United States Patent
Kanasty et al.

(10) Patent No.: US 12,023,406 B2
(45) Date of Patent: *Jul. 2, 2024

(54) GASTRIC RESIDENCE SYSTEMS WITH RELEASE RATE-MODULATING FILMS

(71) Applicant: Lyndra Therapeutics, Inc., Watertown, MA (US)

(72) Inventors: Rosemary Kanasty, Cambridge, MA (US); Nupura Bhise, Cambridge, MA (US); Stephen Zale, Hopkinton, MA (US); Bennett Carter, Stoughton, MA (US); Jung Hoon Yang, Brookline, MA (US); Andrew Bellinger, Wellesley, MA (US); Susan Low, Pepperell, MA (US); James Wright, Lexington, MA (US); David Altreuter, Wayland, MA (US); Colin Gardner, Concord, MA (US)

(73) Assignee: LYNDRA THERAPEUTICS, INC., Watertown, MA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/618,759

(22) PCT Filed: Jun. 8, 2018

(86) PCT No.: PCT/US2018/036743
§ 371 (c)(1),
(2) Date: Dec. 2, 2019

(87) PCT Pub. No.: WO2018/227147
PCT Pub. Date: Dec. 13, 2018

(65) Prior Publication Data
US 2020/0146979 A1  May 14, 2020

Related U.S. Application Data

(60) Provisional application No. 62/652,128, filed on Apr. 3, 2018, provisional application No. 62/566,111, filed on Sep. 29, 2017, provisional application No. 62/517,732, filed on Jun. 9, 2017.

(51) Int. Cl.
| | |
|---|---|
| *A61K 9/00* | (2006.01) |
| *A61K 9/14* | (2006.01) |
| *A61K 31/445* | (2006.01) |
| *A61K 31/65* | (2006.01) |
| *A61K 47/10* | (2017.01) |
| *A61K 47/14* | (2017.01) |
| *A61K 47/34* | (2017.01) |

(52) U.S. Cl.
CPC ............ *A61K 9/0065* (2013.01); *A61K 9/146* (2013.01); *A61K 31/445* (2013.01); *A61K 31/65* (2013.01); *A61K 47/10* (2013.01); *A61K 47/14* (2013.01); *A61K 47/34* (2013.01)

(58) Field of Classification Search
CPC .... A61K 9/0065; A61K 9/146; A61K 31/445; A61K 31/65; A61K 47/10; A61K 47/14; A61K 47/34; A61K 31/519; A61K 47/32
See application file for complete search history.

(56) References Cited

U.S. PATENT DOCUMENTS

| | | |
|---|---|---|
| 1,957,564 A | 5/1934 | West |
| 3,154,461 A | 10/1964 | Johnson |
| 3,531,368 A | 9/1970 | Okamoto |
| 3,716,614 A | 2/1973 | Watanabe |
| 3,844,285 A | 10/1974 | Laby |
| 3,976,764 A | 8/1976 | Watanabe |
| 4,304,767 A | 12/1981 | Heller |
| 4,451,260 A | 5/1984 | Mitra |
| 4,525,358 A | 6/1985 | Baltes |
| 4,676,507 A | 6/1987 | Patterson |
| 4,735,804 A | 4/1988 | Caldwell |
| 4,758,436 A | 7/1988 | Caldwell |
| 4,767,627 A | 8/1988 | Caldwell |
| 4,812,012 A | 3/1989 | Terada |

(Continued)

FOREIGN PATENT DOCUMENTS

| | | |
|---|---|---|
| AU | 643219 B2 | 1/1991 |
| AU | 6199090 A | 3/1991 |

(Continued)

OTHER PUBLICATIONS

Woodruff, Polymer-Polycaprolactone, Progress in Polym. Sci. p. 1217, Apr. 2010.*

(Continued)

*Primary Examiner* — Sarah Alawadi
*Assistant Examiner* — Thurman Wheeler
(74) *Attorney, Agent, or Firm* — MORRISON & FOERSTER LLP

(57) ABSTRACT

The invention provides gastric residence systems, or components of gastric residence system such as segments or elongate members of gastric residence systems, with release rate-modulating films and methods for making and using such systems. The release rate-modulating films provide good control over release of agents (such as therapeutic, diagnostic, or nutritional agents) present in the gastric residence system. The films also permit higher drug loading in the gastric residence systems and components of gastric residence systems while maintaining good control over release of agents. Some embodiments of the films can provide resistance against burst release of agent upon exposure to alcohol.

57 Claims, 39 Drawing Sheets

(56) References Cited

U.S. PATENT DOCUMENTS

| | | | |
|---|---|---|---|
| 4,996,058 A | 2/1991 | Sinnreich | |
| 5,002,772 A | 3/1991 | Curatolo | |
| 5,007,790 A | 4/1991 | Shell | |
| 5,047,464 A | 9/1991 | Pogany | |
| 5,121,329 A | 6/1992 | Crump | |
| 5,340,433 A | 8/1994 | Crump | |
| 5,369,142 A | 11/1994 | Culbertson | |
| 5,443,843 A | 8/1995 | Curatolo | |
| 5,491,586 A | 2/1996 | Phillips | |
| 5,762,637 A | 6/1998 | Berg et al. | |
| 5,840,332 A | 11/1998 | Lerner | |
| 5,939,467 A * | 8/1999 | Wnuk | A61L 15/62 523/128 |
| 6,120,802 A | 9/2000 | Breitenbach et al. | |
| 6,120,803 A | 9/2000 | Wong | |
| RE37,314 E | 8/2001 | Hirai | |
| 6,306,420 B1 | 10/2001 | Cheikh | |
| 6,306,439 B1 | 10/2001 | Penners | |
| 6,316,460 B1 | 11/2001 | Creekmore | |
| 6,375,649 B1 | 4/2002 | Jellie | |
| 6,436,069 B1 | 8/2002 | Jellie | |
| 6,488,962 B1 | 12/2002 | Berner | |
| 6,500,168 B1 | 12/2002 | Jellie | |
| 6,548,083 B1 | 4/2003 | Wong | |
| 6,685,962 B2 | 2/2004 | Friedman | |
| 6,776,999 B1 | 8/2004 | Krumme | |
| 6,780,168 B2 | 8/2004 | Jellie | |
| 6,825,308 B1 | 11/2004 | Kulkarni | |
| 6,962,579 B2 | 11/2005 | Jellie | |
| 7,276,252 B2 | 10/2007 | Payumo | |
| 7,691,151 B2 | 4/2010 | Kutsko | |
| 7,964,196 B2 | 6/2011 | De | |
| 8,021,384 B2 | 9/2011 | Weiss | |
| 8,038,659 B2 | 10/2011 | Boyden | |
| 8,158,143 B2 | 4/2012 | Lendlein | |
| 8,267,888 B2 | 9/2012 | Marco | |
| 8,277,843 B2 | 10/2012 | Singh | |
| 8,298,574 B2 | 10/2012 | Tsabari | |
| 8,377,453 B2 | 2/2013 | Han | |
| 8,414,559 B2 | 4/2013 | Gross | |
| 8,586,083 B2 | 11/2013 | Mohammad | |
| 8,609,136 B2 | 12/2013 | Tsabari | |
| 8,753,678 B2 | 6/2014 | Tsabari | |
| 8,771,730 B2 | 7/2014 | Navon | |
| 9,072,663 B2 | 7/2015 | Navon | |
| 9,107,816 B2 | 8/2015 | Lee | |
| 9,220,688 B2 | 12/2015 | Alon | |
| 9,259,387 B2 | 2/2016 | Navon | |
| 10,182,985 B2 | 1/2019 | Bellinger | |
| 10,195,143 B2 | 2/2019 | Zalit et al. | |
| 10,485,758 B2 | 11/2019 | Menachem et al. | |
| 10,517,819 B2 | 12/2019 | Bellinger et al. | |
| 10,517,820 B2 | 12/2019 | Bellinger | |
| 10,532,027 B2 | 1/2020 | Bellinger | |
| 10,596,110 B2 | 3/2020 | Bellinger | |
| 10,610,482 B2 | 4/2020 | Bellinger | |
| 10,716,751 B2 | 7/2020 | Bellinger et al. | |
| 10,716,752 B2 | 7/2020 | Bellinger et al. | |
| 11,077,056 B2 | 8/2021 | Bellinger et al. | |
| 11,246,829 B2 | 2/2022 | Bellinger et al. | |
| 11,357,723 B2 | 6/2022 | Bellinger et al. | |
| 11,389,399 B2 | 7/2022 | Bellinger et al. | |
| 11,576,866 B2 * | 2/2023 | Bellinger | A61K 9/4866 |
| 2002/0022048 A1 | 2/2002 | Bromberg | |
| 2002/0132008 A1 | 9/2002 | Mumper | |
| 2003/0021822 A1 | 1/2003 | Lloyd | |
| 2003/0232895 A1 | 12/2003 | Omidian | |
| 2004/0180086 A1 | 9/2004 | Ramtoola | |
| 2004/0219186 A1 | 11/2004 | Ayres | |
| 2005/0033331 A1 | 2/2005 | Burnett | |
| 2005/0165136 A1 | 7/2005 | Mays | |
| 2005/0175702 A1 | 8/2005 | Muller-schulte | |
| 2005/0249807 A1 | 11/2005 | Brown et al. | |
| 2006/0069214 A1 | 3/2006 | Deiss | |
| 2006/0142794 A1 | 6/2006 | Lendlein | |
| 2006/0182788 A1 | 8/2006 | Singh | |
| 2007/0048383 A1 | 3/2007 | Helmus | |
| 2007/0104754 A1 | 5/2007 | Sterling | |
| 2007/0123809 A1 | 5/2007 | Weiss | |
| 2007/0129784 A1 | 6/2007 | Lendlein | |
| 2007/0131144 A1 | 6/2007 | Winter et al. | |
| 2007/0264307 A1 | 11/2007 | Chen | |
| 2008/0075766 A1 | 3/2008 | Li | |
| 2008/0153779 A1 | 6/2008 | Liao | |
| 2008/0241238 A1 | 10/2008 | Dharmadhikari | |
| 2008/0249156 A1 | 10/2008 | Palepu | |
| 2008/0260824 A1 | 10/2008 | Nangia | |
| 2008/0292691 A1 | 11/2008 | Lloyd | |
| 2009/0092415 A1 | 4/2009 | Murakami | |
| 2009/0105531 A1 | 4/2009 | Boyden | |
| 2009/0155326 A1 | 6/2009 | Mack | |
| 2009/0182424 A1 | 7/2009 | Marco | |
| 2009/0246142 A1 | 10/2009 | Bhatia | |
| 2009/0324694 A1 | 12/2009 | Mohammad | |
| 2010/0152410 A1 | 6/2010 | East | |
| 2010/0168439 A1 | 7/2010 | Olson | |
| 2010/0256342 A1 | 10/2010 | Salemme | |
| 2010/0266655 A1 | 10/2010 | Dadey | |
| 2010/0297009 A1 | 11/2010 | Olson | |
| 2010/0316712 A1 | 12/2010 | Nangia | |
| 2011/0038912 A1 * | 2/2011 | Darby | A61L 29/16 424/423 |
| 2011/0040318 A1 | 2/2011 | Marco | |
| 2011/0052700 A1 | 3/2011 | Han | |
| 2011/0097395 A1 | 4/2011 | Babul et al. | |
| 2011/0125091 A1 | 5/2011 | Abbate | |
| 2011/0245909 A1 | 10/2011 | Schmid | |
| 2011/0268666 A1 | 11/2011 | Friedman | |
| 2011/0305685 A1 | 12/2011 | Tseng | |
| 2012/0009261 A1 | 1/2012 | Sesha | |
| 2012/0116285 A1 | 5/2012 | Duggirala | |
| 2012/0165793 A1 | 6/2012 | Ortiz | |
| 2012/0165794 A1 | 6/2012 | Ortiz | |
| 2012/0301547 A1 | 11/2012 | Gan | |
| 2012/0321706 A1 | 12/2012 | Masri | |
| 2013/0045530 A1 | 2/2013 | Gracias | |
| 2013/0131637 A1 | 5/2013 | Dicesare et al. | |
| 2013/0226104 A1 | 8/2013 | Hyde | |
| 2013/0273135 A1 | 10/2013 | Brooks | |
| 2014/0050784 A1 | 2/2014 | Kagan | |
| 2014/0052171 A1 | 2/2014 | Tegels | |
| 2014/0249499 A1 | 9/2014 | Selaru | |
| 2015/0265536 A1 | 9/2015 | Muley | |
| 2015/0335592 A1 | 11/2015 | Barnscheid | |
| 2015/0342877 A1 | 12/2015 | Menachem | |
| 2016/0317796 A1 | 11/2016 | Zhang | |
| 2017/0051099 A1 | 2/2017 | Diciccio | |
| 2017/0106099 A1 | 4/2017 | Bellinger | |
| 2017/0128576 A1 | 5/2017 | Zhang | |
| 2017/0135954 A1 | 5/2017 | Bellinger | |
| 2017/0266112 A1 | 9/2017 | Bellinger | |
| 2018/0250226 A1 | 9/2018 | Betser et al. | |
| 2018/0311154 A1 | 11/2018 | Kanasty | |
| 2018/0369138 A1 | 12/2018 | Zalit et al. | |
| 2019/0070107 A1 | 3/2019 | Bellinger | |
| 2019/0070108 A1 | 3/2019 | Bellinger | |
| 2019/0125667 A1 | 5/2019 | Bellinger | |
| 2019/0133936 A1 | 5/2019 | Bellinger | |
| 2019/0175500 A1 | 6/2019 | Bellinger | |
| 2019/0231697 A1 | 8/2019 | Bellinger | |
| 2019/0254966 A1 | 8/2019 | Bellinger | |
| 2019/0262265 A1 | 8/2019 | Bellinger | |
| 2019/0290799 A1 | 9/2019 | Arshi et al. | |
| 2019/0298652 A1 | 10/2019 | Bellinger et al. | |
| 2019/0365645 A1 | 12/2019 | Traverso et al. | |
| 2019/0365646 A1 | 12/2019 | Menachem et al. | |
| 2019/0366064 A1 | 12/2019 | Traverso et al. | |
| 2020/0030589 A1 | 1/2020 | Ben Menachem et al. | |
| 2020/0085736 A1 | 3/2020 | Bellinger et al. | |
| 2020/0085737 A1 | 3/2020 | Bellinger et al. | |
| 2020/0230244 A1 | 7/2020 | Traverso et al. | |
| 2020/0376242 A1 | 12/2020 | Ben Menachem et al. | |
| 2020/0405635 A1 | 12/2020 | Menachem et al. | |
| 2021/0093564 A1 | 4/2021 | Bellinger et al. | |

(56) References Cited

U.S. PATENT DOCUMENTS

| | | | |
|---|---|---|---|
| 2021/0113460 A1 | 4/2021 | Bellinger et al. | |
| 2021/0128460 A1 | 5/2021 | Bellinger et al. | |
| 2021/0177750 A1 | 6/2021 | Bellinger et al. | |
| 2023/0039421 A1 | 2/2023 | Bellinger et al. | |

FOREIGN PATENT DOCUMENTS

| | | | |
|---|---|---|---|
| CA | 2951884 A1 | 12/2015 | |
| CN | 1049787 A | 3/1991 | |
| CN | 1754898 A | 4/2006 | |
| CN | 102245127 A | 11/2011 | |
| CN | 103654903 A | 3/2014 | |
| EP | 0202159 A2 | 11/1986 | |
| EP | 0253554 A2 | 1/1988 | |
| EP | 0253554 A3 | 7/1988 | |
| EP | 0344939 A2 | 12/1989 | |
| EP | 0388234 A1 | 9/1990 | |
| EP | 0406015 A1 | 1/1991 | |
| EP | 0415671 A2 | 3/1991 | |
| EP | 0202159 B1 | 7/1991 | |
| EP | 0344939 B1 | 1/1993 | |
| EP | 0820258 B1 | 10/2002 | |
| EP | 1124534 B1 | 1/2004 | |
| EP | 1687379 A1 | 8/2006 | |
| EP | 1911518 A1 | 4/2008 | |
| EP | 2324822 A2 | 5/2011 | |
| EP | 2329810 A1 | 6/2011 | |
| EP | 1528916 B1 | 12/2012 | |
| JP | S58174312 A | 10/1983 | |
| JP | S6226215 A | 2/1987 | |
| JP | S6323815 A | 8/1987 | |
| JP | H0229268 A | 11/1989 | |
| JP | H03044318 A | 2/1991 | |
| JP | H03128934 A | 5/1991 | |
| JP | H03163011 A | 7/1991 | |
| JP | 2006518392 A | 8/2006 | |
| JP | 2013500293 A | 1/2013 | |
| JP | 2013530193 A | 7/2013 | |
| JP | 2004325508 A | 11/2018 | |
| RU | 2070029 C1 | 12/1996 | |
| RU | 2242219 C2 | 12/2004 | |
| WO | 199738969 A1 | 10/1997 | |
| WO | 200025742 A1 | 5/2000 | |
| WO | 200137812 A2 | 5/2001 | |
| WO | 200137812 A3 | 2/2002 | |
| WO | 2003015745 A1 | 2/2003 | |
| WO | 2004010978 A1 | 2/2004 | |
| WO | 2004073690 A1 | 9/2004 | |
| WO | 2004112755 A1 | 12/2004 | |
| WO | 2005065660 A2 | 7/2005 | |
| WO | 2006072948 A2 | 7/2006 | |
| WO | 2006084164 A2 | 8/2006 | |
| WO | 2006072948 A3 | 11/2006 | |
| WO | 2006084164 A3 | 11/2006 | |
| WO | 2007027812 A2 | 3/2007 | |
| WO | 2007048223 A2 | 5/2007 | |
| WO | 2005065660 A3 | 6/2007 | |
| WO | 2007048223 A3 | 6/2007 | |
| WO | 2007083309 A2 | 7/2007 | |
| WO | 2007093999 A1 | 8/2007 | |
| WO | 2007083309 A3 | 9/2007 | |
| WO | 2008015162 A1 | 2/2008 | |
| WO | 2008039698 A1 | 4/2008 | |
| WO | 2008140651 A2 | 11/2008 | |
| WO | 2008140651 A3 | 1/2009 | |
| WO | 2007027812 A3 | 4/2009 | |
| WO | 2009132461 A1 | 11/2009 | |
| WO | 2009144558 A1 | 12/2009 | |
| WO | 2010035273 A2 | 4/2010 | |
| WO | 2010042879 A2 | 4/2010 | |
| WO | 2010042879 A3 | 6/2010 | |
| WO | 2010064100 A1 | 6/2010 | |
| WO | 2010064139 A2 | 6/2010 | |
| WO | 2010035273 A3 | 7/2010 | |
| WO | 2010064139 A3 | 9/2010 | |
| WO | 2010099466 A2 | 9/2010 | |
| WO | 2010099466 A3 | 1/2011 | |
| WO | 2011012369 A2 | 2/2011 | |
| WO | 2011032087 A2 | 3/2011 | |
| WO | 2011032087 A3 | 6/2011 | |
| WO | 2011012369 A3 | 9/2011 | |
| WO | 2011139796 A2 | 11/2011 | |
| WO | 2012003968 A1 | 1/2012 | |
| WO | 2011139796 A3 | 3/2012 | |
| WO | 2012087658 A1 | 6/2012 | |
| WO | 2013011438 A1 | 1/2013 | |
| WO | 2013049188 A1 | 4/2013 | |
| WO | 2014014348 A1 | 1/2014 | |
| WO | 2015083171 A1 | 6/2015 | |
| WO | 2015187746 A1 | 12/2015 | |
| WO | 2015191920 A1 | 12/2015 | |
| WO | 2015191922 A1 | 12/2015 | |
| WO | 2015191925 A1 | 12/2015 | |
| WO | WO2017070612 * | 4/2017 | ............... A61K 9/00 |
| WO | WO-2017070612 A1 * | 4/2017 | ........... A61K 31/505 |
| WO | 2017100367 A1 | 6/2017 | |
| WO | 2017205844 A2 | 11/2017 | |
| WO | 2017205844 A3 | 1/2018 | |
| WO | 2018064630 A1 | 4/2018 | |
| WO | 2018227147 A1 | 12/2018 | |
| WO | 2019060458 A1 | 3/2019 | |
| WO | 2019111132 A1 | 6/2019 | |
| WO | 2020102650 A2 | 5/2020 | |
| WO | 2020102650 A3 | 8/2020 | |

OTHER PUBLICATIONS

Agrawal, A. et al. (Jul. 2006). "Clinical Relevance of the Nutcracker Esophagus: Suggested Revision of Criteria for Diagnosis," J Clin Gastroenterol. 40(6):504-509.

Ajili, S.H. et al. (Jun. 2009, e-pub. Jan. 3, 2009). "Polyurethane/ Polycaprolactane Blend With Shape Memory Effect as a Proposed Material for Cardiovascular Implants," Acta Biomaterialia 5(5):1519-1530.

Alhnan, M.A. et al. (Aug. 2016; e-published on May 18, 2016). "Emergence of 3D Printed Dosage Forms: Opportunities and Challenges," Pharm. Res. 33(8):1817-1832, 38 pages.

Barbucci, R. et al. (1989). "Vinyl Polymers Containing Amido and Carboxyl Groups as Side Substituents, 2 a). Thermodynamic and Fourier-Transform Infrared Spectroscopic Studies for the Protonation of poly(N-Acryloylglycine) and the poly(N-N-acryoyl-6-aminocaproic acid)," Makromol. Chem. 190:2627-2638.

Belknap, R. et al. (Jan. 7, 2013). "Feasibility of an Ingestible Sensor-Based System for Monitoring Adherence to Tuberculosis Therapy," Plos One 8(1):e53373, pp. 1-5.

Bellinger, A.M. et al. (Nov. 16, 2016). "Oral, Ultra-Long-Lasting Drug Delivery: Application Toward Malaria Elimination Goals," Sci. Transl. Med. 8(365ra157): 1-12., (with Supplementary Material), 21 pages.

Byrne, C. et al. (Mar. 2007; e-pub. Dec. 18, 2006). "The Ingestible Telemetric Body Core Temperature Sensor: A Review of Validity and Exercise Applications," Brit J Sport Med. 41(3):126-133.

Cargill, R. et al. (Aug. 1988). "Controlled Gastric Emptying. 1. Effects of Physical Properties on Gastric Residence Times of Nondisintegrating Geometric Shapes in Beagle Dogs," Pharm Res. 5(8):533-536.

Cargill, R. et al. (Jun. 1989). "Controlled Gastric Emptying. II. In Vitro Erosion and Gastric Residence Times of an Erodible Device in Beagle Dogs," Pharm Res. 6(6):506-509.

Choudhry, N.K. et al. (Dec. 1, 2011; e-pub. Nov. 14, 2011). "Full Coverage for Preventive Medications After Myocardial Infarction," N Engl J Med. 365:2088-2097.

Cirillo, G. et al. (Jan. 21, 2014). "Carbon Nanotubes Hybrid Hydrogels in Drug Delivery: A Perspective Review," BioMed Res Intl. 2014(Article ID 825017), 17 pages.

Cong, H.-P. et al. (2013, e-pub. Jul. 23, 2013). "Stretchable and Self-Healing Graphene Oxide-Polymer Composite Hydrogels: A Dual-Network Design," Chem Mater. 25:3357-3362.

(56) References Cited

OTHER PUBLICATIONS

Dash, S. et al. (May-Jun. 2010). "Kinetic Modeling on Drug Release From Controlled Drug Delivery Systems," Acta Poloniae Pharmaceutica 67(3):217-223.

Davies, G.C. et al. (Mar. 1993). "Release Characteristics, Ovarian Activity and Menstrual Bleeding Pattern with a Single Contraceptive Implant Releasing 3-Ketodesogestrel," Contraception 47(3):251-261.

Dumortier, G. et al. (Dec. 2006, e-pub. Nov. 11, 2006). "A Review of Poloxamer 407 Pharmaceutical and Pharmacological Characteristics," Pharmaceutical Research 23(12):2709-2728.

Dunn, D.L. et al. (2005). Wound Closure Manual Ethicon, Inc. A Johnson and Johnson company, 127 pages.

Edwards, D.A.W. (Nov. 1961). "Physiological Concepts of the Pylorus," Proceedings of the Royal Society of Medicine 54:930-933.

Ereqat, S. et al. (Sep. 2011). "MDR Tuberculosis and Non-Compliance With Therapy," Lancet Infect Dis. 11(9):662.

European Extended Search Report dated Jul. 5, 2019, for Application No. EP 16873798.9, filed on Apr. 26, 2018, 9 pages.

European Search Report dated May 27, 2019 for Application No. EP 16858392.0, filed on Apr. 26, 2018, 10 pages.

Evonik Industries AG, (Dec. 2012). Eudragit Technical Information Sheet, Eudragit L 100 and Eudragit S 100, Specification and Test Methods, 7 pages.

Extended European Search Report dated Feb. 23, 2018 for Application No. EP 15806483.2, filed Jun. 11, 2015, 8 pages.

Extended European Search Report dated Dec. 20, 2017 for Application No. EP 15806017.8, filed on Apr. 26, 2018, 10 pages.

Extended European Search Report dated Jun. 4, 2021 for Application No. EP 18813515.6, 8 pages.

Extended European Search Report dated Nov. 20, 2019 for Application No. EP 17803732.1, 9 pages.

Fallon, S.C. et al. (Apr. 2013). "The Surgical Management of Rapunzel Syndrome: A Case Series and Literature Review," J Pediatr Surg. 48(4):830-834.

Farra, R. et al. (Feb. 22, 2012; e-pub Feb. 16, 2012.). "First-In-Human Testing of a Wirelessly Controlled Drug Delivery Microchip," Sci Transl Med. 4(122):122ra21, 12 pages.

Fix, J.A. et al. (1993). "Controlled Gastric Emptying. III. Gastric Residence Time of a Nondisintegrating Geometric Shape in Human Volunteers," Pharm. Res. 10(7):1087-1089.

Fuhrmann, G. et al. (Jul. 2013). "Sustained Gastrointestinal Activity of Dendronized Polymer-Enzyme Conjugates," Nat Chem. 5:582-589.

Genco, A. et al. (2005). "Bioenterics Intragastric Balloon: The Italian Experience With 2,515 Patients," Obes Surg. 15:1161-1164.

Gordi, T. et al. (May 2008). "Pharmacokinetics of Gabapentin After A Single Day and at Steady State Following The Administration of Gastric-Retentive-Extended-Release And Immediate-Release Tablets: A Randomized, Open-Label, Multiple-Dose, Three-Way Crossover, Exploratory Study in Healthy Subjects," Clin Ther. 30(5):909-916.

Harrison, S.K. et al. (2006). "Comparison of Shear Modulus Test Methods," Virginia Tech. 8 pages.

Haslauer, C.M. et al. (Jul. 2015; e-published on Sep. 17, 2014). "Translating Textiles To Tissue Engineering: Creation And Evaluation Of Microporous, Biocompatible, Degradable Scaffolds Using Industry Relevant Manufacturing Approaches And Human Adipose Derived Stem Cells," J. Biomed. Mater. Res. B Appl. Biomater. 103(5):1050-1058, 22 pages.

Hiemke, C. et al. (Sep. 2011; e-published on Sep. 27, 2011). "AGNP Consensus Guidelines for Therapeutic Drug Monitoring in Psychiatry: Update 2011," Pharmacopsychiatry 44(6):195-235.

Huang, W.M. et al. (Jul.-Aug. 2010). "Shape Memory Materials," Materials Today 13(7-8):54-61.

Hwang, S.-J. et al. (1998). "Gastric Retentive Drug-Delivery Systems," Crit Rev Ther Drug Carrier Syst. 15(3):243-284.

International Preliminary Report on Patentability for PCT/US2015/035425 dated Dec. 15, 2016, filed Jun. 11, 2015, 6 pages.

International Preliminary Report on Patentability for PCT/US2015/035429 dated Dec. 15, 2016, filed Jun. 11, 2015, 8 pages.

International Preliminary Report on Patentability dated Dec. 10, 2019 for PCT Application No. PCT/US2018/036743 filed on Jun. 8, 2018, 16 pages.

International Preliminary Report on Patentability dated Apr. 11, 2019 for PCT Application No. PCT/US2017/054608 filed on Sep. 29, 2017, 16 pages.

International Preliminary Report on Patentability dated Dec. 6, 2018 for PCT Application No. PCT/US2017/034856, filed on May 26, 2017, 11 pages.

International Preliminary Report on Patentability dated Dec. 22, 2016 for PCT Application No. PCT/US2015/035423 filed on Jun. 11, 2015, 11 pages.

International Preliminary Report on Patentability dated Jun. 21, 2018 for PCT Application No. PCT/US2016/065453 filed on Dec. 7, 2016, 11 pages.

International Preliminary Report on Patentability dated May 3, 2018 for PCT Application No. PCT/US2016/058309 filed on Oct. 21, 2016, 6 pages.

International Preliminary Report on Patentability dated Nov. 16, 2017 for PCT Application No. PCT/US2016/030020 filed on Apr. 29, 2016, 8 pages.

International Search Report and Written Opinion for PCT/US2015/035425 dated Sep. 15, 2015, filed Jun. 11, 2015, 8 pages.

International Search Report and Written Opinion for PCT/US2015/035429 dated Sep. 15, 2015, filed Jun. 11, 2015, 9 pages.

International Search Report and Written Opinion dated Dec. 14, 2017 for PCT Application No. PCT/US2017/054608 filed on Sep. 29, 2017, 18 pages.

International Search Report and Written Opinion dated Dec. 29, 2016 for PCT Application No. PCT/US2016/058309 filed on Oct. 21, 2016, 8 pages.

International Search Report and Written Opinion dated Feb. 28, 2017 for PCT Application No. PCT/US2016/065453 filed on Dec. 7, 2016, 14 pages.

International Search Report and Written Opinion dated Jul. 21, 2016 for PCT Application No. PCT/US2016/030020 filed on Apr. 29, 2016, 10 pages.

International Search Report and Written Opinion dated Nov. 13, 2017 for PCT Application No. PCT/US2017/034856, filed on May 26, 2017, 15 pages.

International Search Report and Written Opinion dated Sep. 10, 2018 for PCT Application No. PCT/US2018/036743 filed on Jun. 8, 2018, 26 pages.

International Search Report and Written Opinion dated Sep. 15, 2015 for PCT Application No. PCT/US2015/035423 filed on Jun. 11, 2015, 13 pages.

Invitation to Pay Additional Fees and, Where Applicable, Protest Fee, dated Sep. 5, 2017, for PCT Application No. PCT/US2017/034856, filed on May 26, 2017, 3 pages.

Jantratid, E. et al. (Jul. 2008; e-pub. Apr. 11, 2008). "Dissolution Media Simulating Conditions in the Proximal Human Gastrointestinal Tract: An Update," Pharm. Res. 25(7):1663-1676.

Javed, I. et al. (2014). "Drug Release Optimization From Microparticles of Poly(ε-caprolactone) and Hydroxypropyl Methylcellulose Polymeric Blends: Formulation and Characterization," J. Drug Del. Sci. Tech. 24(6);607-612.

Kanis, L.A. et al. (2014). "Cellulose Acetate Butyrate/Poly(caprolactonetriol) Blends: Miscibility, Mechanical Properties, and in vivo Inflammatory Response," J. of Biomaterials Applications 29(5):654-661.

Kao, E.C. et al. (Jan. 1996). "Preparation of Glass Ionomer Cement Using N-acryloyl Substituted Amino Acid Monomers-Evaluationof Physical Properties," Dent Mater. 12:44-51.

Karim, Q.A. et al. (Sep. 3, 2010, e-pub. Jul. 19, 2010). "Effectiveness And Safety Of Tenofovir Gel, An Antiretroviral Microbicide, For The Prevention Of HIV Infection In Women," Science 329(5996):1168-1174, 19 pages.

Kethu, S.R. et al. (2012). "Endoluminal Bariatric Techniques," Gastrointestinal Endoscopy 76(1):1-7.

(56) References Cited

OTHER PUBLICATIONS

Khaled, S.A. et al. (Jan. 30, 2014). "Desktop 3D Printing of Controlled Release Pharmaceutical Bilayer Tablets," International Journal of Pharmaceutics 461(1-2):105-111, 17 pages.

Khanna, S.C. et al. (Sep. 1969). "Epoxy Resin Beads as a Pharmaceutical Dosage Form. I.: Method of Preparation," Journal of Pharmaceutical Sciences 58(9):1114-1117.

Kim, B.K. et al. (1996). "Polyurethanes Having Shape Memory Effects," Polymer 37(26):5781-5793.

Kim, Y.J. et al. (Dec. 24, 2013). "Biologically Derived Melanin Electrodes In Aqueous Sodium-Ion Energy Storage Devices," P Natl Acad Sci USA. 110(52): 20912-20917.

Lam, P.L. et al. (2014). "Advanced Progress of Microencapsulation Technologies: In Vivo and In Vitro Models for Studying Oral and Transdermal Drug Deliveries," J. Control Release 178:25-45.

Laulicht, B. et al. (Feb. 8, 2011). "Localization of Magnetic Pills," Proc Natl Acad Sci. 108(6):2252-2257.

Li, L.C. et al. (Oct. 16, 2002). "Polyanhydride Implant for Antibiotic Delivery—From the Bench to the Clinic," Adv Drug Deliv Rev. 54(7):963-986.

Lipton, S.A. (Jan. 2004). "Failures and Successes of NMDA Receptor Antagonists: Molecular Basis For the Use of Open-Channel Blockers Like Memantine in the Treatment of Acute and Chronic Neurologic Insults," NeuroRx: The Journal of the American Society for experimental Neuro Therapeutics 1(1):101-110.

Liu, Y. et al. (2009; e-pub. Aug. 29, 2008). "Review of Electro-Active Shape-Memory Polymer Composite," Compos Sci and Technol. 69(13):2064-2068.

López-Pousa, S. et al. (Sep. 2012). "Consumption of Pharmaceuticals in Primary Non-Alzheimer's Degenerative Dementias: A Cross-Sectional Study By the Registry of Dementias of Girona (ReDeGi)," Drugs Aging 29(9):733-740, 22 pages.

Marrazzo, J.M. et al. (Feb. 5, 2015). "Tenofovir-Based Preexposure Prophylaxis for HIV Infection Among African Women," N Engl J Med. 372(6):509-518.

Meng, Q. et al. (2009). "A Review of Shape Memory Polymer Composites and Blends," Composites Part A: Applied Science and Manufacturing 40(11):1661-1672.

Miao, L. et al. (2015). "Exploring the Tumor Microenvironment With Nanoparticles," Cancer Treat Res. 166:193-226, 36 pages.

Mintchev, M.P. et al. (Feb. 2010; e-pub Dec. 11, 2009). "Pilot Study of Temporary Controllable Gastric Pseudobezoars for Dynamic Non-Invasive Gastric Volume Reduction," Physiol Meas. 31(2):131-144.

Moes, A.J. (Jan. 1993). "Gastroretentive Dosage Forms," Crit Rev Ther Drug Carrier Syst. 10(2):143-195.

Mohr, R. et al. (Mar. 7, 2006; e-pub Feb. 28, 2006.). "Initiation of Shape-Memory Effect by Inductive Heating of Magnetic Nanoparticles in Thermoplastic Polymers," Proc Natl Acad Sci USA. 103(10):3540-3545.

Murphy, C.S. et al. (Oct. 2009). "Gastro-Retentive Drug Delivery Systems: Current Developments in Novel System Design and Evaluation," Curr. Drug Deliv. 6(5):451-460.

Muthu, M.S. et al. (2008). "Studies on Biodegradable Polymeric Nanoparticles of Risperidone: in vitro and in vivo Evaluation," Nanomedicine 3(3):305-319.

Nakamichi, K. (2004). "The Preparation of Enteric Solid Dispersions With Hydroxypropylmethylcellulose Acetate Succinate Using a Twin-Screw Extruder," J. Drug Del. Sci. Tech. 3(14):193-198.

Neto-Ferreira, R. et al. (2013). "Pleiotropic Effects of Rosuvastatin on the Glucose Metabolism and the Subcutaneous and Visceral Adipose Tissue Behavior in C57Bl/6 Mice," Diabetology Metabol Synd. 5:32, 10 pages.

Olson, A.J. et al. (Dec. 26, 2007; e-pub Dec. 18, 2007). "Chemical Mimicry of Viral Capsid Self-Assembly," Proc Natl Acad Sci USA 104(52):20731-20736.

Osterberg, L. et al. (Aug. 4, 2005). "Adherence to Medication," N Engl J Med. 353(5):487-497.

Phadke, A. et al. (Mar. 20, 2012; e-pub Mar. 5, 2012). "Rapid Self-Healing Hydrogels," Proc Natl Acad Sci USA 109(12):4383-4388.

Phillips, M.R. et al. (Jul. 1998). "Gastric Trichobezoar: Case Report and Literature Review," Mayo Clin Proc. 73(7):653-656.

Pittenger, C. (Jun. 2015, e-published on Jun. 11, 2015). "Glutamate Modulators in the Treatment of Obsessive-Compulsive Disorder," Psychiatr. Ann. 45(6):308-315, 13 pages.

Puso, M. A. et al. (Jan. 1, 2006). "A Stabilized Nodally Integrated Tetrahedral," International Journal for Numerical Methods in Engineering 67(6):841-867.

Rammes, G. et al. (Mar. 2008). "Pharmacodynamics of Memantine: An Update," Curr. Neuropharmacol. 6(1):55-78.

Ren, S. et al. (2009). "Noncovalently Connected Micelles Based on a β-cyclodextrin-Contaiing Polymer and Adamantane End-Capped Poly(e-ecaprolactone) via Host-Guest Interactions," J Polym Sci. 47:4267-4278.

Richter, J.E. et al. (Jun. 1987). "Esophageal Manometry in 95 Healthy Adult Volunteers. Variability of Pressures With Age and Frequency of "Abnormal" Contractions," Dig Dis Sci. 32(6):583-592.

Salessiotis, N. (Sep. 1972). "Measurement of the Diameter of the Pylorus in Man: Part I. Experimental Project for Clinical Application," The Amer J of Surgery. 124:331-333.

Salunke, D.M. et al. (Sep. 12, 1986). "Self-Assembly of Purified Polyomavirus Capsid Protein VP1," Cell 46(6):895-904, 10 pages.

Singer, S.J. et al. (Feb. 18, 1972). "The Fluid Mosaic Model of the Structure of Cell Membranes," Science 175(4023):720-731.

Singh, B.N. et al. (Feb. 3, 2000). "Floating Drug Delivery Systems: An Approach to Oral Controlled Drug Delivery Via Gastric Retention," J Control Release 63(3):235-259.

Singh, P. et al. (2015, e-pub, Dec. 18, 2014). "Synthesis and Characterization of Nano Micelles of poly(N-acrylamidohexanoic acid)-b-poly(N-vinylcaprolactam) Via RAFT Process: Solubilizing and Releasing of Hydrophobic Molecules," Polymer. 57:51-61.

Six-Pentagons (Dec. 23, 2017). "Six-Pentagons Polylink," retrieved from http://makingmathvisible.com/polylinks/polylinks-3.html, lasted visited Dec. 23, 2017, 4 pages.

Szakács, R. et al. (2012). "The "Blue" Side of Glutamatergic Neurotransmission: NMDA Receptor Antagonists as Possible Novel Therapeutics for Major Depression," Neuropsychopharmacol. Hung. 14(1):29-40.

Tao, H. et al. (Feb. 21, 2012). "Silk-Based Conformal, Adhesive, Edible Food Sensors," Adv Mater. 24(8):1067-1072.

Timmer, C.J. et al. (Sep. 2000). "Pharmacokinetics of Etonogestrel and Ethinylestradiol Released From a Combined Contraceptive Vaginal Ring," Clin Pharmacokinet. 39(3):233-242.

Traverso, G. et al. (Mar. 26, 2015). "Special Delivery for the Gut," Nature. 519:S19.

Uhrich, K.E. et al. (1999, e-pub. Oct. 26, 1999). "Polyermic Systems for Controlled Drug Relase," Chem. Rev. 99:3181-3198.

Ursan, I.D. et al. (Mar.-Apr. 2013). "Three-Dimensional Drug Printing: A Structured Review," J. Am. Pharm. Assoc. 53(2):136-144.

US Dept Health "Q3C—Tables and List Guidance for Industy," (2017). Retrieved from www.fda.gov/downloads/drugs/guidances/ucm073395.pdf, last visited Jun. 2017, 10 pages.

US Dept. Health "Guidance for Industry: Size, Shape, and Other Physical Attributes of Generic Tables and Capsules," (2013). Retrieved from www.v.regulations.gov/#!documentDetail;D=FDA-2013-N-1434-0002, last visited Dec. 2013, 11 pages.

Welding Techniques for Thermoplastics (2021). retrieved from the Internet: URL:https://www.twi-global.com/technical-knowledge/job-knowledge/welding-techniques-forthermoplastics-055 (http://web.archive.org/web/20150416235739/http://www.twiglobal.com/technical-knowledge/job-knowledge/welding-techniques-for-thermoplastics-055/, last visited Mar. 17, 2021, 8 pages.

Whitesides, G.M. et al. (Mar. 29, 2002). "Self-Assembly at all Scales," Science 295(5564):2418-2421.

Wilber, A.W. et al. (Nov. 7, 2009). "Self-Assembly of Monodisperse Clusters: Dependence on Target Geometry," J Chem Phys. 131(17):175101, 14 pages.

(56) References Cited

OTHER PUBLICATIONS

Wilber, A.W. et al. (Nov. 7, 2009; e-pub. Nov. 2, 2009). "Monodisperse Self-Assembly in a Model With Protein-Like Interactions," J Chem Phys. 131(17):175102, 11 pages.

Won, Y.W. et al. (Dec. 2014). "Oligopeptide Complex for Targeted Non-Viral Gene Delivery to Adipocytes," Nat Mater.13:1157-1164.

Yang X, et al. (May 14, 2014), e-pub. May 5, 2014). "Triple Shape Memory Effect of Star-Shaped Polyurethane," ACS Appl Mater Interfaces 6(9):6545-6554.

Yerragunta, B. et al. (Jan.-Mar. 2015). "Development of a Novel 3-Month Drug Releasing Risperidone Microspheres," J. Pharm Bioall Sci. 7(1):37-44.

Yu, D.G. et al. (Sep. 2008). "Three-Dimensional Printing in Pharmaceutics: Promises and Problems," J. Pharm. Sci. 97(9):3666-3690.

Zhang, S. et al. (Oct. 2015; e-pub. Jul. 27, 2015). "A Ph-Responsive Supramolecular Polymer Gel as an Enteric Elastomer for Use in Gastric Devices," Nature Materials 14(10):1065-1071, 19 pages.

Zhang, X. et al. (2013; e-pub Oct. 15, 2012). "Biodegradable Shape Memory Nanocomposites With Thermal and Magnetic Field Responsiveness," J Biomater Sci Polym Ed. 24(9):1057-1070.

Zu, Y. et al. (2008, e-pub. Sep. 26, 2008). "Effect of Neutralization of poly(methacrylic acid-co-ethyl acrylate) on Drug Release from Enteric-Coated Pellets Upon Accelerated Storage," Drug Dev. Ind. Pharm. 33(4):457-473.

Abraham, N. (May 15, 2015). "Dow Corning QP1-2 Liquid Silicone Rubber Supports Cost-Effective Medical Device Designs," Medical Design & Outsourcing, retrieved from the Internet https://www.medicaldesignandoutscourcing.com/dow-coming-qp1-2-liquid-silicone-rubber-supports-cost-effective-medical device-designs/, last visited Nov. 16, 2021, 8 pages.

Chourasia, M.K. et al. (2003). "Pharmaceutical Approaches To Colon Targeted Drug Delivery Systems," J. Pharm. Pharmaceut Sci. 6(1):33-66.

Pubchem (Oct. 27, 2022). "472403627—Polyoxyl 40 Hydrogenated Castor Oil," retrieved from the Internet: https://pubchem.ncbi.nlm.nih.gov/substance/472403627#section=Source, last visited Apr. 10, 2023, 5 pages.

* cited by examiner

| Coating Identifier | Coating solution composition |
|---|---|
| C5 | 1g Eudragit RS, 3 mL Dichloromethane |
| C8 | 1g PCL 55K, 6 mL Dichloromethane |
| C31 | 1.5 g Cellulose Acetate, 15mL Acetone |
| C25 | 1g Ethyl Cellulose, 15mL Acetone |

FIG. 3A

| Solvent | Maximum PCL concentration observed | Dissolution conditions | Coating appearance | Coating performance |
|---|---|---|---|---|
| Dichloromethane | Up to 25% wt/vol | Dissolution of PCL in minutes at room temperature. | Acceptable at low PCL concentrations, Uneven at >10% wt/vol | Able to modulate release profile |
| Ethyl acetate | Up to 15% wt/vol | Requires heating to 40°C for several hours for dissolution. Precipitates slowly after cooling to room temperature | Acceptable | Able to modulate release profile |
| Acetone | Up to 10% wt/vol | Requires heating to 40°C for several hours for dissolution. Precipitates slowly after cooling to room temperature | Appears uneven, possibly poorly adhered to underlying matrix | No reliable control over release profile |

FIG. 4

GASTRIC RESIDENCE SYSTEMS WITH RELEASE RATE-MODULATING FILMS

CROSS REFERENCE TO RELATED APPLICATIONS

This application is a national stage application under 35 U.S.C. § 371 of International Application No. PCT/US2018/036743 having an International Filing Date of Jun. 8, 2018, which claims priority benefit of U.S. Provisional Patent Application No. 62/517,732 filed Jun. 9, 2017, of U.S. Provisional Patent Application No. 62/566,111 filed Sep. 29, 2017, and of U.S. Provisional Patent Application No. 62/652,128 filed Apr. 3, 2018. The entire contents of those patent applications are hereby incorporated by reference herein.

FIELD OF THE INVENTION

The invention relates to systems which remain in the stomach for extended periods for sustained release of pharmaceuticals, and methods of use thereof.

BACKGROUND OF THE INVENTION

Gastric residence systems are delivery systems for agents which remain in the stomach for days to weeks, or even over longer periods, during which time drugs or other agents can elute from the systems for absorption in the gastrointestinal tract. Examples of such systems are described in International Patent Application Nos. WO 2014/191920, WO 2015/191925, WO 2017/070612, WO 2017/100367, and PCT/US2017/034856.

Gastric residence systems are designed to be administered to the stomach of a patient, typically in a capsule which is swallowed or introduced into the stomach by an alternate method of administration (for example, feeding tube or gastric tube). Upon dissolution of the capsule in the stomach, the systems expand or unfold to a size which remains in the stomach and resists passage through the pyloric sphincter over the desired residence period (such as three days, seven days, two weeks, etc.). This requires mechanical stability over the desired residence period. Over the period of residence, the system releases an agent or agents, such as one or more drugs, preferably with minimal burst release, which requires careful selection of the carrier material for the agent in order to provide the desired release profile. While resident in the stomach, the system should not interfere with the normal passage of food or other gastric contents. The system should pass out of the stomach at the end of the desired residence time, and be readily eliminated from the patient. If the system prematurely passes from the stomach into the small intestine, it should not cause intestinal obstruction, and again should be readily eliminated from the patient. These characteristics require careful selection of the materials from which the system is constructed, and the dimensions and arrangement of the system.

The current invention describes the use of release rate-modulating films for use in gastric residence systems, which provide good control over release rates of agents from the systems.

SUMMARY OF THE INVENTION

The invention provides gastric residence systems which have segments covered with release rate-modulating polymer films. The invention also provides elongate members of gastric residence systems which have segments covered with release rate-modulating polymer films. The invention also provides segments covered with release rate-modulating polymer films suitable for use in gastric residence systems. The invention also provides elongate members covered with release rate-modulating polymer films suitable for use in gastric residence systems. Methods of making the segments, elongate members, and gastric residence systems are also provided. Methods of using the gastric residence systems are also provided.

In some embodiments, the invention provides gastric residence systems which comprise a therapeutically effective amount of an agent or a pharmaceutically acceptable salt thereof, where the gastric residence system has a compacted configuration and an uncompacted configuration, the gastric residence system comprises a plurality of elongate members affixed to a central elastomer, each elongate member comprises at least two segments joined by linkers, where the linkers are configured such that they no longer join the at least two segments of each elongate member after a specified gastric residence period; and where the elongate members comprise a carrier polymer, and the agent or the pharmaceutically acceptable salt thereof; where the gastric residence system is configured to release the agent or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. In some embodiments, the gastric residence systems as disclosed herein can have a gastric residence period of about four days to about eight days when administered to a human patient. In some embodiments, the gastric residence systems as disclosed herein can have a gastric residence period of about four days to about ten days when administered to a human patient. In some embodiments, the gastric residence systems as disclosed herein can have a gastric residence period of about seven days, or at least about seven days, when administered to a human patient. In some embodiments, the gastric residence systems as disclosed herein can have a gastric residence period of about seven days to about ten days when administered to a human patient In any of the embodiments described herein, the invention can provide gastric residence systems which comprise a therapeutically effective amount of an agent or a pharmaceutically acceptable salt thereof, where the gastric residence system has a compacted configuration and an uncompacted configuration, the gastric residence system comprises a plurality of elongate members affixed to a central elastomer, each elongate member comprises at least two segments joined by linkers, where the linkers are configured to weaken or degrade to allow passage of the gastric residence system through the pylorus after the specified gastric residence period (for example, the linkers may soften and become flexible, or the linkers may no longer join the at least two segments of each elongate member after the specified gastric residence period); and where the segments of the elongate members comprise a carrier polymer and the adamantane-class drug or the pharmaceutically acceptable salt thereof, or the segments of the elongate members comprise a) a carrier polymer, b) at least one excipient, and c) the agent or the pharmaceutically acceptable salt thereof; where the gastric residence system is configured to release the agent or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the embodiments described herein, the invention can provide gastric residence systems which comprise a therapeutically effective amount of an adamantane-class drug or a pharmaceutically acceptable salt thereof, where the gastric residence system has a compacted configuration and an uncompacted configuration, the gastric residence system comprises a plurality of elongate members affixed to a central elastomer by linkers, where the linkers are configured to weaken or degrade to allow passage of the gastric residence system through the pylorus after the specified gastric residence period (for example, the linkers may soften and become flexible, or the linkers may no longer join the elongate members to the central elastomer after the specified gastric residence period). The elongate members comprise a carrier polymer and the adamantane-class drug or the pharmaceutically acceptable salt thereof. In another embodiment, the elongate members further comprise at least one excipient. The gastric residence system is configured to release the adamantane-class drug or the pharmaceutically acceptable salt thereof over the specified gastric residence period. The adamantine-class drug or a pharmaceutically acceptable salt thereof can be memantine or a pharmaceutically acceptable salt thereof. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the embodiments described herein, the invention can provide gastric residence systems which comprise a therapeutically effective amount of risperidone or a pharmaceutically acceptable salt thereof, where the gastric residence system has a compacted configuration and an uncompacted configuration, the gastric residence system comprises a plurality of elongate members affixed to a central elastomer by linkers, where the linkers are configured to weaken or degrade to allow passage of the gastric residence system through the pylorus after the specified gastric residence period (for example, the linkers may soften and become flexible, or the linkers may no longer join the elongate members to the central elastomer after the specified gastric residence period). The elongate members comprise a carrier polymer and risperidone or pharmaceutically acceptable salt thereof. In another embodiment, the elongate members further comprise at least one excipient. The gastric residence system is configured to release risperidone or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the embodiments described herein, the invention can provide gastric residence systems which comprise a therapeutically effective amount of doxycycline or a pharmaceutically acceptable salt thereof, where the gastric residence system has a compacted configuration and an uncompacted configuration, the gastric residence system comprises a plurality of elongate members affixed to a central elastomer by linkers, where the linkers are configured to weaken or degrade to allow passage of the gastric residence system through the pylorus after the specified gastric residence period (for example, the linkers may soften and become flexible, or the linkers may no longer join the elongate members to the central elastomer after the specified gastric residence period). The elongate members comprise a carrier polymer and doxycycline or pharmaceutically acceptable salt thereof. In another embodiment, the elongate members further comprise at least one excipient. The gastric residence system is configured to release doxycycline or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the embodiments described herein, the invention can provide gastric residence systems which comprise a therapeutically effective amount of donepezil or a pharmaceutically acceptable salt thereof, where the gastric residence system has a compacted configuration and an uncompacted configuration, the gastric residence system comprises a plurality of elongate members affixed to a central elastomer by linkers, where the linkers are configured to weaken or degrade to allow passage of the gastric residence system through the pylorus after the specified gastric residence period (for example, the linkers may soften and become flexible, or the linkers may no longer join the elongate members to the central elastomer after the specified gastric residence period). The elongate members comprise a carrier polymer and donepezil or pharmaceutically acceptable salt thereof. In another embodiment, the elongate members further comprise at least one excipient. The gastric residence system is configured to release donepezil or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In some embodiments, the invention provides gastric residence systems which comprise an agent or a pharmaceutically acceptable salt thereof, where the gastric residence system has a compacted configuration and an uncompacted configuration, the gastric residence system comprises a plurality of elongate members affixed to a central elastomer by linkers, where the linkers are configured such that they no longer join the elongate members to the central elastomer after a specified gastric residence period. The elongate members comprise a carrier polymer and the agent or the pharmaceutically acceptable salt thereof. In another embodiment, the elongate members further comprise at least one excipient. The gastric residence system is configured to release the agent or the pharmaceutically acceptable salt thereof over the specified gastric residence period. At least one of the linkers can comprise an enteric polymer, or can comprise a polymer that degrades in a time-dependent manner in an aqueous environment. The gastric residence period of the system can be about four days, at least about four days, about seven days, or at least about seven days. The gastric residence period of the system can be about four days to about ten days, about four days to about eight days, or about seven days to about ten days.

In any of the gastric residence systems disclosed herein, the carrier polymer can be polycaprolactone. One or more additional excipients can be mixed in with the carrier polymer. The one or more additional excipients can be selected from the group consisting of soluble excipients, insoluble wicking excipients, degradable excipients, insoluble swellable excipients, and surfactants. The one or more additional excipients can be selected from the group consisting of P407, Eudragit E, PEG, Polyvinylpyrrolidone (PVP), Polyvinyl acetate (PVAc), Polyvinyl alcohol (PVA), Eudragit RS, Eudragit RL, PLA, PLGA, PLA-PCL, polydioxanone, Crospovidone, Croscarmellose, HPMCAS, Lecithin, Taurocholate, SDS, Soluplus, Fatty acids, Kolliphor RH40; and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate, such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%); linear copolymers of caprolactone (95%) and glycolide (5%); polyaxial block copolymers of glycolide (68%), caprolactone (29%), and trimethylene carbonate (3%); polyaxial block copolymers of glycolide (86%), trimethylene carbonate (9%), and lactide (5%); polyaxial block copolymers of glycolide (70%), trimethylene carbonate (27%) and polypropylene succinate (2%); polyaxial block copolymers of caprolactone (35%), lactide (34%), glycolide (17%), and trimethylene carbonate (14%); polyaxial block copolymers of glycolide (55%), trimethylene carbonate (25%), and caprolactone (20%); and linear block copolymers of lactide (39%), caprolactone (33%), and trimethylene carbonate (28%).

In any of the gastric residence systems disclosed herein, when at least one of the linkers is an enteric polymer, the enteric polymer can be selected from the group consisting of poly(methacrylic acid-co-ethyl acrylate), cellulose acetate phthalate, cellulose acetate succinate, hydroxypropyl methylcellulose phthalate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methacrylic acid methylmethacrylate copolymer, methyl acrylate-methacrylic acid copolymer, methacrylate-methacrylic acid-octyl acrylate copolymer; and copolymers, mixtures, blends and combinations thereof. Hydroxypropyl methylcellulose acetate succinate (HPMCAS) is a particularly useful enteric polymer, and can be used alone or in a copolymer, mixture, blend, or combination with any one or more of the other foregoing enteric polymers.

In any of the gastric residence systems disclosed herein having a central elastomer, the central elastomer can comprise silicone rubber.

In any of the gastric residence systems disclosed herein, the system can further comprise a dispersant selected from the group comprising silicon dioxide, hydrophilic fumed silicon dioxide, a stearate salt, calcium stearate, magnesium stearate, microcrystalline cellulose, carboxymethylcellulose, hydrophobic colloidal silica, hypromellose, magnesium aluminum silicate, a phospholipid, a polyoxyethylene stearate, zinc acetate, alginic acid, lecithin, a fatty acid, sodium lauryl sulfate, a non-toxic metal oxide, aluminum oxide, a porous inorganic material, and a polar inorganic material.

In any of the gastric residence systems disclosed herein, the agent or pharmaceutically acceptable salt thereof can comprise particles of the agent or a pharmaceutically acceptable salt thereof in the form of particles disposed in the carrier polymer, where at least about 80% of the mass of particles have sizes between about 1 micron and about 50 microns in diameter.

In any of the gastric residence systems disclosed herein, the gastric residence system can comprise about 10 mg to about 600 mg of agent or a pharmaceutically acceptable salt thereof.

In one embodiment, the invention provides a formulation for extended release of an agent or a pharmaceutically acceptable salt thereof, comprising about 10% to about 30% of an agent or a pharmaceutically acceptable salt thereof; about 0.1% to about 4% of silica; about 5% to about 30% of an acrylate polymer or co-polymer; and about 0.2% to about 10% of a polyalkylene glycol; where the remainder of the composition comprises a polylactone. The formulation can further comprise about 0.1% to about 2% of an anti-oxidant material. The anti-oxidant material can comprise one or more compounds selected from the group consisting of Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate. (Vitamin E can refer to alpha-tocopherol, beta-tocopherol, gamma-tocopherol, delta-tocopherol, alpha-tocotrienol, beta-tocotrienol, gamma-tocotrienol, or delta-tocotrienol, or to any combinations of any two or more of the foregoing.) The silica can comprise hydrophilic fumed silica particles. The acrylate polymer or co-polymer can comprise a co-polymer of ethyl acrylate, methyl methacrylate and trimethylammonioethyl methacrylate, such as a co-polymer comprising ethyl acrylate, methyl methacrylate and trimethylammonioethyl methacrylate in a molar ratio of about 1:2:0.1. The polyalkylene glycol can be selected from the group consisting of polyethylene glycol (PEG), polypropylene glycol (PPG), and a block copolymer of PEG and PPG. When the polyalkylene glycol comprises a block copolymer of PEG and PPG, it can comprise a copolymer of the formula $H-(OCH2CH2)_x-(O-CH(CH3)CH2)_y-(OCH2CH2)_z-OH$, where x and z are about 101 and y is about 56. The polylactone can comprise polycaprolactone, such as a polycaprolactone having an average Mn of about 60,000 to about 100,000, an average Mn of about 75,000 to about 85,000, or an average Mn of about 80,000 (80 k PCL).

In some embodiments, the invention provides one or more elongate members formed from a material comprising a formulation for extended release of an agent or a pharmaceutically acceptable salt thereof as described herein. In some embodiments, the invention provides gastric residence systems comprising one or more elongate members formed from a material comprising a formulation for extended release of an agent or a pharmaceutically acceptable salt thereof as described herein.

In one embodiment, the invention provides a method of making a gastric residence system, comprising preparing at least three elongate members formed from a material comprising any of the formulations for extended release of an agent or a pharmaceutically acceptable salt thereof as described herein; and attaching the elongate members to a central elastomer, to form a gastric residence system having elongate members projecting radially from the central elastomer.

In any embodiment of the methods of treatment disclosed herein, the gastric residence system can administered to the patient on an approximately weekly basis over a period of at least about one month, at least about two months, at least about three months, or indefinitely, or for a period up to about one month, about two months or about three months.

The invention additionally provides gastric residence systems for administration of agents or salts thereof which have segments or elongate members covered with release rate-modulating polymer films, as well as elongate members of such gastric residence systems which have segments covered with release rate-modulating polymer film, segments covered with release rate-modulating polymer films suitable for use in such gastric residence systems, and elongate members covered with release rate-modulating polymer films suitable for use in such gastric residence systems. Methods of making the segments, elongate members, and gastric residence systems containing agents and salts thereof are also provided. Methods of using the gastric residence systems containing agents and salts thereof are also provided.

In one embodiment, the invention provides a segment of a gastric residence system, the segment comprising a carrier polymer; an agent or a salt thereof; and a release-rate modulating polymer film configured to control the release rate of the agent, wherein over a seven-day incubation of the segment in simulated gastric fluid, the amount of the agent or salt thereof released during day 5 is at least about 40% of the amount of agent or salt thereof released during day 2; and wherein at least about 7% of the total amount of agent in the segment is released on day 2 and at least about 7% of the total amount of agent is released on day 5.

In one embodiment, the invention provides a segment of a gastric residence system, the segment comprising a carrier polymer; an agent or a salt thereof; and a release-rate modulating polymer film configured to control the release rate of the agent, wherein over a seven-day incubation of the segment in simulated gastric fluid, the amount of the agent or salt thereof released from the segment during day 7 is at least about 20; of the amount of agent or salt thereof released during day 1; and wherein at least about 4% of the total amount of agent in the segment is released on day 1 and at least about 4% of the total amount of agent is released on day 7.

In one embodiment, the invention provides a segment of a gastric residence system, the segment comprising a carrier polymer, an agent or a salt thereof; and a release-rate modulating polymer film configured to control the release rate of the agent, wherein the release-rate modulating polymer film is configured such that the release of agent from the segment in 40% ethanol/60% simulated gastric fluid over one hour is no more than about 40% higher compared to release of agent from an equivalent segment in 100% simulated gastric fluid over one hour.

In one embodiment, the invention provides a segment of a gastric residence system, the segment comprising a carrier polymer, an agent or a salt thereof; and a release-rate modulating polymer film configured to control the release rate of the agent, wherein the release-rate modulating polymer film is configured such that the release of agent from the segment in 40% ethanol/60% simulated gastric fluid over one hour is at least about 40% lower than the release of agent from a second segment in 40% ethanol/60% simulated gastric fluid over one hour, the second segment comprising the same combination of carrier polymer and agent or salt thereof but lacking the release-rate modulating polymer film.

In one embodiment, the invention provides a segment of a gastric residence system, the segment comprising a carrier polymer, an agent or a salt thereof; and a release-rate modulating polymer film configured to control the release rate of the agent, wherein the release-rate modulating polymer film is configured such that the release of agent from the segment in simulated gastric fluid over an initial 6 hour period is at least about 40% lower than the release of agent from a second segment in simulated gastric fluid over an initial 6 hour period, the second segment comprising the same combination of carrier polymer and agent or salt thereof but lacking the release-rate modulating polymer film; and wherein the release of agent from the segment in simulated gastric fluid over a seven-day period is at least about 60%, at least 70%, or at least 80% of the total amount of agent originally present in the segment.

In one embodiment, the invention provides a segment of a gastric residence system, the segment comprising a carrier polymer; an agent or a salt thereof; and a release-rate modulating polymer film, wherein the polymer film is configured to control the release rate of the agent such that a best-fit linear regression model of the release rate of agent from the segment in simulated gastric fluid has a coefficient of determination $R^2$ of at least about 0.8, at least 0.85, or at least 0.9 over an initial period of seven days; and wherein the segment releases about 40% to about 60% of the agent or salt thereof within a time of about 40% to about 60% of the seven-day period.

In one embodiment, the invention provides a segment of a gastric residence system, the segment comprising a carrier polymer; an agent or a salt thereof; and a release-rate modulating polymer film, wherein the polymer film is configured to control the release rate of the agent from the segment over a seven-day period in simulated gastric fluid such that the release rate from the segment over any one of the seven days varies by no more than about 25% from the average daily total release from the segment over the seven days.

In any of the embodiments of the invention described herein, the release-rate modulating polymer film can comprise one or more polyester materials. The polymer film can comprise polyester with a repeating unit of the form: —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms. The polymer film can comprise polycaprolactone or polydioxanone, such as polycaprolactone of about 10,000 to about 150,000 Mn, polycaprolactone of about 50,000 Mn to about 110,000 Mn, polycaprolactone of about 80,000 Mn to about 110,000 Mn, polycaprolactone of about 60,000 Mn to about 100,000 Mn, polycaprolactone of about 90,000 Mn, polycaprolactone of about 80,000 Mn, polycaprolactone of about 70,000 Mn, or polycaprolactone having intrinsic viscosity of about 1.0 dL/g to about 2.5 dL/g, about 1.0 dL/g to about 2.1 dL/g, or about 1.5 dL/g to about 2.1 dL/g.

In any of the embodiments of the invention described herein, the release-rate modulating polymer film can comprise one or more porogens. The porogen can comprise a water-soluble polymer, a water-soluble small molecule, an inorganic salt, or an organic salt. The porogen can comprise about 1% to about 40% by weight of the film. The porogen can comprise about 1% to about 30% by weight of the film. The porogen can comprise about 5% to about 40% by weight of the film. The porogen can comprise about 5% to about 30% by weight of the film. The porogen can be selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, dials and polyols, polyhydric alcohols, poly (alkylene glycols), polyglycols, alkylene glycols, poly(a,m) alkylenediol esters, alkylene glycols, poly vinylalcohol, poly vinyl pyrrolidone, water soluble polymeric materials. Poloxamer, hypromellose Kolliphor RH40, polyvinyl caprolactam, polyvinyl acetate (PVAc), polyethylene glycol (PEG) Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum. The porogen can be selected from the group consisting of povidone, copovidone, and polyoxyl castor oil.

In one embodiment, the invention provides a segment of a gastric residence system, the segment comprising a carrier polymer; an agent or a salt thereof; and a release-rate modulating polymer film, wherein the polymer film comprises a material selected from the group consisting of polycaprolactone, cellulose acetate, and ethyl cellulose.

In any of the embodiments disclosed herein, the release-rate modulating polymer film can comprise about 0.1% to about 20% of the total weight of the segment. In any of the embodiments disclosed herein, the release-rate modulating polymer film can comprise about 0.1% to about 15% of the total weight of the segment. In any of the embodiments disclosed herein, the release-rate modulating polymer film can comprise about 0.1% to about 10% of the total weight of the segment, about 0.1% to about 5% of the total weight of the segment, about 0.5% to about 5% of the total weight of the segment, about 0.5% to about 2% of the total weight of the segment, or about 1% to about 2% of the total weight of the segment.

In any of the embodiments disclosed herein, the release-rate modulating polymer film can comprise a thickness between about 1 micron and about 20 microns, such as between about 5 microns and about 15 microns.

In any of the embodiments disclosed herein, the release-rate modulating polymer film can further comprise a plasticizer. The plasticizer can comprise about 1% to about 40% by weight of the film, such as about 1% to about 30%, or about 1% to about 20%, or about 1% to about 15%, or about 5% to about 20%, or about 10% to about 20%. The plasticizer can be selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, and poloxamer. The plasticizer can be selected from the group consisting of triethyl citrate and triacetin.

In any of the embodiments disclosed herein, the release-rate modulating polymer film can further comprise a permeable component which is permeable to the agent or salt thereof and permeable to water. The permeable component can be a polymer or a swellable material. The permeable component can comprise about 1% to about 30% by weight of the film. The permeable component can be selected from the group consisting of SSG, crospovidone, croscarmellose, and Carbopol (PAA; polyacrylic acid). At least one of the rate of passage of water and the rate of passage of agent or salt thereof through the permeable component should be higher, as compared to the rate of passage of water or the rate of passage of agent through the release-rate modulating polymer film lacking permeable agent and lacking pores produced by removal of porogens. In various embodiments, the rate of passage of water and the rate of passage of agent or salt thereof through the permeable component is up to about 1.5 times, up to about 2 times, up to about 3 times, up to about 4 times, up to about 5 times, up to about 6 times, up to about 7 times, up to about 8 times, about to about 10 times, up to about 15 times, up to about 20 times, up to about 25 times, up to about 50 times, or up to about 100 times faster, as compared to the rate of passage of water or the rate of passage of agent through the release-rate modulating polymer film lacking permeable agent and lacking pores produced by removal of porogens.

The invention further provides gastric residence systems for administration to a patient, comprising at least one segment of any of the segment embodiments disclosed herein.

The invention further provides gastric residence systems for administration to a patient, comprising an elastomer component, and at least three elongate members attached to the elastomer component, wherein each elongate member comprises a proximal end, a distal end, and an outer surface therebetween, the proximal end of each elongate member is attached to the elastomer component and projects radially from the elastomer component, each elongate member has its distal end not attached to the elastomer component and located at a larger radial distance from the elastomer component than the proximal end; wherein at least one elongate member comprises a segment of any of the segment embodiments disclosed herein, such as a segment coated with a release rate-modulating polymer film or wherein at least one elongate member is coated with a release rate-modulating polymer film. The central elastomer of the gastric residence system can be formed from liquid silicone rubber. The elongate members of the gastric residence system can be attached to the central elastomer via a disintegrating matrix, such as a disintegrating matrix comprising HPMC-AS and polycaprolactone.

The invention further provides methods of making a segment of a gastric residence system comprising coating a segment comprising a carrier polymer and an agent or a salt thereof with a solution of a polymer film formulation to produce a film-coated segment; and drying the film-coated segment. The coating can be performed by dip coating, pan coating, spray coating, or fluidized bed coating. The solvent used in the solution of polymer film formulation can comprise an organic solvent, such as ethyl acetate, dichloromethane, acetone, isopropyl alcohol, or any combination thereof.

The invention further provides methods of making an elongate member of a gastric residence system comprising coating an elongate member comprising a carrier polymer and an agent or a pharmaceutically acceptable salt thereof with a solution of a polymer film formulation to produce a film-coated elongate member; and drying the film-coated elongate member. The coating can be performed by dip coating, pan coating, spray coating, or fluidized bed coating. The solvent used in the solution of polymer film formulation can comprise an organic solvent, such as ethyl acetate, dichloromethane, acetone, isopropyl alcohol, or any combination thereof. The invention further provides a method of making an elongate member of a gastric residence system comprising co-extruding a polymer film and a mixture of a carrier polymer and an agent or a pharmaceutically acceptable salt thereof.

The invention further provides a method of making a segment of a gastric residence system comprising co-extruding a polymer film and a mixture of a carrier polymer and an agent or a salt thereof.

The invention further comprises methods of administering a gastric residence system to a patient, comprising administering a container containing any embodiment of the gastric residence systems disclosed herein in a compacted state to a patient, wherein the container enters the stomach of the patient and dissolves after entry into the stomach, releasing the gastric residence system which then adopts its uncompacted state. Preferably, the patient is a human. The container containing the gastric residence system can be administered by swallowing, by feeding tube, or by gastrostomy tube.

In any of the embodiments of the gastric residence systems, elongate members of gastric residence systems, segments, or segments covered with a release rate-modulating polymer film, the agent in the systems, members, or segments does not comprise an adamantane-class drug or a pharmaceutically acceptable salt thereof. In any of the embodiments of the gastric residence systems, elongate members of gastric residence systems, segments, or segments covered with a release rate-modulating polymer film, the agent in the systems, members, or segments does not comprise memantine; amantadine; adapromine; nitromemantine; rimantadine; bromantane; tromantadine; neramexane; or a pharmaceutically acceptable salt of memantine, amantadine, adapromine, nitromemantine, rimantadine, bromantane, tromantadine, or neramexane.

In any of the embodiments of the release rate-modulating polymer films, or any of the embodiments of segments covered with a release rate-modulating polymer film, the release rate-modulating polymer film do not contain agents; that is, the films do not contain any substance intended for therapeutic, diagnostic, or nutritional use.

In any of the embodiments of the release rate-modulating polymer films, or any of the embodiments of segments covered with a release rate-modulating polymer film, the release-rate modulating polymer film does not add substantially to the strength of the carrier polymer-agent segment that it covers.

It is contemplated that any features from any embodiment disclosed herein can be combined with any features from any other embodiment disclosed herein where possible. In this fashion, hybrid configurations of the disclosed features are within the scope of the present invention.

In any of the embodiments disclosed herein, the term "about" used with numerical values can indicate that both the value specified, as well as values reasonably close to the value specified, are included.

BRIEF DESCRIPTION OF THE DRAWINGS

FIG. 3A depicts compositions of coating solutions used in ethanol release studies.

FIG. 4 depicts solvents used for dip coating PCL films. Dichloromethane and ethyl acetate were both able to dissolve PCL at high concentrations and to form uniform coatings with good performance.

DETAILED DESCRIPTION OF THE INVENTION

Definitions

Figure 1A:
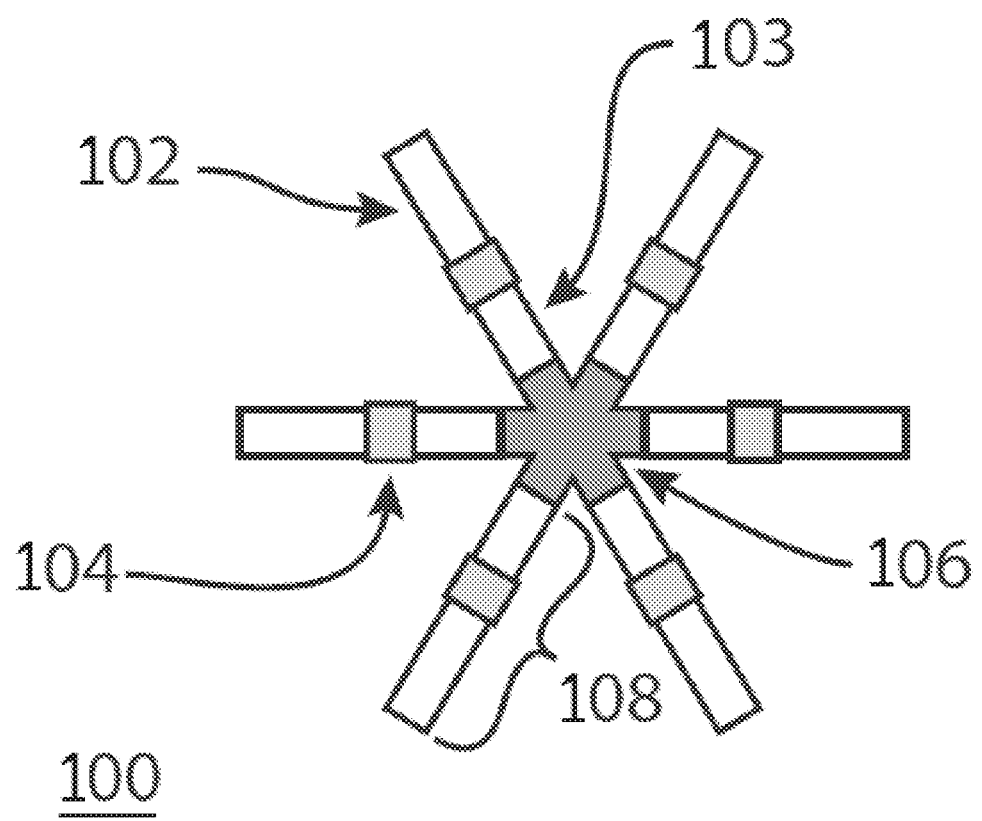
FIG. 1A shows a stellate design of a gastric residence system in its uncompacted state.

A "carrier polymer" is a polymer suitable for blending with an agent, such as a drug, for use in the invention.

An "agent" is any substance intended for therapeutic, diagnostic, or nutritional use in a patient, individual, or subject. Agents include, but are not limited to, drugs, nutrients, vitamins, and minerals.

A "dispersant" is defined as a substance which aids in the minimization of particle size of agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of an agent that is not the agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component. Coupling polymers typically form the linker regions between other components.

A "time-dependent polymer" or "time-dependent coupling polymer" is a polymer that degrades in a time-dependent manner when a gastric residence system is deployed in the stomach. A time-dependent polymer is typically not affected by the normal pH variations in the stomach.

"Approximately constant plasma level" refers to a plasma level that remains within a factor of two of the average plasma level (that is, between 50% and 200% of the average plasma level) measured over the period that the gastric residence system is resident in the stomach.

"Substantially constant plasma level" refers to a plasma level that remains within plus-or-minus 25% of the average plasma level measured over the period that the gastric residence system is resident in the stomach.

A "hydrophilic therapeutic agent," "hydrophilic agent," or "hydrophilic drug" is an agent which readily dissolves in water. A hydrophilic agent is defined as an agent which has a solubility in water of 1 mg/ml or greater. Alternatively, a hydrophilic agent can be defined as an agent which has a log $P_{oct}$ (log partition coefficient $P_{oct}$, where $P_{oct}$=(concentration in 1-octanol)/(concentration in H$_2$O)) in a 1-octanol/water system of less than 0.5. The pH at which solubility or log P$_{oct}$ is measured is 1.6, approximating the gastric environment.

A "hydrophobic therapeutic agent," "hydrophobic agent," or "hydrophobic drug" is an agent which does not readily dissolve in water. A hydrophobic agent is defined as an agent which has a solubility in water of less than 1 mg/ml. Alternatively, a hydrophobic agent can be defined as an agent which has a log P$_{oct}$ (log partition coefficient) in a 1-octanol/water system of greater than 1. Alternatively, a hydrophobic therapeutic agent can be defined as an agent which has a higher solubility in ethanol than in water. Alternatively, a hydrophobic therapeutic agent can be defined as an agent which has a higher solubility in 40% ethanol/60% simulated gastric fluid than in 100% simulated gastric fluid.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

A "patient," "individual," or "subject" refers to a mammal, preferably a human or a domestic animal such as a dog or cat. In a most preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of an agent is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Partitioning behavior of an agent can be measured between a polycaprolactone phase (PCL phase) and a simulated gastric fluid phase (SGF phase), to give the partition coefficient P$_{PCL-SGF}$ between the two phases for the agent. Log P$_{PCL-SGF}$ can also be calculated. A 5:1 mixture of polycaprolactone diol (MW 530):ethyl acetate can be used as the PCL phase, and fasted-state simulated gastric fluid (FaSSGF) can be used as the SGF phase, such that P$_{PCL-SGF}$=(concentration in polycaprolactone diol)/(concentration in FaSSGF)).

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

In addition to the embodiments and methods disclosed here, additional embodiments of gastric residence systems, and methods of making and using such systems, are disclosed in International Patent Application Nos. WO 2015/191920, WO 2015/191925, WO 2017/070612, WO 2017/100367, and PCT/US2017/034856, which are incorporated by reference herein in their entirety.

Drug Polymer Formulations and Excipients for Gastric Residence Systems

Selection of the carrier material for the agent or pharmaceutically acceptable salt thereof in a gastric residence system influences the release profile of drug during the period of gastric residence, and is discussed in more detail below in the section "Carrier polymers for segments and elongate members (carrier polymer-agent component)." Release of drug can be modulated by a wide variety of excipients included in the carrier polymer-agent component. Soluble excipients include P407, Eudragit E, PEG, Polyvinylpyrrolidone (PVP), and Polyvinyl alcohol (PVA). Insoluble, wicking excipients include Eudragit RS and Eudragit RL. Degradable excipients include PLA, PLGA, PLA-PCL, polydioxanone, and linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate; such as linear copolymers of caprolactone (95%) and glycolide (5%); polyaxial block copolymers of glycolide (68%), caprolactone (29%), and trimethylene carbonate (3%); polyaxial block copolymers of glycolide (86%), trimethylene carbonate (9%), and lactide (5%); polyaxial block copolymers of glycolide (70%), trimethylene carbonate (27%) and polypropylene succinate (2%), polyaxial block copolymers of caprolactone (35%), lactide (34%), glycolide (17%), and trimethylene carbonate (14%), polyaxial block copolymers of glycolide (55%), trimethylene carbonate (25%), and caprolactone (20%); and linear block copolymers of lactide (39%), caprolactone (33%), and trimethylene carbonate (28%). Insoluble, swellable excipients include Polyvinyl acetate (PVAc), Crospovidone, Croscarmellose, HPMCAS, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%). Surfactants include Lecithin, Taurocholate, SDS, Soluplus, Fatty acids, and Kolliphor RH40.

Release Rate-Modulating Polymer Films

The current invention provides, inter alia, gastric residence systems, elongate m embers s of gastric residence systems, and segments for use in gastric residence systems and elongate members of gastric residence systems, which are coated with a release rate-modulating film. Use of a release rate-modulating polymer film with the gastric residence systems, such as on the carrier polymer-agent segments of the gastric residence systems or on the elongate members of the gastric residence systems, provides several significant advantages over systems with carrier polymer-agent segments lacking a release rate-modulating film. Release rate-modulating polymer films reduce the burst release of agent upon initial contact with gastric fluid. Linearity of agent release over the residence period is improved by using release rate-modulating polymer films. Both of these advantages provide better regulation of dosing from the gastric residence systems. Some compositions of the release rate-modulating polymer films can also significantly reduce burst release upon exposure to alcohol, as compared to systems lacking such films.

The release rate-modulating polymer films are coatings which can coat all or part of a carrier polymer-agent segment. The films can be continuous, discontinuous, flat, or textured. They can be a smooth coating over a segment, or can follow contours of pores that may be present on the surface of a segment.

In a preferred embodiment, the release rate modulating film of any of the gastric residence systems disclosed herein does not cover the coupling polymers, enteric polymers, enteric linkers, time-dependent linkers, disintegrating polymers, disintegrating matrices, or other linkers of the gastric residence system. If a release-rate modulating polymer film is coated on the surface of an elongate member which comprises one or more linkers, such as a coupling polymer, enteric polymer, enteric linker, time-dependent linker, disintegrating polymer, disintegrating matrix, or other linker, the film is discontinuous and does not cover or coat the linkers. This is readily accomplished by applying a release rate-modulating film to segments which will comprise an elongate member, and then linking the coated segments together with linkers to form an elongate member; the segments comprising carrier polymer-agent (or agent salt) will thus be coated with the release rate-modulating film, but the linkers will not be coated with the release rate-modulating film.

The films are typically applied to segments of the gastric residence systems. The films can also be applied to multi-segment elongate members prior to attachment of the multi-segment elongate members to a central elastomer. The films can also be applied to non-segmented elongate members (that is, elongate members which comprise only one segment) prior to attachment of the non-segmented elongate members to a central elastomer. The non-segmented elongate member can be attached to the central elastomer either directly or via a linker, such as a disintegrating matrix or coupling polymer. An example of segments of a gastric residence system is shown in FIG. 1A, where segment 102 and segment 103 are linked by linker 104, and attached to a central elastomer 106. The segments 102 and 104 comprise carrier polymer and agent (such as a drug). Using a release rate-modulating polymer film on the segments of the gastric residence system provides the advantageous characteristics described herein.

Several parameters of the films can be adjusted in order to generate desired agent release characteristics, and are discussed below.

Chemical Composition of Release Rate-Modulating Polymer Films

Various polymers can be used to form the release-rate modulating polymer films. Polyesters are a useful class of compounds for preparation of release rate-modulating polymer films. Polyesters that can be used in the invention include polyesters with aliphatic groups as their main chains, including polylactones such as polycaprolactone (PCL); polyglycolic acid (PGA); polylactic acid (PLA); poly(lactic-co-glycolic acid) (PLGA); polyhydroxyalkanoates (PHA) such as polyhydroxybutyrate (PHB), polyhydroxyvalerate (PHV), and poly(3-hydroxybutyrate-co-3-hydroxyvalerate) (PHBV); polyethylene adipate (PEA); polybutylene succinate (PBS); and polyesters with aromatic groups in their main chains, such as polyethylene terephthalate (PET), polybutylene terephthalate (PBT), polytrimethylene terephthalate (PTT), and polyethylene naphthalate (PEN). Heteropolymers, including block or random copolymers, such as block or random copolymers incorporating the monomer constituents of the above polyesters, can also be used, including copolymers of lactide and caprolactone (poly-lactide-co-caprolactone; PLC). Mixtures of two or more polyesters can also be used.

In addition to polyesters, cellulose acetate (CA), ethyl cellulose (EC), and copolymers of acrylate and methacrylate esters (e.g., Eudragit RS) can also be used as release rate-modulating polymer films.

Mixtures of polymers from two or more different chemical classes of polymers can also be employed to form the release-rate modulating polymer films.

Release rate modulating polymer films can comprise polyesters with a repeating unit of the form:

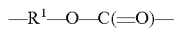
—R$^1$—O—C(=O)— wherein R$^1$ is selected from the group consisting of C$_1$-C$_{12}$ alkylene groups, such as C$_1$-C$_8$ alkylene groups or C$_1$-C$_4$ alkylene groups, ethers containing between two and twelve carbon atoms, two and eight carbon atoms or two and four carbon atoms, and polyethers containing between three and twelve carbon atoms or between three and eight carbon atoms. The polyesters can terminate with hydroxy groups, hydrogens, —C$_1$—C12 alkyl groups, —C$_1$-C$_8$ alkyl groups, or —C$_1$-C$_4$ alkyl groups, or —C$_1$-C$_{12}$—OH, —C$_1$-C$_8$—OH, or —C$_1$-C$_4$—OH (alcohol) groups as appropriate. In some embodiments, the R$^1$ groups can be the same moiety throughout the polymer to form a homopolymer. In some embodiments, the R$^1$ groups can be chosen from two or more different moieties, to form a heteropolymer. The heteropolymer can be a random copolymer, or a block copolymer.

The release-rate modulating polymer film can comprise at least two different polyesters, each different polyester with a repeating unit of the form:

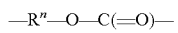
—R″—O—C(=O)— wherein when at least two or more of the different polyesters are homopolymers, the R″ group of any one of the homopolymers is different from the R″ group of any other of the homopolymers; and when at least two or more of the different polyesters are heteropolymers, each heteropolymer has a different varying pattern of R″ groups than the varying pattern of R″ groups of any of the other heteropolymers; and each R″ is selected from the group consisting of C$_1$-C$_{12}$ alkylene groups, ethers containing between two and twelve carbon atoms, and polyethers containing between three and twelve carbon atoms.

Preferred polyesters for use as release rate-modulating polymer films are polycaprolactone and polydioxanone, particularly polycaprolactone (PCL). PCL having number-average molecular weight of about 10,000 Mn to about 150,000 Mn; about 20,000 Mn to about 120,000 Mn; about 30,000 Mn to about 120,000 Mn; about 40,000 Mn to about 120,000 Mn; about 50,000 Mn to about 110,000 Mn; about 80,000 to about 120,000 Mn; about 80,000 Mn to about 110,000 Mn, about 60,000 Mn to about 100,000 Mn; about 70,000 Mn to about 90,000 Mn; about 80,000 Mn; about 90,000 Mn; about 100,000 Mn; about 10,000 Mn to about 100,000 Mn; about 10,000 Mn to about 80,000 Mn; about 40,000 Mn to about 70,000 Mn; about 50,000 Mn to about 60,000 Mn; or about 55,000 Mn can be used for release rate-modulating polymer films. PCL of about 80,000 Mn to about 110,000 Mn is preferred, such as about 85,000 Mn to about 95,000 Mn, or about 90,000 Mn.

Polycaprolactone can also be characterized by its intrinsic viscosity. PCL of about 1.0 dL/g to about 2.5 dL/g or about 1.5 dL/g to about 2.1 dL/g can be used. The intrinsic viscosity can be measured in $CHCl_3$ at 25° C.

Porogens, plasticizers, and Other Additives to Release Rate-Modulating Polymer Films Porogens, plasticizers, or both porogens and plasticizers can be added to the release rate-modulating polymer films to further tune the release rate of the agent in the carrier polymer-agent segment.

Porogens are soluble additives that dissolve out of the release rate-modulating polymer films, creating pores in the films. In some embodiments, the porogens dissolve out of the films when the gastric residence systems are deployed in the gastric environment. That is, after preparation of the segments, the porogens are left in the segments which are assembled into the gastric residence system, and in the gastric residence system as administered to a patient; the porogens then dissolve out of the release rate-modulating polymer film when the gastric residence system is administered to the patient and contacts the gastric environment. In another embodiment, the porogens are removed from the film-covered carrier polymer-agent segments before the segments are assembled into the gastric residence system, or the porogens are removed from the gastric residence system before deployment of the gastric residence system in the gastric environment.

Porogens can be organic or inorganic materials. Examples of porogens include alkali metal salts such as sodium chloride, sodium bromide, potassium chloride, potassium sulfate, potassium phosphate, sodium benzoate, sodium acetate, sodium citrate, potassium nitrate and the like; alkaline earth metal salts such as calcium chloride, calcium nitrate, and the like; and transition metal salts such as ferric chloride, ferrous sulfate, zinc sulfate, cupric chloride, and the like. Additional examples of porogens include saccharides and sugars, such as sucrose, glucose, fructose, mannose, galactose, aldohexose, altrose, talose, lactose, cellulose, monosaccharides, disaccharides, and water soluble polysaccharides. Additional examples of porogens include sorbitol, mannitol, organic aliphatic and aromatic oils, including diols and polyols, as exemplified by polyhydric alcohols, poly(alkylene glycols), polyglycols, alkylene glycols, poly(a,m)alkylenediol esters or alkylene glycols, poly vinylalcohol, poly vinyl pyrrolidone, and water soluble polymeric materials. Further examples of porogens that can be used include Poloxamer; hypromellose (HPMC); Kolliphor M40; polyvinyl caprolactam; polyvinyl acetate (PVAc); polyethylene glycol (PEG); Soluplus (available from BASF; a copolymer of polyvinyl caprolactam, polyvinyl acetate, and polyethylene glycol); copovidone; Eudragits (E, RS, RL); poly(methyl vinyl ether-alt-maleic anhydride); polyoxyethylene alkyl ethers; polysorbates; polyoxyethylene stearates; polydextrose; polyacrylic acid; alginates; sodium starch glycolate (SSG); crosslinked polyactylic acid (carbopol); crosslinked PVP (crospovidone); crosslinked cellulose (croscarmellose); calcium silicate; xanthan gum; and gellan gum. Some particularly useful porogens include povidone, copovidone, and polyoxyl castor oil.

Porogens can be added to make up between about 1% to about 30% by weight of the release rate-modulating polymer film. Porogens can be added to make up about 1% to about 25%, about 1% to about 20%, about 1% to about 15%, about 10% to about 10%, about 1% to about 8%, about 1% to about 5%, about 1% to about 3%, about 5% to about 30%, about 10% to about 30%, about 15% to about 30%, about 20% to about 30%, or about 25% to about 30% by weight of the release rate-modulating polymer film. A preferred range of porogen is about 5% to about 20%, more preferably about 10% to about 20%, by weight of the release rate-modulating polymer film.

Plasticizers can also be added to further tune the properties of the release rate-modulating polymer films. Plasticizers that can be used include the classes of phthalates, phosphates, citrates, tartrates, adipates, sebacates, sulfonamides, succinates, glycolates, glycerolates, benzoates, myristates, and halogenated phenyls. Specific plasticizers that can be used include triacetin, triethyl citrate, PEG, poloxamer, tributyl citrate, and dibutyl sebacate. Triacetin and triethyl citrate (TEC) are particularly useful.

Plasticizers can be added to make up about 1% to about 35%, about 1% to about 30%, about 1% to about 25%, about 1% to about 20%, about 1% to about 15%, about 1% to about 10%, about 1% to about 8%, about 1% to about 5%, about 1% to about 3%, about 5% to about 40%, about 10% to about 40%, about 15% to about 40%, about 20% to about 40%, about 25% to about 40%, about 30% to about 40%, about 10% to about 30%, about 15% to about 30%, about 20% to about 30%, about 25% to about 30%, or about 10%, about 15%, about 20%, about 25%, about 30%, about 35%, or about 40% by weight of the release rate-modulating polymer film. A preferred range of plasticizer is about 5% to about 20%, more preferably about 10% to about 20%, by weight of the release rate-modulating polymer film.

Processing aids can also be added to release rate-modulating polymer films. Anti-tack agents, such as magnesium stearate, talc, or glycerol monostearate can be added to aid in processing of the films. Such anti-tack agents be added in amounts of about 0.5% to about 5%, about 1% to about 3%, or about 2%.

Permeable Components in Release-Rate Modulating Polymer Films

The release-rate modulating polymer film can further comprise a permeable component which is permeable to the agent or pharmaceutically acceptable salt thereof, permeable to water, or permeable both to the agent or salt thereof and to water. Permeability components can thus function to increase the rate of water influx into the carrier polymer of the gastric residence system, and increase the rate of release of agent or salt thereof out of the gastric residence system. The permeable component can be a polymer or a swellable material. The permeable component can comprise about 1% to about 30% by weight of the film. The permeable component can be selected from the group consisting of SSG (sodium starch glycolate), crospovidone, croscarmellose, and Carbopol (PAA; crosslinked polyacrylic acid). At least one of the rate of passage of water and the rate of passage of agent or salt thereof through the permeable component should be higher, as compared to the rate of passage of water or the rate of passage of agent through the release-rate modulating polymer film lacking permeable agent and lacking pores produced by removal of porogens. In various embodiments, the rate of passage of water, the rate of passage of agent or salt thereof, or both the rate of passage of water and the rate of passage of agent or salt thereof through the permeable component is up to about 1.5 times, up to about 2 times, up to about 3 times, up to about 4 times, up to about 5 times, up to about 6 times, up to about 7 times, up to about 8 times, about to about 10 times, up to about 15 times, up to about 20 times, up to about 25 times, up to about 50 times, or up to about 100 times faster, as compared to the rate of passage of water or the rate of passage of agent or salt thereof, or both the rate of passage of water and the rate of passage of agent or salt thereof through the release-rate modulating polymer film lacking permeable agent and lacking pores produced by removal of porogens.

Film Combinations

Various options that can be used for the release rate-modulating polymer film for segments and elongate members are as follows (percentages are weight percentages):

Polymer used in film, about 40% to about 80%; porogen, about 3% to about 20%; plasticizer, about 3% to about 20%; anti-tack agent, about 0.5% to about 5%;

Polymer used in film, about 50% to about 72%; porogen, about 5% to about 20%; plasticizer, about 5% to about 20%; anti-tack agent, about 0.5% to about 5%; or Polymer used in film, about 53% to about 65%; porogen, about 10% to about 20%; plasticizer, about 10% to about 20%; anti-tack agent, about 1% to about 3%.

Examples of polymers that can be used in any of these options are polycaprolactone and polydioxanone; preferably, polycaprolactone is used as the polymer.

Examples of porogens that can be used in any of these options are povidone, copovidone, and polyoxyl castor oil.

Examples of plasticizers that can be used in any of these options include triethyl citrate, triacetin, PEG, poloxamer, tributyl citrate, and dibutyl sebacate.

Examples of anti-tack agents that can be used in any of these options include magnesium stearate, talc, and glycerol monostearate.

A preferred combination for the release-rate modulating polymer film is polycaprolactone, copovidone, triethyl citrate, and Mg stearate.

Specific polymer-porogen-plasticizer-anti-tack agent combinations that can be used include polycaprolactone-povidone-triethyl citrate-Mg stearate; polycaprolactone-copovidone-triethyl citrate-Mg stearate; polycaprolactone-polyoxyl castor oil-triethyl citrate-Mg stearate; polycaprolactone-povidone-triacetin-Mg stearate; polycaprolactone-copovidone-triacetin-Mg stearate; polycaprolactone-polyoxyl castor oil-triacetin-Mg stearate; polycaprolactone-povidone-PEG-Mg stearate; polycaprolactone-copovidone-PEG-Mg stearate; polycaprolactone-polyoxyl castor oil-PEG-Mg stearate; polycaprolactone-povidone-poloxamer-Mg stearate; polycaprolactone-copovidone-poloxamer-Mg stearate; polycaprolactone-polyoxyl castor oil-poloxamer-Mg stearate; polycaprolactone-povidone-tributyl citrate-Mg stearate; polycaprolactone-copovidone-tributyl citrate-Mg stearate; polycaprolactone-polyoxyl castor oil-tributyl citrate-Mg stearate; polycaprolactone-povidone-dibutyl sebacate-Mg stearate; polycaprolactone-copovidone-dibutyl sebacate-Mg stearate; polycaprolactone-polyoxyl castor oil-dibutyl sebacate-Mg stearate; polycaprolactone-povidone-triethyl citrate-talc; polycaprolactone-copovidone-triethyl citrate-talc; polycaprolactone-polyoxyl castor oil-triethyl citrate-talc; polycaprolactone-povidone-triacetin-talc; polycaprolactone-copovidone-triacetin-talc; polycaprolactone-polyoxyl castor oil-triacetin-talc; polycaprolactone-povidone-PEG-talc; polycaprolactone-copovidone-PEG-talc; polycaprolactone-polyoxyl castor oil-PEG-talc; polycaprolactone-povidone-poloxamer-talc; polycaprolactone-copovidone-poloxamer-talc; polycaprolactone-polyoxyl castor oil-poloxamer-talc; polycaprolactone-povidone-tributyl citrate-talc; polycapmlactone-copovidone-tributyl citrate-talc; polycaprolactone-polyoxyl castor oil-tributyl citrate-talc; polycaprolactone-povidone-dibutyl sebacate-talc; polycaprolactone-copovidone-dibutyl sebacate-talc; polycaprolactone-polyoxyl castor oil-dibutyl sebacate-talc; polycaprolactone-povidone-triethyl citrate-glycerol monostearate; polycaprolactone-copovidone-triethyl citrate-glycerol monostearate; polycaprolactone-polyoxyl castor oil-triethyl citrate-glycerol monostearate; polycaprolactone-povidone-triacetin-glycerol monostearate; polycaprolactone-copovidone-triacetin-glycerol monostearate; polycaprolactone-polyoxyl castor oil-triacetin-glycerol monostearate; polycaprolactone-povidone-PEG-glycerol monostearate; polycaprolactone-copovidone-PEG-glycerol monostearate; polycaprolactone-polyoxyl castor oil-PEG-glycerol monostearate; polycaprolactone-povidone-poloxamer-glycerol monostearate; polycaprolactone-copovidone-poloxamer-glycerol monostearate; polycaprolactone-polyoxyl castor oil-poloxamer-glycerol monostearate; polycapmlactone-povidone-tributyl citrate-glycerol monostearate; poiycaprolactone-copovidone-tributyl citrate-glycerol monostearate; polycaprolactone-polyoxyl castor oil-tributyl citrate-glycerol monostearate; polycaprolactone-povidone-dibutyl sebacate-glycerol monostearate; polycaprolactone-copovidone-dibutyl sebacate-glycerol monostearate; and polycaprolactone-polyoxyl castor oil-dibutyl sebacate-glycerol monostearate.

In addition to the coatings listed above, any coating from Table COAT-1 and Table COAT-2 may be used as a release rate-modulating polymer film, for example in amounts of 1%, 1.5%, 2%, 2.5%, 3%, 3.5%, 4%, 4.5%, or 5% by weight of the elongate member or segment to which they are applied. The coatings can be used in any amount disclosed herein for the release-rate polymer films, such as about 1% to about 20%. Each row of the table below represents a coating formulation.

TABLE COAT-1
Coating Formulation

Eudragit RS
PCL 55 k
Ethyl Cellulose
75:25 PLGA
50:50 PLGA
25:75 PLGA
50:50 PLGA
Ethyl Cellulose
Cellulose Acetate
PCL 55 k
PCL 15 k
PLGA 50:50 Ester Terminated 35-45 k
PLGA 50:50 Acid Terminated 35-45 k
PCL 80 k
Ethyl Cellulose Cp 10
Ethyl Cellulose Cp 10
Polycaprolactone, copovidone, triethyl citrate, Mg stearate
Ethyl Cellulose:PVP 1.3M
PCL 80 k:TEC
Ethyl Cellulose Cp10:TEC
80 k PCL:PVP
80 k PCL:Kolliphor RH40
80 k PCL:Kollidon VA64
PCL 80 k:TEC
Ethyl Cellulose Cp10:TEC
PCL 55 k:P407
PCL 55 k:P188
PCL 55 k:PEG 10 k
PCL 55 k:PEG 100 k
PCL 55 k:P407
PCL 55 k:P188
PCL 55 k:PVP 1M
Ethyl Cellulose:PEG 1M
Ethyl Cellulose:PEG 100 k
PCL 80 k:TEC
Ethyl Cellulose Cp10:TEC
PVP
80 k PCL:Kolliphor RH40
80 k PCL:Kollidon VA64

Table COAT-2 lists specific amounts of ingredients that can be used in the film formulations. The amounts listed in Table COAT-2 can be varied by plus-or-minus 20% of each ingredient (for example, a composition with 10% P407 can vary between 8% P407 to 12% P407). The coatings can be used in any amount disclosed herein for the release-rate polymer films, such as about 1% to about 20%. Each row of the table below represents a coating formulation.

TABLE COAT-2

| Coating Formulation |
|---|
| 9:1, PCL 55 k:P407 |
| 9:1, PCL 55 k:P188 |
| Eudragit RS |
| 9:1 PCL 55 k:PEG 10 k |
| 9:1 PCL 55 k:PEG 100 k |
| PCL 55 k |
| 9:1, PCL 55 k:P407 |
| 9:1, PCL 55 k:P188 |
| 9:1 PCL 55 k:PVP 1M |
| Ethyl Cellulose |
| 9:1 Ethyl Cellulose:PVP 1.3M |
| 9:1 Ethyl Cellulose:PEG 1M |
| 9:1 Ethyl Cellulose:PEG 100 k |
| 75:25 PLGA |
| 25:75 PLGA |
| 50:50 PLGA |
| Ethyl Cellulose |
| Cellulose Acetate |
| 9:1 Ethyl Cellulose:PEG 1M |
| 9:1 Cellulose Acetate TEG 1M |
| Cellulose Acetate |
| PCL 55 k |
| PCL 15 k |
| PLGA 50:50 Ester Terminated 35-45 k |
| PLGA 50:50 Acid Terminated 35-45 k |
| PCL 80 k |
| 9:1 PCL 80 k:TEC |
| 8:2 PCL 80 k:TEC |
| 7:3 PCL 80 k:TEC |
| Ethyl Cellulose |
| Ethyl Cellulose Cp 10 |
| 9:1 Ethyl Cellulose Cp10:TEC |
| 8:2 Ethyl Cellulose Cp10:TEC |
| 7:3 Ethyl Cellulose Cp10:TEC |
| 7:3 80 k PCL:PVP |
| 9:1 PVP |
| 7:3 80 k PCL:Kolliphor RH40 |
| 9:1 80 k PCL:Kolliphor RH40 |
| 7:3 80 k PCL:Kollidon VA64 |
| 9:1 80 k PCL:Kollidon VA64 |
| polycaprolactone 83.8%, copovidone 4.4%, Triethyl citrate 9.%8, Magnesium stearate % 2.0 |
| polycaprolactone 66.7%, copovidone 16.6%, Triethyl citrate 14.7%, Magnesium stearate 2.0% |
| polycaprolactone 48.0%, copovidone 20.6%, Triethyl citrate, 29.4%, Magnesium stearate 2.0%, |
| polycaprolactone 54.9%, copovidone 13.7%, Triethyl citrate 29.4%, Magnesium stearate 2.0% |
| polycaprolactone 54.9%, copovidone 23.5%, Triethyl citrate 19.6%, Magnesium stearate 2.0% |
| polycaprolactone 62.7%, copovidone 15.7%, Triethyl citrate 19.6%, Magnesium stearate 2.0% |
| polycaprolactone 62.5%, copovidone 20.8%, Triethyl citrate 14.7%, Magnesium stearate 2.0% |
| polycaprolactone 70.6%, copovidone 17.6%, Triethyl citrate 9.8%, Magnesium stearate 2.0% |

Film Thickness

The release-rate modulating polymer films should be very thin in comparison to the carrier polymer-agent segment of the gastric residence system that they cover. This allows for diffusion of water into the carrier polymer-agent segment, and diffusion of agent out of the segment.

The thickness of the release-rate modulating polymer films can be between about 1 micrometer to about 40 micrometers, between about 1 micrometer to about 30 micrometers, or between about 1 micrometer to about 25 micrometers. The films are typically between about 1 micrometer to about 20 micrometers, such as between about 1 micrometer to about 20 micrometers, about 1 micrometer to about 15 micrometers, about 1 micrometer to about 10 micrometers, about 1 micrometer to about 5 micrometers, about 1 micrometer to about 4 micrometers, about 1 micrometer to about 3 micrometers, about 1 micrometer to about 2 micrometers, about 2 micrometers to about 10 micrometers, about 5 micrometers to about 20 micrometers, about 5 micrometer to about 10 micrometers, about 10 micrometer to about 15 micrometers, or about 15 micrometers to about 20 micrometers.

In further embodiments, the release-rate modulating polymer film does not add substantially to the strength of the carrier polymer-agent segment that it covers. In further embodiments, the release-rate modulating polymer film adds less than about 20%, less than about 10%, less than about 5%, or less than about 1% to the strength of the segment. The strength of the segment can be measured by the four-point betiding flexural test (ASTM D790) described in Example 18 of WO 2017/070612 and Example 13 of WO 2017/100367.

Film Weight

The release-rate modulating polymer films can make up about 0.1% to 20% of the weight of the film-covered carrier polymer-agent segment of the gastric residence system. The release-rate modulating polymer films can make up about 0.1% to 15% of the weight of the film-covered carrier polymer-agent segment of the gastric residence system. The release-rate modulating polymer films can make up about 0.1% to 10% of the weight of the film-covered carrier polymer-agent segment of the gastric residence system. The weight of the film can make up about 0.1% to about 8%, about 0.1% to about 5%, about 0.1% to about 4%, about 0.1% to about 3%, about 0.1% to about 2%, about 0.1% to about 1%, about 0.5% to about 10%, about 0.5% to about 8%, about 0.5% to about 5%, about 0.5% to about 4%, about 0.5% to about 3%, about 0.5% to about 2%, about 0.5% to about 1%, about 1% to about 10%, about 1% to about 8%, about 1% to about 5%, about 1% to about 4%, about 1% to about 3%, or about 1% to about 2% of the film-covered carrier polymer-agent segment of the gastric residence system.

Application of Release Rate-Modulating Polymer Films onto Segments for Use in Gastric Residence Systems The release rate-modulating polymer films can be applied to segments for use in gastric residence systems using various techniques. Several of the techniques involve coating a segment, comprising a carrier polymer and agent, with a solution of a formulation of a release rate-modulating polymer film, producing a film-coated segment. The film-coated segment is then dried.

Various methods of coating films onto objects are known in the art, and include dip coating, pan coating, spray coating, and fluidized bed coating. Fluidized bed coating is also known as Wurster coating or air suspension coating. For these coating methods, a formulation of a release-rate modulating polymer film, including the polymer, and any porogens and plasticizers if present, is prepared as a solution. The solvent used for the solution of the polymer film formulation is typically an organic solvent, such as ethyl acetate, dichloromethane, acetone, methanol, ethanol, isopropanol, or any combination thereof. Preferably, Class 3 solvents as listed in the guidance from the United States Food and Drug Administration at URL www.fda.gov/downloads/drugs/guidances/ucm073395.pdf (which include ethanol, acetone, and ethyl acetate) are used; however, Class 2 solvents (which include dichloromethane and methanol) can be used if necessary for the formulation. Class 1 and Class 4 solvents should be used only when the formulation cannot be prepared with a suitable Class 3 or Class 2 solvent.

Release rate-modulating polymer films can also be integrated onto segments by co-extrusion, where the segment formulation is co-extruded with a surrounding thin layer of the release rate-modulating polymer film.

The Examples below illustrate the use of some of these coating techniques for preparation of segments with a release rate-modulating polymer film.

Overall System Configuration

The current invention provides, inter alia, gastric residence systems, elongate members of gastric residence systems, and segments for use in gastric residence systems and elongate members of gastric residence systems, which are coated with a release rate-modulating film. As discussed, the release rate-modulating film provides a number of advantages.

Figure 1B:
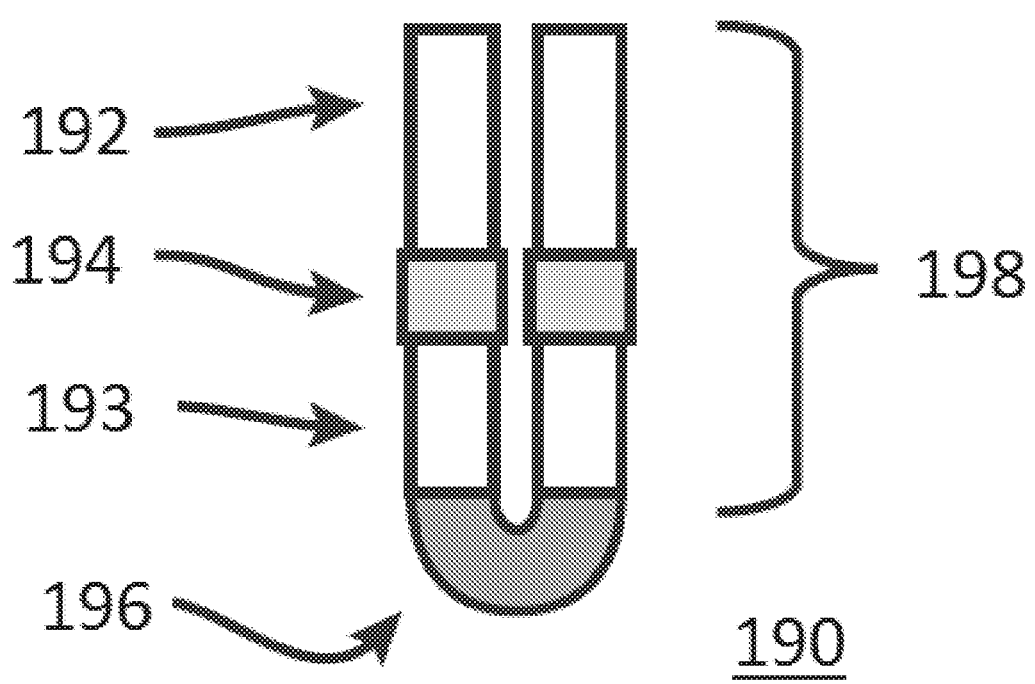
FIG. 1B shows a stellate design of a gastric residence system in a compacted or folded state.

Gastric residence systems can be prepared in different configurations. The "stellate" configuration of a gastric residence system is also known as a "star" (or "asterisk") configuration. An example of a stellate system 100 is shown schematically in FIG. 1A. Multiple elongate members, or "arms" (only one such arm, 108, is labeled for clarity), are affixed to disk-shaped central elastomer 106. The elongate members or arms depicted in FIG. 1A are comprised of segments 102 and 103, joined by a coupling polymer or linker region 104 (again, the components are only labeled in one arm for clarity) which serves as a linker region. This configuration permits the system to be folded or compacted at the central elastomer. FIG. 1B shows a folded configuration 190 of the gastric residence system of FIG. 1A (for clarity, only two arms are illustrated in FIG. 1B). Segments 192 and 193, linker region 194, elastomer 196, and arm 198 of FIG. 1B correspond to segments 102 and 103, linker region 104, elastomer 106, and arm 108 of FIG. 1A, respectively. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

While the linker regions 104 are shown as slightly larger in diameter than the segments 102 and 103 in FIG. 1A, they can be the same diameter as the segments, so that the entire elongate member 102-104-103 has a smooth outer surface.

In some embodiments, the stellate system may have an elongate member or arm composed of only one segment, which is attached to the central elastomer by a linker region. This corresponds to FIG. 1A with the segments 103 omitted. The single-segment elongate members comprising segments 102 are then directly attached to central elastomer 106 via the linkers 104. The linkers can comprise a coupling polymer or a disintegrating matrix.

A stellate system can be described as a gastric residence system for administration to the stomach of a patient, comprising an elastomer component, and a plurality of at least three carrier polymer-agent components comprising a carrier polymer and an agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member independently comprises one or more segments, each segment comprising a proximal end, a distal end, and an outer surface therebetween; and wherein, when two or more segments are present in an elongate member, each segment is attached to an adjacent segment via a linker region. The linker region can be a coupling polymer or a disintegrating matrix. The elongate members can be attached to the central elastomer via a coupling polymer or a disintegrating matrix, and can have intervening portions of interfacing polymers. For the plurality of at least three elongate members, or for a plurality of elongate members, a preferred number of elongate members is six, but three, four, five, seven, eight, nine, or ten elongate members can be used. The elongate members should be equally spaced around the central elastomer; if there are N elongate members, there will be an angle of about 360/N degrees between neighboring elongate members.

Figure 1C:
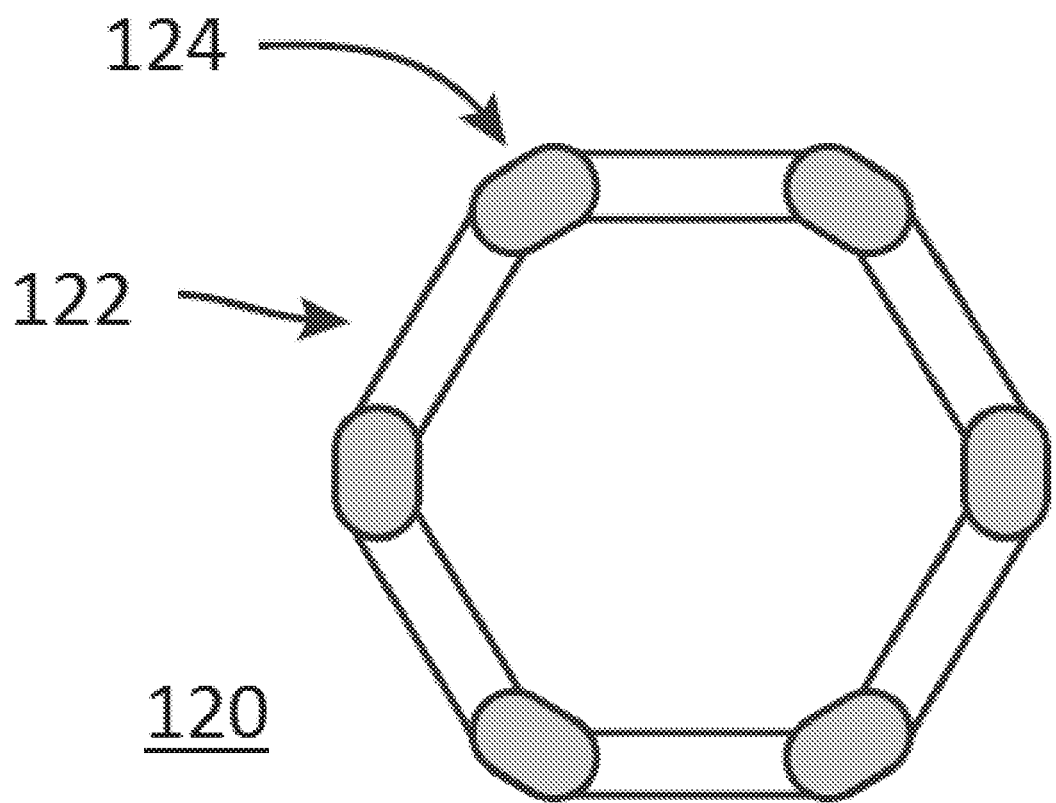
FIG. 1C shows a ring design of a gastric residence system in an uncompacted state.

FIG. 1C shows another possible overall configuration 120 for a gastric residence system, which is a ring configuration. Segments 122 are joined by coupling polymer or linker region 124 (only one segment and one coupling linkage are labeled for clarity). The coupling polymer/linker region in this design must also function as an elastomer, to enable the ring to be twisted into a compacted state for placement in a container, such as a capsule.

In one embodiment of the stellate configuration, the segments 102 and 103 comprise a carrier polymer blended with an agent or drug. In one embodiment of the ring configuration, the segments 122 comprise a carrier polymer blended with an agent or drug.

The coupling polymers of the gastric residence system, which serve as linker regions, are designed to break down gradually in a controlled manner during the residence period of the system in the stomach. If the gastric residence system passes prematurely into the small intestine in an intact form, the system is designed to break down much more rapidly to avoid intestinal obstruction. This is readily accomplished by using enteric polymers as coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient. In the system shown in FIG. 1A, at least the coupling polymer used for the couplings 104 are made from such enteric polymers.

In additional embodiments, a time-dependent coupling polymer or linker can be used. Such a time-dependent coupling polymer or linker degrades in a predictable, time-dependent manner. In some embodiments, the degradation of the time-dependent coupling polymer or linker may not be affected by the varying pH of the gastrointestinal system.

In additional embodiments, different types of linkers can be used in the gastric residence systems. That is, both enteric linkers (or enteric coupling polymers) and time-dependent linkers (or time-dependent coupling polymers) can be used. In some embodiments, a single multi-segment elongate member arm of a stellate system can use both an enteric linker at some linker regions between segments, and a time-dependent linker at other linker regions between segments.

Linker regions are typically about 100 microns to about 1 millimeter in width, such as about 200 um to about 1000 um, about 300 um to about 1000 um, about 400 um to about 1000 um, about 500 um to about 1000 um, about 600 um to about 1000 um, about 700 um to about 1000 um, about 800 um to about 1000 um, or about 900 um to about 1000 um; or about 100 um to about 900 um about 100 um to about 800 um, about 100 um to about 700 um, about 100 um to about 600 um, about 100 um to about 500 um, about 100 um to about 400 um, about 100 um to about 300 um, or about 100 um to about 200 um. Linker regions can be about 100 um, about 200 um, about 300 um, about 400 um, about 500 um, about 600 um, about 700 um, about 800 um, about 900 um, or about 1000 um in width, where each value can be plus or minus 50 um (±50 um).

The central elastomeric polymer of a stellate system is typically not an enteric polymer; however, the central elastomeric polymer can also be made from such an enteric polymer where desirable and practical.

The central elastomer should have a specific durometer and compression set. The durometer is important because it determines the folding force of the dosage form and whether it will remain in the stomach; a preferred range is from about 60 to about 90 A. The compression set should be as low as possible to avoid having permanent deformation of the gastric residence system when stored in the capsule in its compacted configuration. A preferred range is about 10% to about 20% range. Materials that fit these requirements are the QP1 range of liquid silicone rubbers from Dow Corning. In any embodiment with a central elastomer, the QP1-270 (70 A durometer) liquid silicone rubber can be used.

Segments and elongate members of the gastric residence systems can have cross-sections in the shape of a circle (in which case the segments are cylindrical), a polygon (such as segments with a triangular cross-section, rectangular cross-section, or square cross-section), or a pie-shaped cross-section (in which case the segments are cylindrical sections). Segments with polygon-shaped or pie-shaped cross-sections, and ends of cylindrically-shaped sections which will come into contact with gastric tissue, can have their sharp edges rounded off to provide rounded corners and edges, for enhanced safety in vivo. That is, instead of having a sharp transition between intersecting edges or planes, an arc is used to transition from one edge or plane to another edge or plane. Thus, a "triangular cross-section" includes cross-sections with an approximately triangular shape, such as a triangle with rounded corners. An arm with a triangular cross-section includes an arm where the edges are rounded, and the corners at the end of the arm are rounded. Rounded corners and edges are also referred to as fillet corners, filleted corners, fillet edges, or filleted edges.

As discussed herein, the segments of the gastric residence system, comprising carrier polymer and agent, can be covered with a release rate-modulating polymer film. In some embodiments, one or more of any coupling polymer, disintegrating matrix, or interfacing polymer affixed to the segments are also covered by the release rate-modulating polymer film. In some embodiments, one or more of any coupling polymer, disintegrating matrix, or interfacing polymer affixed to the segments arc not covered by the release rate-modulating polymer film. If the coupling polymer (which may be an enteric polymer) or the disintegrating matrix is covered by the release rate-modulating polymer film, the kinetics of de-coupling or disintegration should be determined on the film-covered coupling polymer or the film-covered disintegrating matrix.

Evaluation of Release Characteristics

The release characteristics of agent from segments, elongate members, and gastric residence systems can be evaluated by various assays. Assays for agent release arc described in detail in the examples. Release of agent in vitro from segments, elongate members, and gastric residence systems can be measured by immersing a segment, elongate member, or gastric residence system in a liquid, such as water, 0.1N HCl, fasted state simulated gastric fluid (FaSSGF), or fed state simulated gastric fluid (FeSSGF). Fasted state simulated gastric fluid (FaSSGF) is preferred for release assays. Simulated gastric fluid indicates either fasted state simulated gastric fluid (FaSSGF) or fed state simulated gastric fluid (FeSSGF); when a limitation is specified as being measured in simulated gastric fluid (SGF), the limitation is met if the limitation holds in either fasted state simulated gastric fluid (FaSSGF) or fed state simulated gastric fluid (FeSSGF). For example, if a segment is indicated as releasing at least 10% of an agent over the first 24 hours in simulated gastric fluid, the limitation is met if the segment releases at least 10% of the agent over the first 24 hours in fasted state simulated gastric fluid, or if the segment releases at least 10% of the agent over the first 24 hours in fed state simulated gastric fluid.

Ethanol burst release is typically measured by immersing a segment, elongate member, or gastric residence system in a solution of 40% ethanol and 60% fasted state simulated gastric fluid for one hour, followed by immersing the same segment, elongate member, or gastric residence system in 100% fasted state simulated gastric fluid for the remainder of the test period, and measuring release of agent at appropriate time points. This test is designed to simulate the effects of consumption of alcoholic beverages by a patient having a gastric residence system of the invention deployed in the patient's stomach.

While in vitro tests can be performed using segments, elongate members, or gastric residence systems, use of segments for in vitro tests is most convenient for rapid evaluation of the release characteristics. When in vitro tests are done to compare release rates under different conditions (such as release in 100% FaSSGF versus release in 40% ethanol/60% FaSSGF), the comparison solutions are kept at the same temperature, such as room temperature, 25° C., or 37° C. Room temperature (ambient temperature) is a preferred temperature for comparisons; in one embodiment, the ambient temperature does not drop below 20° C. or exceed 25° C. (although it may fluctuate between 20° C. and 25° C.).

In vivo tests can be performed in animals such as dogs (for example, beagle dogs or hound dogs) and swine. For in vivo tests, a gastric residence system is used, since an individual segment or elongate member would not be retained in the stomach of the animal. Blood samples can be obtained at appropriate time points, and, if desired, gastric contents can be sampled by cannula or other technique.

Clinical trials in humans, conducted in accordance with appropriate laws, regulations, and institutional guidelines, also provide in vivo data.

Release Profiles

The increased linearity profiles of the segments with release rate-modulating polymer films provides advantageous release characteristics over a segment with the same carrier polymer-agent composition, but lacking the release rate-modulating polymer films. For example, a segment of a gastric residence system comprising a carrier polymer, an agent or a salt thereof, and a release-rate modulating polymer film configured to control the release rate of the agent, can have a release profile where the release-rate modulating polymer film is configured such that, over a seven-day incubation in simulated gastric fluid, the amount of the agent or salt thereof released during day 5 is at least about 40% of the amount of agent or salt thereof released during day 2. That is, over the seven day incubation period, the amount of the agent or salt thereof released from hours 96-120 (day 5) is at least about 40% of the amount of agent or salt released during hours 24-48 (day 2) of the incubation. In some embodiments, release over day 5 is at least about 50%, at least about 60%, at least about 70%, at least about 80%, or at least about 90% of the amount of agent or salt released over day 2. In some embodiments, release over day 5 is at least about 40% to about 90%, at least about 50% to about 90%, at least about 60% to about 90%, at least about 70% to about 90%, at least about 80% to about 90%, or at least about 40% to about 100%, of the amount of agent or salt released over day 2, in any of these embodiments, at least about 5% of the total amount of agent is released on day 2 and at least about 5% of the total amount of agent is released on day 5, at least about 5% of the total amount of agent is released on day 2 and at least about 7% of the total amount of agent is released on day 5, or at least about 7% of the total amount of agent is released on day 2 and at least about 7% of the total amount of agent is released on day 5. "Total amount of agent" refers to the amount of agent originally present in the segment.

In another embodiment, a segment of a gastric residence system comprising a carrier polymer, an agent or a salt thereof, and a release-rate modulating polymer film configured to control the release rate of the agent, can have a release profile where the release-rate modulating polymer film is configured such that, over a seven-day incubation in simulated gastric fluid, the amount of the agent or salt thereof released during day 7 is at least about 20% of the amount of agent or salt thereof released during day 1. That is, over the seven day incubation period, the amount of the agent or salt thereof released from hours 144-168 (day 7) is at least about 20% of the amount of agent or salt released during hours 0-24 (day 1) of the incubation, in some embodiments, release over day 7 is at least about 30%, at least about 40%, at least about 50%, at least about 60%, or at least about 70% of the amount of agent or salt released over day 1. In some embodiments, release over day 7 is at least about 20% to about 70%, at least about 30% to about 70%, at least about 40% to about 70%, at least about 50% to about 70%, at least about 60% to about 70%, or at least about 20% to about 100%, of the amount of agent or salt released over day 1. In any of these embodiments, at least about 7% of the total amount of agent is released on day 1 and at least about 4% of the total amount of agent is released on day 7, at least about 4% of the total amount of agent is released on day 1 and at least about 4% of the total amount of agent is released on day 7, or at least about 7% of the total amount of agent is released on day 1 and at least about 7% of the total amount of agent is released on day 7. "Total amount of agent" refers to the amount of agent originally present in the segment.

Segments with release rate-modulating polymer films of the invention also have lower burst release when initially immersed in simulated gastric fluid. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release of agent from the segment in simulated gastric fluid over an initial 24 hour period is at least about 40% lower than the release of agent from a second segment in simulated gastric fluid over an initial 6 hour period, where the second segment comprises the same combination of carrier polymer and agent or salt thereof, but lacks the release-rate modulating polymer film; and wherein the release of agent from the segment with the polymer film in simulated gastric fluid over a seven-day period is either i) at least about 60% of the release of agent from the second segment lacking the polymer film over a seven-day period, or ii) at least 60% of the total amount of agent originally present in the segment. In further embodiments, the release of agent from the segment with the film in simulated gastric fluid over an initial 24 hour period is at least about 40% lower, about 40% to about 50% lower, about 40% to about 60% lower, or about 40% to about 70% lower than the release of agent from a second segment without the film in simulated gastric fluid over an initial 6 hour period, while the release of agent from the segment with the film in simulated gastric fluid over a seven day period is either i) at least about 60%, at least about 70%, at least about 80%, or about 60% to about 80% of the release of agent from the second segment in simulated gastric fluid lacking the polymer film over a seven-day period, or ii) at least about 60%, at least about 70%, at least about 80%, or about 60% to about 80% of the total amount of agent originally present in the segment. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) at least about 60%, at least about 70%, at least about 75%, or at least about 80% (such as about 60% to about 70%, about 60% to about 80%, about 60% to about 90%, or about 60% to about 99%) of the total amount of agent originally present in the segment.

Segments with release rate-modulating polymer films of the invention also have lower burst release in an ethanol challenge as compared to segments lacking the films. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release of agent from the segment in 40% ethanol/60% simulated gastric fluid over one hour is at least about 40% lower than the release of agent from a second segment in 40% ethanol/60% simulated gastric fluid over one hour, the second segment comprising the same combination of carrier polymer and agent or salt thereof but lacking the release-rate modulating polymer film. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) i) at least about 60%, at least about 70%, at least about 75%, or at least about 80% (such as about 60% to about 70%, about 60% to about 80%, about 60% to about 90%, or about 60% to about 99%) of the total amount of agent originally present in the segment. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release of agent from the segment in 40% ethanol/60% simulated gastric fluid over one hour is no more than about 40% higher compared to release of agent from an equivalent segment in 100% simulated gastric fluid over one hour. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) at least about 60%, at least about 70%, at least about 75%, or at least about 80% (such as about 60% to about 70%, about 60% to about 80%, about 60% to about 90%, or about 60% to about 99%) of the total amount of agent originally present in the segment.

Linearity of release of agent from segments having a release rate-modulating polymer film coating is also improved. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that a best-fit linear regression model of the release rate of agent has a coefficient of determination $R^2$ of at least about 0.8, at least about 0.85, or at least about 0.9 over an initial period of seven days in simulated gastric fluid (where the initial period of seven days is measured from the start time when the segment is initially immersed in simulated gastric fluid; that is, the period of seven days includes the time at t=0 or origin point of the release profile); and wherein the segment releases about 30% to about 70% of the agent or salt thereof within a time of about 40% to about 60% of the seven-day period.

In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release rate over any one of the seven days varies by no more than about 50%, no more than about 40%, no more than about 30%, no more than about 25%, no more than about 20%, or no more than about 10% from the average daily total release over the seven days.

Carrier Polymers for Segments and Elongate Members (Carrier Polymer-Agent Component)

The segments and elongate members of the gastric residence system comprise a carrier polymer-agent component, which comprises the agent (or a pharmaceutically acceptable salt of an agent) to be eluted from the gastric residence system in the gastric environment. The agent is blended into the carrier polymer to form a carrier polymer-agent mixture. This mixture can be formed into the desired shape or shapes for use as carrier polymer-agent components in the systems. After the drug or drug salt is blended into the carrier polymer to form the carrier polymer-drug mixture, the drug or drug salt is distributed or dispersed throughout the blended mixture. If excipients, anti-oxidants, or other ingredients are included in the carrier polymer-drug blend, they will also be distributed or dispersed throughout the blended mixture.

Preferably, carrier polymers have the following characteristics. They should be thermoplastic, to allow extrusion using hot melt extrusion or 3D printing techniques. They should also have a high enough melt strength and viscosity to enable extrusion into the required geometry. They should have low melting temperatures (for example, less than about 120° C.), to avoid exposing agents or drugs to high temperatures during manufacture. They should have sufficient mechanical strength (Young's modulus, compression strength, tensile strength) to avoid breaking in the stomach during the desired residence period. They should be capable of forming stable blends with agents, therapeutic agents, drugs, excipients, dispersants, and other additives.

Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly(vinyl pyrrolidone), ethylene/vinyl alcohol copolymer, poly(vinyl alcohol), carboxyvinyl polymer (Carbomer), Carbopol® acidic carboxy polymer, polycarbophil, poly(ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutatnic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly(ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer. In another embodiment, polydioxanone is used as the carrier polymer. In any of the embodiments of the gastric residence system, the carrier polymer used in the gastric residence system can comprise polycaprolactone, such as linear polycaprolactone with a number-average molecular weight (Mn) range between about 60 kiloDalton (kDa) to about 100 kDa; 75 kDa to 85 kDa; or between about 80 kDa; or between about 45 kDa to about 55 kDa; or between about 50 kDa to about 110,000 kDa, or between about 80 kDa to about 110,000 kDa.

Other excipients can be added to the carrier polymers to modulate the release of agent. Such excipients can be added in amounts from about 1% to 15%, preferably from about 5% to 10%, more preferably about 5% or about 10%. Examples of such excipients include Poloxamer 407 (available as Kolliphor P407, Sigma Cat #62035), poly(ethylene glycol)-block-poly(propylene glycol)-block-poly(ethylene glycol), CAS No. 9003-11-6; H—(OCH2CH2)x-(O—CH(CH3)CH2)y-(OCH2CH2)z-OH where x and z are about 101 and y is about 56); Pluronic P407, Eudragit E, Eudragit EPO (available from Evonik); hypromellose (available from Sigma, Cat #H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), and Soluplus (available from BASF; a copolymer of polyvinyl caprolactam, polyvinyl acetate, and polyethylene glycol). Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. Preferred insoluble, swellable excipients include crospovidone, croscarmellose, hypromellose acetate succinate (HPMCAS), and carbopol. EUDRAGIT RS and EUDRAGIT RL are registered trademarks of Evonik (Darmstadt, Germany) for copolymers of ethyl acrylate, methyl methacrylate and methacrylic acid ester with quaternary ammonium groups (trimethylammonioethyl methacrylate chloride), having a molar ratio of ethyl acrylate, methyl methacrylate and trimethylammonioethyl methacrylate of about 1:2:0.2 in Eudragit® RL and about 1:2:0.1 in Eudragit® RS. Preferred insoluble, swellable excipients include crospovidone, croscarmellose, hypromellose acetate succinate (HPMCAS), carbopol, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%).

Further examples of excipients that can be used in the segments of the gastric residence system are listed in the Excipient Table below.

| Excipient Table | | |
|---|---|---|
| Function | General examples | Specific examples |
| Polymeric and non-polymeric solubilizers | Polyalkylene oxides<br>Polyethoxylated castor oil<br>Detergents | Kolliphor RH, Kolliphor P407, Soluplus, Cremophor, SDS |
| Release-enhancing excipient (porogen or wicking agent) | Acrylate polymers<br>Acrylate co-polymers<br>Polyvinylpyrrolidone | Eudragit RL<br>Eudragit RS<br>Eudragit E<br>Linear block copolymer of dioxanone and ethylene glycol (e.g., 80:20 ratio) |
| Dispersant | porous inorganic material<br>polar inorganic material<br>non-toxic metal oxides<br>amphiphilic organic molecules<br>polysaccharides, cellulose, cellulose derivatives | silica, hydrophilic-fumed silica, hydrophobic colloidal silica, magnesium aluminum silicate, stearate salts, calcium stearate, magnesium stearate, microcrystalline cellulose, |

| | Excipient Table | |
|---|---|---|
| Function | General examples | Specific examples |
| | fatty acids<br>detergents | carboxymethylcellulose,<br>hypromellose, phospholipids,<br>polyoxyethylene stearates, zinc<br>acetate, alginic acid, lecithin,<br>sodium lauryl sulfate, aluminum<br>oxide |
| Stabilizer/Preservative agent | Anti-oxidants<br>Anti-microbial agents<br>Buffering substances/<br>pH stabilizers | Tocopherols<br>Alpha-tocopherol<br>Ascorbic acid; ascorbate salts<br>Carotenes<br>Butylated hydroxytoluene (BHT)<br>Butylated hydroxyanisole (BHA)<br>Fumaric acid<br>calcium carbonate<br>calcium lactate<br>calcium phosphate<br>sodium phosphate<br>sodium bicarbonate |

Agents for Use in Gastric Residence Systems

Agents which can be administered to or via the gastrointestinal tract can be used in the gastric residence systems of the invention. The agent is blended with the carrier polymer, and any other excipients or other additives to the carrier polymer, and formed into a segment for use in a gastric residence system. Agents include, but are not limited to, drugs, pro-drugs, biologics, and any other substance which can be administered to produce a beneficial effect on an illness or injury. Agents that can be used in the gastric residence systems of the invention include statins, such as rosuvastatin; nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; antidementia drugs, such as memantine; cardiac glycosides such as digoxin; alpha blockers such as tamsulosin; cholesterol absorption inhibitors such as ezetimibe; anti-gout treatments, such as colchicine, antihistamines, such as loratadine and cetirizine, opioids, such as loperamide; proton-pump inhibitors, such as omeprazole, antiviral agents, such as entecavir; antibiotics, such as doxycycline, ciprofloxacin, and azithromycin; antimalarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as agents in the gastric residence systems of the invention include proteins, polypeptides, polynucleotides, and hormones. Exemplary classes of agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; antimuscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "agent" includes salts, solvates, polymorphs, and co-crystals of the aforementioned substances. In certain embodiments, the agent is selected from the group consisting of cetirizine, rosuvastatin, escitalopram, citalopram, risperidone, olanzapine, donepezil, and ivermectin. In another embodiment, the agent is one that is used to treat a neuropsychiatric disorder, such as an anti-psychotic agent or an anti-dementia drug such as memantine.

In some embodiments of the invention disclosed herein, the agent can exclude adamantane-class drugs. In some embodiments of the invention disclosed herein, the agent can exclude any one or more of memantine; amantadine; adapromine; nitromemantine; rimantadine; bromantane; neramexane; or tromantadine; or a pharmaceutically acceptable salt of memantine, amantadine, adapromine, nitromemantine, rimantadine, bromantane, or tromantadine. In some embodiments of the invention disclosed herein, the agent can exclude memantine. In some embodiments of the invention disclosed herein, the agent can exclude a salt of memantine or a pharmaceutically acceptable salt of memantine.

Crystalline and Amorphous Forms of Agents

Agents can be used in the gastric residence systems of the invention in any suitable crystalline form, or in amorphous form, or in both crystalline form or forms and amorphous forms. That is, agent or drug particles contained in the gastric residence systems can be used in crystalline form, in amorphous form, or in a mixture of crystalline forms (either a single crystalline form, or multiple crystalline forms) and amorphous forms, so as to provide a desired rate of release or desired physical or chemical properties.

Agent Classes of Interest

Gastric residence systems are well-suited for use in treatment of diseases and disorders which present difficulties with patient compliance, and thus in some embodiments, the gastric residence systems are used to treat a disease or disorder where patient compliance with a medication regimen is problematic. Such diseases and disorders include neuropsychiatric diseases and disorders, dementia and other diseases and disorders which affect memory, Alzheimer's disease, psychoses, schizophrenia, and paranoia. Accordingly, agents which can be used in the gastric residence systems include, but are not limited to, anti-dementia agents, anti-Alzheimer's disease agents, and anti-psychotics.

Hydrophilic Agents

Exemplary hydrophilic agents which can be used in the systems include risperidone, cetirizine, memantine, and olanzapine.

Hydrophobic Agents

Exemplary hydrophobic agents which can be used in the systems include aripiprazole, ivermectin, rosuvastatin, citalopram, and escitalopram.

Agent Loading of Elongate Members and Segments

The elongate members, or segments of which the elongate members are comprised, comprise agent or a pharmaceutically acceptable salt thereof. In some embodiments, the agent or salt thereof (for example, a drug) makes up about 10% to about 40% by weight of the elongate member or segment, and thus the carrier polymer and any other components of the elongate member or segment blended into the carrier polymer together make up the remainder of the weight of the elongate member or segment. In some embodiments, the agent or salt thereof makes up about 10% to about 35%, about 10% to about 30%, about 10% to about 25%, about 10% to about 20%, about 10% to about 15%, about 15% to about 40%, about 20% to about 40%, about 25% to about 40%, about 30% to about 40%, about 35% to about 40%, about 15% to about 35%, about 20% to about 35%, or about 25% to about 40% by weight of the elongate member or segment.

Further embodiments of elongate members or segments, where the agent or salt thereof makes up more than about 40% by weight of the elongate member or segment, are described below under "high agent loading of elongate members and segments."

High Agent Loading of Elongate Members and Segments

In some embodiments of the invention, the elongate members, or segments of which the elongate members are comprised, can have a high loading of agent or pharmaceutically acceptable salt thereof. "High loading" generally refers to elongate members or segments where the agent or salt thereof (for example, a drug) makes up more than about 40% by weight of the elongate member or segment, and thus the carrier polymer and any other components of the elongate member or segment blended into the carrier polymer together make up less than about 60% by weight of the elongate member or segment. Any components of the elongate members or segments which are not blended into the carrier polymer are not included in the calculation of the weight percentage; for example, if an elongate member has one or more disintegrating matrices interspersed between segments of the elongate member, the weight of such matrices would not be included as part of the weight of the elongate member in the calculation of the weight percentage of agent in the elongate member. Once the loading of the agent increases to about 60%, it becomes increasingly difficult to properly blend the agent with the carrier polymer, and phase separation of the agent and polymer tends to occur. Thus, the loading of the agent in an elongate member or segment should not exceed about 60% of the total weight of the elongate member.

Thus, in some embodiments, the amount of agent by weight in the elongate members, or segments of which the elongate members are comprised, can comprise at least about 40%, at least about 45%, at least about 50%, at least about 55%, or about 60%. In some embodiments, the amount of agent by weight in the elongate members, or segments of which the elongate members are comprised, can comprise about 40% to about 60%, about 45% to about 60%, about 50% to about 60%, about 55% to about 60%, about 40% to about 55%, about 40% to about 50%, or about 40% to about 45%. In some embodiments, the amount of agent by weight in the elongate members, or segments of which the elongate members are comprised, can comprise about 25% to about 60%, about 30% to about 60%, or about 35% to about 60%. In some embodiments, the amount of agent by weight in the elongate members, or segments of which the elongate members are comprised, can comprise about 51% to about 60%, about 52% to about 60%, about 53% to about 60%, about 54% to about 60%, about 55% to about 60%, about 56% to about 60%, or about 57% to about 60%. In some embodiments, the agent or pharmaceutically acceptable salt thereof is present in an amount by weight of between about 67% and about 150% of the weight of the carrier polymer.

The combination of the high agent or agent salt loading with the release rate-controlling polymer film provides gastric residence systems with increased amounts of agent or agent salt, while maintaining good release kinetics over the residence period of the system.

The release-rate modulating polymer films can also be used with loadings lower than the high-loading values above, such as an amount of agent by weight in the elongate members, or segments of which the elongate members are comprised, of about 20% to about 35%. Loading ranges covering both high-loading and lower-than-high-loading can be used, such as between about 20% to about 60%, between about 25% to about 60%, between about 30% to about 60%, between about 35% to about 60%, between about 20% to about 50%, between about 20% to about 40%, or between about 25% to about 50%.

Dispersants for Modulation of Agent Release and Stability of Polymer Blend

The use of a dispersant in the carrier polymer-agent component provides numerous advantages. The rate of elution of agent from the carrier polymer-agent component is affected by numerous factors as previously noted, including the composition and properties of the carrier polymer (which may itself comprise multiple polymeric and non-polymeric components); the physical and chemical properties of the agent; and the gastric environment. Avoiding burst release of agent, especially hydrophilic agents, and maintaining sustained release of the agent over the effective release period or residence period is an important characteristic of the systems. The use of a dispersant according to the invention enables better control of release rate and suppression of burst release. Burst release and release rate can be tuned by using varied concentrations of dispersant. For example, different dispersants and different excipients, at varying concentrations, can tune burst release of cetirizine in simulated gastric fluid.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant. One particularly useful silicon dioxide is sold by Cabot Corporation (Boston, Massachusetts, USA) under the registered trademark CAB-O-SIL® M-5P (CAS #112945-52-5), which is hydrophilic-fumed silicon dioxide having a BET surface area of about 200 m2/g±15 m2/g The mesh residue for this product on a 45 micron sieve is less than about 0.02%. The typical primary aggregate size is about 150 to about 300 nm, while individual particle sizes may range from about 5 nm to about 50 nm.

In addition to anti-aggregation/anti-flocculation activity, the dispersant can help prevent phase separation during fabrication and/or storage of the systems. This is particularly useful for manufacture of the systems by hot melt extrusion.

The weight/weight ratio of dispersant to agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 15%, about 0.1%, to about 1%, about 0.1% to about 0.5%, or about 0.2% to about 0.8%.

Dispersants can also be used to modulate the amount of burst release of agent or pharmaceutically acceptable salt thereof during the initial period when the gastric residence system is administered. In embodiments of a gastric residence system that is to be administered once weekly, the burst release over the approximately first six hours after initial administration is less than about 8%, preferably less than about 6%, of the total amount of agent (or salt thereof) in the system. In embodiments of a gastric residence system that is to be administered once every three days, the burst release over the approximately first six hours after initial administration is less than about 12%, preferably less than about 10%, of the total amount of agent (or salt thereof) in the system. In embodiments of a gastric residence system that is to be administered once daily, the burst release over the approximately first six hours after initial administration is less than about 40%, preferably less than about 30%, of the total amount of agent (or salt thereof) in the system. In general, if a new gastric residence system is administered every D days, and the total mass of agent (or salt thereof) is M, then the gastric residence system releases less than about [(M divided by D) times 0.5], preferably less than about [(M divided by D) multiplied by 0.4], or less than about [(M divided by D) multiplied by ⅜], more preferably less than about [(M divided by D) multiplied by 0.3], over the approximately first six hours after initial administration. In further embodiments, the gastric residence system releases at least about [(M divided by D) multiplied by 0.25] over the approximately first six hours after initial administration, that is, the system releases at least about one-quarter of the daily dosage over the first one-quarter of the first day of administration.

Stabilizers for Use in Gastric Residence Systems

Many agents are prone to oxidative degradation when exposed to reactive oxygen species, which can be present in the stomach. An agent contained in the system may thus oxidize due to the prolonged residence in the stomach of the system, and the extended release period of agent from the system. Accordingly, it is desirable to include stabilizers or preservatives in the systems, in order to stabilize the agent to prevent oxidative and other degradation.

Stabilizers, such as anti-oxidants including tocopherols, alpha-tocopherol, ascorbic acid, ascorbyl palmitate, butylated hydroxytoluene, butylated hydroxyanisole, and fumaric acid, can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Anti-oxidant stabilizers that can be included in the systems to reduce or prevent oxidation of the agent include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm). Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate can be used as anti-oxidant stabilizers.

Certain agents can be pH-sensitive, especially at the low pH present in the gastric environment. Buffering or pH-stabilizer compounds that can be included in the systems to reduce or prevent degradation of agent at low pH include calcium carbonate, calcium lactate, calcium phosphate, sodium phosphate, and sodium bicarbonate. They are typically used in an amount of up to about 2% w/w. The buffering or pH-stabilizer compounds can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

The anti-oxidant stabilizers, pH stabilizers, and other stabilizer compounds are blended into the polymers containing the agent (or pharmaceutically acceptable salt thereof) by blending the stabilizer(s) into the molten carrier polymer-agent or agent salt mixture. The stabilizer(s) can be blended into molten carrier polymer prior to blending the agent (or salt thereof) into the polymer-stabilizer mixture; or the stabilizer(s) can be blended with agent (or salt thereof) prior to formulation of the blended agent (or salt thereof)-stabilizer mixture in the carrier polymer; or stabilizer(s), agent (or salt thereof), and molten carrier polymer can be blended simultaneously. Agent (or salt thereof) can also be blended with molten carrier polymer prior to blending the stabilizer(s) into the polymer-agent or agent salt mixture.

In one embodiment, less than about 10% of the agent (or salt thereof) remaining in the system is degraded or oxidized after a gastric residence period of about 24 hours. In one embodiment, less than about 10% of the agent (or salt thereof) remaining in the system is degraded or oxidized after a gastric residence period of about 48 hours. In one embodiment, less than about 10% of the agent (or salt thereof) remaining in the system is degraded or oxidized after a gastric residence period of about 72 hours. In one embodiment, less than about 10% of the agent (or salt thereof) remaining in the system is degraded or oxidized after a gastric residence period of about 96 hours. In one embodiment, less than about 10% of the agent (or salt thereof) remaining in the system is degraded or oxidized after a gastric residence period of about five days. In some embodiments, less than about 10% of the agent (or salt thereof) remaining in the system is degraded or oxidized after a gastric residence period of about a week. In some embodiments, less than about 10% of the agent (or salt thereof) remaining in the system is degraded or oxidized after a gastric residence period of about two weeks.

In one embodiment, less than about 5% of the agent (or salt thereof) remaining in the system is degraded or oxidized after a gastric residence period of about 24 hours. In one embodiment, less than about 5% of the agent (or salt thereof) remaining in the system is degraded or oxidized after a gastric residence period of about 48 hours. In one embodiment, less than about 5% of the agent (or salt thereof) remaining in the system is degraded or oxidized after a gastric residence period of about 72 hours. In one embodiment, less than about 5% of the agent (or salt thereof) remaining in the system is degraded or oxidized after a gastric residence period of about 96 hours. In one embodiment, less than about 5% of the agent (or salt thereof) remaining in the system is degraded or oxidized after a gastric residence period of about five days. In some embodiments, less than about 5% of the agent (or salt thereof) remaining in the system is degraded or oxidized after a gastric residence period of about a week. In some embodiments, less than about 5% of the agent (or salt thereof) remaining in the system is degraded or oxidized after a gastric residence period of about two weeks.

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours, in one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days (about one week), or up to about 7 days (about one week). In one embodiment, the gastric residence system has a residence time of about 10 days, or up to about 10 days. In one embodiment, the gastric residence system has a residence time of about 14 days (about two weeks), or up to about 14 days (about two weeks).

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

The gastric residence system releases a therapeutically effective amount of agent (or salt thereof) during at least a portion of the residence time or residence period during which the system resides in the stomach. In one embodiment, the system releases a therapeutically effective amount of agent (or salt thereof) during at least about 25% of the residence time. In one embodiment, the system releases a therapeutically effective amount of agent (or salt thereof) during at least about 50% of the residence time. In one embodiment, the system releases a therapeutically effective amount of agent (or salt thereof) during at least about 60% of the residence time. In one embodiment, the system releases a therapeutically effective amount of agent (or salt thereof) during at least about 70% of the residence time. In one embodiment, the system releases a therapeutically effective amount of agent (or salt thereof) during at least about 75% of the residence time. In one embodiment, the system releases a therapeutically effective amount of agent (or salt thereof) during at least about 80% of the residence time, in one embodiment, the system releases a therapeutically effective amount of agent (or salt thereof) during at least about 85% of the residence time. In one embodiment, the system releases a therapeutically effective amount of agent (or salt thereof) during at least about 90% of the residence time. In one embodiment, the system releases a therapeutically effective amount of agent (or salt thereof) during at least about 95% of the residence time. In one embodiment, the system releases a therapeutically effective amount of agent (or salt thereof) during at least about 98% of the residence time. In one embodiment, the system releases a therapeutically effective amount of agent (or salt thereof) during at least about 99% of the residence time.

Radiopacity

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or are added to a small portion of the system. Examples of suitable radiopaque substances are barium sulfate, bismuth subcarbonate, bismuth oxychloride, and bismuth trioxide. It is preferable that these materials should not be blended into the polymers used to construct the gastric residence system, so as not to alter drug release from the carrier polymer, or desired properties of other system polymers. Metal striping or tips on a small portion of the system components can also be used, such as tungsten.

Carrier Polymer-Agent/Agent Salt Combinations With Excipients and Other Additives The blend of carrier polymer-agent or carrier polymer-agent salt can comprise various excipients and other additives. The following Table CPE-1 lists combinations of excipients and other additives that can be used in combination with agent or salt thereof and carrier polymer in the compositions making up the elongate members or segments of elongate members of the gastric residence systems. These excipients and other additives can be combined with agent or salt thereof (where the agent or agent salt comprises between about 10% to about 60% by weight of the composition) with the carrier polymer, such as polycaprolactone, making up the remainder of the composition. Excipients include the following, which can be used individually or in any combination, in amounts ranging from about 1% to about 30%, such as about 5% to 20%, by weight of the composition: Kolliphor P407 (poloxamer 407, poly(ethylene glycol)-block-poly(propylene glycol)-block-poly(ethylene glycol)), Eudragit RS (Poly[Ethyl acrylate, methyl methacrylate, trimethylammonioethyl methacrylate chloride] 1:2:0.1), Eudragit RL (Poly[Ethyl acrylate, methyl methacrylate, trimethylammonioethyl methacrylate chloride] 1:2:0.2), PDO (polydioxanone), PEG-PCL, SIF (FaSSIF/FaSSGF powder from BioRelevant), EPO (dimethylaminoethyl methacrylate—butyl methacrylate—methyl methacrylate copolymer), Kollidon VA64 (vinylpyrrolidone—vinyl acetate copolymer in a ratio of 6:4 by mass), polyvinyl acetate, polyvinyl pyrrolidine.

Other additives include silicon dioxide (comprising, for example, about 0.1% to about 5% by weight of the composition, such as about 0.1% to 1% or about 0.5%) and an anti-oxidant, such as alpha-tocopherol (comprising, for example, about 0.1% to about 5% by weight of the composition, such as about 0.1% to 1% or about 0.5%). Each row of the table below represents a formulation of excipients and other additives for use with the carrier polymer and agent or salt thereof.

TABLE CPE-1
Excipients and additives, in combination with agent or salt thereof and carrier polymer EPO, P407, Silica, α-tocopherol
EPO, Silica, α-tocopherol
Eudragit RL, Eudragit RS, Kolliphor P407, Silica, α-tocopherol
Eudragit RL, Kolliphor P407, Silica, α-tocopherol
Eudragit RL, Eudragit RS, Kolliphor P407, Silica, α-tocopherol
Eudragit RL, Kolliphor P407, Silica, α-tocopherol
Eudragit RL, Kolliphor P407, Silica, α-tocopherol
Eudragit RS, P407, Silica, α-tocopherol
Eudragit RS, Silica, α-tocopherol
Kollidon VA64, Silica, α-tocopherol
Kolliphor P407, Silica, α-tocopherol
Kolliphor RH40, Silica, α-tocopherol
PDO, Silica, α-tocopherol
PEG-PCL, Silica, α-tocopherol
Poly Vinyl Acetate, Silica, α-tocopherol
PVP, Silica, α-tocopherol
SIF, Silica, α-tocopherol
Silica, P188, P407, α-tocopherol
Silica, α-tocopherol Table CPE-2 lists specific amounts of excipients and other additives that can be used in combination with agent or salt thereof and carrier polymer in the compositions making up the elongate members or segments of elongate members of the gastric residence systems.

The amounts listed in Table CPE-2 can be varied by plus-or-minus 20% of each ingredient (for example, 0.5% silica can vary between 0.4% and 0.6% silica, as 20% of 0.5% is 0.1%). Each row of the table below represents a formulation of excipients and other additives for use with the carrier polymer and agent or salt thereof.

TABLE CPE-2
Excipients and additives, in combination with agent or salt thereof and carrier polymer 0.5% Silica, 0.5% α-tocopherol
0.5% Silica, 2% P407, 0.5% α-tocopherol
0.5% Silica, 2% P188, 2% P407, 0.5% α-tocopherol
0.5% Silica, 3% Eudragit RS, 2% P407, 0.5% α-tocopherol
1% Kolliphor P407, 0.5% Silica, 0.5% α-tocopherol
10% Eudragit RS, 2.5% P407, 2% Silica, 0.5% α-tocopherol
10% Eudragit RS, 5% P407, 0.5% Silica, 0.5% α-tocopherol
10% Eudragit RS, 5% P407, 2% Silica, 0.5% α-tocopherol
12% Eudragit RL, 3% Kolliphor P407, 0.5% Silica, 0.5% α-tocopherol
12% Eudragit RL, 5% Kolliphor P407, 0.5% Silica, 0.5% α-tocopherol
14.78% Eudragit RS, 0.226% P407, 0.5% Silica, 0.5% α-tocopherol
17.5% Eudragit RS, 5% P407, 0.5% Silica, 0.5% α-tocopherol
19.8% Eudragit RS, 0.5% Silica, 0.5% α-tocopherol
2% Kolliphor P407, 0.5% Silica, 0.5% α-tocopherol
2% P407, 0.5% Silica, 0.5% α-tocopherol
20% Eudragit RS, 2% P407, 0.5% Silica, 0.5% α-tocopherol
21.25% Eudragit RS, 2.5% P407, 0.5% Silica, 0.5% α-tocopherol
25% Eudragit RL, 5% P407, 0.5% Silica, 0.5% α-tocopherol
25% Eudragit RS, 0.5% Silica, 0.5% α-tocopherol
25% Eudragit RS, 5% P407, 0.5% Silica, 0.5% α-tocopherol
3% Eudragit RL, 9% Eudragit RS, 5% Kolliphor P407, 0.5% Silica, 0.5% α-tocopherol
3.5% Eudragit RS, 2.5% P407, 2% Silica, 0.5% α-tocopherol

TABLE CPE-2
Excipients and additives, in combination with agent or salt thereof and carrier polymer 3.5% Eudragit RS, 5% P407, 2% Silica, 0.5% α-tocopherol
30% PDO, 0.5% Silica, 0.5% α-tocopherol
39.5% PEG-PCL, 0.36% Silica, 0.36% α-tocopherol
4.5% EPO, 4.5% P407, 0.5% Silica, 0.5% α-tocopherol
5% Kolliphor P407, 0.5% Silica, 0.5% α-tocopherol
5% Kolliphor RH40, 0.5% Silica, 0.5% α-tocopherol
5% SIF, 0.5% Silica, 0.5% α-tocopherol
6% Eudragit RL, 5% Kolliphor P407, 0.5% Silica, 0.5% α-tocopherol
6% Eudragit RL, 6% Eudragit RS, 5% Kolliphor P407, 0.5% Silica, 0.5% α-tocopherol
6.75% Eudragit RS, 3.75% P407, 2% Silica, 0.5% α-tocopherol
7% EPO, 2% P407, 0.5% Silica, 0.5% α-tocopherol
9% EPO, 0.5% Silica, 0.5% α-tocopherol
9% Eudragit RL, 3% Eudragit RS, 5% Kolliphor P407, 0.5% Silica, 0.5% α-tocopherol
9% Kollidon VA64, 0.5% Silica, 0.5% α-tocopherol
9% Poly Vinyl Acetate, 0.5% Silica, 0.5% α-tocopherol
9% PVP, 0.5% Silica, 0.5% α-tocopherol
9% SIF, 0.5% Silica, 0.5% α-tocopherol Manufacture/Assembly of System: Three-Dimensional Printing Three-dimensional printing of components of the gastric residence system, such as arm or arm segments, is performed using commercially-available equipment. Three-dimensional printing has been used for pharmaceutical preparation; see Khaled et al., "Desktop 3D printing of controlled release pharmaceutical bilayer tablets," International Journal of Pharmaceutics 461:105-111 (2014); U.S. Pat. No. 7,276,252; Alhnan et al., "Emergence of 3D Printed Dosage Forms: Opportunities and Challenges," Pharm. Res., May 18, 2016, PubMed PMID: 27194002); Yu et al., "Three-dimensional printing in pharmaceutics: promises and problems," J. Pharm. Sci. 97(9):3666-3690 (2008); and Ursan et al., "Three-dimensional drug printing: A structured review," J. Am. Pharm. Assoc. 53(2):136-44 (2013).

The initial feedstocks for three-dimensional printing are polymers or polymer blends (e.g. enteric polymers, time-dependent polymers, or blends of one or more of an agent, an agent salt, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer or blended polymer material is extruded through a circular die, creating a cylindrical fiber which is wound around a spool.

Multiple spools are fed into the 3D printer (such as a Hyrel Printer, available from Hyrel 3D, Norcross, Georgia, United States), to be fed into their representative print heads. The print heads heat up and melt the material at the nozzle, and lay down a thin layer of material (polymer or polymer blend) in a specific position on the piece being manufactured. The material cools and hardens within seconds, and the next layer is added until the complete structure is formed. The quality of the dosage form is dependent on the feed rate, nozzle temperature, and printer resolution; feed rate and nozzle temperature can be adjusted to obtain the desired quality.

Three-dimensional printing can be used to manufacture individual elongate members, or segments of elongate members. Three-dimensional printing can also be used to prepare a bulk configuration, such as a consolidated "slab," similar to that prepared by co-extrusion methods described herein. The bulk configuration can be cut into individual pieces (that is, individual elongate members or individual segments) as needed.

In some embodiments of the invention, producing an entire elongate member, or "arm," of the gastric residence system by three-dimensional printing of the elongate member is contemplated. In some embodiments of the invention, producing a segment of an elongate member, or "arm," of the gastric residence system by three-dimensional printing of the segment of an elongate member is contemplated. In some embodiments, an elongate member or a segment thereof is produced by three-dimensional printing of adjacent portions of carrier polymer-agent or polymer-agent salt blend and linker material in a bulk configuration, such as a slab configuration. The three-dimensional printing can be followed by cutting the bulk configuration into pieces which have the desired shape of the elongate member or segment thereof. The three-dimensional printing can be followed by compression molding of portions of the bulk configuration into pieces which have the desired shape of the elongate member or segment thereof.

Three-dimensional printing is often accomplished by feeding a rod or fiber of a solid material to a print head, where it is melted and deposited with subsequent solidification, in a technique known as fused deposition modeling (sometimes also called extrusion deposition); see U.S. Pat. Nos. 5,121,329 and 5,340,433. The methods described herein for the manufacture of carrier polymer-drug components can also be used to manufacture feed material, which can be used in the manufacture via three-dimensional printing of components of the gastric residence systems.

Manufacture/Assembly of System: Co-Extrusion

Components of the gastric residence systems can be manufactured by co-extrusion. Most of the various configurations for the segments discussed herein, such as the "islands-in-the-sea" configurations, can be made by either three-dimensional printing or co-extrusion. However, co-extrusion is less expensive, and can be run as a continuous process, as opposed to three-dimensional printing, which is generally run as a batch process.

Co-extrusion of the "islands-in-the-sea" configuration is used in the textile industry and for production of fiber optics, but has rarely been applied in biomedical systems. See U.S.

Pat. Nos. 3,531,368; 3,716,614; 4,812,012; and Haslauer et al., J. Biomed. Mater. Res. B Appl. Biomater. 103(5):1050-8 (2015)).

Co-extrusion of components of the gastric residence system, such as an elongate member (arm), or a segment of an elongate member (arm), can be performed using commercially-available equipment, combined with customized co-extruder plumbing and customized dies for the desired configuration. The initial feedstocks for co-extrusion are polymers or polymer blends (e.g. enteric polymers, time-dependent polymers, or blends of one or more of an agent, an agent salt, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer pellets thus formed are placed into hoppers above single screw extruders and dried to remove surface moisture. Pellets are gravimetrically fed into individual single-screw extruders, where they are melted and pressurized for co-extrusion.

The appropriate molten polymers are then pumped through custom designed dies with multiple channels where they form the required geometry. The composite polymer block is cooled (water-cooled, air-cooled, or both) and cut or stamped into the desired shape, including, but not limited to, such shapes as triangular prisms, rectangular prisms, or cylinder sections (pie-shaped wedges).

In some embodiments of the invention, producing an entire elongate member, or "arm," of the gastric residence system by co-extruding the elongate member is contemplated. In some embodiments of the invention, producing a segment of an elongate member, or "arm," of the gastric residence system by co-extruding the segment of an elongate member is contemplated. In some embodiments, an elongate member or a segment thereof is produced by co-extruding adjacent portions of carrier polymer-agent or carrier polymer-agent salt blend and linker material in a bulk configuration, such as a slab configuration. The co-extruding can be followed by cutting the bulk configuration into pieces which have the desired shape of the elongate member or segment thereof. The co-extruding can be followed by compression molding of portions of the bulk configuration into pieces which have the desired shape of the elongate member or segment thereof.

In some embodiments, an elongate member or a segment thereof is produced by co-extruding adjacent portions of carrier polymer-agent or carrier polymer-agent salt blend and linker material in a bulk configuration, such as a slab configuration, while also co-extruding an additional polymer or polymers within the carrier polymer-agent or carrier polymer-agent salt blend, the linker material, or both the carrier polymer-agent (or agent salt) blend and the linker material. The co-extruding the additional polymer or polymers within the carrier polymer-agent or carrier polymer-agent salt blend, the linker material, or both the carrier polymer-agent (or agent salt) blend and the linker material can be performed in an islands-in-the-sea configuration. The co-extruding can be followed by cutting the bulk configuration into pieces which have the desired shape of the elongate member or segment thereof. The co-extruding can be followed by compression molding of portions of the bulk configuration into pieces which have the desired shape of the elongate member or segment thereof.

Agent Particle Size and Milling

Control of particle size used in the gastric residence systems is important for both optimal release of agent and mechanical stability of the systems. The particle size of the agents affects the surface area of the agents available for dissolution when gastric fluid permeates the carrier polymer-agent segments of the system. Also, as the "arms" (elongate members) of the systems are relatively thin in diameter (for example, 1 millimeter to 5 millimeters), the presence of a particle of agent of a size in excess of a few percent of the diameter of the arms will result in a weaker arm, both before the agent elutes from the device, and after elution when a void is left in the space formerly occupied by the agent particle. Such weakening of the arms is disadvantageous, as it may lead to premature breakage and passage of the system before the end of the desired residence period.

In one embodiment, the agent particles used for blending into the carrier polymer-agent components are smaller than about 100 microns in diameter. In another embodiment, the agent particles are smaller than about 75 microns in diameter. In another embodiment, the agent particles are smaller than about 50 microns in diameter. In another embodiment, the agent particles are smaller than about 40 microns in diameter. In another embodiment, the agent particles are smaller than about 30 microns in diameter. In another embodiment, the agent particles are smaller than about 25 microns in diameter. In another embodiment, the agent particles are smaller than about 20 microns in diameter. In another embodiment, the agent particles are smaller than about 10 microns in diameter. In another embodiment, the agent particles are smaller than about 5 microns in diameter.

In one embodiment, at least about 80% of the agent particles used for blending into the carrier polymer-agent components are smaller than about 100 microns in diameter. In another embodiment, at least about 80% of the agent particles are smaller than about 75 microns in diameter. In another embodiment, at least about 80% of the agent particles are smaller than about 50 microns in diameter. In another embodiment, at least about 80% of the agent particles are smaller than about 40 microns in diameter. In another embodiment, at least about 80% of the agent particles are smaller than about 30 microns in diameter. In another embodiment, at least about 80% of the agent particles are smaller than about 25 microns in diameter. In another embodiment, at least about 80% of the agent particles are smaller than about 20 microns in diameter. In another embodiment, at least about 80% of the agent particles are smaller than about 10 microns in diameter. In another embodiment, at least about 80% of the agent particles are smaller than about 5 microns in diameter.

In one embodiment, at least about 80% of the mass of the agent particles used for blending into the carrier polymer-agent components have sizes between about 1 micron and about 100 microns in diameter. In another embodiment, at least about 80% of the mass of the agent particles have sizes between about 1 micron and about 75 microns in diameter. In another embodiment, at least about 80% of the mass of the agent particles have sizes between about 1 micron and about 50 microns in diameter. In another embodiment, at least about 80% of the mass of the agent particles have sizes between about 1 micron and about 40 microns in diameter. In another embodiment, at least about 80% of the mass of the agent particles have sizes between about 1 micron and about 30 microns in diameter. In another embodiment, at least about 80% of the mass of the agent particles have sizes between about 1 micron and about 25 microns in diameter. In another embodiment, at least about 80% of the mass of the agent particles have sizes between about 1 micron and about 20 microns in diameter. In another embodiment, at least about 80% of the mass of the agent particles have sizes between about 1 micron and about 10 microns in diameter. In another embodiment, at least about 80% of the mass of the agent particles have sizes between about 1 micron and about 5 microns in diameter.

In one embodiment, at least about 80% of the mass of the agent particles used for blending into the carrier polymer-agent components have sizes between about 2 microns and about 100 microns in diameter. In another embodiment, at least about 80% of the mass of the agent particles have sizes between about 2 microns and about 75 microns in diameter. In another embodiment, at least about 80% of the mass of the agent particles have sizes between about 2 microns and about 50 microns in diameter. In another embodiment, at least about 80% of the mass of the agent particles have sizes between about 2 microns and about 40 microns in diameter. In another embodiment, at least about 80% of the mass of the agent particles have sizes between about 2 microns and about 30 microns in diameter. In another embodiment, at least about 80% of the mass of the agent particles have sizes between about 2 microns and about 25 microns in diameter. In another embodiment, at least about 80% of the mass of the agent particles have sizes between about 2 microns and about 20 microns in diameter. In another embodiment, at least about 80% of the mass of the agent particles have sizes between about 2 microns and about 10 microns in diameter. In another embodiment, at least about 80% of the mass of the agent particles have sizes between about 2 microns and about 5 microns in diameter.

In one embodiment, at least about 80% of the mass of the agent particles used for blending into the carrier polymer-agent components have sizes between about 5 microns and about 100 microns in diameter. In another embodiment, at least about 80% of the mass of the agent particles have sizes between about 5 microns and about 75 microns in diameter. In another embodiment, at least about 80% of the mass of the agent particles have sizes between about 5 microns and about 50 microns in diameter. In another embodiment, at least about 80% of the mass of the agent particles have sizes between about 5 microns and about 40 microns in diameter. In another embodiment, at least about 80% of the mass of the agent particles have sizes between about 5 microns and about 30 microns in diameter. In another embodiment, at least about 80% of the mass of the agent particles have sizes between about 5 microns and about 25 microns in diameter. In another embodiment, at least about 80% of the mass of the agent particles have sizes between about 5 microns and about 20 microns in diameter. In another embodiment, at least about 80% of the mass of the agent particles have sizes between about 5 microns and about 10 microns in diameter.

The particle size of the agents can be readily adjusted by milling. Several milling techniques are available to reduce larger particles to smaller particles of desired size. Fluid energy milling is a dry milling technique which uses interparticle collisions to reduce the size of particles. A type of fluid energy mill called an air jet mill shoots air into a cylindrical chamber in a manner so as to maximize collision between agent particles. Ball milling utilizes a rolling cylindrical chamber which rotates around its principal axis. The agent and grinding material (such as steel balls, made from chrome steel or CR-NI steel; ceramic balls, such as zirconia; or plastic polyamides) collide, causing reduction in particle size of the agent. Ball milling can be performed in either the dry state, or with liquid added to the cylinder where the agent and the grinding material are insoluble in the liquid. Further information regarding milling is described in the chapter by R. W. Lee et al. entitled "Particle Size Reduction" in *Water-Insoluble Drug Formulation, Second Edition* (Ron Liu, editor), Boca Raton, Florida: CRC Press, 2008; and in the chapter by A. W. Brzeczko et al. entitled "Granulation of Poorly Water-Soluble Drugs" in *Handbook of Pharmaceutical Granulation Technology, Third Edition* (Dilip M. Parikh, editor), Boca Raton, Florida: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Willing Additives

Substances can be added to the agent material during milling to assist in obtaining particles of the desired size, and minimize aggregation during handling. Silica (silicon dioxide, $SiO_2$) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 5% of milling additive, such as silica, can be used for fluid milling or ball milling, or about 0.1% to about 4%, about 0.1% to about 3%, about 0.1% to about 2%, about 0.1% to about 1%, about 1% to about 5%, about 1% to about 4%, about 1% to about 3%, about 1% to about 2 or about 0.1%, about 0.5%, about 1%, about 2%, about 3%, about 4% or about 5%.

Particle Sizing

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

Coupling Polymers

The coupling polymer is used to link one or more carrier polymer-agent components to one or more carrier polymer-agent components, to link one or more carrier polymer-agent components to one or more elastomer components, or to link one or more elastomer components to one or more elastomer components. Thus, the coupling polymers form linker regions between other components of the system. Enteric polymers and time-dependent polymers are preferred for use as coupling polymers. In some embodiments, enteric polymers are used as coupling polymers. In some embodiments, time-dependent polymers which are pH-resistant, that is, less sensitive to changes in pH than enteric polymers, are used as coupling polymers. In some embodiments, both enteric polymers and time-dependent polymers which are less sensitive to changes in pH than enteric polymers are used as coupling polymers.

Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. Thus, the gastric residence systems are designed to uncouple rapidly in the intestinal environment by dissolution of the coupling polymer, within 48 hours, preferably within 24 hours, more preferably within 12 hours, yet more preferably within 1-2 hours, so as to avoid potential intestinal blockage. If, during treatment, the gastric residence system must be removed quickly for any reason, the patient can drink a mildly basic aqueous solution (such as a bicarbonate solution) in order to induce immediate de-coupling of the gastric residence system.

By "time-dependent polymer which are pH-resistant" (or equivalently, "pH-resistant time-dependent polymers") is meant that, under conditions where an enteric polymer would degrade to the point that it would no longer link the components together, the time-dependent polymer will still have sufficient mechanical strength to link the components together. In some embodiments, the time-dependent polymer retains about the same linking capacity, that is, about 100% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 90% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 75% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 60% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 50% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 25% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer resists breaking under a flexural force of about 0.2 Newtons (N), about 0.3 N, about 0.4 N, about 0.5 N, about 0.75 N, about 1 N, about 1.5 N, about 2 N, about 2.5 N, about 3 N, about 4 N, or about 5 N, after exposure to a solution between about pH 7 to about pH 8, where the exposure is for about an hour, about a day, about three days, or about a week. Linkage strength can be measured by any relevant test that serves to test coupling ability, such as a four-point bending flexural test (ASTM D790).

Exemplary coupling polymers include, but are not limited to, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in the Enteric Polymer Table, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Röhm GmbH, Darmstadt, Germany) is a preferred enteric polymer. Another preferred enteric polymer is hydroxypropylmethylcellulose acetate succinate (hypromellose acetate succinate or HPMCAS; Ashland, Inc., Covington, Kentucky, USA), which has a tunable pH cutoff from about 5.5 to about 7.0. Cellulose acetate phthalate, cellulose acetate succinate, and hydroxypropyl methylcellulose, phthalate are also suitable enteric polymers.

In one embodiment, the enteric polymers used in the gastric residence system dissolve at a pH above about 4. In some embodiments, the enteric polymers used in the gastric residence system dissolve at a pH above about 5. In some embodiments, the enteric polymers used in the gastric residence system dissolve at a pH above about 6. In some embodiments, the enteric polymers used in the gastric residence system dissolve at a pH above about 7. In some embodiments, the enteric polymers used in the gastric residence system dissolve at a pH above about 7.5. In some embodiments, the enteric polymers used in the gastric residence system dissolve at a pH between about 4 and about 5. In some embodiments, the enteric polymers used in the gastric residence system dissolve at a pH between about 4 and about 6. In some embodiments, the enteric polymers used in the gastric residence system dissolve at a pH between about 4 and about 7. In some embodiments, the enteric polymers used in the gastric residence system dissolve at a pH between about 4 and about 7.5. In some embodiments, the enteric polymers used in the gastric residence system dissolve at a pH between about 5 and about 6. In some embodiments, the enteric polymers used in the gastric residence system dissolve at a pH between about 5 and about 7. In some embodiments, the enteric polymers used in the gastric residence system dissolve at a pH between about 5 and about 7.5. In some embodiments, the enteric polymers used in the gastric residence system dissolve at a pH between about 6 and about 7. In some embodiments, the enteric polymers used in the gastric residence system dissolve at a pH between about 6 and about 7.5.

| Enteric Polymer Table | |
|---|---|
| Polymer | Dissolution pH |
| Cellulose acetate phthalate | 6.0-6.4 |
| Hydroxypropyl methylcellulose phthalate 50 | 4.8 |

-continued

Enteric Polymer Table

| Polymer | Dissolution pH |
|---|---|
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are time-dependent polymers, that is, polymers that degrade in a time-dependent manner in the gastric environment. For example, the liquid plasticizer triacetin releases from a polymer formulation in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture (that is, using less triacetin in the mixture), while the degradation time can be decreased by decreasing the amount of Plastoid B used in the mixture (that is, using more triacetin in the mixture).

A variety of time-dependent mechanisms are available. Water-soluble time-dependent polymers break down as water penetrates through the polymer. Examples of such polymers are hydroxypropyl methylcellulose and poly vinyl acetate. Acid soluble time-dependent polymers break down over time in an acidic environment. Examples include Eudragit EPO. Time-dependent polymers can use water soluble plasticizers; as plasticizer is released, the remaining polymer becomes brittle and breaks under gastric forces. Examples of such polymers include triacetin and triethyl citrate.

In some embodiments, the carrier polymer-agent components are elongate members comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

In some embodiments, the carrier polymer-drug components are non-segmented elongate members attached to the elastomer component of the system by enteric polymers, time-dependent linkers, or disintegrating matrices, or by any combination of enteric polymers, time-dependent linkers, and/or disintegrating matrices.

In any of the embodiments of the gastric residence systems described herein, the coupling polymers or linkers can comprise hydroxypropyl methyl cellulose acetate succinate (HPMCAS) and polycaprolactone (PCL). These blends can be used to form disintegrating linkers or disintegrating matrices. The ratio of HPMCAS to polycaprolactone in the disintegrating linker or disintegrating matrix can be between about 80% HPMCAS:20% PCL to about 20% HPMCAS:80% PCL. the ratio of HPMCAS to polycaprolactone can be between about 80% HPMCAS:20% PCL to about 20% PMCAS:80% PCL; between about 70% HPMCAS:30% PCL to about 30% HPMCAS:70% PCL; between about 60% HPMCAS:40% PCL to about 40% HPMCAS:60% PCL; between about 80% HPMCAS:20% PCL to about 50% HPMCAS:50% PCL; between about 80% HPMCAS:20% PCL to about 60% HPMCAS:40% PCL; between about 70% HPMCAS:30% PCL to about 50% HPMCAS:50% PCL; between about 70% HPMCAS:30% PCL to about 60% HPMCAS:40% PCL; between about 20% HPMCAS:80% PCL to about 40% HPMCAS:60% PCL; between about 20% HPMCAS:80% PCL to about 50% HPMCAS:50% PCL; between about 30% HPMCAS:70% PCL to about 40% HPMCAS:60% PCL; between about 30% HPMCAS:70% PCL to about 50% HPMCAS:50% PCL; or about 80% HPMCAS:20% PCL, about 70% HPMCAS:30% PCL, about 60% HPMCAS:40% PCL, about 50% HPMCAS:50% PCL, about 40% HPMCAS:60% PCL, about 30% HPMCAS:70% PCL, or about 20% HPMCAS:80% PCL. The linker can further comprise a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

The linkers are chosen to weaken sufficiently after a specified period of time in order to allow the gastric residence systems to reach a point where they de-couple and pass through the pylorus and out of the stomach after the desired residence period or weaken sufficiently such that the gastric residence system is no longer retained in the stomach; that is, the linkers weaken to the point of uncoupling (the uncoupling point) or to the point where the gastric residence system can pass through the pylorus (the pyloric passage point, or passage point). Thus, in one embodiment, linkers are used that uncouple after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In one embodiment, linkers are used that uncouple after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In one embodiment, linkers are used that uncouple after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In one embodiment, linkers are used that uncouple after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In one embodiment, linkers are used that uncouple after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In one embodiment, linkers are used that uncouple after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In one embodiment, linkers are used that uncouple after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

The de-coupling or pyloric passage point in human, dog, or pig occurs when the system passes out of the stomach, that is, when it passes through the pylorus. For the in vitro measurements in simulated gastric fluid or acidic water, the de-coupling or pyloric passage point occurs when the linker weakens to the point where it will break under the normal compressive forces of the stomach, typically about 0.1 Newton to 0.2 Newton. Linkage strength (breaking point) can be measured by any relevant test that serves to test coupling ability, that is, the force required to break the linker, such as the four-point bending flexural test (ASTM D790) described in Example 18 of WO 2017/070612, or Examples 12, 13, 15, 17, or 18 of WO 2017/100367. In one embodiment, the de-coupling or pyloric passage point is reached when the linkers uncouple at about 0.2 N of force. In another embodiment, the de-coupling or pyloric passage point is reached when the linkers uncouple at about 0.1 N of force.

The gastric residence systems can reach the pyloric passage point without any or all of the linkers actually breaking. If the linkers weaken or degrade to the point where they can no longer hold the gastric residence system in the stomach, even if one, some, or all of the linkers do not break, the gastric residence system will pass through the pylorus and into the small intestine (the pyloric passage point or passage point). In some embodiments, linkers are used that weaken to the passage point after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach: or after about two weeks in a human stomach. In some embodiments, linkers are used that weaken to the passage point after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In some embodiments, linkers are used that weaken to the passage point after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In some embodiments, linkers are used that weaken to the passage point after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In some embodiments, linkers are used that weaken to the passage point after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In some embodiments, linkers are used that weaken to the passage point after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In some embodiments, linkers are used that weaken to the passage point after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

Elastomers

Elastomers (also referred to as elastic polymers or tensile polymers) enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In one embodiment, the elastomer is a silicone elastomer. In one embodiment, the elastomer is formed from a liquid silicone rubber (LSR), such as sold in the Dow Corning QP-1 liquid silicone rubber kit. In one embodiment, the elastomer is crosslinked polycaprolactone. In one embodiment, the elastomer is an enteric polymer, such as those listed in the Enteric Polymer Table. In some embodiments, the coupling polymer(s) used in the system are also elastomers. Elastomers are preferred for use as the central polymer in the star-shaped or stellate design of the gastric residence systems.

In one embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Examples of elastomers which can be used include silicones, such as those formed using Dow Corning QP-1 kits; urethane-cross-linked polycaprolactones; poly(acryloyl 6-aminocaproic acid) (PA6ACA); poly(methacrylic acid-co-ethyl acrylate) (EUDRAGIT L, 100-55); and mixtures of poly(acryloyl 6-aminocaproic acid) (PA6ACA) and poly(methacrylic acid-co-ethyl acrylate) (EUDRAGIT L 100-55).

Flexible coupling polymers, i.e., elastomeric coupling polymers or elastomers, are used as the central polymer in the star-shaped or stellate design of the gastric residence systems. A particularly preferred elastomer for use as the central elastomer of the stellate or star configuration is silicone rubber. Liquid silicone rubber (LSR) can be molded easily and cured into a desired shape. The Dow Corning QP-1 series, comprising cross-linked dimethyl and methylvinyl siloxane copolymers and reinforcing silica, are examples of such silicone rubber polymers (see, for example, the Web site www.dowcoming.com/DataFiles/090276fe8018ed07.pdf. Non-segmented elongate members or elongate members comprising segments of carrier polymer-agent components can then be attached to the central silicone rubber elastomer. Another elastomer which can be used as the central elastomer in the stellate design is cross-linked polycaprolactone.

Specific configurations of gastric residence systems are disclosed in International Patent Application No. WO 2017/100367, and any of those configurations can be used for the gastric residence systems disclosed herein.

System Dimensions

The system must be able to adopt a compacted state with dimensions that enable the patient to swallow the system (or for the system to be introduced into the stomach by alternate means, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in the Capsule Table below (see "Draft Guidance for industry on Size, Shape, and Other Physical Attributes of Generic Tablets and Capsules" at URL www.regulations.gov/#!documentDetail; D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in the Capsule Table.

| Capsule Table | | |
|---|---|---|
| Capsule Size | Outer Diameter (mm) | Length (mm) |
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule, for example, in a manner such as that shown in FIG. 1B. Once the capsule dissolves in the stomach, the system will adopt a configuration suitable for gastric retention, for example, in a manner such as that shown in FIG. 1A. Preferred capsule sizes are 00 and 00el (a 00el-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In another embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter. For star-shaped polymers with N arms (where N is greater than or equal to three, such as N=6), the arms can have dimensions such that the system has at least two perpendicular dimensions, each of length as noted above. These two perpendicular dimensions are chosen as noted above in order to promote retention of the gastric residence system.

The system is designed to eventually break apart in the stomach at the end of the desired residence time (residence period), at which point the remaining components of the system are of dimensions that permit passage of the system through the pyloric sphincter, small intestine, and large intestine. Finally, the system is eliminated from the body by defecation, or by eventual complete dissolution of the system. In the small and large intestines. Thus, coupling polymers or disintegrating matrices are placed in the gastric residence systems of the invention in a configuration such that, at the end of the desired residence period when the coupling polymers or disintegrating matrices break or dissolve, the uncoupled components of the gastric residence system have dimensions suitable for passage through the pyloric sphincter and elimination from the digestive tract.

System Polymeric Composition

The choice of the individual polymers for the carrier polymer, coupling polymer, and elastomer influence many properties of the system, such as drug elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of drug from the carrier polymer-drug component is affected by numerous factors, including the composition and properties of the carrier polymer, which may itself be a mixture of several polymeric and non-polymeric components; the properties of the drug such as hydrophilicity/hydrophobicity, charge state, pKa, and hydrogen bonding capacity; and the properties of the gastric environment. In the aqueous environment of the stomach, avoiding burst release of a drug (where burst release refers to a high initial delivery of active pharmaceutical ingredient upon initial deployment of the system in the stomach), particularly a hydrophilic drug, and maintaining sustained release of the drug over a period of time of days to one or two weeks is challenging.

The residence time of the systems in the stomach is adjusted by the choice of coupling polymers used in the linker regions. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

Methods of Manufacture of Carrier Polymer-Agent (or Agent Salt) Components

Blending temperatures for incorporation of the agent (or a pharmaceutically acceptable salt thereof) into polymeric matrices typically range from about 80° C. to about 120° C., although higher or lower temperatures can be used for polymers which are best blended at temperatures outside that range. When agent (or salt thereof) particles of a particular size are used, and it is desired that the size of the particles be maintained during and after blending, blending can be done at temperatures below the melting point of the agent (or salt thereof), so as to maintain the desired size of the particles. Otherwise, temperatures can be used which melt both the polymer and the agent (or salt thereof). Blending temperatures should be below the degradation temperature of the agent (or salt thereof). In one embodiment, less than about 2% of the agent (or salt thereof) is degraded during manufacture. In one embodiment, less than about 1.5% of the agent (or salt thereof) is degraded during manufacture. In one embodiment, less than about 1% of the agent (or salt thereof) is degraded during manufacture. In one embodiment, less than about 0.75% of the agent (or salt thereof) is degraded during manufacture. In one embodiment, less than about 0.5% of the agent (or salt thereof) is degraded during manufacture. In one embodiment, less than about 0.4% of the agent (or salt thereof) is degraded during manufacture. In one embodiment, less than about 0.3% of the agent (or salt thereof) is degraded during manufacture. In one embodiment, less than about 0.2% of the agent (or salt thereof) is degraded during manufacture. In one embodiment, less than about 0.15% of the agent (or salt thereof) is degraded during manufacture. In one embodiment, less than about 0.1% of the agent (or salt thereof) is degraded during manufacture. In one embodiment, less than about 0.05% of the agent (or salt thereof) is degraded during manufacture. In one embodiment, less than about 0.04% of the agent (or salt thereof) is degraded during manufacture. In one embodiment, less than about 0.03% of the agent (or salt thereof) is degraded during manufacture. In one embodiment, less than about 0.02% of the agent (or salt thereof) is degraded during manufacture. In one embodiment, less than about 0.01% of the agent (or salt thereof) is degraded during manufacture.

Hot melt extrusion can be used to prepare the carrier polymer-agent (or agent salt) components. Single-screw or, preferably, twin-screw systems can be used. As noted, if it is desired that the size of the particles be maintained during and after blending, carrier polymers should be used which can be melted at temperatures which do not degrade the agent or salt thereof. Otherwise, temperatures can be used which melt both the polymer and the agent or salt thereof.

Melting and casting can also be used to prepare the carrier polymer-agent (or salt thereof) components. The carrier polymer and agent (or salt thereof), and any other desired components, are mixed together. The carrier polymer is melted and the melt is mixed so that the agent (or salt thereof) particles are evenly distributed in the melt, poured into a mold, and allowed to cool.

Solvent casting can also be used to prepare the carrier polymer-agent (or salt thereof) components. The polymer is dissolved in a solvent, and particles of agent (or salt thereof) are added. If the size of the agent (or salt thereof) particles are to be maintained, a solvent should be used which does not dissolve the agent (or salt thereof) particles, so as to avoid altering the size characteristics of the particles; otherwise, a solvent which dissolves both the polymer and agent (or salt thereof) particles can be used. The solvent-carrier polymer-agent (or salt thereof) particle mixture (or solvent-carrier particle-agent/agent salt solution), is then mixed to evenly distribute the particles (or thoroughly mix the solution), poured into a mold, and the solvent is evaporated.

Manufacture/Assembly of System: Affixing Elongate Members to Central Elastomer

For a stellate gastric residence system, such as that shown in FIG. 1A, the elongate members, or "arms" of the gastric residence system can be affixed to the central elastomer in a number of ways. The central polymer can be cast or molded with short "asterisk" arms, and a linker polymer can be used to affix the elongate members to the asterisk arms of the central elastomer. Alternatively, the central elastomer can be formed in a mold into which the proximal ends of the elongate members protrude. The elastomer sets, cures, or otherwise hardens into its desired form with a portion of the elongate members extending into the body of the central elastomer. Alternatively, the central elastomer can be prepared with cavities into which the elongate members can be firmly inserted.

The invention thus includes a method of making a gastric residence system, comprising preparing at least three elongate members formed from a material comprising any drug-carrier polymer-excipient formulation as disclosed herein; and attaching the elongate members to a central elastomer to form a gastric residence system. The elongate members can comprise at least one segment with a release rate-controlling polymer film. The elongate members of the gastric residence system project radially from the central elastomer, such as in a "hub and spoke" arrangement. A preferred number of elongate members or "arms" is six. However, stellate systems with three, four, five, seven, or eight elongate members can also be used.

In some embodiments, elongate members or "arms" comprising any carrier polymer-agent formulation, including arms comprising segments having release rate-modulating polymer films, can be heat-welded, solvent-welded, or otherwise affixed to other elements, including disintegrating matrices, coupling polymers, or interfacing polymers, which are then affixed to a central elastomer. In some embodiments, the arms are directly affixed to a central elastomer. Disintegrating matrices, coupling polymers, or interfacing polymer segments can be welded or otherwise affixed to the central elastomer prior to affixing the elongate members.

In some embodiments, arms comprising any drug-carrier polymer-excipient formulation as disclosed herein can be heat-welded to polycaprolactone segments, such as short polycaprolactone "asterisk" arms affixed to a central elastomer. Linker segments can be welded to the short "asterisk" arms prior to affixing the drug-carrier polymer-excipient formulation arms. Heat welding of drug-carrier polymer-excipient formulation arms to MW 80,000 PCL segments at temperatures between 140° C. to 170° C., followed by cooling for 24 hours at 8° C., resulted in stronger welds. Thus, in one embodiment, attaching the elongate members comprising any drug-carrier polymer-excipient formulation as disclosed herein to a central elastomer to form a gastric residence system, can comprise heat-welding the elongate members to other system components, such as asterisk arms or other segments comprising at least about 90%, at least about 95%, or at least about 99% polycaprolactone (such as MW 80,000 PCL), at a temperature between about 140° C. to about 170° C., followed by cooling of the welded members attached to other system components for about 12 to about 48 hours at a temperature of about 2° C. to about 14° C., such as about 5° C. to about 10° C., or about 8° C. The other system components can alternatively be linker elements.

Manufacture/Assembly of System

Once the elongate members of the gastric residence system have been affixed to the central elastomer, the system is ready to be folded into its compacted configuration and placed into a capsule for storage, transport, and eventual administration. The system can be folded in an automated mechanical process, or by hand, and placed into a capsule of the appropriate size and material. More detail regarding manufacture and assembly of gastric residence systems, and of packaging the gastric residence system into capsules, can be found in International Patent Application Nos. WO 2015/191920, WO 2015/191925, WO 2017/070612, WO 2017/100367, and PCT/US2017/034856.

Carrier Polymer-Agent/Release Rate-Modulating Film Combinations

A variety of carrier polymer-agent segment formulations can be used with any given release rate-modulating film to provide desired release characteristics from the film-coated segment. Likewise, a variety of release rate-modulating films can be used with any given carrier polymer-agent segment formulation. One useful combination of carrier polymer-agent/film comprises a segment with about 15% to about 40% agent, about 3% to about 15% of excipients selected from one or more of P407, silica, and vitamin E succinate, with the balance of the segment made up of polycaprolactone (PCL); and a release rate-modulating film that is about 75% to about 95% polycaprolactone with the balance of the film comprising copovidone porogen, where the weight of the film is about 0.5% to about 2% of the weight of the underlying segment, and/or where the thickness of the film ranges from about 3 microns to about 10 microns. An exemplary combination is 27.5% agents, 6% excipients (P407, silica, vitamin E succinate), and 66.5% PCL, with a film that is 90% PCL 10% copovidone porogen, where the weight of the film is about 1% of the weight of the underlying segment.

Another useful combination of carrier polymer-agent/film comprises a segment with about 30% to about 50% agent, about 10% to about 30% plasticizer, about 0% to about 10% of excipients selected from one or more of P407, silica, and vitamin E succinate, with the balance of the segment made up of polycaprolactone (PCL); and a release rate-modulating film that is about 75% to about 95% polycaprolactone with the balance of the film comprising copovidone porogen, where the weight of the film is about 0.5% to about 3% of the weight of the underlying segment, and/or where the thickness of the film ranges from about 3 microns to about 12 microns.

Methods of Treatment Using the Gastric Residence Systems

The gastric residence systems can be used to treat conditions requiring administration of a drug or agent over an extended period of time. In a preferred embodiment, a gastric residence system is administered to a human. For long-term administration of agents or drugs which are taken for months, years, or indefinitely, administration of a gastric residence system periodically, such as once weekly or once every two weeks can provide substantial advantages in patient compliance and convenience. Accordingly, the gastric residence systems of the invention can be administered once every three days, once every five days, once weekly, once every ten days, or once every two weeks. The administration frequency is timed to coincide with the designed gastric residence period of the gastric residence system which is administered, so that at about the same time that a gastric residence system passes out of the stomach after its residence period, a new gastric residence system is administered.

Once a gastric residence system has been administered to a patient, the system provides sustained release of agent or drug over the period of gastric retention. After the period of gastric retention, the system degrades and passes out of the stomach. Thus, for a system with a gastric retention period of one week, the patient will swallow (or have administered to the stomach via other methods) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the agent or drug in the system, comprises introducing a new gastric residence system every D-days into the stomach of the patient, by oral administration or other methods, over the total desired treatment period. The number of gastric residence systems administered to the patient will be (T-total) divided by (D-days). For example, if treatment of a patient for a year (T-total 365 days) is desired, and the gastric residence period of the system is 7 days (D-days=7 days), approximately 52 gastric residence systems will be administered to the patient over the 365 days, as a new system will be administered once every seven days.

Alternatively, the patient can swallow (or have administered to the stomach via other methods) a new gastric residence system at the end of the effective release period of the gastric residence system. The "effective release period" or "effective release time" is the time over which the gastric residence system releases an effective amount of the agent contained in the system. Accordingly, in one embodiment, a method of treatment of a patient with a gastric residence system of the invention having an effective release period of a number of days E (where E-days is the effective release period in days), over a total desired treatment period T-total (where T-total is the desired length of treatment in days) with the agent in the system, comprises introducing a new gastric residence system every E-days into the stomach of the patient, by oral administration or other means, over the total desired treatment period. The number of gastric residence systems administered to the patient will be (T-total) divided by (E-days). For example, if treatment of a patient for a year (T-total=365 days) is desired, and the effective release period of the system is 7 days (E-days=7 days), approximately 52 gastric residence systems will be administered to the patient over the 365 days, as a new system will be administered once every seven days.

Gastric Delivery Pharmacokinetics for Gastric Residence Systems

The gastric residence systems of the invention provide for high bioavailability of the agent as measured by $AUC_{inf}$ after administration of the systems, relative to the bioavailability of a conventional oral formulation of the agent. The systems also provide for maintenance of an approximately constant plasma level or a substantially constant plasma level of the agent.

Relative bioavailability, $F_{REL}$, of two different formulations, formulation A and formulation B, is defined as:

$$F_{REL}=100\times(AUC_A\times Dose_B)/(AUC_B\times Dose_A)$$

where $AUC_A$ is the area under the curve for formulation A, $AUC_B$ is the area under the curve for formulation B, $Dose_A$ is the dosage of formulation A used, and $Dose_B$ is the dosage of formulation B used. AUC, the area under the curve for the plot of agent plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the agent has dropped to a negligible amount.

In one embodiment, the substantially constant plasma level of agent provided by the gastric residence systems of the invention can range from at or above the trough level of the plasma level of agent when administered daily in a conventional oral formulation (that is, $C_{min}$ of agent administered daily in immediate-release formulation) to at or below the peak plasma level of agent when administered daily in a conventional oral formulation (that is, $C_{max}$ of agent administered daily in immediate-release formulation). In some embodiments, the substantially constant plasma level of agent provided by the gastric residence systems of the invention can be about 50% to about 90% of the peak plasma level of agent when administered daily in a conventional oral formulation (that is, $C_{max}$ of agent administered daily in immediate-release formulation). The substantially constant plasma level of agent provided by the gastric residence systems of the invention can be about 75% to about 125% of the average plasma level of agent when administered daily in a conventional oral formulation (that is, $C_{ave}$ of agent administered daily in immediate-release formulation). The substantially constant plasma level of agent provided by the gastric residence systems of the invention can be at or above the trough level of plasma level of agent when administered daily in a conventional oral formulation (that is, $C_{min}$ of agent administered daily in immediate-release formulation), such as about 100% to about 150% of $C_{min}$.

The gastric residence systems of the invention can provide bioavailability of agent released from the system of at least about 50%, at least about 60%, at least about 70%, or at least about 80% of that provided by an immediate release form comprising the same amount of agent. As indicated above, the bioavailability is measured by the area under the plasma concentration-time curve (AUCinf).

Dissolution Profile, Bioavailability and Pharmacokinetics for Gastric Residence Systems Dissolution: The gastric residence systems described herein provide a steady release of an agent or a pharmaceutically acceptable salt thereof over an extended period of time. The systems are designed to release a therapeutically effective amount of an agent or salt thereof over the period of residence in the stomach. The release of agent (or salt thereof) can be measured in vitro or in vivo to establish the dissolution profile (elution profile, release rate) of the agent (or salt thereof) from a given residence system. In a specific environment. The dissolution profile can be specified as a percentage of the original amount of agent (or salt thereof) present in the system which elutes from the system over a given time period.

Thus, in some embodiments, the agent (or salt thereof) contained in a gastric residence system can have a dissolution profile of 10-20% release between zero hours and 24 hours in a given environment. That is, over the 24-hour period after initial introduction of the gastric residence system into the environment of interest, 10-20% of the initial agent (or salt thereof) contained in the system elutes from the system.

The environment of interest can be 1) the stomach of a patient (that is, an in vivo environment), or 2) simulated gastric fluid (that is, an in vitro environment).

The gastric residence systems of the invention provide for high bioavailability of the agent (or salt thereof) as measured by $AUC_{inf}$ after administration of the systems, relative to the bioavailability of a conventional oral formulation of the agent (or salt thereof). The systems also provide for maintenance of a substantially constant plasma level of the agent (or salt thereof).

Parameters of interest for release include the linearity of release over the residence period of the gastric residence systems, the standard deviation of release over the residence period (which is related to linearity of release; a standard deviation of zero indicates that release is linear over the entire residence period), the release over the initial six hours of residence (that is, burst release upon initial administration), and total release of agent (or salt thereof) over the residence period. A preferable residence period is seven days, although other periods, such as two, three, four, five, six, eight, nine, ten, 11, 12, 13, or 14 days can be useful.

Linearity of agent (or salt thereof) release over the residence period refers to the amount released during each 24-hour period of residence. For a seven-day period of residence, it is desirable that about the amount of agent (or salt thereof) is released each day, i.e., that linearity of agent (or salt thereof) release is maximized. This will minimize the standard deviation of daily agent or agent salt release over the residence period. In some embodiments, the gastric release systems have a variation (or a standard deviation) for daily agent (or salt thereof) release of less than about 100%, less than about 90%, less than about 80%, less than about 70%, less than about 60%, less than about 50%, less than about 40%, less than about 30%, less than about 25%, less than about 20%, less than about 15%, less than about 10%, or less than about 5%, over the period of residence. In some embodiments, the period of residence can be about three days, about seven days, about ten days, or about two weeks.

Minimization of burst release, that is, release over the initial period of residence (such as six hours, twelve hours, or 24 hours after administration of a gastric residence system) is desirable in order to maintain a predictable and steady release profile. If T is the total agent (or salt thereof) release over the residence period units of mass), and D is the number of days of the residence period, then completely linear release would mean that about T/D mass of agent (or salt thereof) is released per day. If the period over which burst release is measured is the first six hours, then a linear release profile will result in 0.25×T/D mass of agent (or salt thereof) released during the first six hours. In percentage terms of the total amount of agent (or salt thereof) released over the residence period of D days, linear release would be about 100D % of agent (or salt thereof) per day, and a linear release over the first six hours would be 25/D %. (Note that 100% in this context indicates the total amount of agent (or salt thereof) released, regardless of how much agent (or salt thereof) is contained in the initial formulation.) Thus, for a seven day residence period, linear release over the first six hours would be about 3.6% of the total amount of agent (or salt thereof) released over the seven-day period.

In some embodiments, during the initial six hours of residence after administration the gastric residence systems release about 0.2 to about 2 times T/D of the total mass of agent (or salt thereof) T released over the residence period of D days, or about 0.2 to about 1.75 times T/D of the total mass of agent (or salt thereof) T released over the residence period of D days, or about 0.2 to about 1.5 times T/D of the total mass of agent (or salt thereof) T released over the residence period of D days, or about 0.2 to about 1.25 times T/D of the total mass of agent (or salt thereof) T released over the residence period of D days, or about 0.2 to about 1 times T/D of the total mass of agent (or salt thereof) T released over the residence period of D days, or about 0.2 to about 0.8 times T/D of the total mass of agent (or salt thereof) T released over the residence period of D days, or about 0.2 to about 0.75 times T/D, or about 0.2 to about 0.7 times T/D, or about 0.2 to about 0.6 times T/D, or about 0.2 to about 0.5 times T/D, or about 0.2 to about 0.4 times T/D, or about 0.2 to about 0.3 times T/D, or about 0.25 to about 2 times T/D, or about 0.3 to about 2 times T/D, or about 0.4 to about 2 times T/D, or about 0.5 to about 2 times T/D, or about 0.6 to about 2 times T/D, or about 0.7 to about 2 times T/D, or about 0.25 to about 1.5 times T/D, or about 0.3 to about 1.5 times T/D, or about 0.4 to about 1.5 times T/D, or about 0.5 to about 1.5 times T/D, or about 0.6 to about 1.5 times T/D, or about 0.7 to about 1.5 times T/D, or about 0.25 to about 1.25 times T/D, or about 0.3 to about 1.25 times T/D, or about 0.4 to about 1.25 times T/D, or about 0.5 to about 1.25 times T/D, or about 0.6 to about 1.25 times T/D, or about 0.7 to about 1.25 times T/D, or about 0.25 to about 1 times T/D, or about 0.3 to about 1 times T/D, or about 0.4 to about 1 times T/D, or about 0.5 to about 1 times T/D, or about 0.6 to about 1 times T/D, or about 0.7 to about 1 times T/D, or about 0.25 times T/D, or about 0.25 to about 0.8 times T/D, or about 0.3 to about 0.8 times T/D, or about 0.4 to about 0.8 times T/D, or about 0.5 to about 0.8 times or about 0.6 to about 0.8 times T/D, or about 0.7 to about 0.8 times T/D, or about 0.8 times T/D, about 1 times T/D, about 1.25 times T/D, about 1.5 times T/D, or about 2 times T/D.

In some embodiment of the gastric residence systems, during the initial six hours of residence after administration the gastric residence systems release about 2% to about 10% of the total mass of agent (or salt thereof) released over the residence period, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments of the gastric residence systems, where the gastric residence systems have a residence period of about seven days, during the initial six hours of residence after administration the gastric residence systems release about 2% to about 10% of the total mass of agent (or salt thereof) released over the residence period of seven days, or about 3% to about 10%, or about 4% to about 10%, or about 5% to about 10%, or about 6% to about 10%, or about 7% to about 10%, or about 8% to about 10%, or about 9% to about 10%, or about 2% to about 9%, or about 2% to about 8%, or about 2% to about 7%, or about 2% to about 6%, or about 2% to about 5%, or about 2% to about 4%, or about 2% to about 3%.

In some embodiments, during the initial 24 hours of residence after administration, the gastric residence systems release about 10% to about 35% of the total mass of agent (or salt thereof) released over the residence period, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

In some embodiments, where the gastric residence systems have a residence period of about seven days, during the initial 24 hours of residence after administration the gastric residence systems release about 10% to about 35% of the total mass of agent (or salt thereof) released over the residence period of seven days, or about 10% to about 30%, or about 10% to about 25%, or about 10% to about 20%, or about 10% to about 15%, or about 15% to about 35%, or about 15% to about 35%, or about 15% to about 30%, or about 20% to about 30%, or about 25% to about 35%, or about 25% to about 30%, or about 30% to about 35%.

Reduction of pH Effect on Release Rate

The gastric residence systems, and segments of gastric residence systems, as described herein which comprise release-rate modulating polymer films have reduced variability of release of an agent or pharmaceutically acceptable salt thereof at different pH values, as compared to release from gastric residence systems or segments of gastric residence systems of similar composition but which lack the release-rate modulating polymer films.

The solubility of certain agents, or salts thereof, can vary at different pH values. For example, the solubility of risperidone is significantly higher at the more acidic end of the gastric pH range (e.g., pH 1.5) than at the less acidic end of the gastric pH range (e.g., pH 4.8). Risperidone will thus have a faster dissolution rate at the lower pH, and will have a tendency to be released faster from a gastric residence system at the lower pH. Since the pH of the stomach can vary over time due to several factors, reducing the variation in release rate of a given agent or salt thereof at different pH values aids in providing a linear dissolution profile over a given period of time.

The pH-dependent release rate ratio, $RR_{pH}$, for a given agent or salt thereof at a given first pH value and a given second pH value can be expressed as:

$$RR_{pH} = \text{(rate of release at a first pH) divided by (rate of release at a second pH)}.$$

If the rates of release at the first and second pH are identical, the $RR_{pH}$ will be 1. If the rate of release at the first pH is higher than the rate of release at the second pH, the $RR_{pH}$ will be greater than 1, while if the rate of release at the first pH is lower than the rate of release at the second pH, the $RR_{pH}$ will be less than one. In order to reduce variability of release at different pH values, a value of $RR_{pH}$ as close to 1 as possible is desirable.

A pH-dependent release rate ratio factor, $RRF_{pH}$, can be defined as the factor by which the release rate at the two pH values differ. $RRF_{pH}$ is the same as $RR_{pH}$ when $RR_{pH}$ is greater than one, and is the reciprocal of $RR_{pH}$ when $RR_{pH}$ is less than one.

Release rate ratios for gastric residence systems can be measured at any two different pH values between about 1 and about 6, and generally at pH values at least about 1 pH unit apart, such as at least about 2 pH units apart, at least about 3 pH units apart, or at least about 4 pH units apart. Two useful values are a first pH of about 1.5 and a second pH of about 4.8, to represent typical low-pH and high-pH extremes of stomach pH. Release rate ratios can be measured in simulated gastric fluid adjusted to the pH of interest, such as FaSSGF, including FaSSGF at about pH 1 to pH 2, e.g. at pH 1.5. Release rate ratios can also be measured in buffer systems at the pH of interest, such as ammonium acetate (for example, at about pH 4.8). Release rate ratios can be calculated by measuring release from gastric residence systems at two different pH values over a period of time, such as about one hour, about two hours, about three hours, about six hours, about 12 hours, about 24 hours, about 48 hours, about 72 hours, about 96 hours, about 5 days, about 6 days, about 7 days, about 8 days, about 9 days, about 10 days, or about 2 weeks.

The gastric residence systems and the segments of gastric residence systems described herein, comprising a release-rate modulating film, can have a pH-dependent release rate ratio factor $RRF_{pH}$, where the first pH is 1.5 and the second pH is 4.8, or alternatively where the first pH and the second pH are both between about pH 1 and about pH 6 and are at least about 3 pH units apart, of greater than about 1, of greater than about 2, of greater than about 3, of greater than about 4, of greater than about 5, of greater than about 6, of greater than about 10, of greater than about 20, or of about 1 to about 20, of about 1 to about 10, of about 1 to about 6, of about 1 to about 4, of about 1 to about 3, of about 1 to about 2.5, about 1 to about 2.2, about 1 to about 2, about 1 to about 1.9, about 1 to about 1.8, about 1 to about 1.7, about 1 to about 1.6, about 1 to about 1.5, about 1 to about 1.4, about 1 to about 1.3, about 1 to about 1.2, about 1 to about 1.1, about 1.1 to about 2, about 1.2 to about 2, about 1.3 to about 2, about 1.4 to about 2, or about 1.5 to about 2.

The gastric residence systems and the segments of gastric residence systems described herein, comprising a release-rate modulating film, can have a pH-dependent release rate ratio $RR_{pH}$, where the first pH is about 1.5 and the second pH is about 4.8, or alternatively where the first pH and the second pH are both between about pH 1 and about pH 6 and are at least about 3 pH units apart, of about 0.05 to about 20, of about 0.1 to about 10, of about 0.2 to about 5, of about 0.25 to about 4, about 0.3 to about 3, 0.4 to about 2.5, about 0.5 to about 2, about 0.6 to about 2, about 0.7 to about 2, about 0.8 to about 2, about 0.9 to about 2, about 1 to about 20, about 1 to about 10, about 1 to about 5, about 1 to about 4, about 1 to about 3, about 1 to about 2, about 1.1 to about 2, about 1.2 to about 2, about 1.3 to about 2, about 1.4 to about 2, or about 1.5 to about 2. The gastric residence systems and the segments of gastric residence systems described herein, comprising a release-rate modulating film, can have a pH-dependent release rate ratio $RR_{pH}$, where the first pH is 1.5 and the second pH is 4.8, or alternatively where the first pH and the second pH are both between about pH 1 and about pH 6 and are at least about 3 pH units apart, of about 1 to about 2.5, about 1 to about 2.2, about 1 to about 2, about 1 to about 1.9, about 1 to about 1.8, about 1 to about 1.7, about 1 to about 1.6, about 1 to about 1.5, about 1 to about 1.4, about 1 to about 1.3, about 1 to about 1.2, or about 1 to about 1.1; or of greater than about 1, greater than about 1.5, greater than about 2, greater than about 3, greater than about 4, greater than about 5, greater than about 10, or greater than about 20. The gastric residence systems and the segments of gastric residence systems described herein, comprising a release-rate modulating film, can have a pH-dependent release rate ratio $RR_{pH}$, where the first pH is 1.5 and the second pH is 4.8, or alternatively where the first pH and the second pH are both between about pH 1 and about pH 6 and are at least about 3 pH units apart, of about 0.05 to about 1 of about 0.1 to about 1, of about 0.25 to about 1, about 0.3 to about 1, about 0.4 to about 1, about 0.5 to about 1, about 0.6 to about 1, about 0.7 to about 1, about 0.8 to about 1, or about 0.9 to about 1; or of less than about 0.9, less than about 0.8, less than about 0.7, less than about 0.6, less than about 0.5, less than about 0.4, less than about 0.3, less than about 0.2, less than about 0.1, or less than about 0.05.

pH-dependent release rate ratios of agents and pharmaceutically acceptable salts thereof from gastric residence systems tend to deviate from the ideal value of one when there is a significant difference in solubility of an agent or salt thereof at different pH values. The difference in solubility of an agent or a pharmaceutically acceptable salt thereof at two different pH values used in the gastric residence systems described herein can be about a factor of about 1.25 or more, a factor of about 1.5 or more, a factor of about 3 or more, a factor of about 4 or more, a factor of about 5 or more, a factor of about 10 or more, a factor of about 20 or more, a factor of about 30 or more, a factor of about 40 or more, a factor of about 50 or more, a factor of about 75 or more, or a factor of about 100 or more; or a factor of about 2 to about 100, about 2 to about 75, about 2 to about 50, about 2 to about 20, about 2 to about 10, about 5 to about 100, about 5 to about 75, about 5 to about 50, about 5 to about 20, or about 5 to about 10, where the two different pH values lie between about pH 1 and about pH 6, such as about pH 1.5 and about pH 4.8, or where the first pH and the second pH are at least about 3 pH units apart. Generally, the greater the difference in solubility of an agent or pharmaceutically acceptable salt thereof at two different pH values, the more useful release-rate modulating polymer films become for reducing differences in pH-dependent rates of release from gastric residence systems. For example, when the difference in solubility of an agent or a pharmaceutically acceptable salt thereof at two different pH values between about pH 1 and about pH 6 (such as about pH 1.5 and about pH 4.8) is a factor of about 5 or more, or where the difference in solubility of an agent or a pharmaceutically acceptable salt thereof at a first pH value and a second pH value where the values are at least about 3 pH units apart is a factor of about 5 or more (for example, an agent having a solubility of 12 mg/ml at pH 1.5 and a solubility of 2 mg/ml at pH 4.8 has a difference in solubility at the two different pH values of a factor of 6), release-rate modulating polymer films are very useful in reducing difference in pH-dependent rates of release from gastric residence systems. However, release-rate modulating polymer films can be used to shift the pH-dependent release rate ratio closer to one when there is any difference in solubility of an agent or a pharmaceutically acceptable salt thereof at two different pH values, and release-rate modulating polymer films can be used for the other purposes disclosed herein even if there is no significant difference in solubility of an agent at different pH values.

The release-rate modulating polymer films used for the gastric residence systems and the segments of gastric residence systems described herein, can reduce the deviation from the ideal value of 1 in the pH-dependent release rate ratio factor $RRF_{pH}$ of the gastric residence system as compared to the deviation in the same gastric residence system lacking the release-rate modulating films, by about 10%, about 25%, about 33%, about 50%, about 75%, or by a factor of about 1.25, about 1.5, about 2, or about 3. The deviation in pH-dependent release rate ratio factor $RRF_{pH}$ is defined as $(RRF_{pH}-1)$, and can also be referred to as the deviation from 1 of the pH-dependent release rate ratio factor $RRF_{pH}$. For example, if a first gastric residence system lacking a release-rate modulating polymer film has a release rate in arbitrary units of 9 at pH 1.5 and 3 at pH 4.8, its pH-dependent release rate ratio factor $RRF_{pH}$ is $(9/3)=3$, and it deviates by 2 units from the ideal value of 1 (where release rates at the two pH values are equal). If a second gastric residence system having the same components as the first gastric residence system, but also including a release-rate modulating polymer film, has a release rate in arbitrary units of 4 at pH 1.5 and 2 at pH 4.8, its pH-dependent release rate ratio factor $RRF_{pH}$ is $(4/2)=2$, which deviates by 1 unit from the ideal value of 1. Thus, the release-rate modulating polymer coating has reduced the deviation of the pH-dependent release rate ratio factor $RRF_{pH}$ from the ideal value by a factor of 2, since the deviation from the ideal value for the system lacking the film was 2 units, and the deviation from the ideal value for the system with the film was 1 unit.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days) (rounded to an integral number), for administration every D-days. Alternatively, if the total treatment time in days is (T-total), and the gastric residence systems have an effective release period of (E-days), then the kit will contain a number of gastric residence systems equal to ((T-total) divided by (E-days)) (rounded to an integral number), for administration every E-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the agent or drug contained in the gastric residence systems. For example, if the total treatment period prescribed for the patient is one year, and the gastric residence system has a residence time of one week or an effective release period of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the agent or drug contained in the gastric residence systems, are also included in the invention. The articles of manufacture may be supplied in appropriate packaging, such as dispensers, trays, or other packaging that assists the patient in administration of the gastric residence systems at the prescribed interval.

EXEMPLARY EMBODIMENTS

The invention is further described by the following embodiments. The features of each of the embodiments are combinable with any of the other embodiments where appropriate and practical.

Embodiment 1. A segment of a gastric residence system, the segment comprising: a carrier polymer; an agent or a salt thereof; and a release-rate modulating polymer film configured to control the release rate of the agent or salt thereof, wherein over a seven-day incubation of the segment in simulated gastric fluid, the amount of the agent or salt thereof released from the segment during day 5 is at least about 40% of the amount of agent or salt thereof released during day 2; and wherein at least about 7% of the total amount of agent or salt thereof in the segment is released on day 2 and at least about 7% of the total amount of agent or salt thereof is released on day 5.

Embodiment 2. A segment of a gastric residence system, the segment comprising: a carrier polymer; an agent or a salt thereof; and a release-rate modulating polymer film configured to control the release rate of the agent or salt thereof, wherein over a seven-day incubation of the segment in simulated gastric fluid, the amount of the agent or salt thereof released from the segment during day 7 is at least about 20% of the amount of agent or salt thereof released during day 1; and wherein at least about 4% of the total amount of agent or salt thereof in the segment is released on day 1 and at least about 4% of the total amount of agent or salt thereof is released on day 7.

Embodiment 3. A segment of a gastric residence system, the segment comprising: a carrier polymer, an agent or a salt thereof and a release-rate modulating polymer film configured to control the release rate of the agent or salt thereof, wherein the release-rate modulating polymer film is configured such that the release of agent or salt thereof from the segment in 40% ethanol/60% simulated gastric fluid over one hour is no more than about 40% higher compared to release of agent or salt thereof from an equivalent segment in 100% simulated gastric fluid over one hour.

Embodiment 4. A segment of a gastric residence system, the segment comprising: a carrier polymer, an agent or a salt thereof and a release-rate modulating polymer film configured to control the release rate of the agent or salt thereof, wherein the release-rate modulating polymer film is configured such that the release of agent or salt thereof from the segment in 40% ethanol/60% simulated gastric fluid over one hour is at least about 40% lower than the release of agent or salt thereof from a second segment in 40% ethanol/60%, simulated gastric fluid over one hour, the second segment comprising the same combination of carrier polymer and agent or salt thereof but lacking the release-rate modulating polymer film.

Embodiment 5. A segment of a gastric residence system, the segment comprising: a carrier polymer, an agent or a salt thereof and a release-rate modulating polymer film configured to control the release rate of the agent or salt thereof, wherein the release-rate modulating polymer film is configured such that the release of agent or salt thereof from the segment in simulated gastric fluid over an initial 6 hour period is at least about 40% lower than the release of agent or salt thereof from a second segment in simulated gastric fluid over an initial 6 hour period, the second segment comprising the same combination of carrier polymer and agent or salt thereof but lacking the release-rate modulating polymer film; and wherein the release of agent or salt thereof from the segment in simulated gastric fluid over a seven-day period is at least about 60% of the total amount of agent or salt thereof originally present in the segment.

Embodiment 6. The segment of embodiment 5, wherein the release of agent or salt thereof from the segment in simulated gastric fluid over a seven-day period is at least about 70% of the release of the total amount of agent or salt thereof originally present in the segment.

Embodiment 7. The segment of embodiment 5, wherein the release of agent or salt thereof from the segment in simulated gastric fluid over a seven-day period is at least about 80% of the release of the total amount of agent or salt thereof originally present in the segment.

Embodiment 8. A segment of a gastric residence system, the segment comprising: a carrier polymer; an agent or a salt thereof and a release-rate modulating, polymer film, wherein the polymer film is configured to control the release rate of the agent or salt thereof such that a best-fit linear regression model of the release rate of agent or salt thereof from the segment in simulated gastric fluid has a coefficient of determination $R^2$ of at least about 0.8 over an initial period of seven days; and wherein the segment releases about 40% to about 60% of the agent or salt thereof within a time of about 40% to about 60% of the seven-day period.

Embodiment 9. The segment of embodiment 8, wherein the polymer film is configured to control the release rate of the agent or salt thereof such that a best-fit linear regression model of the release rate of agent or salt thereof from the segment in simulated gastric fluid has a coefficient of determination $R^2$ of at least about 0.9 over an initial period of seven days; and wherein the segment releases about 40% to about 60% of the agent or salt thereof within a time of about 40% to about 60% of the seven-day period.

Embodiment 10. A segment of a gastric residence system, the segment comprising: a earlier polymer; an agent or a salt thereof; and a release-rate modulating polymer film, wherein the polymer film is configured to control the release rate of the agent or salt thereof from the segment over a seven-day period in simulated gastric fluid such that the release rate from the segment over any one of the seven days varies by no more than about 25% from the average daily total release from the segment over the seven days.

Embodiment 11. The segment of a gastric residence system according to any one of embodiments 1-10, wherein the release-rate modulating polymer film comprises one or more polyester materials.

Embodiment 12. The segment of embodiment 11, wherein the polymer film comprises polyester with a repeating unit of the form:

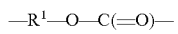

wherein $R^1$ is selected from the group consisting of $C_1$-$C_{12}$ alkylene groups, ethers containing between two and twelve carbon atoms, and polyethers containing between three and twelve carbon atoms.

Embodiment 13. The segment of embodiment 11, wherein the polymer film comprises polycaprolactone or polydioxanone.

Embodiment 14. The segment of embodiment 11, wherein the polymer comprises polycaprolactone, of about 10,000 to about 150,000 Mn.

Embodiment 15. The segment of embodiment 11, wherein the polymer film comprises polycaprolactone of about 80,000 Mn to about 110,000 Mn.

Embodiment 16. The segment of embodiment 11, wherein the polymer film comprises polycaprolactone of about 90,000 Mn.

Embodiment 17. The segment of embodiment 11, wherein the polymer film comprises polycaprolactone having intrinsic viscosity of about 1.5 dL/g to about 2.1 dL/g.

Embodiment 18. The segment of any one of embodiments 1-17, wherein polymer film further comprises a porogen.

Embodiment 19. The segment of any one of embodiments 1-17, wherein the porogen comprises a water-soluble polymer, a water-soluble small molecule, an inorganic salt, or an organic salt.

Embodiment 20. The segment of any one of embodiments 1-17, wherein the porogen comprises about 1% to about 30% by weight of the film.

Embodiment 21. The segment of any one of embodiments 1-17, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, dials and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose Kolliphor RH40 polyvinyl caprolactam, polyvinyl acetate (PVAc), polyethylene glycol (PEG) Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 22. The segment of any one of embodiments 1-17, wherein the porogen is selected from the group consisting of povidone, copovidone, and polyoxyl castor oil.

Embodiment 23. A segment of a gastric residence system, the segment comprising: a carrier polymer; an agent or a salt thereof; a release-rate modulating polymer film, wherein the polymer film comprises one or more polyester materials.

Embodiment 24. The segment of embodiment 23, wherein the polymer film comprises polyester with a repeating unit of the form:

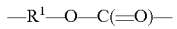

wherein $R^1$ is selected from the group consisting of $C_1$-$C_{12}$ alkylene groups, ethers containing between two and twelve carbon atoms, and polyethers containing between three and twelve carbon atoms.

Embodiment 25. The segment of embodiment 23, wherein the polymer film comprises polycaprolactone or polydioxanone.

Embodiment 26. The segment of embodiment 23, wherein the polymer film comprises polycaprolactone of about 10,000 to about 150,000 Mn.

Embodiment 27. The segment of embodiment 23, wherein the polymer film comprises polycaprolactone of about 80,000 Mn to about 110,000 Mn.

Embodiment 28. The segment of embodiment 23, wherein the polymer film comprises polycaprolactone of about 90,000 Mn.

Embodiment 29. The segment of embodiment 23, wherein the polymer film comprises polycaprolactone having intrinsic viscosity of about 1.5 dL/g to about 2.1 dL/g.

Embodiment 30. A segment of a gastric residence system, the segment comprising: a carrier polymer; an agent or a salt thereof; a release-rate modulating polymer film, wherein the polymer film comprises a material selected from the group consisting of polycaprolactone, cellulose acetate, and ethyl cellulose.

Embodiment 31. A segment of a gastric residence system, the segment comprising: a carrier polymer; an agent or a salt thereof; and a release-rate modulating polymer film, wherein the polymer film comprises about 0.1% to about 10% of the total weight of the segment.

Embodiment 32. The segment of embodiment 31, wherein the polymer film comprises about 0.1% to about 5% of the total weight of the segment.

Embodiment 33. The segment of embodiment 31, wherein the polymer film comprises about 0.5% to about 5% of the total weight of the segment.

Embodiment 34. The segment of embodiment 31, wherein the polymer comprises about 0.5% to about 2% of the total weight of the segment.

Embodiment 35. The segment of embodiment 31, wherein the polymer film comprises about 1% to about 2% of the total weight of the segment.

Embodiment 36. A segment of a gastric residence system, the segment comprising: a carrier polymer; an agent or a salt thereof; and a release-rate modulating polymer film, wherein the polymer film has a thickness between about 1 micron and about 20 microns.

Embodiment 37. The segment of embodiment 36, wherein the polymer has a thickness between about 5 microns and about 15 microns.

Embodiment 38. The segment of any one of embodiments 31-37, wherein the polymer film comprises polyester with a repeating unit of the form:

wherein $R^1$ is selected from the group consisting of $C_1$-$C_{12}$ alkylene groups, ethers containing between two and twelve carbon atoms, and polyethers containing between three and twelve carbon atoms.

Embodiment 39. The segment of any one of embodiments 31-37, wherein the polymer film comprises polycaprolactone or polydioxanone.

Embodiment 40. The segment of any one of embodiments 31-37, wherein the polymer film comprises polycaprolactone of about 10,000 to about 150,000 Mn.

Embodiment 41. The segment of any one of embodiments 31-37, wherein the polymer film comprises polycaprolactone of about 80,000 Mn to about 110,000 Mn.

Embodiment 42. The segment of any one of embodiments 31-37, wherein the polymer film comprises polycaprolactone of about 90,000 Mn.

Embodiment 43. The segment of any one of embodiments 31-37, wherein the polymer film comprises polycaprolactone having intrinsic viscosity of about 1.5 dL/g to about 2.1 dL/g.

Embodiment 44. A segment of a gastric residence system, the segment comprising: a carrier polymer; an agent or a salt thereof; and a release-rate modulating polymer film, wherein the polymer film further comprises a porogen.

Embodiment 45. The segment of embodiment 44, wherein the porogen comprises a water-soluble polymer, a water-soluble small molecule, an inorganic salt, or an organic salt.

Embodiment 46. The segment of embodiment 44 or embodiment 45, wherein the porogen comprises about 1% to about 30% by weight of the film.

Embodiment 47. The segment of any one of embodiments 44-46, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG) Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 48. The segment of any one of embodiments 44-46, wherein the porogen is selected from the group consisting of povidone, copovidone, and polyoxyl castor oil.

Embodiment 49. The segment of any one of embodiments 44-48, wherein the polymer film further comprises a plasticizer.

Embodiment 50. The segment of embodiment 49, wherein the plasticizer comprises about 1% to 40% by weight of the film.

Embodiment 51. The segment of embodiment 49 or embodiment 50, wherein the plasticizer is selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, and poloxamer.

Embodiment 52. The segment of embodiment 49 or embodiment 50, wherein the plasticizer is selected from the group consisting of triethyl citrate and triacetin.

Embodiment 53. The segment of any one of embodiments 44-52, wherein the polymer film comprises polyester with a repeating unit of the form:

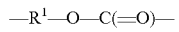

wherein $R^1$ is selected from the group consisting of $C_1$-$C_{12}$ alkylene groups, ethers containing between two and twelve carbon atoms, and polyethers containing between three and twelve carbon atoms.

Embodiment 54. The segment of any one of embodiments 44-52, wherein the polymer film comprises polycaprolactone or polydioxanone.

Embodiment 55. The segment of any one of embodiments 44-52, wherein the polymer film comprises polycaprolactone of about 10,000 to about 150,000 Mn.

Embodiment 56. The segment of any one of embodiments 44-52, wherein the polymer film comprises polycaprolactone of about 80,000 Mn to about 110,000 Mn.

Embodiment 57. The segment of any one of embodiments 44-52, wherein the polymer film comprises polycaprolactone of about 90,000 Mn.

Embodiment 58. The segment of any one of embodiments 44-52, wherein the polymer film comprises polycaprolactone having intrinsic viscosity of about 1.5 dL/g to about 2.1 dL/g.

Embodiment 59. A segment of a gastric residence system, the segment comprising: a carrier polymer; an agent or a salt thereof; and a release-rate modulating polymer film, wherein the polymer film further comprises a permeable component which is permeable to the agent or salt thereof and permeable to water.

Embodiment 60. The segment of embodiment 59, wherein the permeable component is a polymer or a swellable material.

Embodiment 61. The segment of embodiment 59 or embodiment 60, wherein the permeable component comprises about 1% to about 30% by weight of the film.

Embodiment 62. The segment of any one of embodiments 59-61, wherein the permeable component is selected from the group consisting of SSG, crospovidone, croscarmellose, and Carbopol (PAA).

Embodiment 63. The segment of any one of embodiments 59-62, wherein the polymer film further comprises a plasticizer.

Embodiment 64. The segment of embodiment 63, wherein the plasticizer comprises about 1% to 40% by weight of the film.

Embodiment 65. The segment of embodiment 63 or embodiment 64, wherein the plasticizer is selected from the group consisting of phthalates, phosphates, citrates, tartrates, adipates, sebacates, sulfonamides, succinates, glycolates, glycerolates, benzoates, myristates, halogenated phenyls, triacetin, triethyl citrate, PEG, poloxamer, tributyl citrate, and dibutyl sebacate.

Embodiment 66. The segment of embodiment 63 or embodiment 64, wherein the plasticizer is selected from the group consisting of triethyl citrate and triacetin.

Embodiment 67. The segment of any one of embodiments 59-66, wherein the polymer film comprises polyester with a repeating unit of the form:

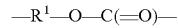

wherein $R^1$ is selected from the group consisting of $C_1$-$C_{12}$ alkylene groups, ethers containing between two and twelve carbon atoms, and polyethers containing between three and twelve carbon atoms.

Embodiment 68. The segment of any one of embodiments 59-66, wherein the polymer film comprises polycaprolactone or polydioxanone.

Embodiment 69. The segment of any one of embodiments 59-66, wherein the polymer film comprises polycaprolactone of about 10,000 to about 150,000 Mn.

Embodiment 70. The segment of any one of embodiments 59-66, wherein the polymer film comprises polycaprolactone of about 80,000 Mn to about 110,000 Mn.

Embodiment 71. The segment of any one of embodiments 59-66, wherein the polymer film comprises polycaprolactone of about 90,000 Mn.

Embodiment 72. The segment of any one of embodiments 59-66, wherein the polymer film comprises polycaprolactone having intrinsic viscosity of about 1.5 dL/g to about 2.1 dL/g.

Embodiment 73. A gastric residence system for administration to a patient, comprising: an elastomer component, and at least three elongate members attached to the elastomer component, wherein each elongate member comprises a proximal end, a distal end, and an outer surface therebetween, the proximal end of each elongate member is attached to the elastomer component and projects radially from the elastomer component, each elongate member has its distal end not attached to the elastomer component and located at a larger radial distance from the elastomer component than the proximal end; wherein at least one elongate member comprises a segment of any one of embodiments 1-72.

Embodiment 74. A gastric residence system for administration to a patient, comprising at least one segment of any one of embodiments 1-72.

Embodiment 75. A method of making a segment of a gastric residence system comprising: coating a segment comprising a carrier polymer and an agent or a salt thereof with a solution of a polymer film formulation to produce a film-coated segment; and drying the film-coated segment.

Embodiment 76. The method of embodiment 75, wherein the coating is performed by dip coating.

Embodiment 77. The method of embodiment 75, wherein the coating is performed by pan coating.

Embodiment 78. The method of embodiment 75, wherein the coating is performed by spray coating.

Embodiment 79. The method of embodiment 75, wherein the coating is performed by fluidized bed coating.

Embodiment 80. The method of any one of embodiments 75-79, wherein the solvent used in the solution of polymer film formulation comprises an organic solvent.

Embodiment 81. The method of embodiment 80, wherein the solvent used in the polymer film formulation comprises ethyl acetate, dichloromethane, acetone, isopropyl alcohol, or any combination thereof.

Embodiment 82. A method of making a segment of a gastric residence system comprising: co-extruding a polymer film and a mixture of a carrier polymer and an agent or a salt thereof.

Embodiment 83. The method of any one of embodiments 75-82, wherein the polymer film formulation comprises polyester with a repeating unit of the form:

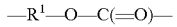

wherein $R^1$ is selected from the group consisting of $C_1$-$C_{12}$ alkylene groups, ethers containing between two and twelve carbon atoms, and polyethers containing between three and twelve carbon atoms.

Embodiment 84. The method of any one of embodiments 75-82, wherein the polymer film formulation comprises polycaprolactone or polydioxanone.

Embodiment 85. The method of any one of embodiments 75-82, wherein the polymer film formulation comprises polycaprolactone of about 10,000 to about 150,000 Mn.

Embodiment 86. The method of any one of embodiments 75-82, wherein the polymer film formulation comprises polycaprolactone of about 80,000 Mn to about 110,000 Mn.

Embodiment 87. The method of any one of embodiments 75-82, wherein the polymer film formulation comprises polycaprolactone of about 90,000 Mn.

Embodiment 88. The method of any one of embodiments 75-82, wherein the polymer film formulation comprises polycaprolactone having intrinsic viscosity of about 1.5 dL/g to about 2.1 dL/g.

Embodiment 89. The method of any one of embodiments 75-88, wherein polymer film further comprises a porogen.

Embodiment 90. The method of any one of embodiments 75-88, wherein the porogen comprises a water-soluble polymer, a water-soluble small molecule, an inorganic salt, or an organic salt.

Embodiment 91. The method of any one of embodiments 75-88, wherein the porogen comprises about 1% to about 30% by weight of the film.

Embodiment 92. The method of any one of embodiments 75-88, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 93. The method of any one of embodiments 75-88, wherein the porogen is selected from the group consisting of povidone, copovidone, and polyoxyl castor oil.

Embodiment 94. The gastric residence system of embodiment 73, wherein the central elastomer is formed from liquid silicone rubber.

Embodiment 95. The gastric residence system of embodiment 73 or embodiment 94, wherein the elongate members are attached to the central elastomer via a disintegrating matrix.

Embodiment 96. The gastric residence system of embodiment 95, wherein the disintegrating matrix comprises HPMC-AS and polycaprolactone.

Embodiment 97. A method of administering a gastric residence system to a patient, comprising: administering a container containing a gastric residence system of any one of embodiments 73, 74, or 94-96 in a compacted state to a patient, wherein the container enters the stomach of the patient and dissolves after entry into the stomach, releasing the gastric residence system which then adopts its uncompacted state.

Embodiment 98. The method of embodiment 97, wherein the patient is a human.

Embodiment 99. The method of embodiment 97 or 98, wherein the container containing the gastric residence system is administered by swallowing, by feeding tube, or by gastrostomy tube.

Embodiment 100. The segment of any one of embodiments 1-72, the gastric residence system of any one of embodiments 73, 74, 94, 95, or 96, or the method of any one of embodiments 75-93 or 97-99, wherein the agent or salt thereof is not an adamantane-class drug or salt of an adamantane-class drug.

Embodiment 101. A gastric residence system comprising a therapeutically effective amount of an agent or a pharmaceutically acceptable salt thereof, wherein: the gastric residence system has a compacted configuration and an uncompacted configuration.

the gastric residence system comprises a plurality of elongate members affixed to a central elastomer, wherein at least one elongate member comprises: a carrier polymer, the agent or the pharmaceutically acceptable salt thereof, and a release-rate modulating polymer film coated on the surface of the at least one elongate member; wherein the gastric residence system is configured to release the agent or the pharmaceutically acceptable salt thereof over a specified gastric residence period.

Embodiment 102. The gastric residence system of embodiment 101, wherein the agent is not an adamantane-class agent or pharmaceutically acceptable salt of an adamantane-class agent.

Embodiment 103. The gastric residence system of embodiment 101 or embodiment 102, wherein the elongate members are affixed to the central elastomer via linkers, wherein the linkers are configured to weaken or degrade to allow passage of the gastric residence system through the pylorus after the specified gastric residence period.

Embodiment 104. The gastric residence system of embodiment 101 or embodiment 102, wherein at least one elongate member comprises at least two segments joined by linkers, wherein the linkers are configured to weaken or degrade to allow passage of the gastric residence system through the pylorus after the specified gastric residence period.

Embodiment 105. The gastric residence system according to any one of embodiments 101-104, wherein the release-rate modulating polymer film comprises one or more polyester materials.

Embodiment 106. The gastric residence system of embodiment 105, wherein the polymer film comprises polyester with a repeating unit of the form:

wherein $R^1$ is selected from the group consisting of $C_1$-$C_{12}$ alkylene groups, ethers containing between two and twelve carbon atoms, and polyethers containing between three and twelve carbon atoms.

Embodiment 107. The gastric residence system of embodiment 106, wherein the polymer film comprises polycaprolactone or polydioxanone.

Embodiment 108. The gastric residence system of embodiment 107, wherein the polymer film comprises polycaprolactone of about 10,000 to about 150,000 Mn.

Embodiment 109. The gastric residence system of embodiment 107, wherein the polymer film comprises polycaprolactone of about 80,000 Mn to about 110,000 Mn.

Embodiment 110. The gastric residence system of embodiment 107, wherein the polymer film comprises polycaprolactone of about 90,000 Mn.

Embodiment 111. The gastric residence system of embodiment 107, wherein the polymer film comprises polycaprolactone having intrinsic viscosity of about 1.5 dL/g to about 2.1 dL/g.

Embodiment 112. The gastric residence system of any one of embodiments 101-111, wherein the polymer film further comprises a porogen.

Embodiment 113. The gastric residence system of embodiment 112, wherein the porogen comprises a water-soluble polymer, a water-soluble small molecule, an inorganic salt, or an organic salt.

Embodiment 114. The gastric residence system of embodiment 112 or embodiment 113, wherein the porogen comprises about 5% to about 30% by weight of the film.

Embodiment 115. The gastric residence system of any one of embodiments 112-114, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, such as sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, diols and polyols, polyhydric alcohols, poly(alkylene glycols), polyglycols, alkylene glycols, poly(a,m)alkylenediol esters, alkylene glycols, poly vinylalcohol, poly vinyl pyrrolidone, water soluble polymeric materials, Poloxamer, hypromellose (HPMC), Kolliphor RH40, polyvinyl caprolactam, polyvinyl acetate (PVAc), polyethylene glycol (PEG), Soluplus (copolymer of polyvinyl caprolactam, polyvinyl acetate, and polyethylene glycol), copovidone, Eudragits (E, RS, RL), poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid (carbopol), crosslinked PVP (crospovidone), crosslinked cellulose (croscarmellose), calcium silicate, xanthan gum, and gellan gum.

Embodiment 116. The gastric residence system of any one of embodiments 112-114, wherein the porogen is selected from the group consisting of povidone, copovidone, and polyoxyl castor oil.

Embodiment 117. The gastric residence system of any one of embodiments 101-116, wherein the polymer film further comprises a plasticizer.

Embodiment 118. The gastric residence system of embodiment 117, wherein the plasticizer comprises triethyl citrate, triacetin, PEG, poloxamer, tributyl citrate, or dibutyl sebacate.

Embodiment 119. The gastric residence system of embodiment 117 or embodiment 118, wherein the plasticizer comprises about 5% to about 30% by weight of the film.

Embodiment 120. The gastric residence system of any one of embodiments 101-119, wherein the polymer film further comprises an anti-tack agent.

Embodiment 121. The gastric residence system of embodiment 120, wherein the anti-tack agent is selected from the group consisting of magnesium stearate, talc, and glycerol monostearate.

Embodiment 122. The gastric residence system of any one of embodiments 101-121, wherein the carrier polymer comprises a polylactone.

Embodiment 123. The gastric residence system of embodiment 122, wherein the polylactone comprises polycaprolactone.

Embodiment 124. The gastric residence system of embodiment 123, wherein the polycaprolactone has an average $M_n$ of about 60,000 to about 100,000.

Embodiment 125. The gastric residence system of embodiment 123, wherein the polycaprolactone has an average $M_n$ of about 75,000 to about 85,000.

Embodiment 126. The gastric residence system of embodiment 123, wherein the polycaprolactone has an average $M_n$ of about 80,000.

Embodiment 127. The gastric residence system of any one of embodiments 101-126, wherein the elongate members further comprise at least one excipient.

Embodiment 128. The gastric residence system of embodiment 127, wherein the at least one excipient comprises a polyalkylene glycol.

Embodiment 129. The gastric residence system of embodiment 128, wherein the polyalkylene glycol is selected from the group consisting of polyethylene glycol (PEG), polypropylene glycol (PPG), and a block copolymer of PEG and PPG.

Embodiment 130. The gastric residence system of embodiment 128, wherein the polyalkylene glycol comprises a block copolymer of PEG and PPG.

Embodiment 131. The gastric residence system of embodiment 130, wherein the block copolymer of PEG and PPG comprises H—$(OCH_2CH_2)_x$—$(O$—$CH(CH_3)CH_2)_y$—$(OCH_2CH_2)_z$—OH, where x and z are about 101 and y is about 56.

Embodiment 132. The gastric residence system of any one of embodiments 101-131, wherein the elongate members further comprise an anti-oxidant.

Embodiment 133. The gastric residence system of any one of embodiments 101-132, wherein the elongate members further comprise silica.

Embodiment 134. The gastric residence system of any one of embodiments 101-133, wherein the central elastomer comprises silicone rubber. Embodiment 135. The gastric residence system of any one of embodiments 101-134, wherein the plurality of elongate members comprises at least three elongate members.

Embodiment 136. The gastric residence system of any one of embodiments 101-134, wherein the plurality of elongate members is six elongate members.

Embodiment 137. The gastric residence system of any one of embodiments 101-136, wherein the system has a gastric residence period of about four days to about eight days when administered to a human patient.

Embodiment 138. The gastric residence system of any one of embodiments 101-136, wherein the system has a gastric residence period of about seven days to about ten days when administered to a human patient.

Embodiment 139. The gastric residence system of any one of embodiments 101-138, wherein the system is configured to have a dissolution profile characterized by about 10% to 20% dissolution of the initial amount of the agent or pharmaceutically acceptable salt thereof present in the system during an initial 24 hour period in an aqueous environment.

Embodiment 140. The gastric residence system of any one of embodiments 101-138, wherein the system is configured to have a dissolution profile characterized by about 20% to 40% dissolution of the initial amount of the agent or pharmaceutically acceptable salt thereof present in the system during an initial 48 hour period in an aqueous environment.

Embodiment 141. The gastric residence system of embodiment 139 or embodiment 140, wherein the aqueous environment is the stomach of a mammal.

Embodiment 142. The gastric residence system of embodiment 139 or embodiment 140, wherein the aqueous environment is the stomach of a human patient.

Embodiment 143. The gastric residence system of embodiment 139 or embodiment 140, wherein the aqueous environment is simulated gastric fluid, fasted state simulated gastric fluid, or fed state simulated gastric fluid.

Embodiment 144. The gastric residence system of any one of embodiments 101-143, wherein the system comprises between about 10 mg to about 400 mg of agent or pharmaceutically acceptable salt thereof.

Embodiment 145. A gastric residence system comprising: a carrier polymer;
an agent or a salt thereof; and a release-rate modulating polymer film configured to control the release rate of the agent or salt thereof; wherein over a seven-day incubation of the system in simulated gastric fluid, the amount of the agent or salt thereof released from the system during day 5 is at least about 40% of the amount of agent or salt thereof released during day 2; and wherein at least about 7% of the total amount of agent or salt thereof in the system is released on day 2 and at least about 7% of the total amount of agent or salt thereof is released on day 5.

Embodiment 146. A gastric residence system comprising: a carrier polymer; an agent or a salt thereof; and a release-rate modulating polymer film configured to control the release rate of the agent or salt thereof, wherein over a seven-day incubation of the system in simulated gastric fluid, the amount of the agent or salt thereof released from the system during day 7 is at least about 20% of the amount of agent or salt thereof released during day 1; and wherein at least about 4% of the total amount of agent or salt thereof in the system is released on day 1 and at least about 4% of the total amount of agent or salt thereof is released on day 7.

Embodiment 147. A gastric residence system comprising: a carrier polymer, an agent or a salt thereof; and a release-rate modulating polymer film configured to control the release rate of the agent or salt thereof; wherein the release-rate modulating polymer film is configured such that the release of agent or salt thereof from the system in 40% ethanol/60% simulated gastric fluid over one hour is no more than about 40% higher compared to release of agent or salt thereof from an equivalent system in 100% simulated gastric fluid over one hour.

Embodiment 148. A gastric residence system comprising: a carrier polymer; an agent or a salt thereof; and a release-rate modulating polymer film configured to control the release rate of the agent or salt thereof, wherein the release-rate modulating polymer film is configured such that the release of agent or salt thereof from the system in 40% ethanol/60% simulated gastric fluid over one hour is at least about 40% lower than the release of agent or salt thereof from a second system in 40% ethanol/60% simulated gastric fluid over one hour, the second system comprising the same combination of carrier polymer and agent or salt thereof but lacking the release-rate modulating polymer film.

Embodiment 149. A gastric residence system comprising: a carrier polymer; an agent or a salt thereof; and a release-rate modulating polymer film configured to control the release rate of the agent or salt thereof, wherein the release-rate modulating polymer film is configured such that the release of agent or salt thereof from the system in simulated gastric fluid over an initial 6 hour period is at least about 40% lower than the release of agent or salt thereof from a second system in simulated gastric fluid over an initial 6 hour period, the second system comprising the same combination of carrier polymer and agent or salt thereof but lacking the release-rate modulating polymer film; and wherein the release of agent or salt thereof from the system in simulated gastric fluid over a seven-day period is at least about 60% of the total amount of agent or salt thereof originally present in the system.

Embodiment 150. The gastric residence system of embodiment 149, wherein the release of agent or salt thereof from the system in simulated gastric fluid over a seven-day period is at least about 70% of the release of the total amount of agent or salt thereof originally present in the system.

Embodiment 151. The gastric residence system of embodiment 149, wherein the release of agent or salt thereof from the system in simulated gastric fluid over a seven-day period is at least about 80% of the release of the total amount of agent or salt thereof originally present in the system.

Embodiment 152. A gastric residence system comprising: a carrier polymer; an agent or a salt thereof; and a release-rate modulating polymer film, wherein the polymer film is configured to control the release rate of the agent or salt thereof such that a best-fit linear regression model of the release rate of agent or salt thereof from the system in simulated gastric fluid has a coefficient of determination $R^2$ of at least about 0.8 over an initial period of seven days; and wherein the system releases about 40% to about 60% of the agent or salt thereof within a time of about 40% to about 60% of the seven-day period.

Embodiment 153. A gastric residence system providing an extended release agent dosage form, comprising: a plurality of elongate members comprising a therapeutically effective amount of an agent or a pharmaceutically acceptable salt thereof and a carrier polymer, wherein the agent or pharmaceutically acceptable salt thereof is blended with the carrier polymer such that the agent or salt thereof is distributed throughout the elongate member, and a release-rate modulating polymer film coating at least one elongate member; wherein the plurality of elongate members are attached to a central elastomer; and wherein said gastric residence system provides extended release of the agent or pharmaceutically acceptable salt thereof.

Embodiment 154. The gastric residence system of embodiment 153, wherein the elongate members further comprise one or more additional component selected from the group consisting of an excipient and an anti-oxidant, wherein the one or more additional component is blended together with the agent or pharmaceutically acceptable salt thereof and the carrier polymer, such that the agent or salt thereof and one or more additional components are distributed throughout the elongate member.

Embodiment 155. The gastric residence system of embodiment 153 or embodiment 154, wherein the carrier polymer is blended with the agent or pharmaceutically acceptable salt thereof and the one or more additional component if present, by melting and mixing together the carrier polymer, the agent or pharmaceutically acceptable salt thereof, and the one or more additional component if present.

Embodiment 156. The gastric residence system of any one of embodiments 153-155, wherein the elongate members are attached to the central elastomer via linkers, wherein the linkers are configured to weaken or degrade to allow passage of the gastric residence system through the pylorus after the specified gastric residence period.

Embodiment 157. The gastric residence system of any one of embodiments 153-155, wherein at least one elongate member comprises at least two segments joined by linkers, wherein the linkers are configured to weaken or degrade to allow passage of the gastric residence system through the pylorus after the specified gastric residence period.

Embodiment 158. The gastric residence system of embodiment 156, wherein the release-rate modulating polymer film is coated onto the elongate member by coating the elongate member with a solution of a polymer film formulation to produce a film-coated elongate member; and drying the film-coated elongate member.

Embodiment 159. The gastric residence system of embodiment 157, wherein the release-rate modulating polymer film is coated onto the segments by coating the segments with a solution of a polymer film formulation to produce a film-coated segment; and drying the film-coated segment.

Embodiment 160. The gastric residence system of embodiment 158 or embodiment 159, wherein the coating is performed by dip coating.

Embodiment 161. The gastric residence system of embodiment 158 or embodiment 159, wherein the coating is performed by pan coating.

Embodiment 162. The gastric residence system of embodiment 158 or embodiment 159, wherein the coating is performed by spray coating.

Embodiment 163. The gastric residence system of embodiment 158 or embodiment 159, wherein the coating is performed by fluidized bed coating.

Embodiment 164. The gastric residence system of any one of embodiments 158-163, wherein the solvent used in the solution of polymer film formulation comprises an organic solvent.

Embodiment 165. The gastric residence system of embodiment 164, wherein the solvent used in the polymer film formulation comprises ethyl acetate, dichloromethane, acetone, isopropyl alcohol, or any combination thereof.

Embodiment 166. A segment of a gastric residence system coated with a release-rate modulating polymer film or an elongate member of a gastric residence system coated with a release-rate modulating polymer film, prepared by co-extruding a polymer film and a mixture of a carrier polymer and an agent or a pharmaceutically acceptable salt thereof to form the segment or elongate member.

Embodiment 167. A method of making a segment of a gastric residence system coated with a release-rate modulating polymer film or an elongate member of a gastric residence system coated with a release-rate modulating polymer film, comprising: co-extruding a polymer film and a mixture of a carrier polymer and an agent or a pharmaceutically acceptable salt thereof to form the segment or elongate member.

Embodiment 168. A method of making a gastric residence system, comprising: blending an agent comprising an agent or a pharmaceutically acceptable salt thereof with a carrier polymer to form a carrier polymer-agent blend or a carrier polymer-agent salt blend, such that the agent or salt thereof is distributed throughout the carrier polymer-agent blend or the carrier polymer-agent salt blend; forming a plurality of elongate members from the carrier polymer-agent blend or the carrier polymer-agent salt blend, wherein the agent or salt thereof is distributed throughout the elongate member; coating the plurality of elongate members with a release-rate modulating polymer film; and attaching the plurality of elongate members to a central elastomer.

Embodiment 169. The method of embodiment 168, wherein at least one elongate member comprises at least two segments joined by linkers, wherein the linkers are configured such that they no longer join the at least two segments of each elongate member after the specified gastric residence period.

Embodiment 170. A method of making a gastric residence system, comprising: blending an agent comprising an agent or a pharmaceutically acceptable salt thereof with a carrier polymer to form a carrier polymer-agent blend or a carrier polymer-agent salt blend, such that the agent or salt thereof is distributed throughout the carrier polymer-agent blend or the carrier polymer-agent salt blend; forming a plurality of segments from the carrier polymer-agent blend or the carrier polymer-agent salt blend, wherein the agent or salt thereof is distributed throughout the segments; coating the segments with a release-rate modulating polymer film; forming a plurality of elongate members by joining at least two segments together via a linker to make the elongate members; and attaching the plurality of elongate members to a central elastomer.

Embodiment 171. The method of any one of embodiments 168-170, further comprising blending one or more additional component selected from the group consisting of an excipient and an anti-oxidant with the agent or pharmaceutically acceptable salt thereof and the carrier polymer, such that the agent or salt thereof and one or more additional components are distributed throughout the carrier polymer-agent blend or the carrier polymer-agent salt blend.

Embodiment 172. The method of any one of embodiments 168-171, wherein the blending of the agent or pharmaceutically acceptable salt thereof and the one or more additional components if present, comprises melting and mixing together the carrier polymer, the agent or pharmaceutically acceptable salt thereof, and the one or more additional component if present.

Embodiment 173. The method of any one of embodiments 168-172, wherein the elongate members are attached to the central elastomer via linkers, wherein the linkers are configured such that they no longer join the elongate members to the central elastomer after a specified gastric residence period.

Embodiment 174. The method of any one of embodiments 168-173, wherein the coating of the release-rate modulating polymer film onto the elongate members or the segments comprises: coating the elongate members or segments with a solution of a polymer film formulation to produce a film-coated elongate member or a film-coated segment; and drying the film-coated elongate member or film-coated segment.

Embodiment 175. The method of any one of embodiments 168-174, wherein the coating comprises dip coating.

Embodiment 176. The method of any one of embodiments 168-174, wherein the coating comprises pan coating.

Embodiment 177. The method of any one of embodiments 168-174, wherein the coating comprises spray coating.

Embodiment 178. The method of any one of embodiments 168-174, wherein the coating comprises fluidized bed coating.

Embodiment 179. The method of any one of embodiments 174-178, wherein the solvent used in the solution of polymer film formulation comprises an organic solvent.

Embodiment 180. The method of embodiment 179, wherein the solvent used in the polymer film formulation comprises ethyl acetate, dichloromethane, acetone, isopropyl alcohol, or any combination thereof.

Embodiment 181. A gastric residence system, made by any of the methods of embodiments 168-180.

Embodiment 182. A method of making a segment of a gastric residence system coated with a release-rate modulating polymer film or an elongate member of a gastric residence system coated with a release-rate modulating polymer film, comprising: co-extruding a polymer film and a mixture of a carrier polymer and an agent or a pharmaceutically acceptable salt thereof to form the segment or elongate member.

Embodiment 183. A gastric residence system providing an extended release agent dosage form, comprising a therapeutically effective amount of an agent or a pharmaceutically acceptable salt thereof and a release rate-modulating polymer film adapted to provide extended release of the agent or salt thereof in an aqueous environment, wherein the system has a dissolution profile characterized by about 10% to 20% dissolution of the initial amount of agent present in the system during an initial 24 hour period in the aqueous environment.

Embodiment 184. The gastric residence system of embodiment 183, wherein the system has a dissolution profile characterized by about 20% to 40% dissolution of the initial amount of agent present in the system during an initial 48 hour period in the aqueous environment.

Embodiment 185. The gastric residence system of embodiment 183 or embodiment 184, wherein the aqueous environment is the stomach of a human patient.

Embodiment 186. The gastric residence system of embodiment 183 or embodiment 184, wherein the aqueous environment is simulated gastric fluid.

Embodiment 187. The gastric residence system of any one of embodiments 183-186, wherein the system has a gastric residence period of at least about four days when administered to a human patient.

Embodiment 188. The gastric residence system of embodiment 187, wherein the system has a gastric residence period of at about seven days.

Embodiment 189. The gastric residence system of any one of embodiments 183-188, wherein the agent or pharmaceutically acceptable salt thereof is blended with the component adapted to provide extended release of the agent or salt thereof.

Embodiment 190. The gastric residence system of embodiment 189, wherein the gastric residence system further comprises a carrier polymer and at least one excipient, and the agent or a pharmaceutically acceptable salt thereof and the at least one excipient are dispersed within the carrier polymer.

Embodiment 191. A segment of a gastric residence system, the segment comprising: a carrier polymer; an agent or a salt thereof; and a release-rate modulating polymer film configured to control the release rate of the agent or salt thereof, wherein over a seven-day incubation of the segment in simulated gastric fluid, the amount of the agent or salt thereof released from the segment during day 5 is at least about 40% of the amount of agent or salt thereof released during day 2; and wherein at least about 7% of the total amount of agent or salt thereof in the segment is released on day 2 and at least about 7% of the total amount of agent or salt thereof is released on day 5.

Embodiment 192. A gastric residence system providing an extended release agent dosage form, comprising: a plurality of elongate members, wherein at least one elongate member comprises a therapeutically effective amount of an agent or a pharmaceutically acceptable salt thereof and a carrier polymer, and wherein the agent or pharmaceutically acceptable salt thereof is blended with the carrier polymer such that the agent or salt thereof is distributed throughout the at least one elongate member; wherein the agent or pharmaceutically acceptable salt thereof comprises about 40% to about 60% by weight of the at least one elongate member; wherein the plurality of elongate members are attached to a central elastomer; and wherein said gastric residence system provides extended release of the agent or pharmaceutically acceptable salt thereof.

Embodiment 193. A gastric residence system providing an extended release agent dosage form, comprising: a plurality of elongate members, wherein at least one elongate member comprises a therapeutically effective amount of an agent or a pharmaceutically acceptable salt thereof and a carrier polymer, wherein the agent or pharmaceutically acceptable salt thereof is blended with the carrier polymer such that the agent or salt thereof is distributed throughout the at least one elongate member, and a release-rate modulating polymer film coating the at least one elongate member; wherein the agent or pharmaceutically acceptable salt thereof comprises about 40% to about 60% by weight of the at least one elongate member; wherein the plurality of elongate members are attached to a central elastomer; and wherein said gastric residence system provides extended release of the agent or pharmaceutically acceptable salt thereof.

Embodiment 194. The gastric residence system of any one of embodiments 101-144, 152-165, 181, 183-190, 192 or 193, or the segment of embodiment 166 or embodiment 191, wherein the agent or pharmaceutically acceptable salt thereof comprises about 40% to about 60% by weight of the at least one elongate member of embodiments 101-144, 152-165, 181, 183-190, 192 or 193 or about 40% to about 60% by weight of the segment of embodiment 166 or embodiment 191, excluding the weight of any elastomer or linker attached to the at least one elongate member or the segment.

Embodiment 195. The gastric residence system of any one of embodiments 101-144, 152-165, 181, 183-190, 192 or 193, or the segment of embodiment 166 or embodiment 191, wherein the agent or pharmaceutically acceptable salt thereof comprises about 51% to about 60% by weight of the at least one elongate member of embodiments 101-144, 152-165, 181, 183-190, 192 or 193 or about 51% to about 60% by weight of the segment of embodiment 166 or embodiment 191.

Embodiment 196. The gastric residence system of any one of embodiments 145-152, wherein the agent or pharmaceutically acceptable salt thereof is present in an amount by weight of between about 67% and about 150% of the weight of the carrier polymer.

Embodiment 197. The gastric residence system of any one of embodiments 73, 74, 94, 95, 96, 101-165, 181, 183-190, 192 or 193, or the segment of any one of embodiments 1-72, 166, or 191, or the method of any one of embodiments 75-93, 97-99, 167-180, or 182, wherein the agent or pharmaceutically acceptable salt thereof comprises donepezil or a salt thereof.

Embodiment 198. The gastric residence system of any one of embodiments 73, 74, 94, 95, 96, 101-165, 181, 183-190, 192 or 193, or the segment of any one of embodiments 1-72, 166, or 191, or the method of any one of embodiments 75-93, 97-99, 167-180, or 182, wherein the agent or pharmaceutically acceptable salt thereof comprises doxycycline or a salt thereof.

Embodiment 199. The gastric residence system of any one of embodiments 73, 74, 94, 95, 96, 101-165, 181, 183-190, 192 or 193, or the segment of any one of embodiments 1-72, 166, or 191, or the method of any one of embodiments 75-93, 97-99, 167-180, or 182, wherein the agent or pharmaceutically acceptable salt thereof comprises between about 10% to about 40% by weight of the elongate members or segment.

Embodiment 200. The gastric residence system of any one of embodiments 73, 74, 94, 95, 96, 101-165, 181, 183-190, 192 or 193, or the segment of any one of embodiments 1-72, 166, or 191, or the method of any one of embodiments 75-93, 97-99, 167-180, or 182, wherein the agent or pharmaceutically acceptable salt thereof comprises between about 40% to about 60% by weight of the elongate members or segment.

EXAMPLES

The invention is further illustrated by the following non-limiting examples.

Example 1

Drug Release from Monolithic Matrix Formulations Slows Over Time

Figure 2A:
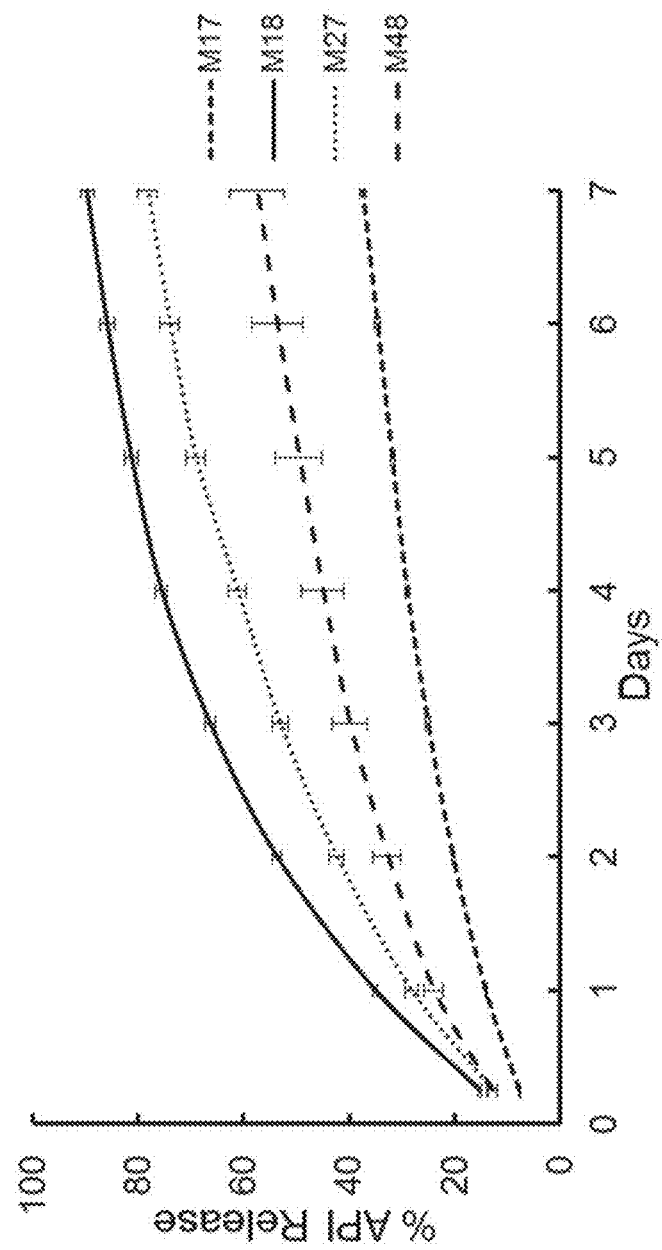
FIG. 2A depicts tapering release profiles for representative formulations of memantine hydrochloride over time.
Figure 2B:
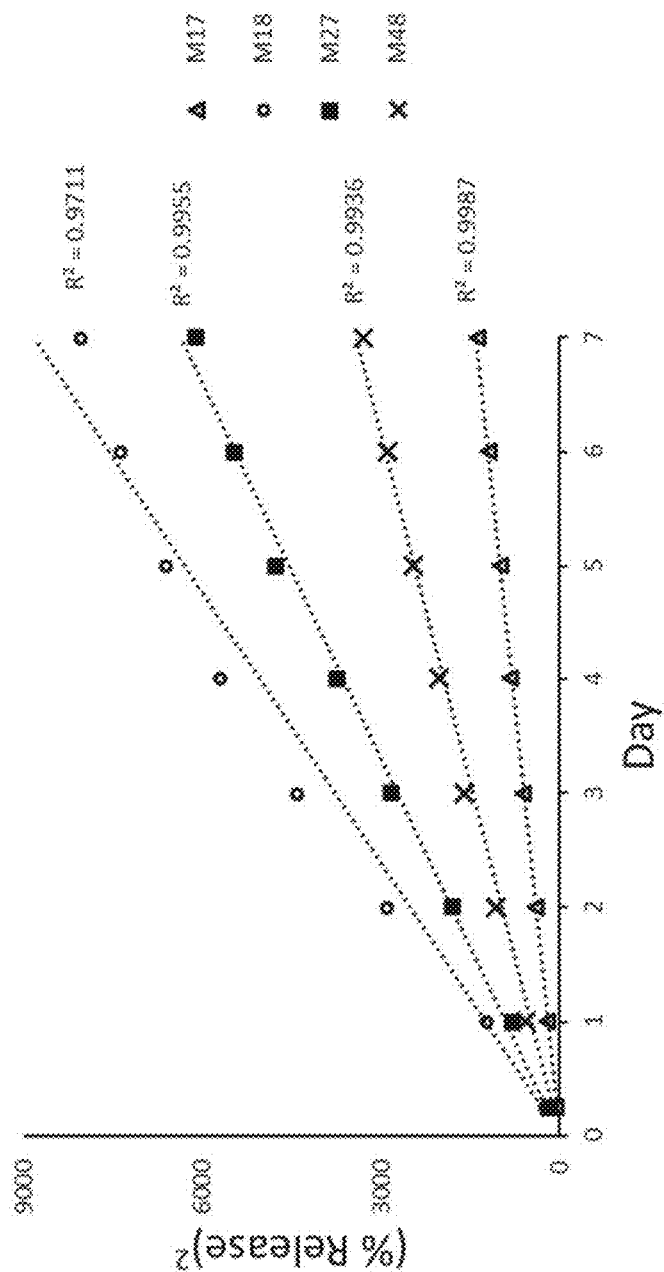
FIG. 2B depicts the linear relationship between the square of cumulative release and time for representative monolithic matrix based formulations, which is consistent with the Higuchi model for matrix-based drug release.
Figure 2C:
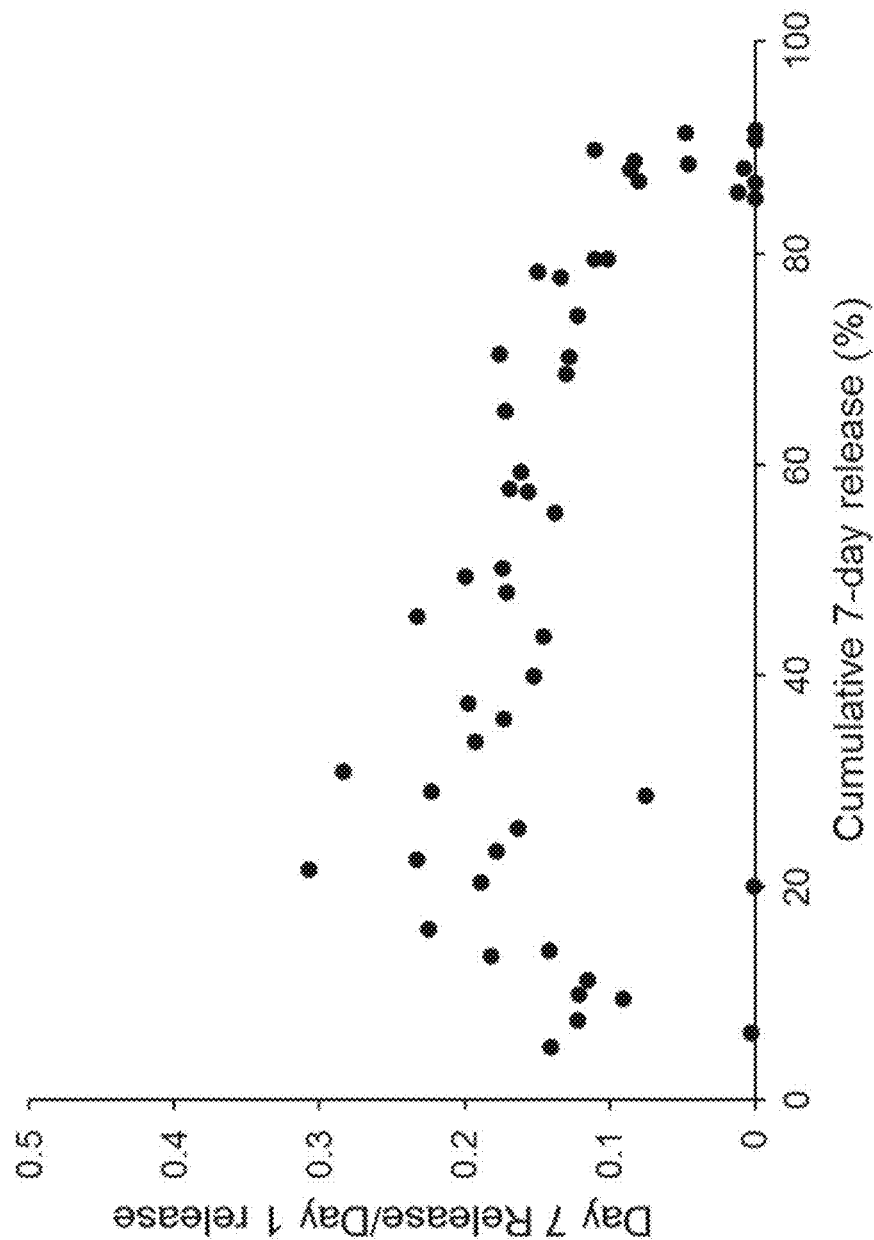
FIG. 2C depicts linearity versus extent of release for about 50 formulations of memantine hydrochloride studied.

Monolithic polymer matrix formulations were tested for their drug release rate over time. As can be seen from FIG. 2A, representative monolithic polymer matrix formulations of memantine hydrochloride showed tapering release rates over time (see Table 1 below). All formulations contained 0.5% w/w silica, 0.5% w/w alpha tocopherol, drug content and excipients listed below, and the balance 80 k polycaprolactone (PCL). M17: 20% w/w memantine, 7% Eudragit E, 2% P407; M18: 20% w/w memantine, 25% Eudragit RS, 5% P407; M27: 20% w/w memantine, 10% Eudragit RS, 5% P407; M48: 35% w/w memantine, 2% Poloxamer P188. This slowing over time drug release manner for monolithic polymer matrix formulations is consistent with the Higuchi model for matrix-based drug release. In the Higuchi model, cumulative release is proportional to the square root of time and the proportionality constant depends on the properties of the matrix (porosity, tortuosity) and drug solubility (Dash et al, Acta Poloniae Pharmaceutica—Drug Research, Vol. 67 No. 3 pp. 217n223, 2010). A linear relationship between time and the square of cumulative release was observed for a wide range of drug-polymer blends studied, with representatives shown in FIG. 2B. While drug release from the matrix could be accelerated or decelerated by varying the properties of the polymer matrix, in each case the release rate slowed significantly over time. In the monolithic matrix systems studied, the dose of drug delivered on day 1 was typically four- to six-fold greater than the dose delivered on day 7. While this tapering dose profile may be acceptable for certain applications, a more linear release profile is desired for many indications. The linearity versus extent of release for about 50 formulations of memantine hydrochloride studied is shown in FIG. 2C. Total release over 7 days (X-value in Table 1) is plotted versus the ratio of (Day 7 Release/Day 1 Release) (Y-value in Table 1) in FIG. 2C. Formulations closer to the upper right corner of the plot (where good total release and good linearity of release occur) are preferable. As can be seen from FIG. 2C, drug release on day 7 was typically 10-30% of release on day 1. Linearity of release, as measured by the ratio of release on day 7 to release on day 1, correlated negatively with total release at 7 days. Thus, in developing matrix-based systems, achieving complete release in a 7-day treatment time requires sacrificing linearity of release, which is consistent with the Higuchi model.

Example 2A

Dip Coated Polycaprolactone Provides Superior Ethanol Resistance

Cellulose acetate (CA), ethyl cellulose (EC), copolymers of acrylate and methacrylate esters (e.g., Eudragit RS) and polycaprolactone (PCL) were tested as release rate-modulating polymer films.

Formulation Preparation

Memantine hydrochloride was blended with PCL and other excipients on a Haake MiniCTW micro-compounder. The components were batch mixed at 100-120° C. for 10 min and then extruded into 2-mm cylinders. The molten extrudate was pressed into a compression mold in the shape of a 20-mm rod of triangular cross section and allowed to cool at room temperature.

Representative formulations are listed in Table 1.

TABLE 1

Representative formulations of memantine.

| Formulation Code | Memantine (% ww) | 80K PCL (% ww) | Excipient (% ww) | Y-value | X-value |
|---|---|---|---|---|---|
| M1 | 20 | 70 | 9% EPO, 0.5% Silica, 0.5% α-tocopherol | 0.16 | 59.35 |
| M2 | 20 | 70 | 9% P407, 0.5% Silica, 0.5% α-tocopherol | 0.18 | 23.36 |

TABLE 1-continued

Representative formulations of memantine.

| Formulation Code | Memantine (% ww) | 80K PCL (% ww) | Excipient (% ww) | Y-value | X-value |
|---|---|---|---|---|---|
| M3 | 20 | 70 | 4.5% EPO, 4.5% P407, 0.5% Silica, 0.5% α-tocopherol | 0.16 | 25.48 |
| M4 | 20 | 70 | 9% Poly Vinyl Acetate, 0.5% Silica, 0.5% α-tocopherol | 0.14 | 4.87 |
| M5 | 20 | 70 | 9% PVP, 0.5% Silica, 0.5% α-tocopherol | 0.18 | 13.47 |
| M6 | 20 | 70 | 9% Kollidon VA64, 0.5% Silica, 0.5% α-tocopherol | 0.08 | 28.63 |
| M7 | 20 | 74 | 5% Kolliphor RH40, 0.5% Silica, 0.5% α-tocopherol | 0.09 | 9.41 |
| M16 | 20 | 70 | 9% EPO, 0.5% Silica, 0.5% α-tocopherol | 0.19 | 33.77 |
| M17 | 20 | 70 | 7% EPO, 2% P407, 0.5% Silica, 0.5% α-tocopherol | 0.20 | 37.33 |
| M18 | 20 | 49 | 25% Eudragit RS, 5% P407, 0.5% Silica, 0.5% α-tocopherol | 0.11 | 89.73 |
| M19 | 20 | 74 | 5% SIF, 0.5% Silica, 0.5% α-tocopherol | 0.12 | 9.81 |
| M20 | 20 | 70 | 9% SIF, 0.5% Silica, 0.5% α-tocopherol | 0.22 | 28.97 |
| M21 | 20 | 49 | 25% Eudragit RL, 5% P407, 0.5% Silica, 0.5% α-tocopherol | 0.00 | 91.57 |
| M22 | 20 | 49 | 30% PDO, 0.5% Silica, 0.5% α-tocopherol | 0.00 | 20.04 |
| M23 | 20 | 70 | 9% EPO, 0.5% Silica, 0.5% α-tocopherol | 0.17 | 50.17 |
| M24 | 20 | 57 | 20% Eudragit RS, 2% P407, 0.5% Silica, 0.5% α-tocopherol | 0.17 | 57.73 |
| M25 | 20 | 59.2 | 19.8% Eudragit RS, 0.5% Silica, 0.5% α-tocopherol | 0.31 | 21.61 |
| M26 | 20 | 56.5 | 17.5% Eudragit RS, 5% P407, 0.5% Silica, 0.5% α-tocopherol | 0.18 | 70.45 |
| M27 | 20 | 64 | 10% Eudragit RS, 5% P407, 0.5% Silica, 0.5% α-tocopherol | 0.15 | 78.20 |
| M28 | 20 | 64 | 14.78% Eudragit RS, 0.226% P407, 0.5% Silica, 0.5% α-tocopherol | 0.22 | 16.08 |
| M29 | 20 | 54 | 25% Eudragit RS, 0.5% Silica, 0.5% α-tocopherol | 0.28 | 30.93 |
| M30 | 20 | 55.25 | 21.25% Eudragit RS, 2.5% P407, 0.5% Silica, 0.5% α-tocopherol | 0.23 | 45.59 |
| M31 | 20 | 49 | 25% Eudragit RS, 5% P407, 0.5% Silica, 0.5% α-tocopherol | 0.10 | 79.42 |
| M32 | 14.37 | 56.63 | 39.5% PEG-PCL, 0.36% Silica, 0.36% α-tocopherol | 0.00 | 6.27 |
| M33 | 20 | 62.5 | 10% Eudragit RS, 5% P407, 2% Silica, 0.5% α-tocopherol | 0.13 | 68.62 |
| M34 | 20 | 65 | 10% Eudragit RS, 2.5% P407, 2% Silica, 0.5% α-tocopherol | 0.23 | 22.65 |
| M35 | 20 | 69 | 3.5% Eudragit RS, 5% P407, 2% Silica, 0.5% α-tocopherol | 0.17 | 35.89 |
| M36 | 20 | 71.5 | 3.5% Eudragit RS, 2.5% P407, 2% Silica, 0.5% α-tocopherol | 0.12 | 11.14 |
| M37 | 22.5 | 64.5 | 6.75% Eudragit RS, 3.75% P407, 2% Silica, 0.5% α-tocopherol | 0.20 | 49.37 |
| M38 | 25 | 57.5 | 10% Eudragit RS, 5% P407, 2% Silica, 0.5% α-tocopherol | 0.12 | 74.11 |
| M39 | 25 | 64 | 3.5% Eudragit RS, 5% P407, 2% Silica, 0.5% α-tocopherol | 0.13 | 77.66 |
| M40 | 25 | 66.5 | 3.5% Eudragit RS, 2.5% P407, 2% Silica, 0.5% α-tocopherol | 0.19 | 20.43 |
| M41 | 20 | 64 | 10% Eudragit RS, 5% P407, 0.5% Silica, 0.5% α-tocopherol | 0.17 | 65.14 |
| M42 | 35 | 64 | 0.5% Silica, 0.5% α-tocopherol | 0.12 | 7.40 |
| M43 | 35 | 62 | 2% P407, 0.5% Silica, 0.5% α-tocopherol | 0.17 | 47.96 |
| M44 | 35 | 62 | 0.5% Silica, 2% P407, 0.5% α-tocopherol | 0.13 | 70.22 |
| M45 | 35 | 62 | 0.5% Silica, 2% P407, 0.5% α-tocopherol | 0.15 | 39.91 |
| M46 | 35 | 62 | 0.5% Silica, 2% P407, 0.5% α-tocopherol | 0.14 | 55.38 |
| M47 | 35 | 62 | 0.5% Silica, 2% P407, 0.5% α-tocopherol | 0.15 | 43.59 |
| M48 | 35 | 62 | 0.5% Silica, 2% P407, 0.5% α-tocopherol | 0.16 | 57.47 |
| M49 | 35 | 59 | 0.5% Silica, 3% Eudragit RS, 2% P407, 0.5% α-tocopherol | 0.08 | 86.84 |
| M50 | 35 | 60 | 0.5% Silica, 2% P188, 2% P407, 0.5% α-tocopherol | 0.09 | 87.84 |
| M51 | 40 | 57 | 0.5% Silica, 2% P407, 0.5% α-tocopherol | 0.05 | 91.39 |
| M52 | 40 | 59 | 0.5% Silica, 0.5% α-tocopherol | 0.14 | 14.08 |
| M53 | 45 | 52 | 0.5% Silica, 2% P407, 0.5% α-tocopherol | 0.00 | 86.72 |
| M54 | 45 | 54 | 0.5% Silica, 0.5% α-tocopherol | 0.11 | 79.42 |
| M55 | 50 | 47 | 0.5% Silica, 2% P407, 0.5% α-tocopherol | 0.00 | 85.24 |
| M56 | 50 | 49 | 0.5% Silica, 0.5% α-tocopherol | 0.00 | 90.63 |
| M57 | 20 | 62 | 12% Eudragit RL, 5% Kolliphor P407, 0.5% Silica, 0.5% α-tocopherol | 0.01 | 85.77 |
| M58 | 20 | 62 | 6% Eudragit RL, 6% Eudragit RS, 5% Kolliphor P407, 0.5% Silica, 0.5% α-tocopherol | 0.05 | 88.40 |
| M59 | 20 | 62 | 9% Eudragit RL, 3% Eudragit RS, 5% Kolliphor P407, 0.5% Silica, 0.5% α-tocopherol | 0.01 | 87.95 |
| M60 | 20 | 62 | 3% Eudragit RL, 9% Eudragit RS, 5% Kolliphor P407, 0.5% Silica, 0.5% α-tocopherol | 0.08 | 88.63 |
| M62 | 20 | 68 | 6% Eudragit RL, 5% Kolliphor P407, 0.5% Silica, 0.5% α-tocopherol | 0.00 | 86.67 |
| M77 | 27.5 | 66.5 | 5% Kolliphor P407, 0.5% Silica, 0.5% α-tocopherol | 1.42 | 91.30 |
| M104 | 40 | 58 | 1% Kolliphor P407, 0.5% Silica, 0.5% α-tocopherol | 0.01 | 103.8 |
| M107 | 45 | 52 | 2% Kolliphor P407, 0.5% Silica, 0.5% α-tocopherol | 0.00 | 94.8 |

Dip Coating

Coating solutions were prepared by dissolving coating components into appropriate organic solvents. Compositions of coating solutions used in ethanol release studies are shown in FIG. 3A. Drug arms were gripped with forceps, completely submerged in the coating solution, and immediately removed. Coated arms were dried in a fume hood overnight.

In Vitro Release

Fasted state simulated gastric fluid (FaSSGF) was prepared per the manufacturer's instructions (www.biorelevant.com). Individual coated drug arms were incubated in 10 mL release media in a shaking incubator at 37° C. for 7 days. Drug content in the release media was typically analyzed after 6 hours, 24 hours, and then daily for up to 7 days by HPLC. At each time point, the entire volume of release media was replaced with fresh media. For ethanol release studies, drug arm were incubated in 40% ethanol in FaSSGF for the first hour of the study. After one hour, the release media was sampled for analysis and the ethanolic release media was replaced with FaSSGF for the remainder of the 7-day study.

Coating Stability to Ethanol

Drug arms were prepared as above and contained 20% w/w memantine hydrochloride, 0.5% silica, 0.5% alpha tocopherol, 25% Eudragit RS, 5% P407, and balance 80 k PCL. Arms were coated by dip coating using the coating solutions described in FIG. 3A. Memantine release from coated drug arms was evaluated over 7 days in FaSSGF as well as 1 hour in 40% ethanol in FaSSGF followed by the remainder of the 7 days in FaSSGF. During the 1 hour in 40% ethanol, drug content was analyzed at 15-minute intervals. Results are shown in FIGS. 3B-3E.

Figure 3B:
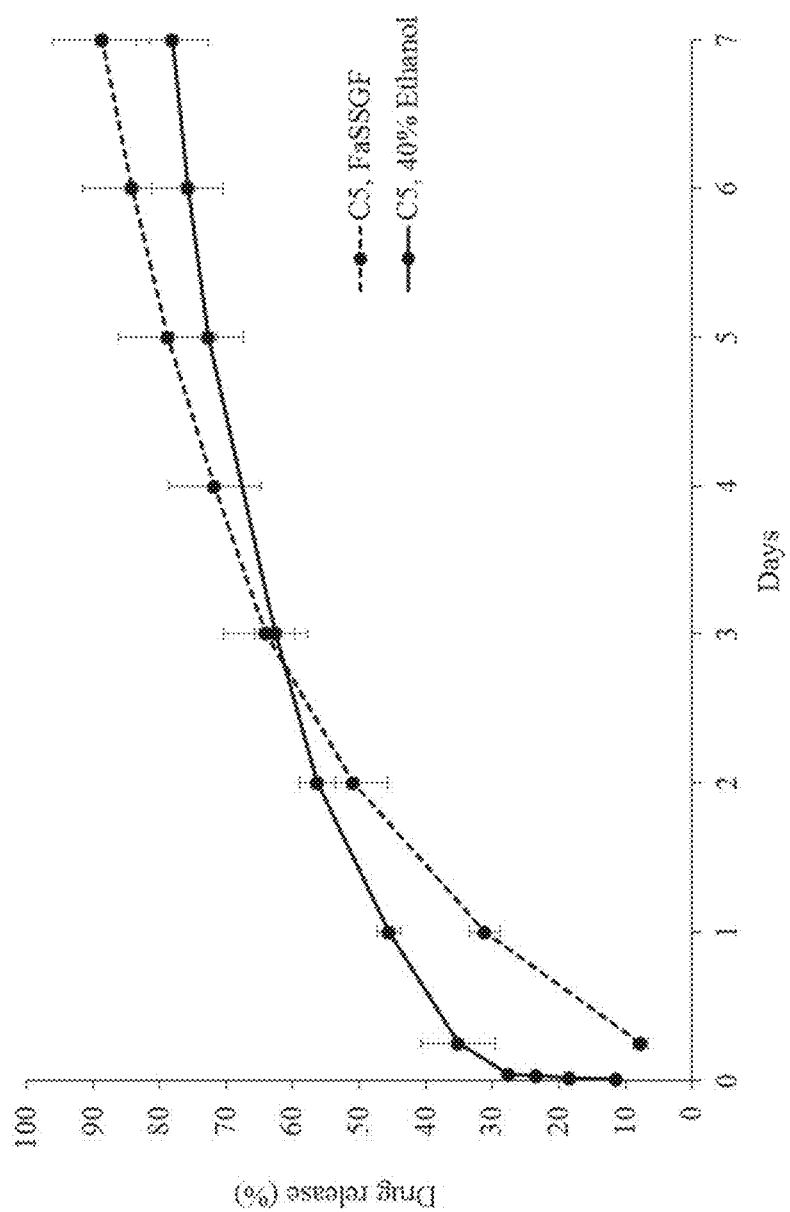
FIGS. 3B, 3C, 3D, and 3E depict drug release profiles for coating C5 (1 g Eudragit RS in 3 mL dichloromethane) on M18 release (FIG. 3B), coating C8 (1 g 55K PCL in 6 mL dichloromethane) on M18 release (FIG. 3C), coating C25 (1 g ethyl cellulose in 15 mL acetone) on M18 release (FIG. 3D), and coating C31 (1.5 g cellulose acetate in 15 mL acetone) on M18 release (FIG. 3E) in FaSSGF for 7 days and in 40% ethanol, 60% FaSSGF for one hour followed by the remainder of the 7 days in FaSSGF.
Figure 3C:
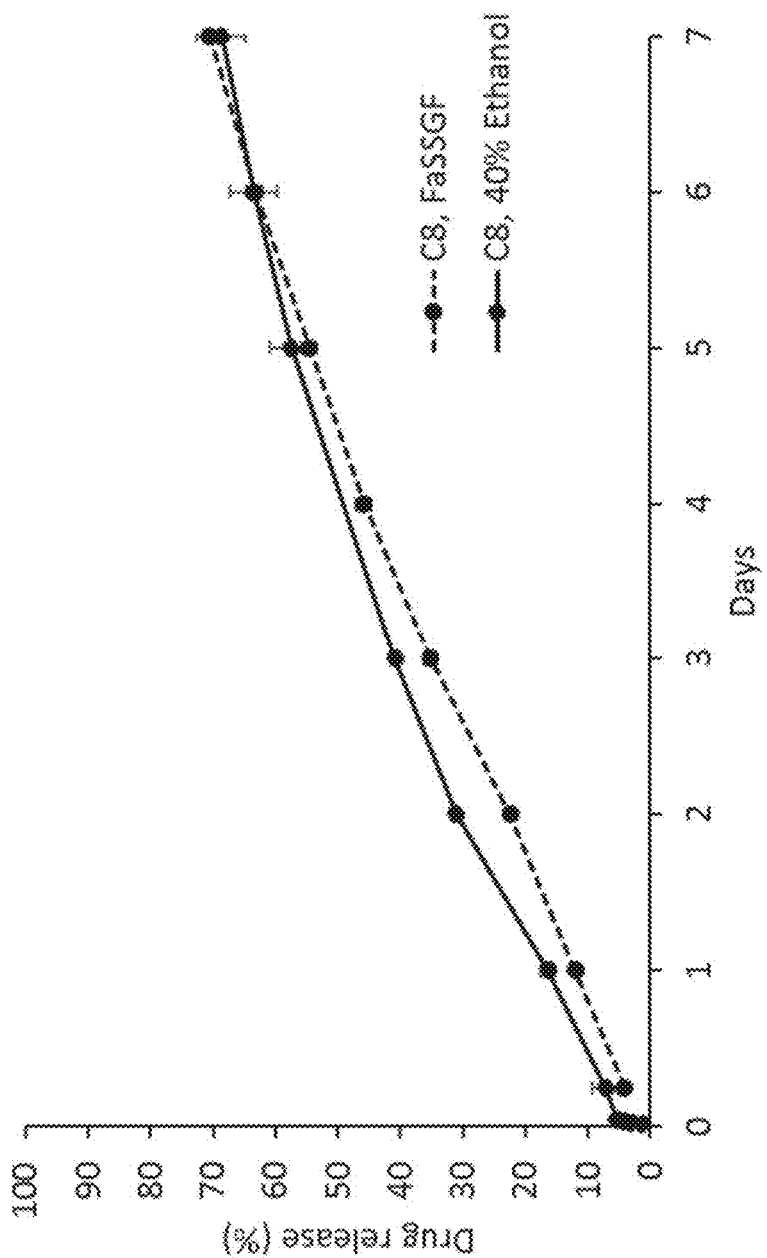
Figure 3D:
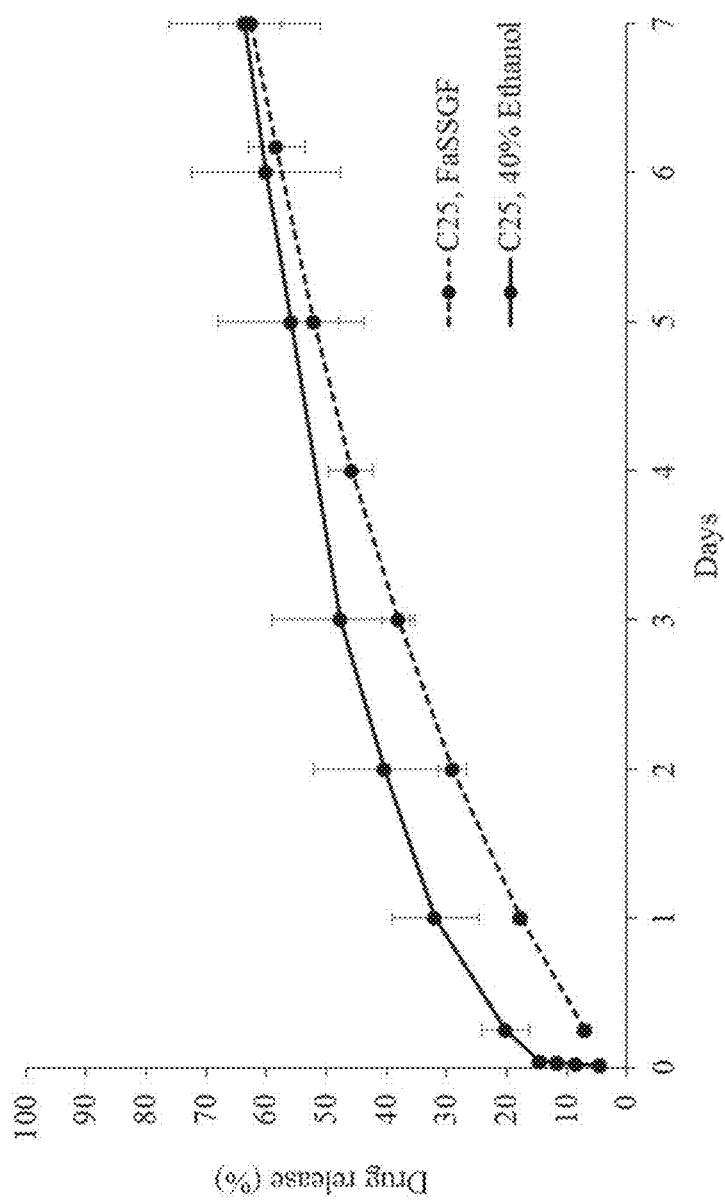
Figure 3E:
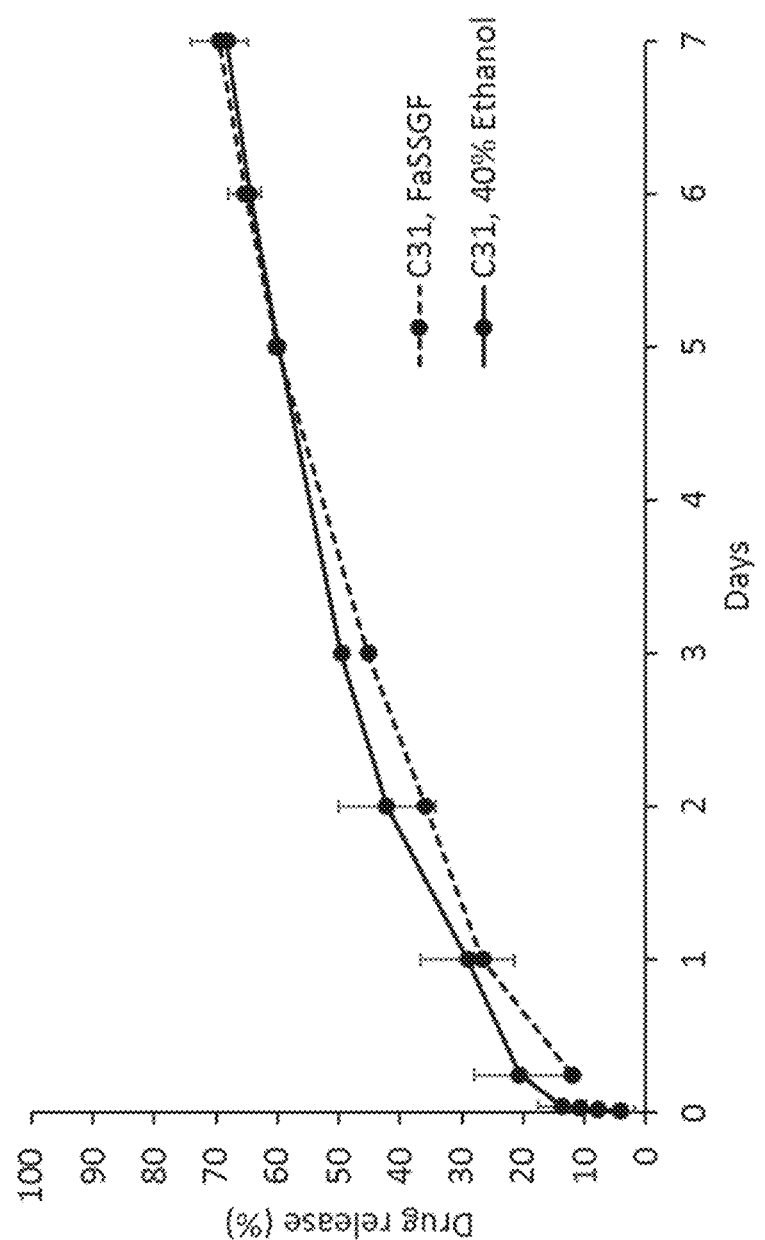

In each case, release was accelerated upon exposure to ethanol during the first hour, Clear differences were observed among coatings with regard to their ability to resist dose dumping in ethanol. Ethanol soluble coatings, such as Eudragit RS, were most susceptible to dose dumping, with a greater than five-fold increase in drug release in 6 hours (FIG. 3B). Coatings that are insoluble in ethanol, such as PCL, demonstrated minimal change in drug release upon exposure to ethanol (FIG. 3C). Ethyl cellulose (FIG. 3D) and cellulose acetate (FIG. 3E) coatings displayed intermediate ethanol stability. After switching from ethanol to FaSSGF, the remainder of the release profile was generally similar to the release profile observed in FaSSGF without ethanol exposure.

Example 2B

Pan Coated Polycaprolactone

Pan Coating

This experiment was performed to explore Ethyl Cellulose (EC) coatings on M57 (20% w/w memantine, 62% w/w 80 k PCL, 12% w/w Eudragit RL, 5% w/w Kolliphor P407, 0.5% w/w silica, 0.5% w/w α-tocopherol) drug loaded arms using a pharmaceutical pan coating process in an effort to create a dosage form with linear release over seven days.

Solutions of EC were prepared in both 100% acetone and 80:20 acetone:isopropyl alcohol with the plasticizer triethyl citrate (TEC) in an EC:TEC ratio of 9:1 and solid concentrations of 2.3-10% w/v. The solution was then applied to drug loaded arms using a Vector LDCS pharmaceutical pan coater. The coating solution was applied to a pre-weighed bed of placebo arms with a small quantity of drug loaded arms spiked in. The pan speed was set at 20 RPM and the product temperature was approximately 35-40° C. After coating, the arms were dried for approximately 5 minutes to drive off any residual acetone. The entire batch of coated placebo and drug loaded arms were weighed to determine the percent mass gain of coating applied. Coatings were applied to a percent mass gain of approximately 2-7% w/w.

The resulting drug loaded arms all had coatings that were not well adhered. The coated placebo and active arms had visual imperfections where the coating was clearly not in contact with the drug arm matrix. Coatings could be easily removed by scratching the surface of the drug arm. Lack of coating adhesion was likely due to the drug arm having a smooth surface that does not allow adequate integration of the coating layer and surface.

Example 3

Solvent Selection for Dip Coating With PCL

This example demonstrates investigation of solvents useful for dip coating PCL films.

Dip coating requires dissolution of coating polymers in a volatile solvent at a concentration sufficient to leave a continuous polymer film on a dipped material. Coating thickness, and in turn drug release rate, can be modulated by varying the solution concentration and/or viscosity. For 80 k PCL coatings, a minimum solution concentration of about 3% wt/vol was necessary to deposit a polymer layer that provided some control over drug release. Concentrations of 5-10% wt/vol are preferred for robust coating performance. This requires high solubility of PCL in the coating solvent and limits the possible solvent systems that can be used to apply coatings. FIG. 4 summarizes solvents used for dip coating PCL films. Dichloromethane and ethyl acetate were both able to dissolve PCL at high concentrations and to form uniform coatings with good performance. Ethyl acetate was chosen as the preferred solvent over dichloromethane for operator safety during processing. For coatings incorporating porogens, the appropriate solvent selection criteria include dissolution of an adequate concentration of porogen. If necessary, co-solvent systems such as ethyl acetate/isopropanol allow addition of porogens to a PCL coating solution.

Example 4

Coatings Comprising Porogens Achieve Linear and Complete Release

The burst release from the uncoated drug formulation could be controlled by coating the drug arm matrix with a 5% w/v PCL coating solution, however, it also reduced the total drug released in 7 days from ~90% (uncoated) to ~60% cumulative release. In this experiment, the effect of adding porogens to the 5% w/v PCL coating to speed up the linear release profile and increase the cumulative drug released in 7 days was studied. Dissolution tests were performed for 7 days in fasted state SGF media.

The coating process was performed by dipping the drug-loaded M77 formulation (arms) into a coating solution. Coating solutions of 80 k PCL were prepared in ethyl acetate at 5% w/v with 90:10 PCL to porogens (Kollidon VA64, Kolliphor RH40 and PVP). In case of PVP, a co-solvent system of 8:2 ethyl acetate to isopropyl alcohol (IPA) was used. In vitro release (dissolution) assay described in Example 2A was performed to study the effect of addition of porogen to coating solution using various porogens.

Figure 5:
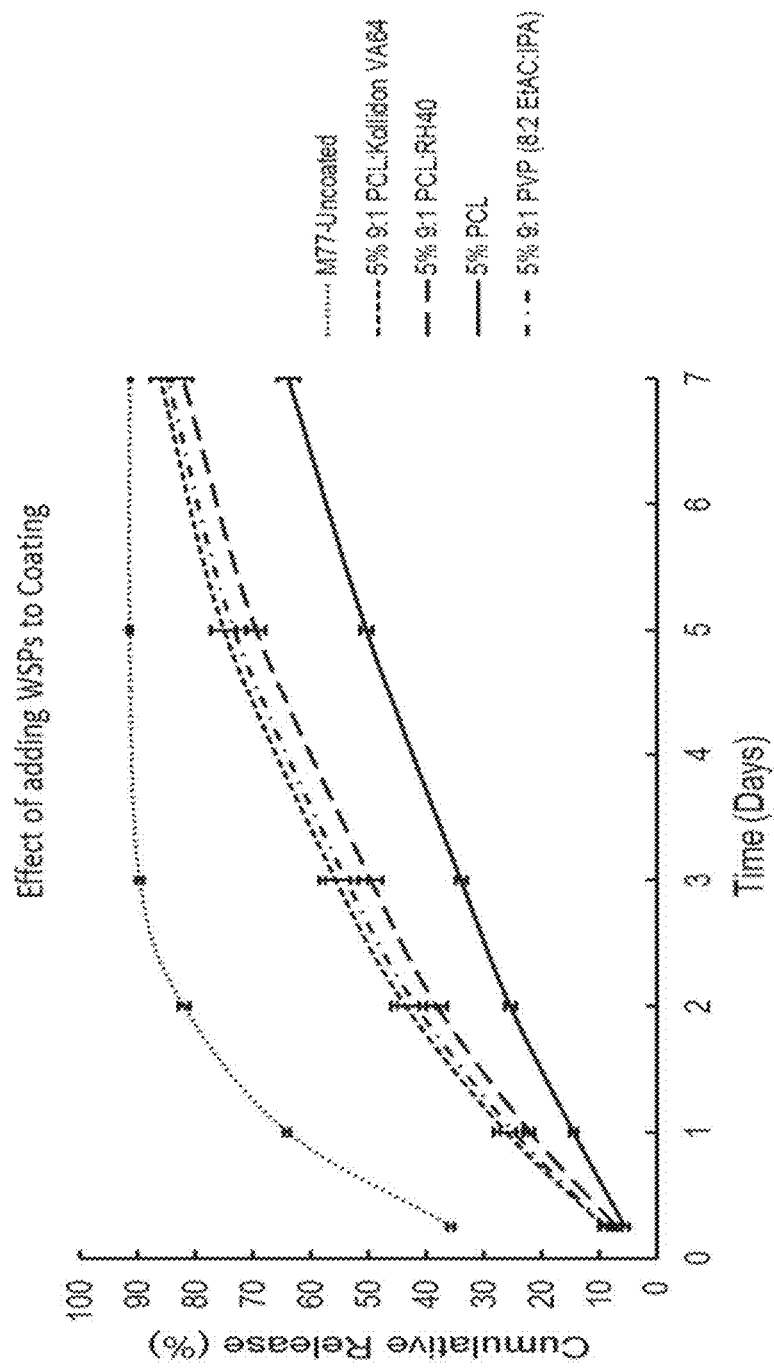
FIG. 5 depicts release rate profiles of M77 uncoated formulation and M77 formulations with coatings of PCL only and PCL with the addition of porogens (Water Soluble Polymers, WSPs) Kollidon VA64 and Kolliphor RH40.

The addition of porogen to the outer coating layer increases the cumulative 7 day release to >80%, similar to the cumulative 7-day release of the uncoated formulation, while controlling the burst release. Dissolution results from this study showed that a controlled release coating with porogens allows control of the burst release and improved linearity of release, while achieving a high 7-day cumulative drug release (FIG. 5).

Example 5

Porogen Incorporation Improves Reproducibility of Release Kinetics for PCL-Based Coatings The coating process was performed by dipping the drug-loaded formulation (arms) into coating solutions as described in Example 2 on two separate experimental runs (Run 1 and Run 2). Two coating solutions were prepared for each run: 5% w/v 80 k PCL only in ethyl acetate and 80 k PCL with porogen (Kollidon VA64) solution was prepared in ethyl acetate at 5% w/v with 90:10 PCL to porogen. For both Run 1 and 2, dissolution assays were performed by incubating dosage forms for 7 days in FaSSGF as described in the in vitro release method in Example 2.

Figure 6:
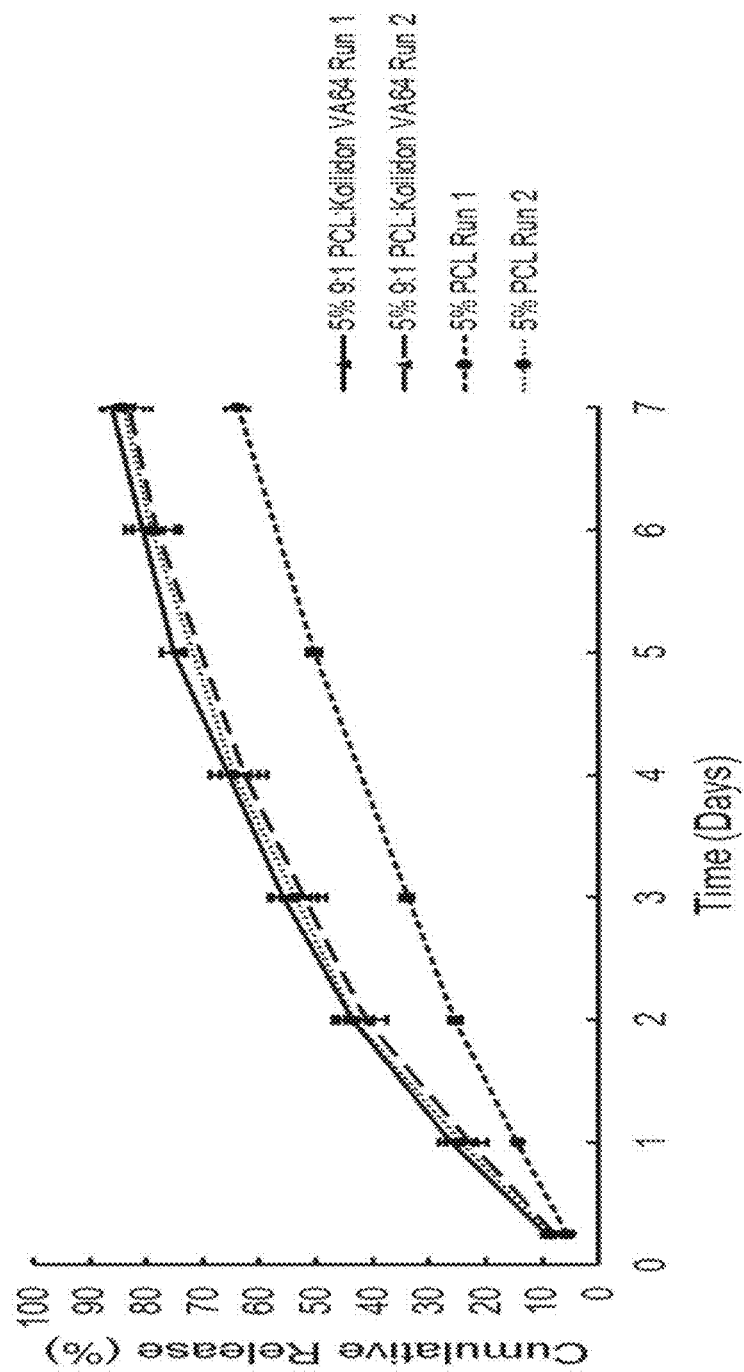
FIG. 6 depicts batch variability of release rate profiles of M77 formulations with dip coatings of PCL only and PCL with the addition of porogens (Kollidon VA64 and Kolliphor RH40)

Dissolution results from this study (FIG. 6) showed that addition of porogen to the 80 k PCL coating solution helps improve batch-to-batch reproducibility of drug release profile of Run 1 and Run 2. The PCL only coating solution leads to variability in the release profile of Run 1 and Run 2 (FIG. 6).

Example 6

Release Rate can be Tuned by Varying the Ratio of Porogens

This experiment was performed to study the effect of changing the composition of the 80 k PCL and porogen coating on tuning the release rate of the dosage form after dip coating. Coating solutions of 80 k PCL and porogens were prepared at 5% w/v with the appropriate solvent as described in Examples 3 and 4 at two different ratios of PCL to porogens, 90:10 and 70:30. Drug arms were dip coated and dissolution tests were performed for 7 days as described in Example 2.

Figure 7:
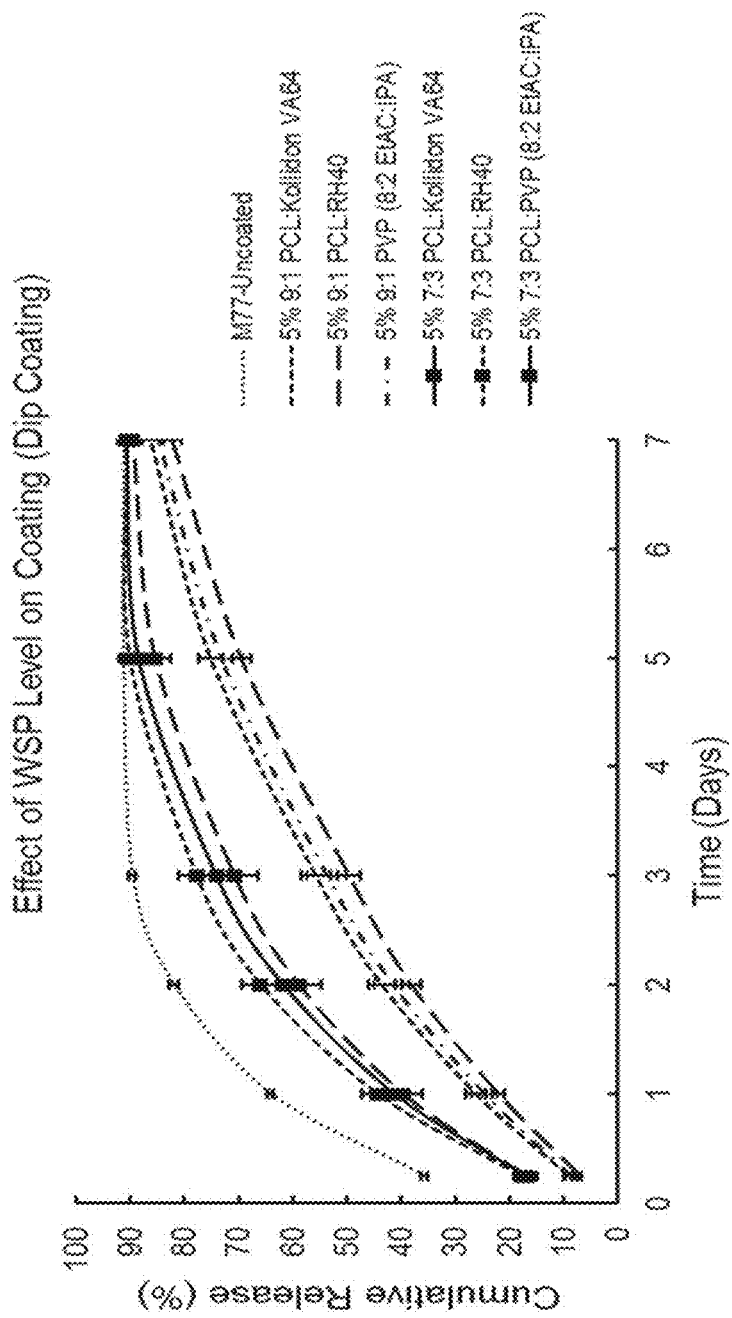
FIG. 7 depicts the tuning effect of release rate profiles for M77 formulations with dip coatings of PCL with the addition of varying levels of porogens.

Dissolution results from this study (FIG. 7) showed that drug arms coated with 70:30 PCL:porogen ratios have a faster release profile than arms coated with 90:10 PCL: porogen ratios, for various porogens tested (Kollidon VA64, Kolliphor RH40 and PVP). Increasing the amount of porogen in the coating solution increases the rate of drug release from the coated formulations in case of various porogens added to the PCL coating solution (FIG. 7). Varying the level of porogen allows tuning the release rate of the coated dosage forms (FIG. 7).

Example 7

Linearity of Release Depends on the Type of Porogen Used in the Coating

This experiment was performed to explore how the level of the porogen poly(ethylene glycol) (PEG 6000) in a PCL coating affects the release rate of the dosage unit. Coating solutions were prepared using fixed amounts of plasticizer with varying ratios of PCL to PEG 6000.

Solutions of PCL, PEG 6000 and TEC were prepared in ethyl acetate at 3.3% w/v with 70:30, 80:20 and 90:10 ratios of PCL to PEG 6000 and 30% triethyl citrate by coating material, with 2% magnesium stearate as a processing aid. The solution was then applied to M57 (20% w/w memantine, 62% w/w 80 k PCL, 12% w/w Eudragit RL, 5% w/w Kolliphor P407, 0.5% w/w Silica, 0.5% w/w α-tocopherol) drug loaded arms using a Vector LDCS pharmaceutical pan coater. The coating solution was applied to a pre-weighed bed of placebo arms (approximately 500 g) with a small quantity (approximately 80 arms) of drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 2.5% w/w mass gain.

Figure 8:
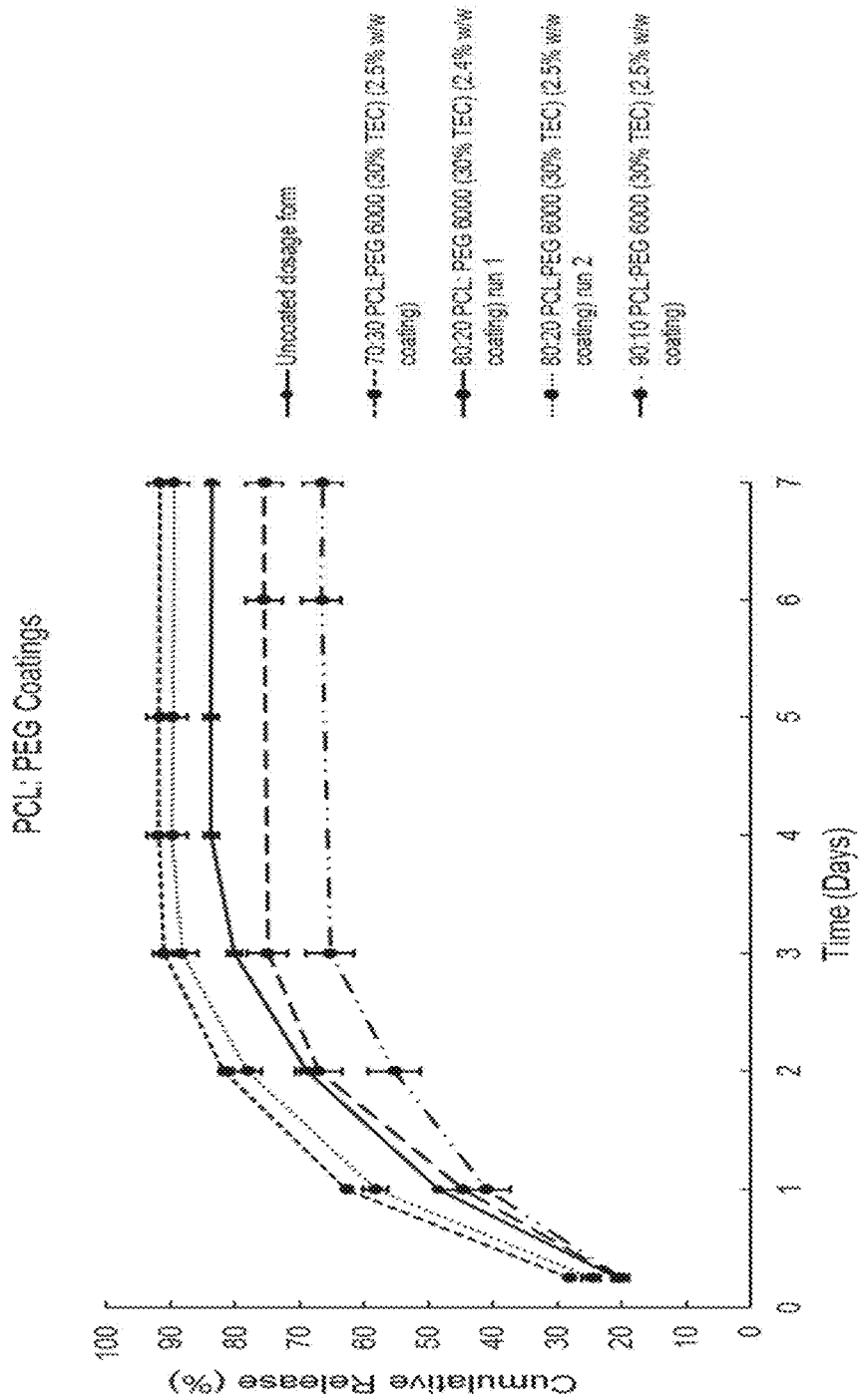
FIG. 8 depicts release rate profiles for formulations with different levels of PEG 6000 in PCL coating.

Dissolution results from this study showed that incorporating PEG 6000 into the coating does not result in a linear release profile and does not create consistent results batch to batch as displayed in runs 1 and 2, both coated with 80:20 PCL: PEG 6000 with 30% TEC at approximately 2.5% mass gain (FIG. 8). Phase separation of PCL and PEG 6000 was observed during the coating which is the likely cause of the lack of controlled release.

Example 8

Plasticizer Concentration in Coatings can be Used to Tune the Release Rate (Pan Coating)

This experiment was performed to explore how the level of the plasticizer TEC in a PCL coating affects the release rate of the dosage unit after coating in a pharmaceutical pan coater. Coating solutions were prepared using fixed ratios of PCL to the porogen copovidone with varying levels of the plasticizer TEC.

Solutions of PCL and copovidone were prepared in ethyl acetate at 3.3% w/v with a 80:20 ratio of PCL to copovidone. Triethyl citrate was added to the solution at a level of 10 or 30% w TEC/w polymer. Magnesium stearate (2% w/w polymer) was added as a processing aid. The solution was then applied to M77 (27.5% w/w memantine, 66.5% w/w 80 k PCL, 5% w/w Kolliphor P407, 0.5% w/w Silica, 0.5% NON α-tocopherol) drug loaded arms using a Vector LDCS pharmaceutical pan coater. The coating solution was applied to a pre-weighed bed of placebo arms (approximately 450 g) with a small quantity (approximately 80 arms) of drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 1.5% and 2.5% w/w mass gain.

Figure 9A:
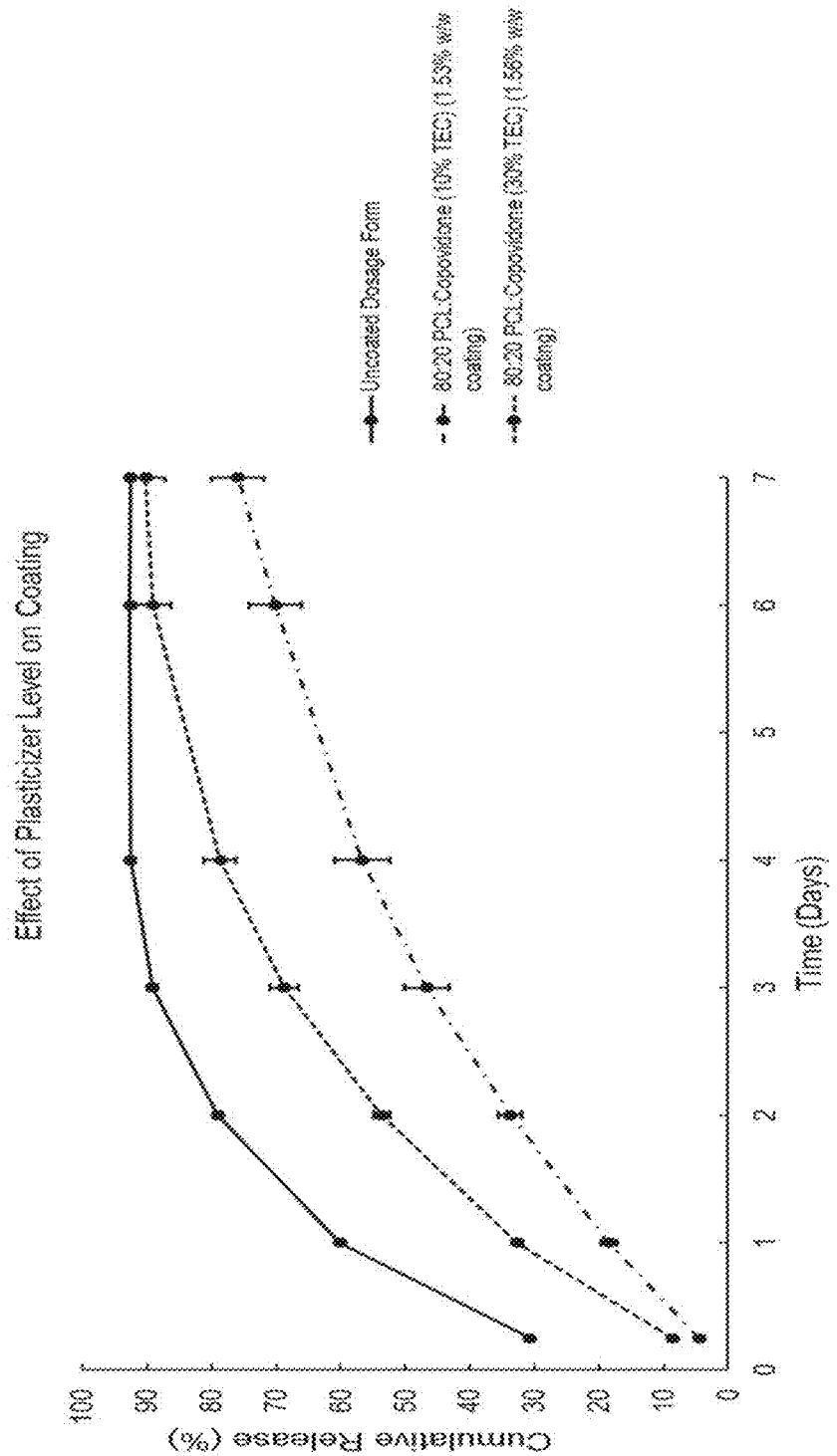
FIG. 9A depicts release rate profiles for formulations with increasing levels of TEC in PCL coating.
Figure 9B:
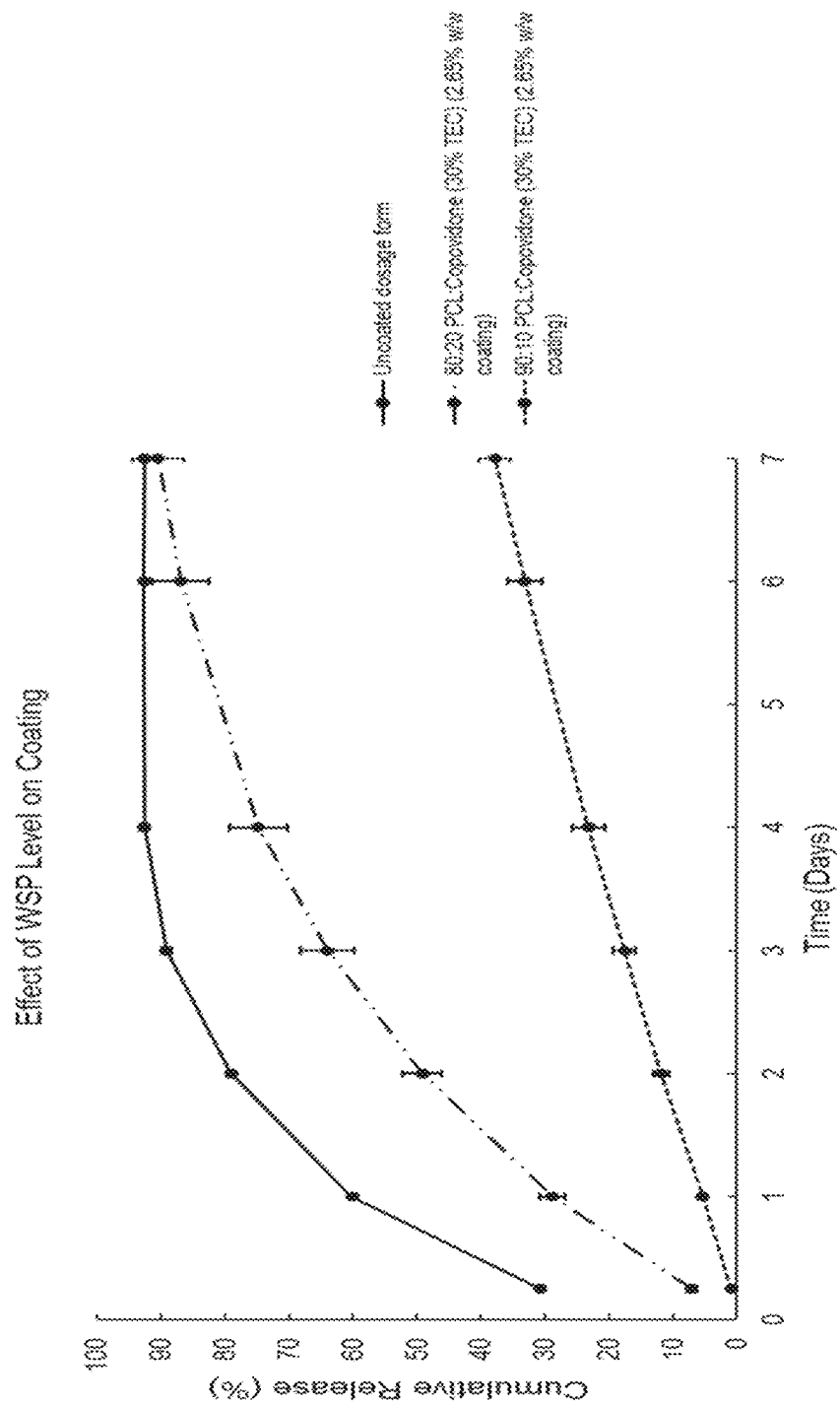
FIG. 9B depicts additional release rate profiles for formulations with increasing levels of TEC in PCL coating.

The dissolution results for these arms show that release rate can be tuned by adjusting the amount of TEC in the coating solution (FIGS. 9A and 9B). Increased ratios of TEC to PCL results in faster dissolution when the ratio of PCL to copovidone and coating % mass gain are held constant.

Example 9

Release Rate can be Tuned by Varying the Ratio of Porogens (Pan Coating)

This experiment was performed to explore how the level of the porogen copovidone in a PCL coating affects the release rate of the dosage unit after pharmaceutical pan coating. Coating solutions were prepared using fixed amounts of plasticizer with varying ratios of PCL to copovidone.

Solutions of PCL and copovidone were prepared in ethyl acetate at 3.3% w/v with a 80:20 ratio of PCL to copovidone. Triethyl citrate was added to the solution at a level of 10 or 30% w TEC/w polymer. Magnesium stearate 2% w/w polymer) was added as a processing aid. The solution was then applied to drug loaded arms using a Vector LDCS pharmaceutical pan coater. The coating solution was applied to a pre-weighed bed of placebo arms (approximately 500 g) with a small quantity (approximately 80 arms) of M77 (27.5% w/w memantine, 66.5% w/w 80 k PCL, 5% w/w Kolliphor P407, 0.5% w/w Silica, 0.5% w/w α-tocopherol) drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 2.5% w/w mass gain.

Figure 10A:
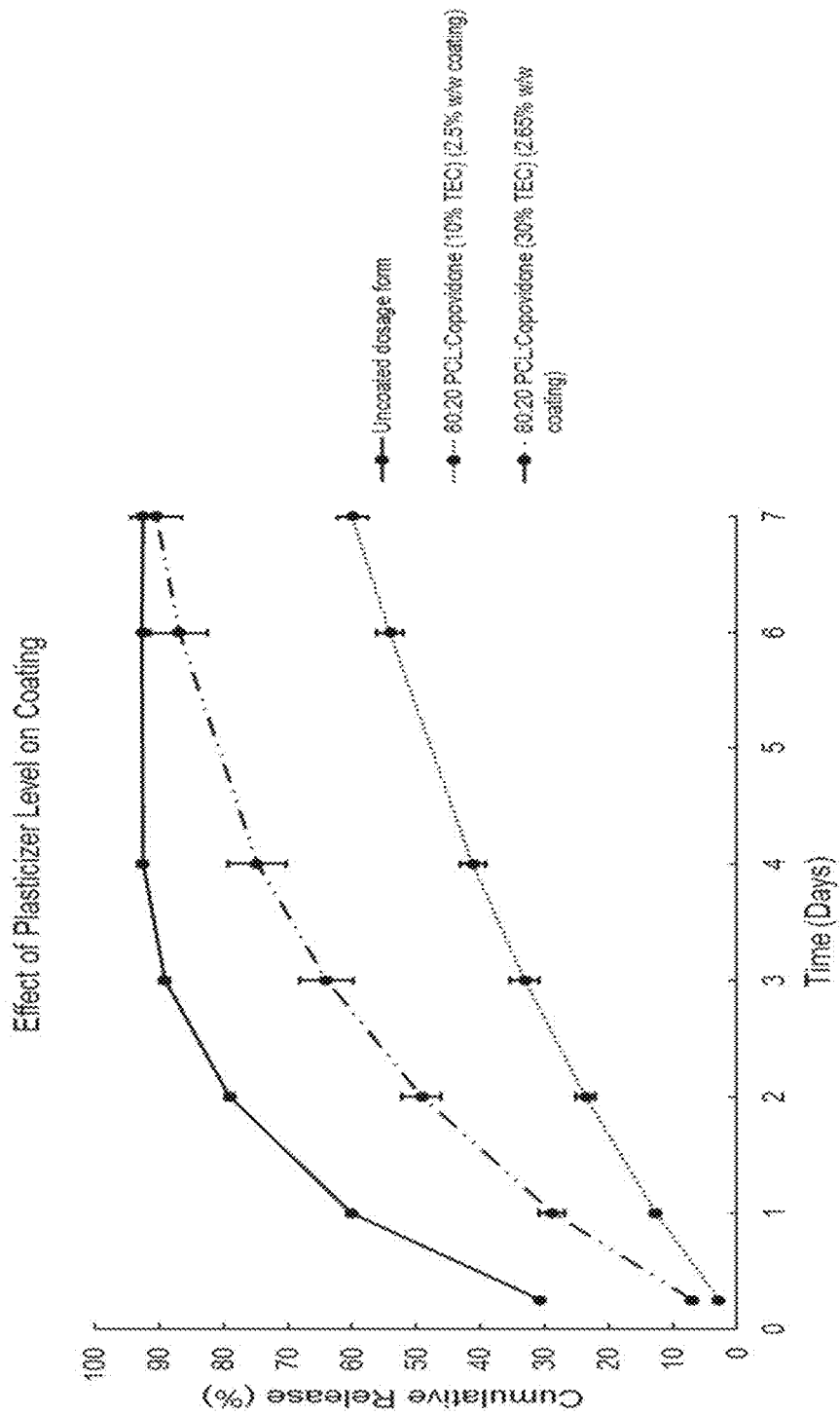
FIG. 10A depicts release rate profiles for formulations with varying ratios of PCL:copovidone and 10% or 30% triethyl citrate in the coating.
Figure 10B:
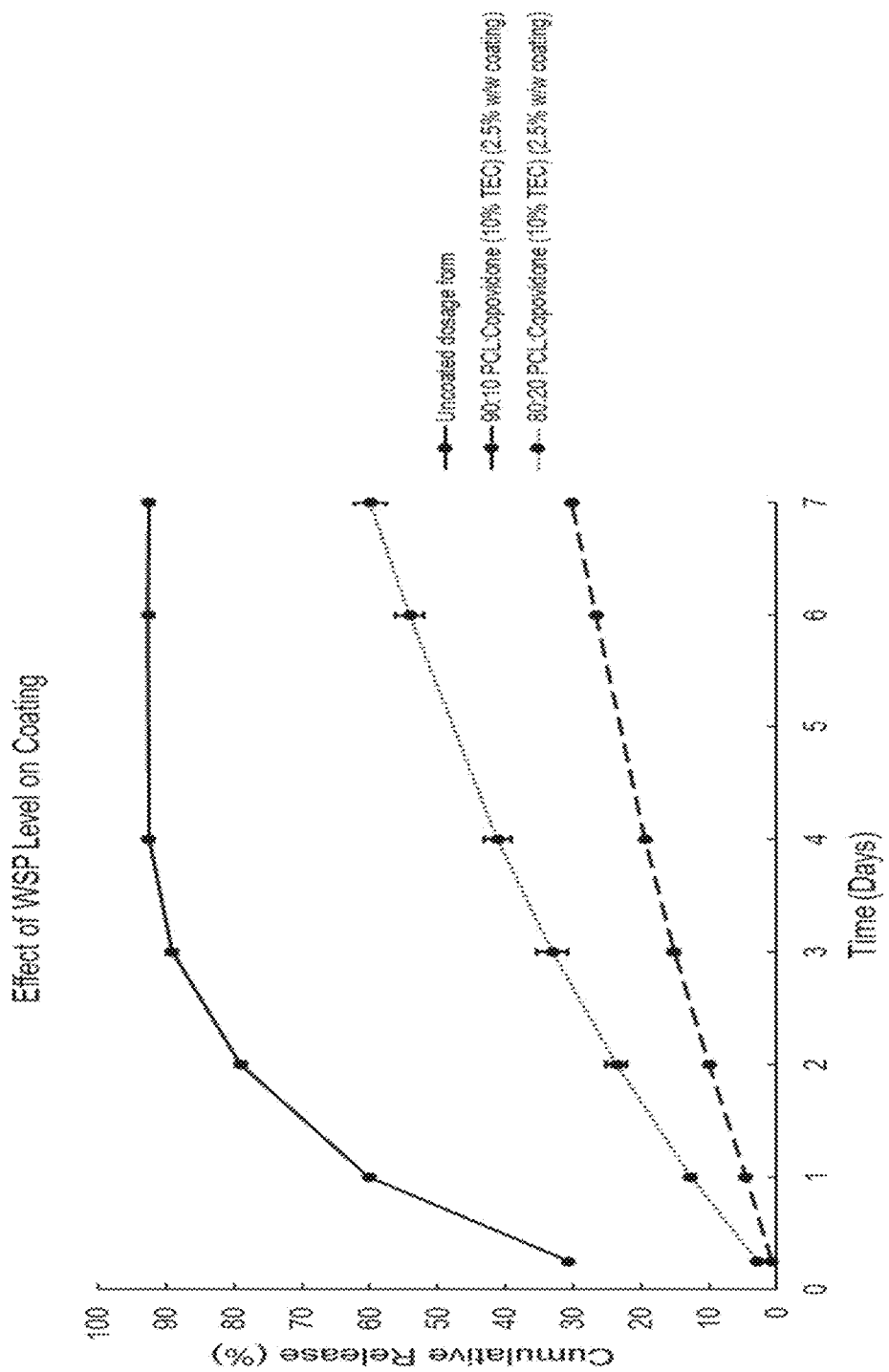
FIG. 10B depicts additional release rate profiles for formulations with varying ratios of PCL:copovidone and 10% or 30% triethyl citrate in the coating.

The dissolution results for these arms show that release rate can be tuned by adjusting the ratio of PCL:copovidone in the coating solution (FIGS. 10A and 10B). Increased ratios of PCL:copovidone results in slower dissolution when the amount of TEC and coating % mass gain is held constant.

Example 10

Coatings Applied by Pan Coating can Control Rate of Release with Minimal Coating Mass This experiment was performed to explore whether low coating weights (<2.5% w/w mass gain which gives about 6 to 12 μm coating thickness range) of PCL pan coated drug loaded arms were able to control release rate and provide linear release for 7 days.

Figure 11:
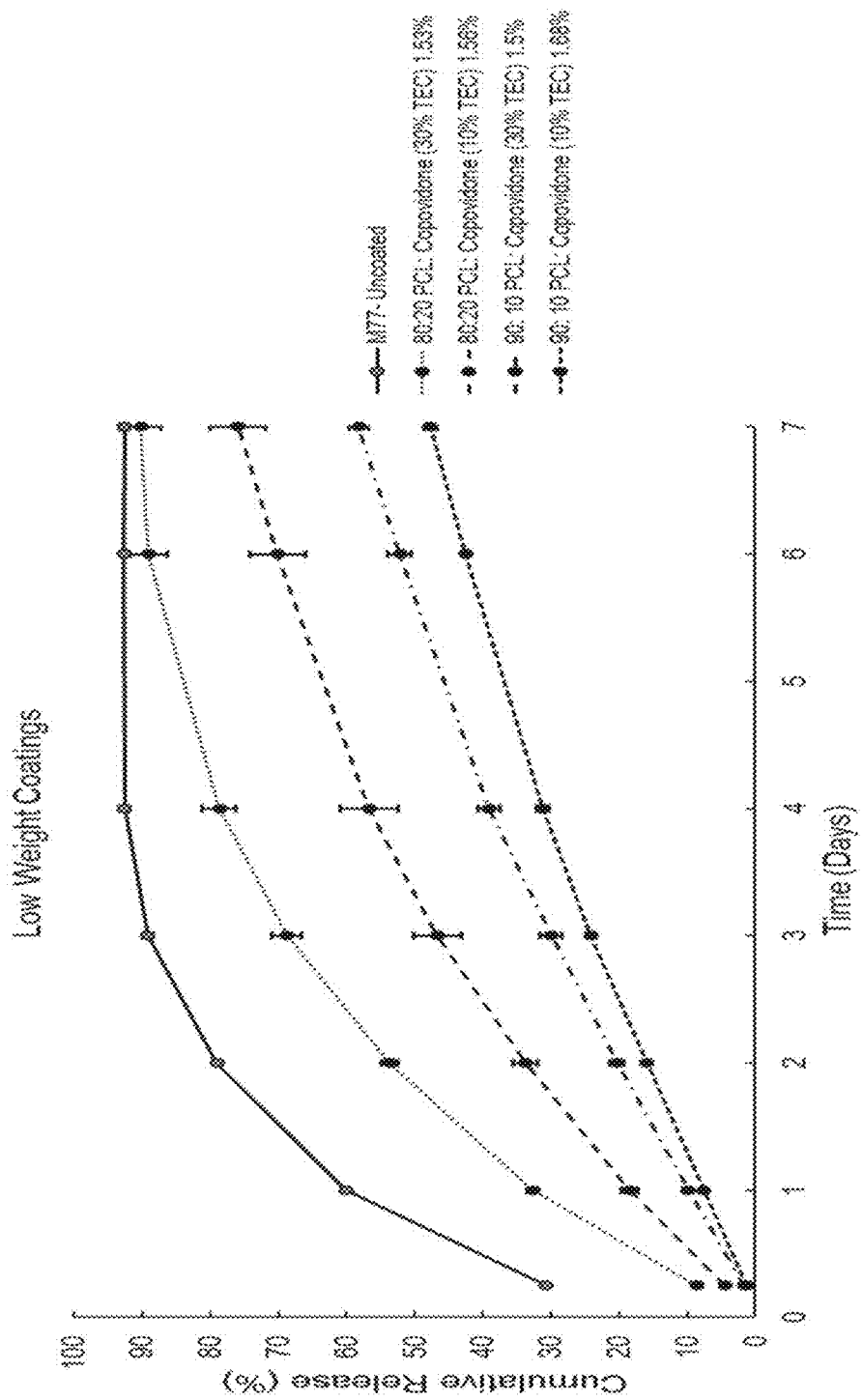
FIG. 11 depicts the effects of low weight coating on drug release rate, with varying ratios of PCL:copovidone and 10% or 30% triethyl citrate in the coating.

Solutions of PCL and copovidone were prepared in ethyl acetate at 3.3% why with a 80:20 ratio of PCL to copovidone. Triethyl citrate was added to the solution at a level of 10 or 30% w TEC/w polymer. Magnesium stearate 2% w/w polymer) was added as a processing aid. The solution was then applied to drug loaded arms using a Vector LDCS pharmaceutical pan coater. The coating solution was applied to a pre-weighed bed of placebo arms (approximately 500 g) with a small quantity (approximately 80 arms; approximately 10 g) of M77 (27.5% w/w memantine, 66.5% w/w 80 k PCL, 5% w/w Kolliphor P407, 0.5% w/w silica, 0.5% w/w α-tocopherol) drug loaded aims spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 1.5% w/w mass gain. The dissolution data for these aims show that release rate can controlled at coating percent mass gains of less than 2.5% and as low as 1.5% (FIG. 11).

Example 11

Coating of Drug-Polymer Arms in Wurster Coater

Drug polymer arms can also be coated in a fluid bed using a Wurster coating process. In this process, the drug polymer arms are fluidized with heated air and coated with a coating solution, e.g., 5% w/w PCL in ethyl acetate, while circulating through the Wurster column. The dissolved coating solution is applied to the drug polymer arms as they enter the Wurster column and pass through the spray zone situated under the column. Solvent evaporation occurs as the arms travel through the column and circulate hack down to the bed of polymer drug arms. This process is continued until the appropriate amount of coating has been applied to the drug polymer arms. Arms are then dried by turning off the coating spray and allowing the heat and air flow to drive off remaining solvent.

Example 12

Coated Drug Arms Lead to More Consistent Drug Serum Levels of Memantine HCl than Uncoated Dose Forms in the Absence of Alcohol Challenge Eight male beagles (n=4/group) weighing between 9.3 and 11.1 kg were used in this study. Dogs were fasted for 12 hr prior to dose administration. Dosage forms consisted of 90 Å durometer polyurethane elastomers heat welded to M57 (20% w/w memantine, 62% w/w 80 k PCL, 12% w/w Eudragit RL, 5% w/w Kolliphor P407, 0.5% w/w Silica, 0.5% w/w α-tocopherol) drug arms that were dip coated with a solution of 6.67% ethyl cellulose w/v in acetone or uncoated. Memantine was incorporated into the drug-polymer arms at a total load of ~155 mg/dosage form for an estimated ~22 mg/day of potential release over 7 days. (Formulations for animal studies in Examples 12-14 are listed in Table 2.)

TABLE 2

Memantine formulations.

| Formulation Code | Memantine (% ww) | 80K PCL (% ww) | Excipient (% ww) | Coating Solution Composition |
|---|---|---|---|---|
| M57 | 20 | 62 | 12% Eudragit RL, 5% Kolliphor P407, 0.5% Silica, 0.5% α-tocopherol | 6.67% ethyl cellulose w/v in acetone |
| M69 | 27.5 | 56.5 | 12% Eudragit RL, 3% Kolliphor P407, 0.5% Silica, 0.5% α-tocopherol | 5% PCL w/v in ethyl acetate |
| M77 | 27.5 | 66.5 | 5% Kolliphor P407, 0.5% Silica, 0.5% α-tocopherol | 4.5% PCL/0.5% Kollidon VA64 w/v in ethyl acetate |

Figure 12:
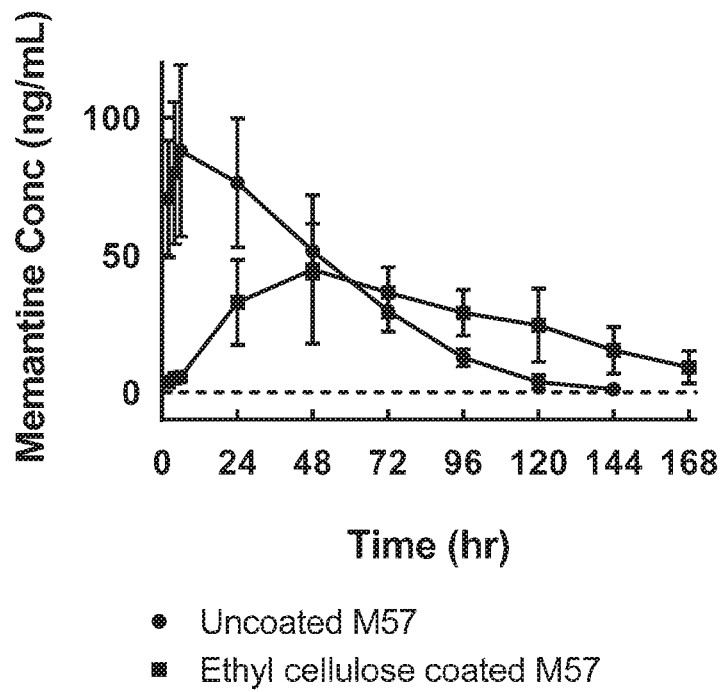
FIG. 12 depicts the effect of ethyl cellulose coating on consistent drug serum levels of Memantine HCl, compared to an uncoated dosage form.

Coated and uncoated dosage forms were placed into capsules immediately before dosing. Capsules were placed at the back of the dog's throat and after swallowing, dogs were offered a food chase of canned food. Blood samples (2 mL) were collected from left or right jugular veins pre-dose and at 2, 4, 6, 24, 48, 72, 96, 120, 144 and 168 hr after dosing. Blood samples were collected into $K_3$EDTA tubes and plasma collected by centrifugation at 5,000 rpm for 5 min. Plasma samples were analyzed for memantine content using a protein precipitation method followed by quantitation on LC-MS/MS (FIG. 12).

Example 13

PCL Coating Results in Near Constant Plasma Drug Concentrations Despite Variations in the Underlying Formulation: Six Dog Study Six male beagles weighing between 9.1 and 10.8 kg were used in this study. Dogs were fasted for 12 hr prior to dose administration. Dosage forms consisted of 90 Å durometer polyurethane elastomers heat welded to M69 (27.5% w/w memantine, 56.5% w/w 80 k PCL, 12% w/w Eudragit RL, 3% w/w Kolliphor P407, 0.5% w/w Silica, 0.5% w/w α-tocopherol) drug arms that were dip coated with a solution of 5% PCL w/v in ethyl acetate. Memantine was incorporated into the drug-polymer arms at a total load of ~183 mg/dosage form for an estimated ~26 mg/day of potential release over 7 days. (See Table 2 above for memantine formulations.) Coated and uncoated dosage forms were placed into capsules immediately before dosing.

Figure 13:
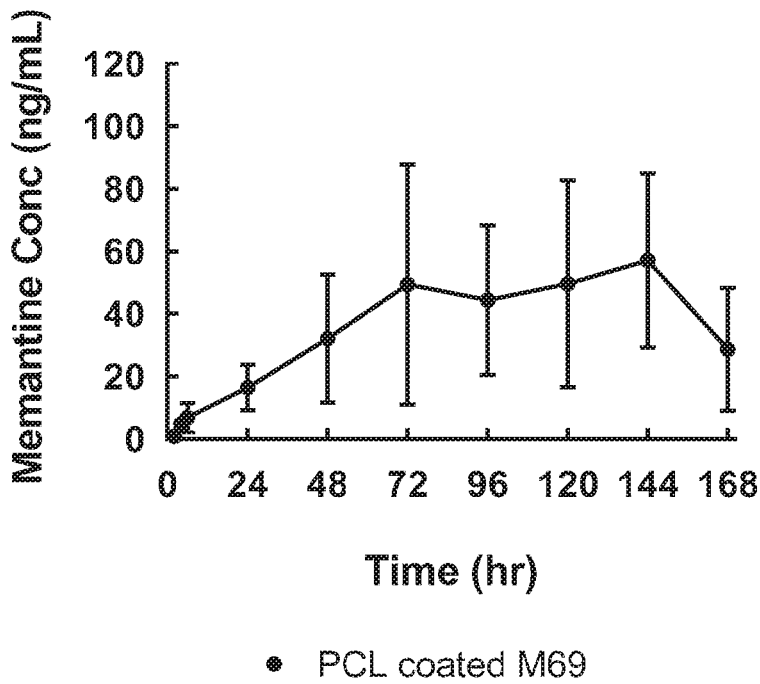
FIG. 13 depicts a near constant plasma drug concentrations for dosage formulations with a PCL coating. The dosage forms consisted of 90 A durometer polyurethane elastomers heat-welded to M69 drug arms that were dip coated with a solution of 5% PCL w/v in ethyl acetate.

Capsules were placed at the back of the dog's throat and after swallowing, dogs were offered a food chase of canned food. Blood samples (2 mL) were collected from left or right jugular veins pre-dose and at 2, 4, 6, 24, 48, 72, 96, 120, 144 and 168 hr after dosing. Blood samples were collected into $K_3$EDTA tubes and plasma collected by centrifugation at 5,000 rpm for 5 min. Plasma samples were analyzed for memantine content using a protein precipitation method followed by quantitation on LC-MS/MS. The results of the study are shown in FIG. 13.

Example 14

PCL Coating Results in Near Constant Plasma Drug Concentrations Despite Variations in the Underlying Formulation: Sixteen Dog Study Sixteen male beagles weighing between 8.2 and 10.1 kg were used in this study. Dogs were fasted for 12 hr prior to dose administration, and then subjected to one of three different feeding regimens: (food 1 hour prior to dose administration. food 1 hour after dose administration, and food 4 hours after dose administration). Dosage forms consisted of 60 Å durometer LSR elastomers IR welded to 50/50 PCL/HPMAS disintegrating matrices and M77 (27.5% w/w memantine, 66.5% w/w 80 k PCL, 5% w/w Kolliphor P407, 0.5% w/w Silica, 0.5% w/w α-tocopherol) drug arms that were coated with a solution of 4.5% PCL/ 0.5% kollidon VA64 w/v in ethyl acetate. Memantine was incorporated into the drug-polymer arms at a total load of ~145 mg/dosage form for an estimated ~21 mg/day of potential release over 7 days. (See Table 2 above for memantine formulations.) Coated and uncoated dosage forms were placed into capsules immediately before dosing.

Figure 14:
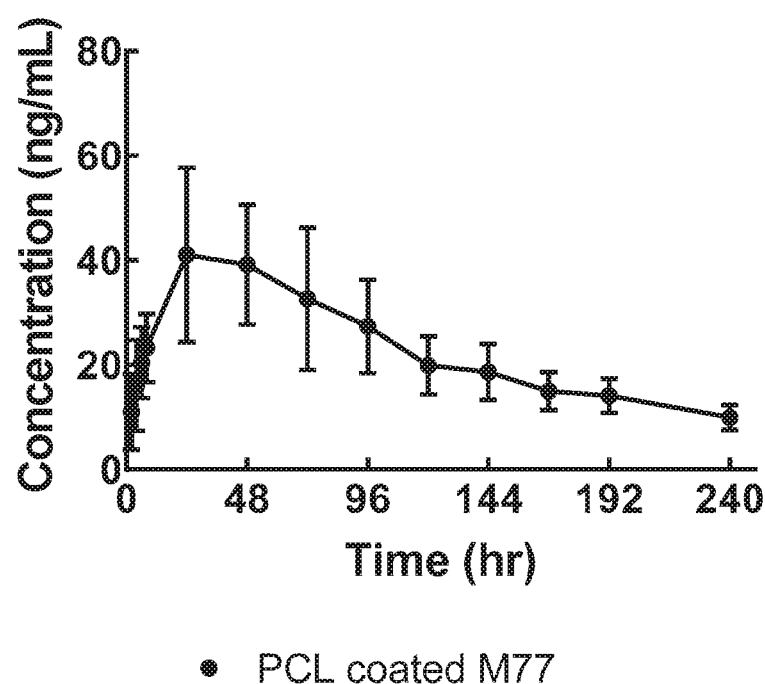
FIG. 14 depicts a near constant plasma drug concentrations for dosage formulations with a PCL coating. The dosage form consisted of 60 A durometer LSR elastomers IR welded to 50/50 PCL/HPMAS disintegrating matrices and M77 drug arms that were coated with a solution of 4.5% PCL/0.5% kollidon VA64 w/v in ethyl acetate.

Capsules were placed at the hack of the dog's throat and after swallowing, dogs were offered a food chase of canned food. Blood samples (2 mL) were collected from left or right jugular veins pre-dose and at 2, 4, 6, 8, 24, 48, 72, 96, 120, 144, 168, 192 and 240 hr after dosing. Blood samples were collected into $K_3$EDTA tubes and plasma collected by centrifugation at 5,000 rpm for 5 min. Plasma samples were analyzed for memantine content using a protein precipitation method followed by quantitation un LC-MS/MS. The results are shown in FIG. 14.

Figure 16:
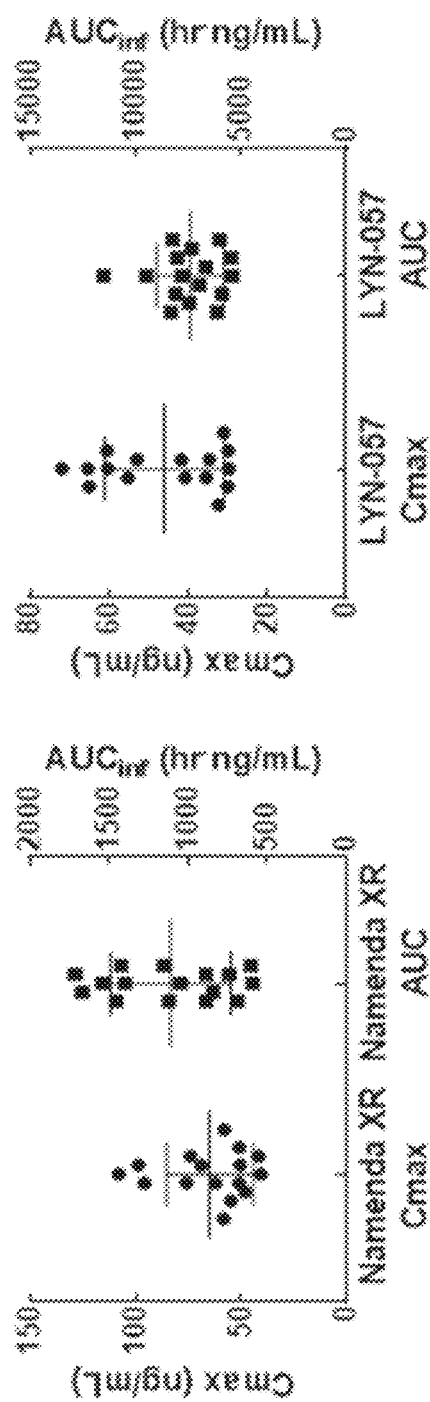
FIG. 16 depicts a comparison of pharmacokinetic parameters for dosage forms consisting of 60 A durometer LSR elastomers IR welded to 50/50 PCL/HPMAS disintegrating matrices and M77 drug arms that were coated with a solution of 4.5% PCL/0.5% kollidon VA64 w/v in ethyl acetate, versus a single dose of Namenda XR, a commercially available extended release formulation of memantine. The left chart shows the Namenda XR reference product single dose variability, with $C_{max}$ (ng/mL) on the left axis and the left grouping of points, and AUC (hr-ng/mL) on the right axis and the right grouping of points. The right chart shows the dosage form variability, with $C_{max}$ (ng/mL) on the left axis and the left grouping of points, and AUC (hr-ng/mL) on the right axis and the right grouping of points. Compared to the reference product, the dosage form achieves nearly 7-fold higher AUC with a lower $C_{max}$ and potentially lower inter-subject variability.

For comparison, the same animals were administered Namenda XR containing 28 mg of memantine and plasma samples were collected and analyzed in a similar manner. Pharmacokinetic parameters for individual animals are shown in FIG. 16. The mean Cmax values for the dosage form and Namenda XR were 46.1±15.2 and 64.9±20.7 ng/mL, respectively, and mean AUC values for the dosage form and Namenda XR were 7438±1590 and 1,113±382 hr*ng/mL, respectively. Despite the range of fed/fasted conditions, the variability of Cmax and AUC observed with coated dosage forms was equal or less than for Namenda XR. The relative standard deviations (RSD) of the dosage form Cmax and AUC were 33% and 21%, respectively, while the corresponding RSDs for Namenda XR were 32% and 34%. In addition, the Cmax observed following dosage form administration was lower than the value observed following the lower dose of Namenda. XR The AUC observed following dosage form administration was approximately 7 times higher than the Namenda XR, AUC, indicating that the bioavailability of memantine was similar for both formulations.

Example 15

Coating of Drug-Polymer Matrix Increases Linearity of Drug Release

Figure 15:
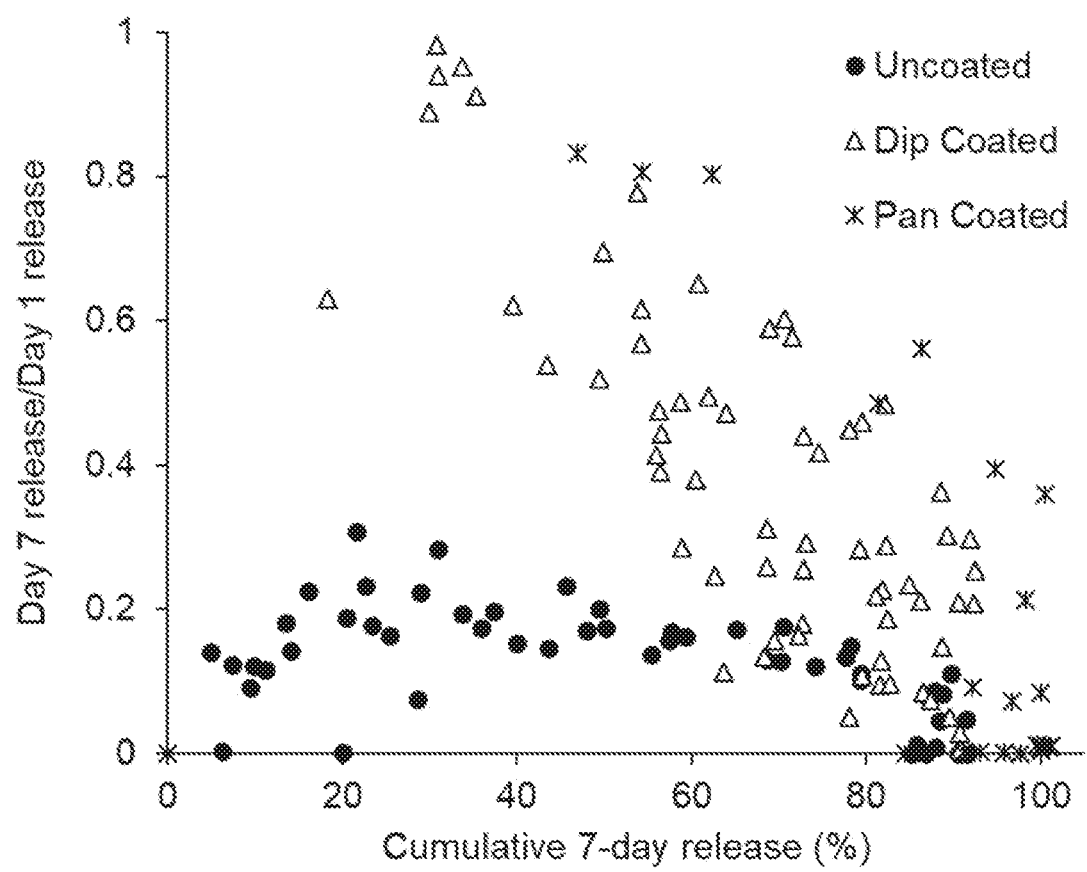
FIG. 15 depicts the linearity versus extent of release comparison between coated drug formulations and those without coating.

Linearity versus extent of release for about 50 formulations of memantine hydrochloride was evaluated, in which drug-polymer matrices were coated in accordance with the present invention in comparison with uncoated formulations (Example 1). Total release over 7 days (X-value in Table 3) is plotted versus the ratio of (Day 7 Release/Day 1 Release) (Y-value in Table 3) in FIG. 15. Formulations closer to the upper right corner of the plot (where good total release and good linearity of release occur) are preferable. As can be seen in FIG. 15, drug release on day 7 was up to 100% of release on day 1. Linearity of release, as measured by the ratio of release on day 7 to release on day 1 was greater than 30% for many formulations, including many formulations that displayed near complete cumulative release at Day 7. In systems of the present invention, achieving complete release in a 7-day treatment time is possible while maintaining near linear release (Day 7 release/Day 1 release>0.3). Coating formulations were as listed in Table 3.

TABLE 3

Coating formulations.

| Formulation Code | Coating Formulation | Coating Solvent | Coating Solution Concentration (% w/v) | Y-value | X-value |
|---|---|---|---|---|---|
| M18 | 9:1, PCL 55 k:P407 | DCM | 33.3 | 0.94 | 30.92 |
| M18 | 9:1, PCL 55 k:P188 | DCM | 33.3 | 0.69 | 49.84 |
| M18 | Eudragit RS | DCM | 33.3 | 0.15 | 88.68 |
| M18 | 9:1 PCL 55 k:PEG 10 k | DCM | 33.3 | 0.95 | 33.73 |
| M18 | 9:1 PCL 55 k:PEG 100 k | DCM | 33.3 | 0.91 | 35.34 |
| M18 | PCL 55 k | DCM | 16.7 | 0.60 | 70.61 |
| M18 | 9:1, PCL 55 k:P407 | DCM | 16.7 | 0.62 | 54.22 |
| M18 | 9:1, PCL 55 k:P188 | DCM | 16.7 | 0.57 | 54.21 |
| M18 | 9:1 PCL 55 k:PVP 1M | DCM | 16.7 | 0.42 | 74.51 |
| M18 | Ethyl Cellulose | Acetone | 6.7 | 0.19 | 82.44 |
| M18 | 9:1 Ethyl Cellulose:PVP 1.3M | Acetone | 6.7 | 0.23 | 81.86 |
| M18 | 9:1 Ethyl Cellulose:PEG 1M | Acetone | 6.7 | 0.44 | 72.87 |
| M18 | 9:1 Ethyl Cellulose:PEG 100 k | Acetone | 6.7 | 0.28 | 79.19 |
| M18 | 75:25 PLGA | Acetone | 16.7 | 0.54 | 43.48 |

TABLE 3-continued

Coating formulations.

| Formulation Code | Coating Formulation | Coating Solvent | Coating Solution Concentration (% w/v) | Y-value | X-value |
|---|---|---|---|---|---|
| M18 | 50:50 PLGA | Acetone | 16.7 | 0.49 | 61.98 |
| M18 | 25:75 PLGA | Acetone | 13.9 | 0.28 | 58.86 |
| M18 | 50:50 PLGA | Acetone | 13.9 | 0.13 | 81.72 |
| M18 | 50:50 PLGA | Acetone | 13.9 | 0.18 | 72.64 |
| M18 | Ethyl Cellulose | Acetone | 6.7 | 0.25 | 62.67 |
| M18 | Cellulose Acetate | Acetone | 6.7 | 0.11 | 79.50 |
| M18 | 9:1 Ethyl Cellulose:PEG 1M | Acetone | 6.7 | 0.16 | 72.18 |
| M18 | 9:1 Cellulose Acetate:PEG 1M | Acetone | 6.7 | 0.10 | 81.60 |
| M18 | Cellulose Acetate | Acetone | 10.0 | 0.16 | 69.48 |
| M18 | PCL 55 k | Acetone | 20.0 | 0.08 | 86.53 |
| M18 | PCL 15 k | Acetone | 20.0 | 0.07 | 87.36 |
| M18 | PLGA 50:50 Ester Terminated 35-45 k | Acetone | 16.7 | 0.39 | 56.45 |
| M18 | PLGA 50:50 Acid Terminated 35-45 k | Acetone | 16.7 | 0.26 | 72.86 |
| M18 | PCL 80 k | Acetone | 10.0 | 0.10 | 82.69 |
| M18 | PCL 80 k | Ethyl Acetate | 10.0 | 0.26 | 68.57 |
| M57 | Ethyl Cellulose | Acetone | 6.7 | 0.29 | 73.18 |
| M57 | PCL 80 k | Ethyl Acetate | 10.0 | 0.49 | 58.76 |
| M58 | Ethyl Cellulose | Acetone | 6.7 | 0.41 | 56.02 |
| M58 | PCL 80 k | Ethyl Acetate | 10.0 | 0.62 | 39.53 |
| M59 | Ethyl Cellulose | Acetone | 6.7 | 0.38 | 60.50 |
| M59 | PCL 80 k | Ethyl Acetate | 10.0 | 0.44 | 56.53 |
| M60 | Ethyl Cellulose | Acetone | 6.7 | 0.47 | 56.19 |
| M60 | PCL 80 k | Ethyl Acetate | 10.0 | 0.52 | 49.40 |
| M57 | PCL 80 k | Ethyl Acetate | 10.0 | 0.48 | 82.11 |
| M57 | PCL 80 k | Ethyl Acetate | 15.0 | 0.78 | 53.78 |
| M57 | 9:1 PCL 80 k:TEC | Ethyl Acetate | 15.0 | 0.65 | 60.77 |
| M57 | 8:2 PCL 80 k:TEC | Ethyl Acetate | 15.0 | 0.59 | 68.87 |
| M57 | 7:3 PCL 80 k:TEC | Ethyl Acetate | 15.0 | 0.36 | 88.57 |
| M57 | Ethyl Cellulose | Acetone | 6.7 | 0.45 | 78.07 |
| M57 | Ethyl Cellulose Cp 10 | Acetone | 6.7 | 0.21 | 92.28 |
| M57 | Ethyl Cellulose Cp 10 | Acetone | 13.3 | 0.21 | 90.63 |
| M57 | 9:1 Ethyl Cellulose Cp10:TEC | Acetone | 13.3 | 0.30 | 89.24 |
| M57 | 8:2 Ethyl Cellulose Cp10:TEC | Acetone | 13.3 | 0.30 | 91.88 |
| M57 | 7:3 Ethyl Cellulose Cp10:TEC | Acetone | 13.3 | 0.25 | 92.46 |
| M62 | PCL 80 k | Ethyl Acetate | 10.0 | 0.46 | 79.46 |
| M77 | PCL 80 k | Ethyl Acetate | 3.0 | 0.22 | 81.19 |
| M77 | PCL 80 k | Ethyl Acetate | 5.0 | 0.47 | 63.90 |
| M77 | PCL 80 k | Ethyl Acetate | 10.0 | 0.58 | 71.51 |
| M77 | 7:3 80 k PCL:PVP | 8:2 Ethyl Acelate:IPA | 5.0 | 0.03 | 90.69 |
| M77 | 9:1 PVP | 8:2 Ethyl Acelate:IPA | 5.0 | 0.23 | 84.89 |
| M77 | 7:3 80 k PCL:Kolliphor RH40 | Ethyl Acetate | 5.0 | 0.01 | 90.74 |
| M77 | 9:1 80 k PCL:Kolliphor RH40 | Ethyl Acetate | 5.0 | 0.29 | 82.26 |
| M77 | 7:3 80 k PCL:Kollidon VA64 | Ethyl Acetate | 5.0 | 0.05 | 89.56 |
| M77 | 9:1 80 k PCL:Kollidon VA64 | Ethyl Acetate | 5.0 | 0.21 | 86.21 |
| M104 | 1.25% weight gain of C3 (Table 5) | Ethyl Acetate | 3.3 | 0.01 | 100.03 |
| M104 | 2.5% weight gain of C3 (Table 5) | Ethyl Acetate | 3.3 | 0.01 | 101.12 |
| M107 | 1.25% weight gain of C3 (Table 5) | Ethyl Acetate | 3.3 | 0.00 | 95.85 |
| M107 | 2.5% weight gain of C3 (Table 5) | Ethyl Acetate | 3.3 | 0.00 | 92.99 |
| M104 | 1.25% weight gain of C4 (Table 5) | Ethyl Acetate | 3.3 | 0.08 | 100.02 |
| M104 | 2.5% weight gain of C4 (Table 5) | Ethyl Acetate | 3.3 | 0.09 | 92.20 |
| M107 | 1.25% weight gain of C4 (Table 5) | Ethyl Acetate | 3.3 | 0.00 | 100.00 |
| M107 | 2.5% weight gain of C4 (Table 5) | Ethyl Acetate | 3.3 | 0.01 | 99.96 |
| M104 | 1.25% weight gain of C5 (Table 5) | Ethyl Acetate | 3.3 | 0.01 | 100.85 |
| M104 | 2.5% weight gain of C5 (Table 5) | Ethyl Acetate | 3.3 | 0.01 | 99.56 |
| M107 | 1.25% weight gain of C5 (Table 5) | Ethyl Acetate | 3.3 | 0.00 | 84.45 |
| M107 | 2.5% weight gain of C5 (Table 5) | Ethyl Acetate | 3.3 | 0.00 | 97.68 |
| M104 | 1.25% weight gain of C6 (Table 5) | Ethyl Acetate | 3.3 | 0.49 | 81.38 |
| M104 | 2.5% weight gain of C6 (Table 5) | Ethyl Acetate | 3.3 | 0.81 | 54.35 |
| M107 | 1.25% weight gain of C6 (Table 5) | Ethyl Acetate | 3.3 | 0.39 | 94.73 |
| M107 | 2.5% weight gain of C6 (Table 5) | Ethyl Acetate | 3.3 | 0.80 | 62.42 |
| M104 | 1.25% weight gain of C7 (Table 5) | Ethyl Acetate | 3.3 | 0.07 | 96.68 |
| M104 | 2.5% weight gain of C7 (Table 5) | Ethyl Acetate | 3.3 | 0.36 | 100.41 |
| M107 | 1.25% weight gain of C7 (Table 5) | Ethyl Acetate | 3.3 | 0.00 | 91.11 |
| M107 | 2.5% weight gain of C7 (Table 5) | Ethyl Acetate | 3.3 | 0.21 | 98.27 |
| M107 | 1.25% weight gain of C8 (Table 5) | Ethyl Acetate | 3.3 | 0.56 | 86.36 |
| M107 | 2.5% weight gain of C8 (Table 5) | Ethyl Acetate | 3.3 | 0.83 | 46.97 |

Example 16

Memantine High Drug Loading

This experiment was performed to explore the extrusion of high drug load memantine formulations. Memantine formulations were extruded at 35, 40, 45 and 55% w/w API (named M103, M104, M105 and M106 respectively). All extrusions were performed at a 500 g scale. The formulations in Table 4 were compounded and profile extruded using a Leistritz 18" hot melt extruder. Each formulation was bag blended to create a homogenous mixture. The blended powder was fed into the extruder hopper and compounded using a feed rate of 0.5 kg/hr. The extrudate was cooled and pelletized using an in-line cutter to make pellets of appropriate size mm) for profile extrusion.

Figure 17:
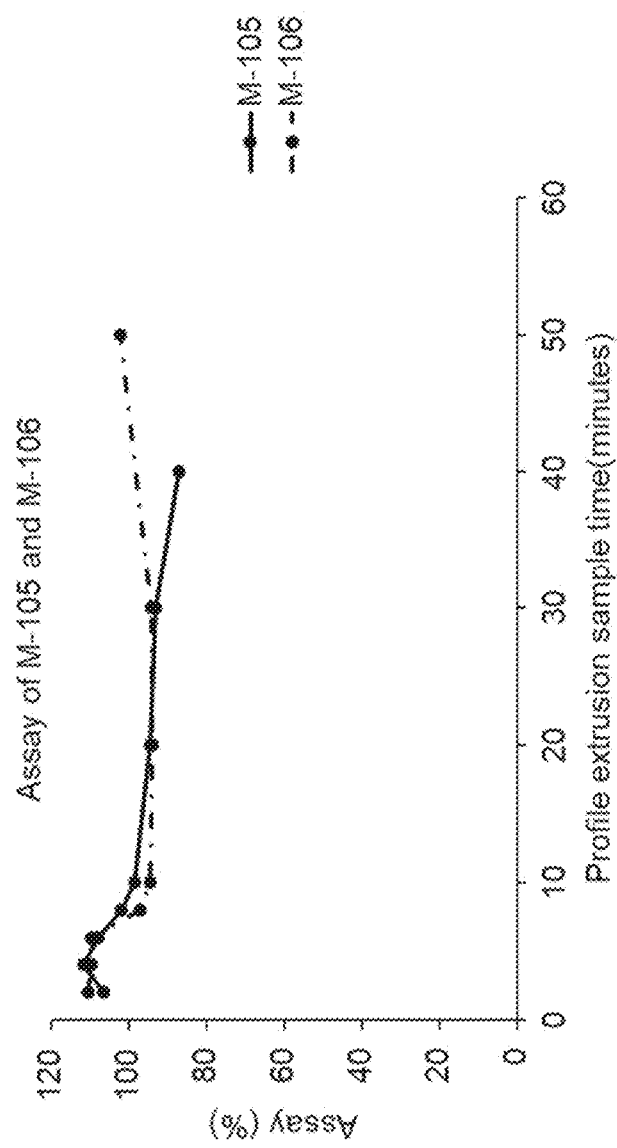
FIG. 17 depicts assays of formulations M105 and M106.
Figure 18:
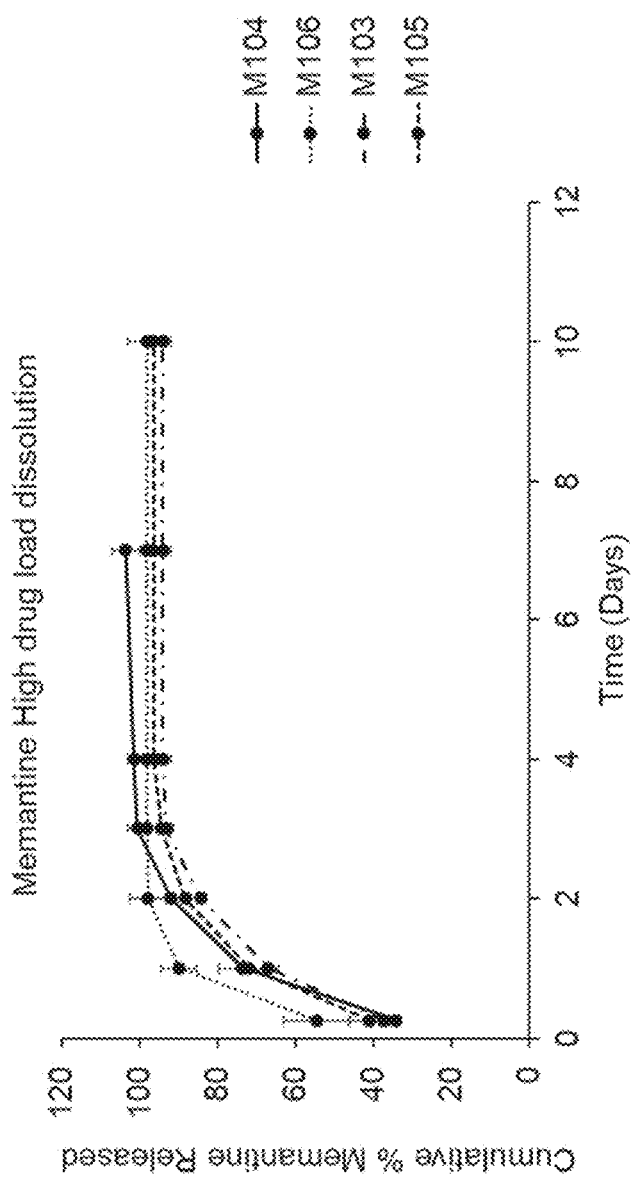
FIG. 18 shows the dissolution of uncoated M103, M104, M105 and M106 formulations in fasted-state simulated gastric fluid (FaSSGF).

The pellets were then fed into the twin screw extruder and profile extruded using a custom triangular die and a feed rate of 0.4-0.5 kg/hr. Samples of the profile extruded drug arms were taken every 2 minutes for the first 10 minutes and one additional sample was taken at the beginning, middle, and end of the process. Samples for M105 and M106 were run for Memantine content analysis. The results show reasonable uniformity with all samples having assay of 85-115% (see FIG. 17). Samples were run for dissolution in fasted simulated gastric fluid (FaSSGF). All samples showed complete release over 3-4 days (see FIG. 18).

TABLE 4

% Composition of Memantine High Drug Load Formulations

| | M103 | M104 | M105 | M106 | M107 |
|---|---|---|---|---|---|
| Memantine HCl | 35.0 | 40.0 | 45.0 | 55.0 | 45.0 |
| Polycaprolactone | 62.0 | 58.0 | 54.0 | 44.0 | 52.0 |
| Poloxamer P407 | 2.0 | 1.0 | 0.0 | 0.0 | 2.0 |
| Colloidal Silicon Dioxide | 0.5 | 0.5 | 0.5 | 0.5 | 0.5 |
| Vitamin E Succinate | 0.5 | 0.5 | 0.5 | 0.5 | 0.5 |
| Total | 100.0 | 100.0 | 100.0 | 100.0 | 100.0 |

Example 17

Coating of High Drug Load Memantine to Control Release Rate

This experiment was performed to explore how coatings containing polycaprolactone, the porogen copovidone and plasticizer triethyl citrate (TEC) can control the release rate of M103, M104, and M105 when applied in a LCDS pan coater.

Two solutions of PCL, copovidone and triethyl citrate were prepared in ethyl acetate at 3.3% w/v. The first coating solution (C1) contained a 95:5 ratio of PCL to copovidone and 10% TEC by coating material, with 2% magnesium stearate as a processing aid. The second solution (C2) contained 80:20 ratio of PCL to copovidone and 15% TEC by coating material, with 2% magnesium stearate as a processing aid. The solution was then applied to drug loaded arms using a Vector LDCS pharmaceutical pan coater. The coating solution was applied to approximately 480 g placebo arms with approximately 5 g of M105 drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 2.5% and 5.0% w/w mass gain.

The process was repeated for M103 and M104. Coating solutions C1 and C2 were prepared again and applied to a coating pan containing approximately 465 g placebo arms with approximately 10 g of M103 and 10 g of M104 drug loaded arms spiked in. Processing conditions were the same as in the previous paragraph.

Figure 19:
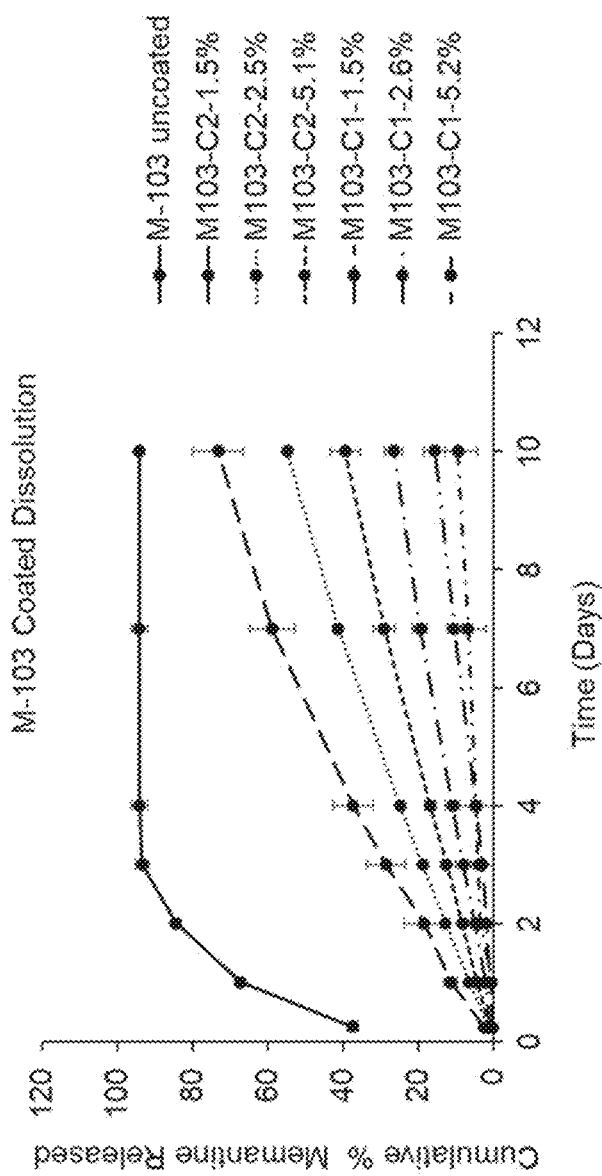
FIG. 19 shows the dissolution of M103 formulations with various coatings (coatings C1, C2 versus uncoated).
Figure 20:
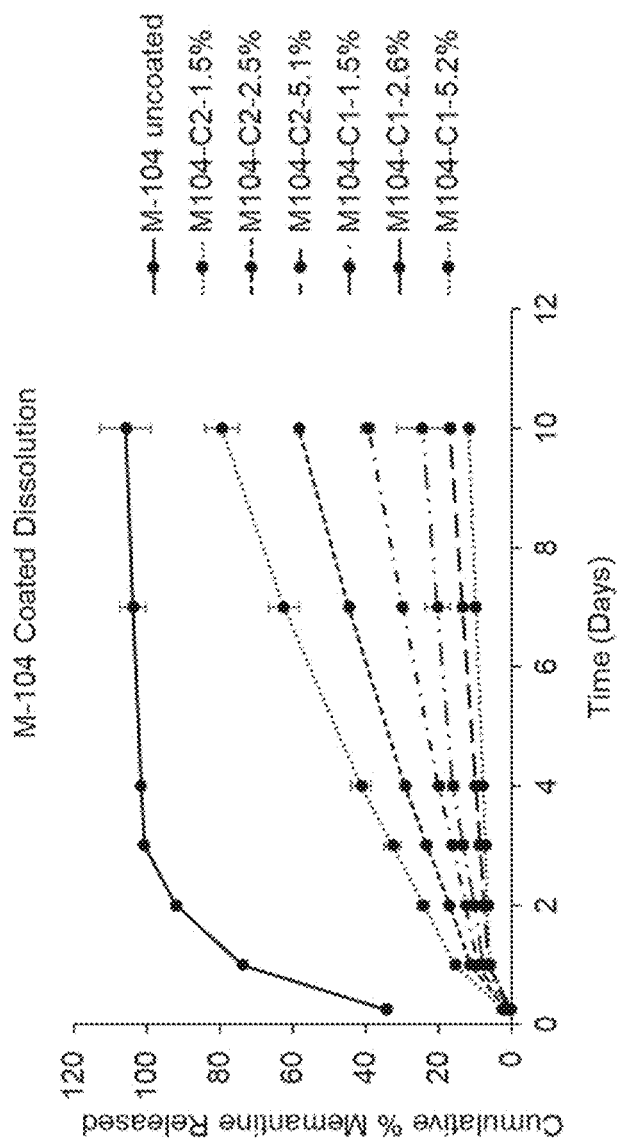
FIG. 20 shows the dissolution of M104 formulations with various coatings (coatings C1, C2 versus uncoated).
Figure 21:
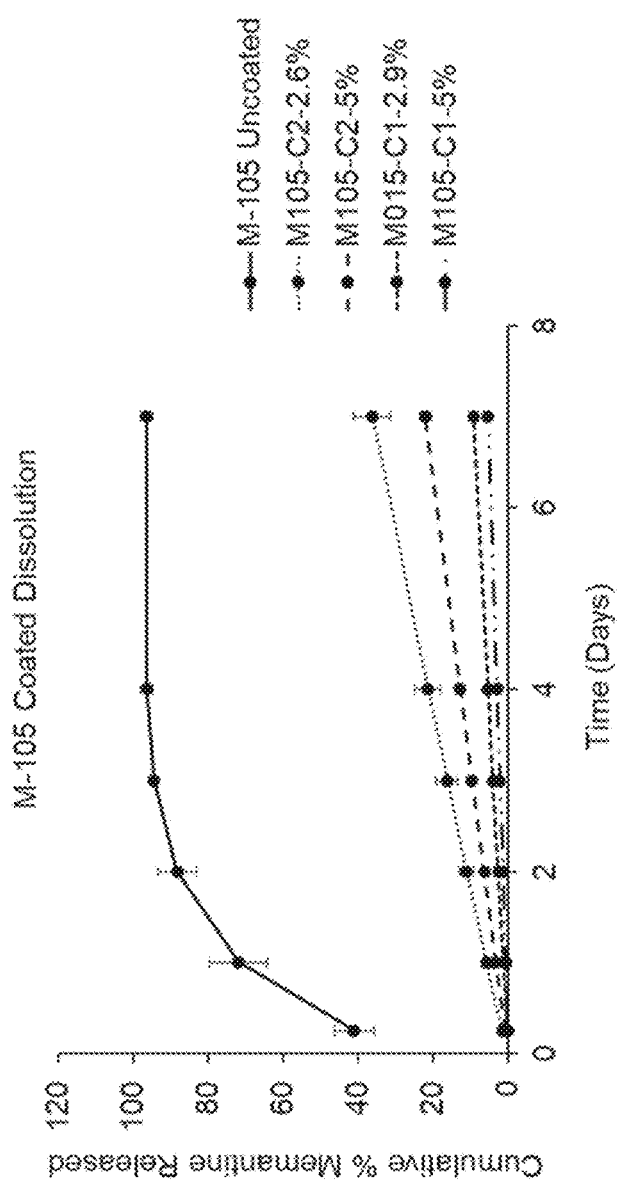
FIG. 21 shows the dissolution of M105 formulations with various coatings (coatings C1, C2 versus uncoated).

All coated material was run for dissolution in FaSSGF. Results showed that the lower amounts of porogen and plasticizer in the C1 coating solution result in relatively slower dissolution at similar coating weights when compared to drug arms coated with the C2 formulation. FIG. 19 shows a graph of dissolution of formulation M103 with C1 coating, C2 coating, and uncoated; FIG. 20 shows a graph of dissolution of formulation M104 with C1 coating, C2 coating, and uncoated; and FIG. 21 shows a graph of dissolution of formulation M105 with C1 coating, C2 coating, and uncoated. For both coating formulations, increased coating weight causes slower dissolution. These dissolution experiments show that the rate of release from all high drug load Memantine formulations tested can be controlled with as little as 1.5% coating weight. Coated formulations show higher linearity than the corresponding uncoated formulation. For example, formulation M104 with C1 coating display correlation co-efficient ($R^2$) values of 0.89, 0.84, 0.73 respectively for coating weights of 1.5%, 2.5%, 5.1% and M104 with C2 coating display correlation co-efficient ($R^2$) values of 0.98, 0.98, 0.96 respectively for coating weights of 1.5%, 2.5%, 5.2% while the uncoated M104 formulation displays a correlation co-efficient ($R^2$) value of 0.58.

Example 18

Coating of High Drug Load Formulations to Increase Extent of Release

This experiment was performed to increase the extent of API release from Example 17 using polycaprolactone coatings, with increased amounts of porogen and the plasticizer triethyl citrate (TEC) to control the release rate of M104 and M107 when applied in a LCDS pan coater.

Six additional solutions of PCL, copovidone and triethyl citrate were prepared in ethyl acetate at 3.3% w/v. The first coating solution (C3) contained a 70:30 ratio of PCL to copovidone and 30% TEC by coating material, with 2% magnesium stearate as a processing aid. The second solution (C4) contained 80:20 ratio of PCL to copovidone and 30% TEC by coating material, with 2% magnesium stearate as a processing aid. The third solution (C5) contained 70:30 ratio of PCL to copovidone and 20% TEC by coating material, with 2% magnesium stearate as a processing aid. The forth solution (C6) contained 80:20 ratio of PCL to copovidone and 20% TEC by coating material, with 2% magnesium stearate as a processing aid. The fifth solution (C7) contained 75:25 ratio of PCL to copovidone and 15% TEC by coating material, with 2% magnesium stearate as a processing aid. The sixth solution (C8) contained 80:20 ratio of PCL to copovidone and 10% TEC by coating material, with 2% magnesium stearate as a processing aid. Coating formulations are summarized in Table 5. The solution was then applied to drug loaded arms using a Vector LDCS pharmaceutical pan coater. The coating solution was applied to approximately 480 g placebo arms with approximately 5 g of M105 drug loaded arms spiked in. The pan speed was set at 20-22 RPM and the product temperature was approximately 40° C. After coating the arms were dried for approximately 5 minutes to drive off any residual ethyl acetate. The entire batch of coated placebo and drug loaded arms were weighed to determine the percent mass gain of coating applied. Drug arms were coated to approximately 1.25% and 2.5% w/w mass gain. For every run M104 and M107 were coated in the same batch.

Figure 22:
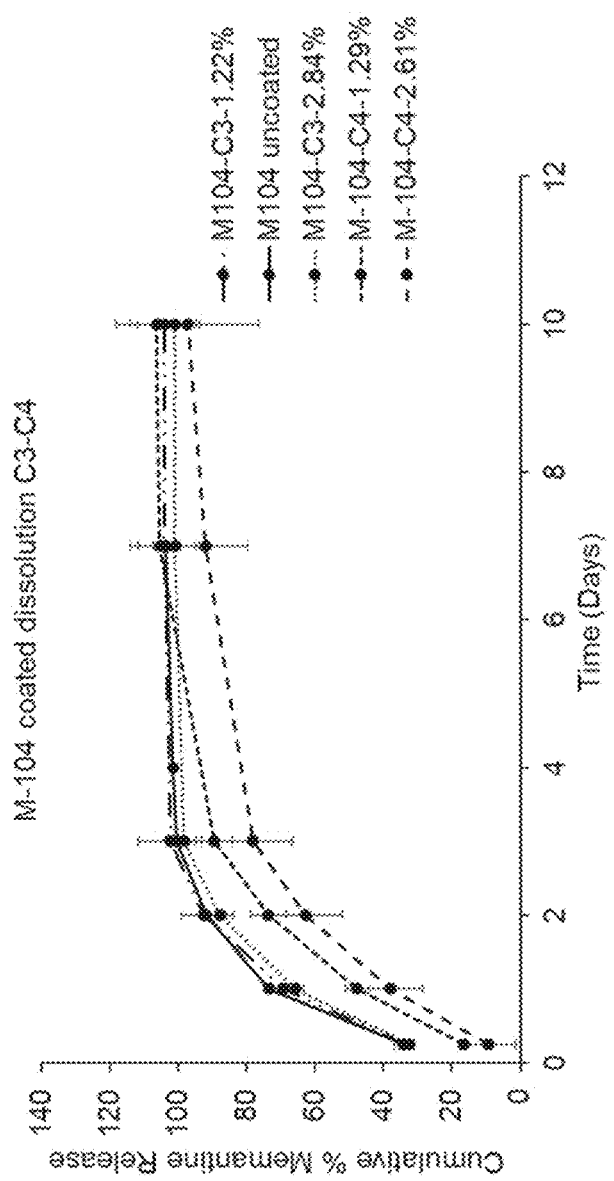
FIG. 22 shows the dissolution of M104 formulations with various coatings (coatings C3, C4 versus uncoated).
Figure 23:
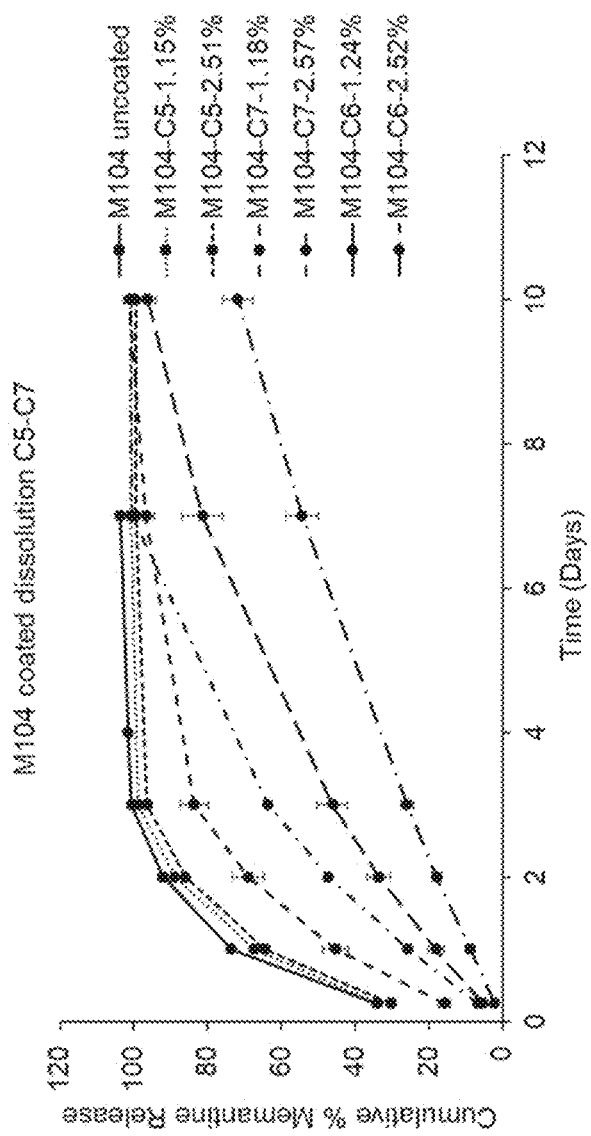
FIG. 23 shows the dissolution of M104 formulations with various coatings (coatings C5, C6, C7 versus uncoated).
Figure 24:
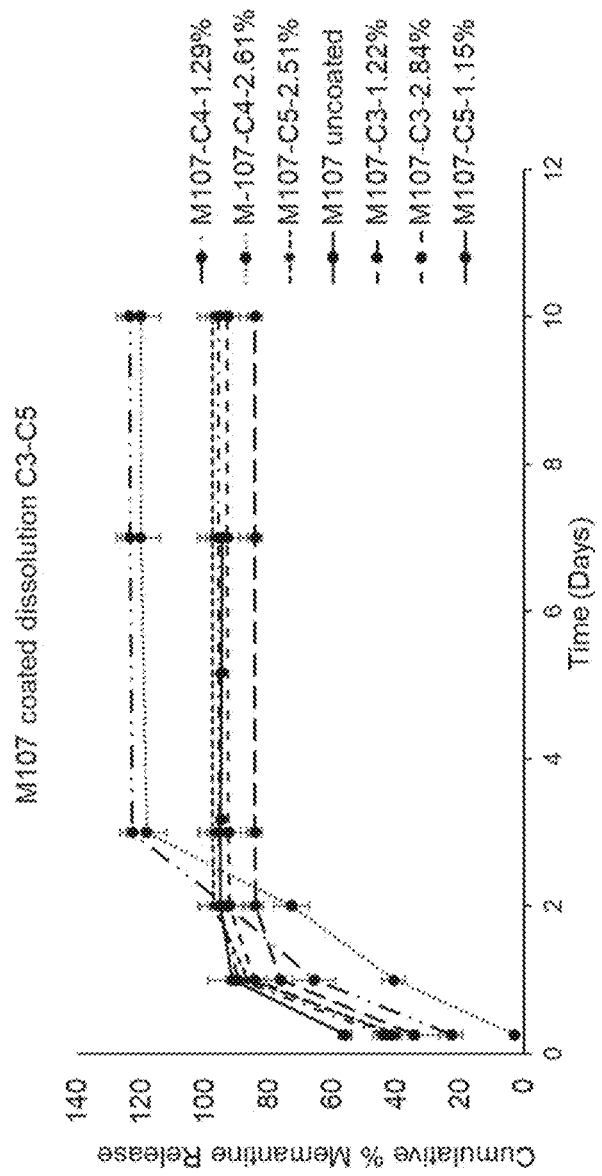
FIG. 24 shows the dissolution of M107 formulations with various coatings (coatings C3, C4, C5 versus uncoated).
Figure 25:
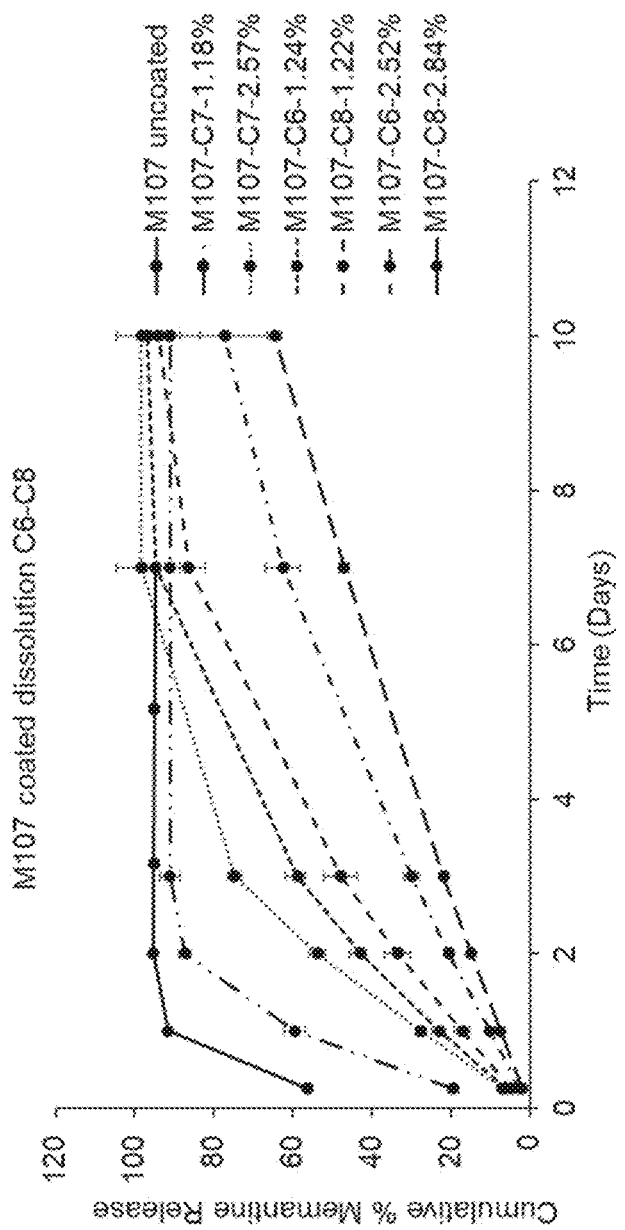
FIG. 25 shows the dissolution of M107 formulations with various coatings (coatings C6, C7, C8 versus uncoated).

All coated material was run for dissolution in FaSSGF. Results showed that the increased amounts of porogen and plasticizer in the C3, C4, C5 and C7 coating solution offer essentially no control of drug release compared to the uncoated arms at the coating weights tested. However, coatings C6 and C8 show sustained release over seven days for both drug arm formulations at all coating weights. Only coatings with <20% copovidone and 20% triethyl citrate show controlled release compared to the uncoated drug arms. FIG. 22 shows a graph of dissolution of formulation M104 with C3 coating, C4 coating, and uncoated. FIG. 23 shows a graph of dissolution of formulation M104 with C5 coating, C6 coating, C7 coating, and uncoated. FIG. 24 shows a graph of dissolution of formulation M107 with C3 coating, C4 coating, C5 coating, and uncoated. FIG. 25 shows a graph of dissolution of formulation M107 with C6 coating, C7 coating, C8 coating, and uncoated.

TABLE 5

% w/w Composition of Coating Formulations

|  | C1 | C2 | C3 | C4 | C5 | C6 | C7 | C8 |
|---|---|---|---|---|---|---|---|---|
| polycaprolactone | 83.8 | 66.7 | 48.0 | 54.9 | 54.9 | 62.7 | 62.5 | 70.6 |
| copovidone | 4.4 | 16.6 | 20.6 | 13.7 | 23.5 | 15.7 | 20.8 | 17.6 |
| Triethyl citrate | 9.8 | 14.7 | 29.4 | 29.4 | 19.6 | 19.6 | 14.7 | 9.8 |
| Magnesium stearate | 2.0 | 2.0 | 2.0 | 2.0 | 2.0 | 2.0 | 2.0 | 2.0 |
| Total | 100.0 | 100.0 | 100.0 | 100.0 | 100.0 | 100.0 | 100.0 | 100.0 |

Example 19

Pan Coating of Donepezil High Drug Load Formulations with PCL

This experiment was performed to demonstrate how a polycaprolactone (PCL) coating affects the release rate of donepezil from the dosage unit after coating in a pharmaceutical pan coater. A solution of PCL, copovidone and triethyl citrate (TEC) was prepared in ethyl acetate at 3.3% w/v with a 70:17:13 ratio of PCL to copovidone to TEC. The solution was applied to drug-loaded arms containing 40% donepezil HCl (w/w) using a Vector LDCS pharmaceutical pan coater. The coating solution was applied to a pre-weighed bed of placebo arms (approximately 450 g) with a small quantity (approximately 80 arms) of drug loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 2.5% and 5% w/w mass gain.

Figure 26:
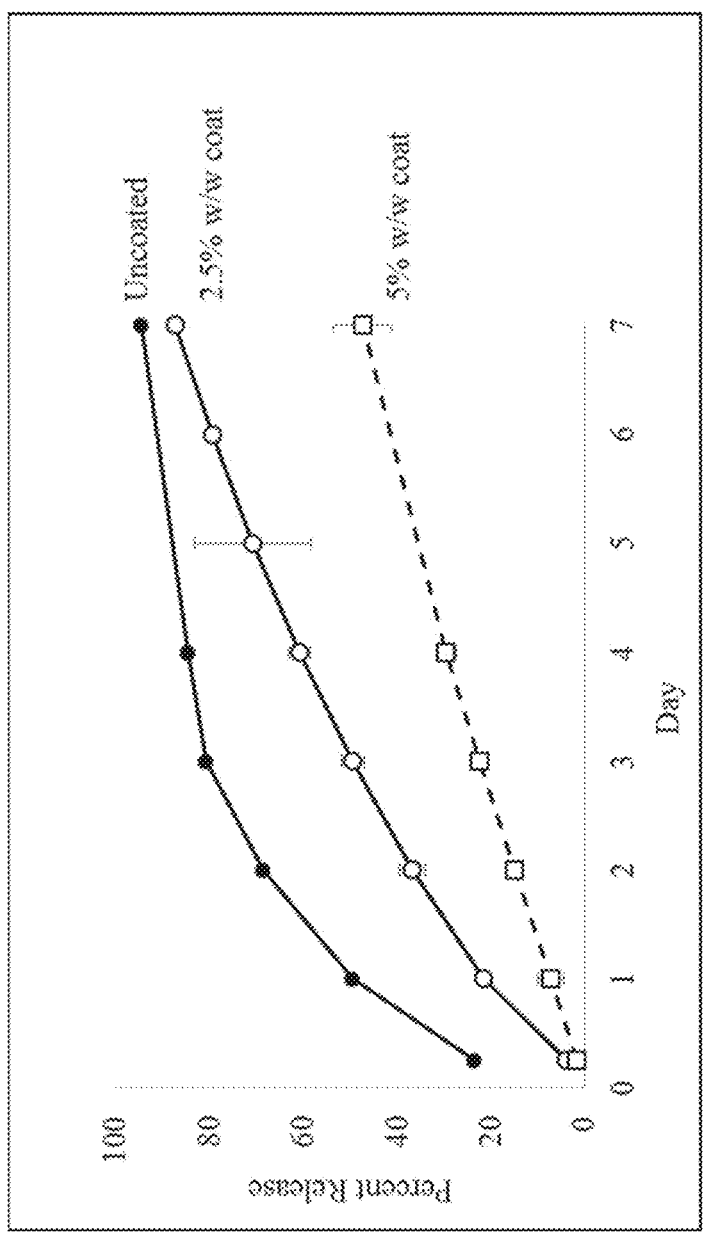
FIG. 26 shows percent release over time of donepezil from formulations with various coatings (2.5% w/w and 5% w/w) versus uncoated formulations.

Triplicate samples of 50 mg of formulated matrix, with or without coating, were placed in 15-ml conical tubes containing 10 ml FaSSGF. Tubes were placed in an incubator shaker at 37° C., 200 rpm. 1 ml aliquots were collected at approximately 0.25, 1, 2, 3, 4, 5, 6 and 7 days. At each sampling the remaining media was discarded and replaced with 10 ml of fresh FaSSGF. Sample aliquots were analyzed directly on HPLC. The results are shown in FIG. 26, and demonstrate that coating improves linearity of release of drug from the arms.

Example 20

Dip Coating Provides Release Rate Control for Doxycycline High Drug Load Formulations Drug Arm Formulation Preparation: Doxycycline hyclate was blended with PCL and other excipients on a Haake MiniCTW micro-compounder by first adding PCL to form a bed on heated screws, followed by the powdered active pharmaceutical ingredient with excipients, then with the balance of required PCL. Batch mixing was performed at 100'C at 75 rpm for 10 minutes and sample was extruded at 20-30 rpm into 2-mm cylinders and compression molded to obtain 18 mm or 20 mm long triangular-cross section forms and allowed to cool and harden at room temperature. Arm formulations used are listed in Table 6.

TABLE 6

| Name | Composition | Function |
|---|---|---|
| DX21 | 7% ERL + 5% P407 | Lead formulations for coating |
| DX23 | 6% ERS + 6% ERL + 2% P407 | Lead formulations for coating |

All formulations contained 25% Doxycycline Hyclate (granulated), 0.5% SiO2, 0.5% alpha-tocopherol, and balance 80 k PCL.
ERL—Eudragit RL;
ERS—Eudragit RS Dip coating: Coating solutions were prepared by weighing excipients into a 20 mL scintillation vial, adding a magnetic stir bar, adding solvent, capping, and vortexing, and were allowed to stir at 25° C. (EC) or 40° C. (PCL) overnight until a clear, homogenous solution had been achieved. Compositions of coating solutions are listed in Table 7, as the percentage of coating material (e.g., 80 k PCL) in solution in the solvent indicated (e.g., ethyl acetate). Drug arms were gripped with forceps, completely submerged in the coating solution, and immediately removed. Coated arms were dried in a fume hood overnight.

TABLE 7

| Base Polymer | Coating solution composition | Solvent |
|---|---|---|
| 80 k PCL (Sigma) | 8% 80 k PCL<br>9% 80 k PCL<br>10% 80 k PCL<br>12% 80 k PCL | Ethyl acetate |

TABLE 7-continued

| Base Polymer | Coating solution composition | Solvent |
|---|---|---|
| Ethyl cellulose (EC) | 15% 80 k PCL<br>18% 80 k PCL<br>10% (9:1) 80 k PCL:TEC<br>12% (9:1) 80 k PCL:TEC<br>6.67% Ethyl cellulose Cp10<br>12% Ethyl cellulose Cp10<br>13.34% Ethyl cellulose CP10<br>15% Ethyl cellulose Cp10<br>18% Ethyl cellulose Cp10 | Acetone |

In Vitro Release: Each formulation was evaluated for release in fasted state simulated gastric fluid (FaSSGF) for seven days. Approximately 50 mg of formulated matrix, with or without coating, was cut and placed in 15-ml conical tubes containing 10 ml FaSSGF. Tubes were placed in an incubator shaker at 37° C., 200 rpm. 1 ml aliquots were collected at approximately 0.25, 1, 2, 3, 4, 5, 6 and 7 days. At each sampling the remaining media was discarded and replaced with 10 ml of fresh FaSSGF. Sample aliquots were analyzed directly on HPLC.

Figure 27:
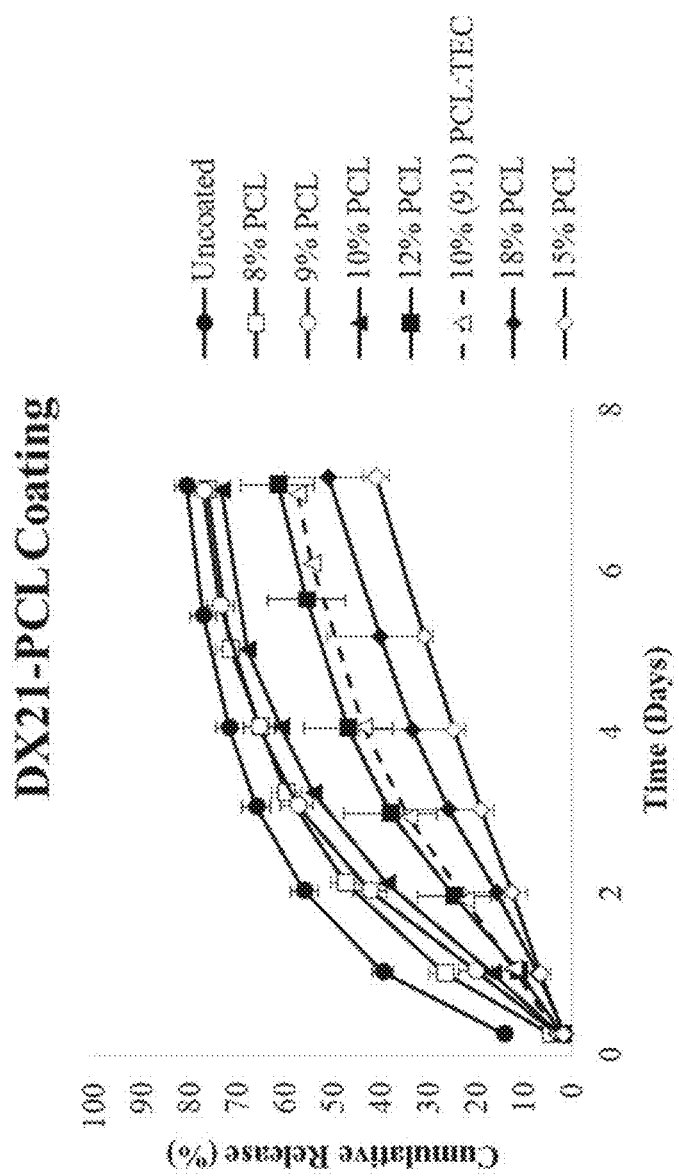
FIG. 27 shows percent release over time of doxycycline from formulations with various polycaprolactone-based coatings ("DX21-PCL" coatings) versus uncoated formulations.
Figure 28:
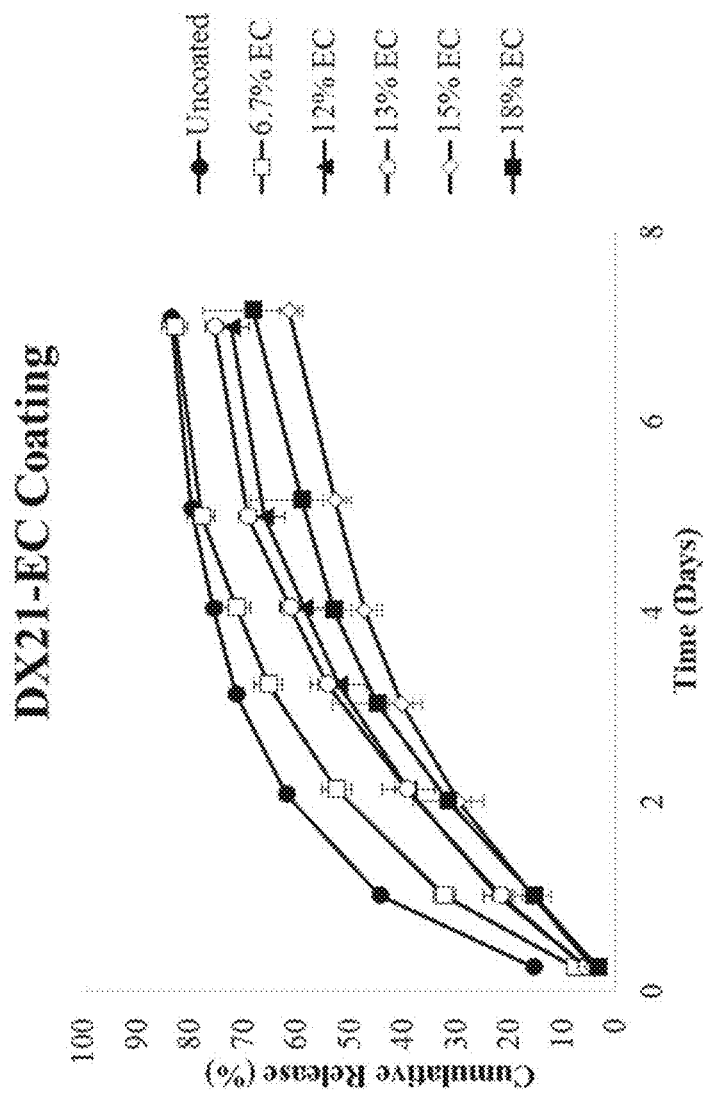
FIG. 28 shows percent release over time of doxycycline from formulations with various ethyl celluose-based coatings ("DX21-EC" coatings) versus uncoated formulations.
Figure 29:
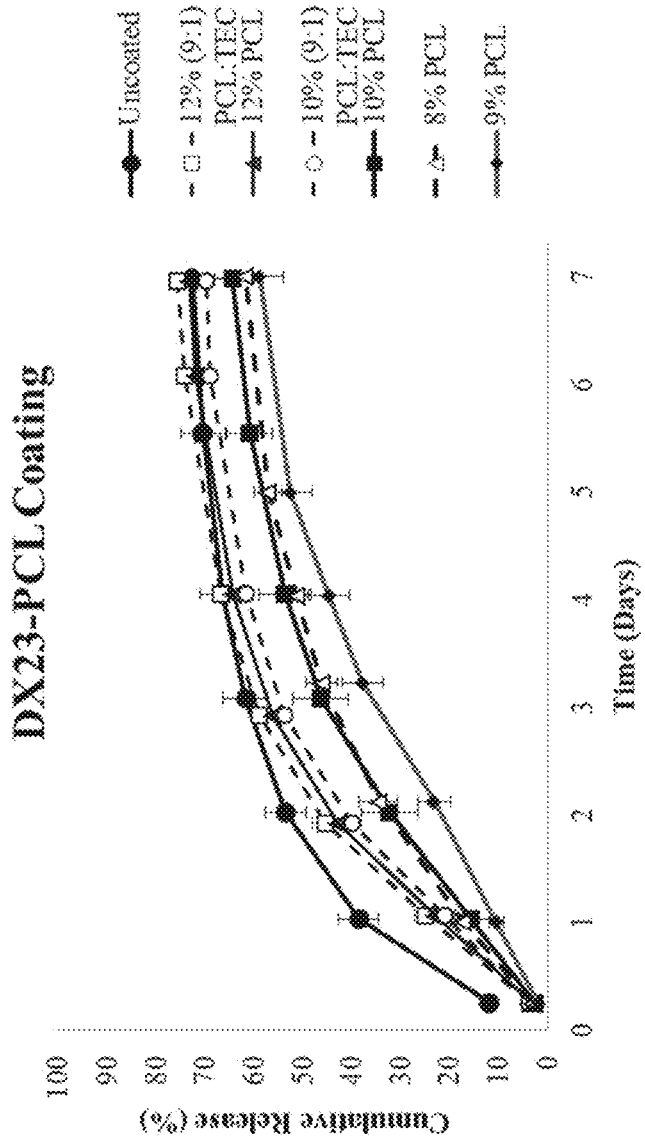
FIG. 29 shows percent release over time of doxycycline from formulations with various polycaprolactone-based coatings ("DX23-PCL" coatings) versus uncoated formulations.
Figure 30:
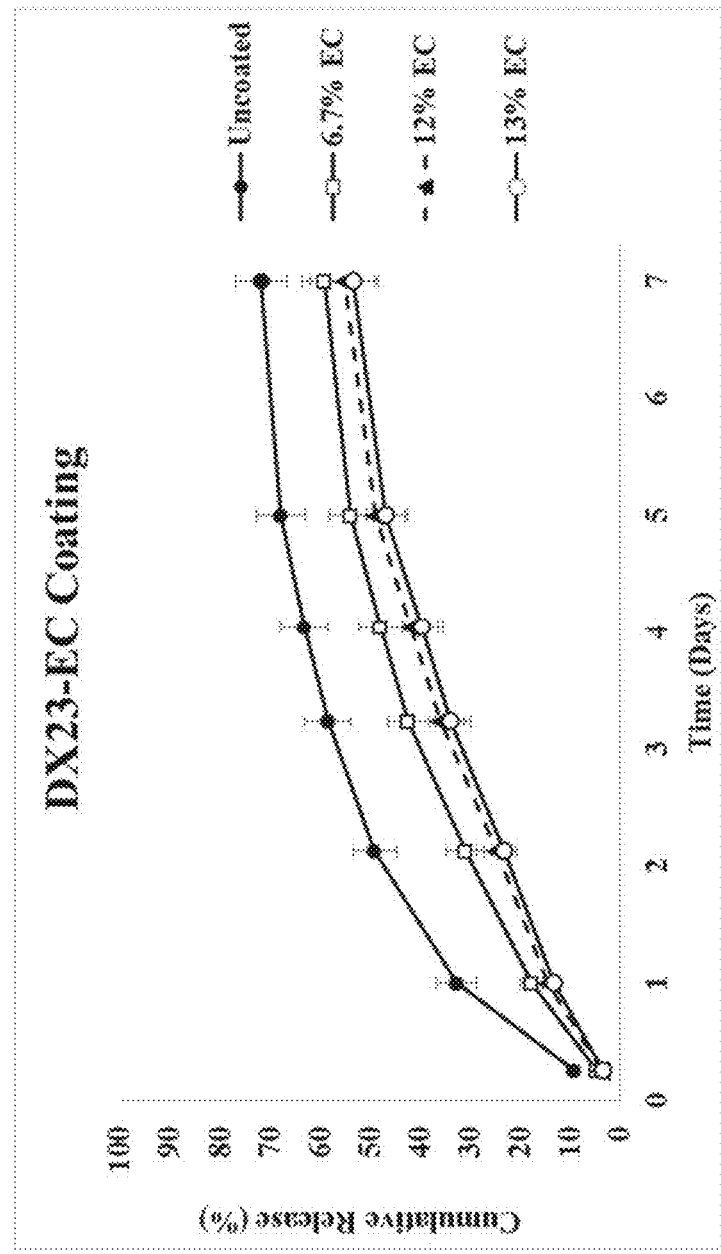
FIG. 30 shows percent release over time of doxycycline from formulations with various ethyl celluose-based coatings ("DX23-EC" coatings) versus uncoated formulations.

FIG. 27 shows release curves from DX21 Doxycycline Hyclate hot melt extrusion (HME) formulations with 80 k PCL coatings. FIG. 28 show release curves from DX21 Doxycycline Hyclate HME formulations with ethyl cellulose coatings. FIG. 29 shows release curves from DX23 Doxycycline Hyclate HME formulations with 80 k PCL coatings. FIG. 30 show release curves from DX23 Doxycycline Hyclate HME formulations with ethyl cellulose coatings.

The results show that release of doxycycline can be modulated and controlled by use of an appropriate release-rate modulating film, such as the highly linear release rate achieved over 7 days by dip-coating into 15% PCL and 18% PCL solutions in ethyl acetate, as shown in FIG. 27.

Example 21

Reduction of pH Effect on Release Due to Pan Coating of Risperidone High Drug Load Formulations With PCL This experiment was performed to evaluate whether a polycaprolactone (PCL) coating affects reduces the effect of media pH on the rate of risperidone release from the dosage unit after coating in a pharmaceutical pan coater. Risperidone is an example of a drug for which the solubility is significantly higher at the more acidic end of the gastric pH range (e.g., pH 1.5) than at the less acidic end of the gastric pH range (e.g., pH 4.8), resulting in faster dissolution rates at the lower pH. The release rate control imparted by PCL-based coating is shown to reduce the ratio between percent drug released at different pHs over time.

A solution of PCL, copovidone and triethyl citrate (TEC) was prepared in ethyl acetate at 3.3% w/v with a 68:22:10 ratio of PCL to copovidone to TEC. The solution was applied to two different formulations of risperidone-loaded aims containing 40% risperidone (w/w) using a Vector LDCS pharmaceutical pan coater. Formulation 1 consisted of 40% risperidone, 10% Soluplus, 5% Kollidon CL, 5% P407, 0.5% α-tocopherol succinate, 0.5% silica MSP, and 39% cryomilled Purac PC17 polycaprolactone. Formulation 2 consisted of 40% risperidone, 5% dicalcium phosphate, 5% P407, 0.5% α-tocopherol succinate, 0.5% silica MSP, and 49% cryomilled Purac PC17 polycaprolactone. The coating solution was applied to a pre-weighed bed of placebo arms (approximately 450 g) with a small quantity (approximately 40 aims) of drug-loaded arms spiked in. The pan speed was set at 20-22 RPM and the product temperature was approximately 40° C. After coating, the arms were dried for approximately 5 minutes to drive off any residual ethyl acetate. The entire batch of coated placebo and drug loaded arms were weighed to determine the percent mass gain of coating applied. Drug arms were coated to approximately 4.5% w/w mass gain.

Samples of ~50 mg of formulated matrix, with or without coating, were placed in 20-ml glass vials containing 10 ml FaSSGF pH 1.5 or ammonium acetate pH 4.8. Tubes were placed in an incubator shaker at 37° C., 200 rpm. 1 ml aliquots were collected at approximately 6 and 24 hours. At each sampling the remaining media was discarded and replaced with 10 ml of fresh FaSSGF or fresh ammonium acetate buffer pH 4.8. Sample aliquots were analyzed directly on HPLC. The presence of the release-rate modulating coating approximately halved the effect of pH on release rate as measured at a 6 hour time point and reduced the effect of pH on release by about ⅓ as measured at a 24 h time point. The results are shown in Table 8, and demonstrate that coating reduces the difference in relative dependence of rates on media pH.

TABLE 8

| | 6 hour % Release | | | 24 hour % Release | | |
|---|---|---|---|---|---|---|
| Formulation | pH 1.5 | pH 4.8 | Rate Ratio (pH 1.5/pH 4.8) | pH 1.5 | pH 4.8 | Rate Ratio (pH 1.5/pH 4.8) |
| Uncoated Formulation 1 | 43.8 | 14.6 | 3.0 | 84.0 | 29.9 | 2.8 |
| Coated Formulation 1 | 16.4 | 10.5 | 1.6 | 55.7 | 27.5 | 2.0 |
| Uncoated Formulation 2 | 42.2 | 15.6 | 2.7 | 81.8 | 33.5 | 2.4 |
| Coated Formulation 2 | 12 9 | 9.4 | 1.4 | 40.8 | 25.1 | 1.6 |

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A gastric residence system comprising a therapeutically effective amount of an agent or a pharmaceutically acceptable salt thereof, wherein:

the gastric residence system has a compacted configuration and an uncompacted configuration, the gastric residence system comprises a plurality of elongate members affixed to a central elastomer, wherein at least one elongate member comprises:
a carrier polymer,
the agent or the pharmaceutically acceptable salt thereof, and
a release-rate modulating polymer film coated on the surface of the at least one elongate member, wherein the release-rate modulating polymer film is configured such that the release of agent or salt thereof from the system in 40% ethanol/60% simulated gastric fluid over one hour is no more than about 40% higher compared to release of agent or salt thereof from an equivalent system in 100% simulated gastric fluid over one hour, wherein the release rate-modulating polymer film comprises one or more polyester materials with a repeating unit of the form $—R^1—O—C(\!=\!O)—$, wherein $R^1$ is selected from the group consisting of $C_1$-$C_{12}$ alkylene groups, ethers containing between two and twelve carbon atoms, and polyethers containing between three and twelve carbon atoms;

wherein the gastric residence system is configured to release the agent or the pharmaceutically acceptable salt thereof over a specified gastric residence period.

2. The gastric residence system of claim 1, wherein the release-rate modulating polymer film comprises polycaprolactone or polydioxanone.

3. The gastric residence system of claim 1, wherein the release-rate modulating polymer film comprises at least two different polyester materials.

4. The gastric residence system of claim 1, wherein the $R^1$ groups in the polymer are the same moiety, such that the polymer is a homopolymer.

5. The gastric residence system of claim 1, wherein the $R^1$ groups are chosen from two or more different moieties, such that the polymer is a heteropolymer.

6. The gastric residence system of claim 5, wherein the heteropolymer is a block copolymer.

7. The gastric residence system of claim 5, wherein the heteropolymer is a random copolymer.

8. The gastric residence system of claim 1, wherein the polymer film comprises at least two different polyesters, each different polyester with a repeating unit of the form:

$$—R''—O—C(\!=\!O)—$$

wherein:
when at least two or more of the different polyesters are homopolymers, the $R''$ group of any one of the homopolymers is different from the $R''$ group of any other of the homopolymers; and
when at least two or more of the different polyesters are heteropolymers, each heteropolymer has a different varying pattern of $R''$ groups than the varying pattern of $R''$ groups of any of the other heteropolymers; and
each $R''$ is selected from the group consisting of $C_1$-$C_{12}$ alkylene groups, ethers containing between two and twelve carbon atoms, and polyethers containing between three and twelve carbon atoms.

9. The gastric residence system of claim 1, wherein the polymer film comprises polycaprolactone.

10. The gastric residence system of claim 1, wherein the polymer film comprises polycaprolactone of about 50,000 Mn to about 110,000 Mn.

11. The gastric residence system of claim 1, wherein the polymer film comprises polycaprolactone of about 80,000 Mn to about 110,000 Mn.

12. The gastric residence system of claim 1, wherein the polymer film comprises polycaprolactone of about 60,000 Mn to about 100,000 Mn.

13. The gastric residence system of claim 1, wherein the polymer film comprises polycaprolactone having intrinsic viscosity of about 1.5 dL/g to about 2.1 dL/g.

14. The gastric residence system of claim 1, wherein the polymer film comprises polycaprolactone having intrinsic viscosity of about 1.0 dL/g to about 2.1 dL/g.

15. The gastric residence system of claim 1, wherein the polymer film further comprises a porogen.

16. The gastric residence system of claim 15, wherein the porogen comprises a water-soluble polymer, a water-soluble small molecule, an inorganic salt, or an organic salt.

17. The gastric residence system of claim 15, wherein the porogen comprises about 5% to about 40% by weight of the film.

18. The gastric residence system of claim 15, wherein the porogen comprises about 5% to about 30% by weight of the film.

19. The gastric residence system of claim 15, wherein the porogen is selected from the group consisting of alkali metal salts, sodium chloride, sodium bromide, potassium chloride, potassium sulfate, potassium phosphate, sodium benzoate, sodium acetate, sodium citrate, potassium nitrate, alkaline earth metal salts, calcium chloride, calcium nitrate, transition metal salts, ferric chloride, ferrous sulfate, zinc sulfate, cupric chloride, saccharides, sugars, sucrose, glucose, fructose, mannose, galactose, aldohexose, altrose, talose, lactose, cellulose, monosaccharides, disaccharides, water soluble polysaccharides, sorbitol, mannitol, organic aliphatic and aromatic oils, dials, polyols, polyhydric alcohols, poly(alkylene glycols), polyglycols, alkylene glycols, poly vinylalcohol, poly vinyl pyrrolidone, water soluble polymeric materials, Poloxamer, hypromellose (HPMC), polyoxyl 40 hydrogenated castor oil, polyvinyl caprolactam, polyvinyl acetate (PVAc), polyethylene glycol (PEG), copolymer of polyvinyl caprolactam, polyvinyl acetate, and polyethylene glycol, copovidone, a cationic copolymer comprising dimethylamino ethyl methylacrylate and neutral methylacrylic acid esters, ammoniomethacrylate copolymers, poly(methyl vinyl ether-alt-maleic anhydride), polyoxyethylene alkyl ethers, polysorbates, polyoxyethylene stearates, polydextrose, polyacrylic acid, alginates, sodium starch glycolate, crosslinked polyacrylic acid, crosslinked PVP crosslinked cellulose, calcium silicate, xanthan gum, and gellan gum.

20. The gastric residence system of claim 1, wherein the polymer film further comprises a plasticizer.

21. The gastric residence system of claim 20, wherein the plasticizer comprises triethyl citrate, triacetin, PEG, poloxamer, tributyl citrate, or dibutyl sebacate.

22. The gastric residence system of claim 20, wherein the plasticizer comprises about 1% to about 30% by weight of the film.

23. The gastric residence system of claim 20, wherein the plasticizer comprises about 5% to about 30% by weight of the film.

24. The gastric residence system of claim 1, wherein the polymer film further comprises an anti-tack agent.

25. The gastric residence system of claim 24, wherein the anti-tack agent is selected from the group consisting of magnesium stearate, talc, and glycerol monostearate.

26. The gastric residence system of claim 1, wherein the polymer film further comprises a permeable component which is permeable to the agent or salt thereof, permeable to water, or both permeable to the agent or salt thereof and permeable to water.

27. The gastric residence system of claim 26, wherein the permeable component is selected from the group consisting of sodium starch glycolate (SSG), crospovidone, croscarmellose, and crosslinked polyacrylic acid.

28. The gastric residence system of claim 1, wherein the carrier polymer comprises a polylactone.

29. The gastric residence system of claim 28, wherein the polylactone of the carrier polymer comprises polycaprolactone.

30. The gastric residence system of claim 29, wherein the polycaprolactone of the carrier polymer has an average $M_n$ of about 50,000 to about 110,000.

31. The gastric residence system of claim 29, wherein the polycaprolactone of the carrier polymer has an average $M_n$ of about 60,000 to about 100,000.

32. The gastric residence system of claim 29, wherein the polycaprolactone of the carrier polymer has an average $M_n$ of about 80,000 to about 110,000.

33. The gastric residence system of claim 1, wherein the elongate members further comprise at least one excipient.

34. The gastric residence system of claim 33, wherein the at least one excipient is selected from the group consisting of poloxamer P407, a cationic copolymer comprising dimethylamino ethyl methylacrylate and neutral methylacrylic acid esters, PEG, Polyvinylpyrrolidone (PVP), Polyvinyl acetate (PVAc), Polyvinyl alcohol (PVA), ammoniomethacrylate copolymers, PLA, PLGA, PLA-PCL, polydioxanone, crospovidone, croscarmellose, HPMCAS, Lecithin, Taurocholate, SDS, copolymer of polyvinyl caprolactam, fatty acids, polyoxyl 40 hydrogenated castor oil, and linear, block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; linear copolymers of caprolactone and glycolide; polyaxial block copolymers of glycolide, caprolactone, and trimethylene carbonate; polyaxial block copolymers of glycolide, trimethylene carbonate, and lactide; polyaxial block copolymers of glycolide, trimethylene carbonate and polypropylene succinate; polyaxial block copolymers of caprolactone, lactide, glycolide, and trimethylene carbonate; polyaxial block copolymers of glycolide, trimethylene carbonate, and caprolactone; and linear block copolymers of lactide, caprolactone, and trimethylene carbonate.

35. The gastric residence system of claim 33, wherein the at least one excipient comprises a polyalkylene glycol.

36. The gastric residence system of claim 1, wherein the elongate members further comprise an anti-oxidant or further comprise silica.

37. The gastric residence system of claim 1, wherein the central elastomer comprises silicone rubber.

38. The gastric residence system of claim 1, wherein the elongate members are affixed to the central elastomer via linkers, wherein the linkers are configured to weaken or degrade to allow passage of the gastric residence system through the pylorus after the specified gastric residence period.

39. The gastric residence system of claim 1, wherein at least one elongate member comprises at least two segments joined by linkers, wherein the linkers are configured to weaken or degrade to allow passage of the gastric residence system through the pylorus after the specified gastric residence period.

40. The gastric residence system of claim 38, wherein the linkers comprise hydroxypropyl methyl cellulose-acetate succinate (HPMCAS) and polycaprolactone.

41. The gastric residence system of claim 1, wherein the system has a gastric residence period of about four days to about ten days when administered to a human patient.

42. The gastric residence system of claim 1, wherein the agent or pharmaceutically acceptable salt thereof comprises about 25% to about 60% by weight of the at least one elongate member.

43. The gastric residence system of claim 1, wherein the agent or pharmaceutically acceptable salt thereof comprises about 40% to about 60% by weight of the at least one elongate member.

44. The gastric residence system of claim 1, wherein the agent or pharmaceutically acceptable salt thereof is present in an amount by weight of between about 67% and about 150% of the weight of the carrier polymer.

45. A gastric residence system providing an extended release agent dosage form, comprising:
a plurality of elongate members, wherein at least one elongate member comprises a therapeutically effective amount of an agent or a pharmaceutically acceptable salt thereof and a carrier polymer,
wherein the agent or pharmaceutically acceptable salt thereof is blended with the carrier polymer such that the agent or salt thereof is distributed throughout the at least one elongate member, and
a release-rate modulating polymer film coating the at least one elongate member, wherein the release-rate modulating polymer film is configured such that the release of agent or salt thereof from the system in 40% ethanol/60% simulated gastric fluid over one hour is no more than about 40% higher compared to release of agent or salt thereof from an equivalent system in 100% simulated gastric fluid over one hour, wherein the release rate-modulating polymer film comprises one or more polyester materials with a repeating unit of the form —$R^1$—O—C(=O)—, wherein $R^1$ is selected from the group consisting of $C_1$-$C_{12}$ alkylene groups, ethers containing between two and twelve carbon atoms, and polyethers containing between three and twelve carbon atoms;
wherein the agent or pharmaceutically acceptable salt thereof comprises about 25% to about 60% by weight of the at least one elongate member;
wherein the plurality of elongate members are attached to a central elastomer; and wherein said gastric residence system provides extended release of the agent or pharmaceutically acceptable salt thereof.

46. The gastric residence system of claim 45, wherein the agent or pharmaceutically acceptable salt thereof comprises about 40% to about 60% by weight of the at least one elongate member.

47. The gastric residence system of claim 1, wherein the agent or pharmaceutically acceptable salt thereof has a difference in solubility of a factor of about 5 or more at two different pH values between about pH 1 and about pH 6.

48. The gastric residence system of claim 1, wherein the gastric residence system has a pH-dependent release rate ratio factor of about 3 or less at two different pH values between about pH 1 and about pH 6.

49. The gastric residence system of claim 1, wherein the gastric residence system has a pH-dependent release rate ratio factor of about 2 or less at two different pH values between about pH 1 and about pH 6.

50. The gastric residence system of claim 47, wherein the two different pH values are pH 1.5 and pH 4.8.

51. The gastric residence system of claim 47, wherein the two different pH values are at least 2 pH units apart.

52. The gastric residence system of claim 47, wherein the gastric residence system has a deviation from 1 of a pH-dependent release rate ratio factor at least about 25% less than a deviation from 1 of a pH-dependent release rate ratio factor of a comparison gastric residence system comprising the same components but lacking the release-rate modulating polymer film.

53. The gastric residence system of claim 47, wherein the gastric residence system has a deviation from 1 of a pH-dependent release rate ratio factor at least about 50% less than a deviation from 1 of a pH-dependent release rate ratio factor of a comparison gastric residence system comprising the same components but lacking the release-rate modulating polymer film.

54. The gastric residence system of claim 1, wherein the system is configured to have a dissolution profile characterized by:

i) about 10% to 20% dissolution of the initial amount of the agent or pharmaceutically acceptable salt thereof present in the system during an initial 24 hour period in an aqueous environment; or ii) about 20% to 40% dissolution of the initial amount of the agent or pharmaceutically acceptable salt thereof present in the system during an initial 48 hour period in an aqueous environment;

wherein the aqueous environment is the stomach of a mammal, the stomach of a human patient, simulated gastric fluid, fasted state simulated gastric fluid, or fed state simulated gastric fluid.

55. A method of administering a gastric residence system to a patient, comprising: administering a container containing the gastric residence system of claim 1 to a patient.

56. The gastric residence system of claim 1, wherein the agent or pharmaceutically salt thereof is selected from the group consisting of donepezil, doxycycline, a pharmaceutically acceptable salt of donepezil, or a pharmaceutically acceptable salt of doxycycline.

57. The gastric residence system of claim 1, wherein the agent or pharmaceutically salt thereof is risperidone or a pharmaceutically acceptable salt of risperidone.

* * * * *